(12) United States Patent
Markowitz et al.

(10) Patent No.: US 11,690,847 B2
(45) Date of Patent: Jul. 4, 2023

(54) COMBINATIONS OF 15-PGDH INHIBITORS WITH CORTICOSTEROIDS AND/OR TNF INHIBITORS AND USES THEREOF

(71) Applicant: CASE WESTERN RESERVE UNIVERSITY, Cleveland, OH (US)

(72) Inventors: Sanford Markowitz, Pepper Pike, OH (US); Won Jin Ho, Cleveland, OH (US); Stephen P. Fink, Avon Lake, OH (US); Vinay Varadan, Westlake, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 651 days.

(21) Appl. No.: 16/465,500

(22) PCT Filed: Nov. 30, 2017

(86) PCT No.: PCT/US2017/063959
§ 371 (c)(1),
(2) Date: May 30, 2019

(87) PCT Pub. No.: WO2018/102552
PCT Pub. Date: Jun. 7, 2018

(65) Prior Publication Data
US 2020/0061073 A1    Feb. 27, 2020

Related U.S. Application Data

(60) Provisional application No. 62/510,166, filed on May 23, 2017, provisional application No. 62/428,259, filed on Nov. 30, 2016.

(51) Int. Cl.
| | |
|---|---|
| A61K 31/5377 | (2006.01) |
| A61P 1/00 | (2006.01) |
| A61K 31/421 | (2006.01) |
| A61K 31/426 | (2006.01) |
| A61K 31/4365 | (2006.01) |
| A61K 31/437 | (2006.01) |
| A61K 31/4439 | (2006.01) |
| A61K 31/4985 | (2006.01) |
| A61K 31/519 | (2006.01) |
| A61K 31/573 | (2006.01) |
| A61K 31/56 | (2006.01) |

(52) U.S. Cl.
CPC ........ *A61K 31/5377* (2013.01); *A61K 31/421* (2013.01); *A61K 31/426* (2013.01); *A61K 31/437* (2013.01); *A61K 31/4365* (2013.01); *A61K 31/4439* (2013.01); *A61K 31/4985* (2013.01); *A61K 31/519* (2013.01); *A61K 31/56* (2013.01); *A61K 31/573* (2013.01); *A61P 1/00* (2018.01)

(58) Field of Classification Search
CPC .............. A61K 31/5377; A61K 31/421; A61K 31/426; A61K 31/4365; A61K 31/437; A61K 31/4439; A61K 31/4985; A61K 31/519; A61K 31/56; A61K 31/573; A61P 1/00
See application file for complete search history.

(56) References Cited

U.S. PATENT DOCUMENTS

| | | |
|---|---|---|
| 3,382,247 A | 5/1968 | Anthony et al. |
| 4,725,676 A | 2/1988 | Agback et al. |
| 4,889,846 A | 12/1989 | Crossley |
| 4,910,226 A | 3/1990 | Holt et al. |
| 4,966,974 A | 10/1990 | Klausener et al. |
| 4,973,474 A | 11/1990 | Hocquaux et al. |
| 5,006,532 A | 4/1991 | Baker et al. |
| 5,015,629 A | 5/1991 | diZerega |
| 5,041,157 A | 8/1991 | Seiler et al. |
| 5,217,521 A | 6/1993 | Durr |
| 5,405,842 A | 4/1995 | Silverman |
| 5,411,981 A | 5/1995 | Gaillard-Kelly et al. |
| 5,438,058 A | 8/1995 | Dufetel et al. |
| 5,445,164 A | 8/1995 | Worthen et al. |
| 5,460,964 A | 10/1995 | McGlave et al. |
| 5,466,694 A | 11/1995 | Terranova et al. |
| 5,468,888 A | 11/1995 | Bouboutou et al. |
| 5,480,913 A | 1/1996 | Liao et al. |
| 5,516,779 A | 5/1996 | Von Langen et al. |
| 5,529,769 A | 6/1996 | Cho et al. |
| 5,565,467 A | 10/1996 | Batchelor et al. |
| 5,631,282 A | 5/1997 | Goetz |
| 5,635,387 A | 6/1997 | Fei et al. |
| 5,650,145 A | 7/1997 | Saint-Leger |

(Continued)

FOREIGN PATENT DOCUMENTS

| | | |
|---|---|---|
| AR | 060498 A1 | 6/2008 |
| AU | 2013/249434 B2 | 10/2017 |

(Continued)

OTHER PUBLICATIONS

Zhang; Science 2015, 348, aaa2340, 8 pages. doi: 10.1126/science. aaa2340 (Year: 2015).*

(Continued)

*Primary Examiner* — Daniel R Carcanague
(74) *Attorney, Agent, or Firm* — Barnes & Thornburg LLP

(57) ABSTRACT

A method of treating intestinal gastrointestinal, or bowel disorders in a subject in need thereof includes administering to the subject a therapeutically effective amount of 15-PGDH inhibitor alone or in combination with a corticosteroid and/or TNF alpha antagonist.

6 Claims, 22 Drawing Sheets

(56) References Cited

U.S. PATENT DOCUMENTS

| | | |
|---|---|---|
| 5,677,136 A | 10/1997 | Simmons et al. |
| 5,681,559 A | 10/1997 | DiGiusto et al. |
| 5,716,827 A | 2/1998 | Tsukamoto et al. |
| 5,750,397 A | 5/1998 | Tsukamoto et al. |
| 5,756,092 A | 5/1998 | Michelet et al. |
| 5,759,793 A | 6/1998 | Schwartz et al. |
| 5,760,043 A | 6/1998 | Dufetel et al. |
| 5,772,990 A | 6/1998 | Hocquaux et al. |
| 5,807,895 A | 9/1998 | Stratton et al. |
| 6,027,896 A | 2/2000 | Roses et al. |
| 6,121,254 A | 9/2000 | Saint-Leger |
| 6,214,533 B1 | 4/2001 | Ho et al. |
| 6,281,227 B1 | 8/2001 | Choi-Sledeski et al. |
| 6,414,027 B1 | 7/2002 | Neal |
| 6,465,421 B1 | 10/2002 | Duranton et al. |
| 6,468,972 B1 | 10/2002 | Pruche et al. |
| 7,004,913 B1 | 2/2006 | Rutenberg et al. |
| 7,022,675 B2 | 4/2006 | Rodgers et al. |
| 7,091,216 B2 | 8/2006 | Toupence et al. |
| 7,131,958 B2 | 11/2006 | Deverre |
| 7,147,626 B2 | 12/2006 | Goodman et al. |
| 7,189,724 B2 | 3/2007 | An et al. |
| 7,294,641 B2 | 11/2007 | Boulle et al. |
| 7,320,967 B2 | 1/2008 | Michelet et al. |
| 7,396,525 B2 | 7/2008 | Rozot et al. |
| 7,629,112 B1 | 12/2009 | Zengerle et al. |
| 7,705,041 B2 | 4/2010 | Michelet et al. |
| 8,068,897 B1 | 11/2011 | Gazdzinski |
| 8,202,882 B2 | 5/2012 | Hoelzemann et al. |
| 8,637,558 B2 | 1/2014 | Cho et al. |
| 8,642,660 B2 | 2/2014 | Goldfarb |
| 9,649,350 B2 | 5/2017 | Choi et al. |
| 9,789,116 B2 | 10/2017 | Markowitz et al. |
| 9,790,233 B2 | 10/2017 | Markowitz et al. |
| 9,801,863 B2 | 10/2017 | Markowitz et al. |
| 10,301,320 B2 | 5/2019 | Markowitz et al. |
| 10,420,752 B2 | 9/2019 | Markowitz et al. |
| 10,869,871 B2 | 12/2020 | Markowitz et al. |
| 10,945,998 B2 | 3/2021 | Markowitz et al. |
| 11,426,420 B2 | 8/2022 | Markowitz et al. |
| 2002/0044953 A1 | 4/2002 | Michelet et al. |
| 2002/0045659 A1 | 4/2002 | Michelet et al. |
| 2003/0083381 A1 | 5/2003 | Kumagai et al. |
| 2003/0096823 A1 | 5/2003 | Asp et al. |
| 2004/0052760 A1 | 3/2004 | Michelet et al. |
| 2004/0087593 A1 | 5/2004 | Clark et al. |
| 2004/0241726 A1 | 12/2004 | Liew |
| 2004/0241727 A1 | 12/2004 | Liew |
| 2004/0241729 A1 | 12/2004 | Liew |
| 2005/0026923 A1 | 2/2005 | An et al. |
| 2005/0187221 A1 | 8/2005 | Matsuda et al. |
| 2006/0019976 A1 | 1/2006 | Karp et al. |
| 2006/0034786 A1 | 2/2006 | Michelet et al. |
| 2006/0051540 A1 | 3/2006 | Kagawa |
| 2006/0089349 A1 | 4/2006 | Gundertofte et al. |
| 2006/0233797 A1 | 10/2006 | Gujrathi |
| 2006/0287284 A1 | 12/2006 | Schutze et al. |
| 2007/0049603 A1 | 3/2007 | Miknis et al. |
| 2007/0059265 A1 | 3/2007 | Boulle |
| 2007/0071699 A1 | 3/2007 | Boulle |
| 2007/0078175 A1 | 4/2007 | Boulle et al. |
| 2007/0155884 A1 | 7/2007 | Pellegatti et al. |
| 2007/0219234 A1 | 9/2007 | Oizumi et al. |
| 2008/0039459 A1 | 2/2008 | Folkes et al. |
| 2008/0206320 A1 | 8/2008 | Michelet et al. |
| 2008/0249117 A1 | 10/2008 | Michelet et al. |
| 2009/0007243 A1 | 3/2009 | Takita et al. |
| 2009/0105210 A1 | 4/2009 | Ashton et al. |
| 2009/0118337 A1 | 5/2009 | Davis |
| 2009/0163545 A1 | 6/2009 | Goldfarb |
| 2010/0022521 A1 | 1/2010 | Nogradi et al. |
| 2010/0076041 A1 | 3/2010 | Kilburn et al. |
| 2010/0099672 A1 | 4/2010 | Karp et al. |
| 2010/0120732 A1 | 5/2010 | Tabunoki |
| 2010/0190853 A1 | 7/2010 | Rethore et al. |
| 2010/0196705 A1 | 8/2010 | Hood et al. |
| 2010/0234369 A1 | 9/2010 | Hoelzemann et al. |
| 2011/0009374 A1 | 1/2011 | Keller |
| 2011/0014250 A1 | 1/2011 | Michelet et al. |
| 2011/0034564 A1 | 2/2011 | Parkkinen |
| 2011/0142816 A1 | 6/2011 | Landry et al. |
| 2011/0195031 A1 | 8/2011 | Du |
| 2011/0269954 A1 | 11/2011 | Cho et al. |
| 2012/0302586 A1 | 11/2012 | Rathod et al. |
| 2013/0078632 A1 | 3/2013 | Krishnadath |
| 2013/0190297 A1 | 7/2013 | De Jonghe |
| 2015/0072998 A1 | 3/2015 | Markowitz |
| 2015/0118744 A1 | 4/2015 | Tanaka et al. |
| 2015/0202241 A1 | 7/2015 | Choi et al. |
| 2016/0136185 A1 | 5/2016 | Shin et al. |
| 2016/0311825 A1 | 10/2016 | Farmer et al. |
| 2016/0376430 A1 | 12/2016 | Kusumoto et al. |
| 2017/0165241 A1 | 6/2017 | Markowitz |
| 2017/0173028 A1 | 6/2017 | Markowitz |
| 2017/0174704 A1 | 6/2017 | Gigstad et al. |
| 2017/0216265 A1 | 8/2017 | Markowitz |
| 2017/0266141 A1 | 9/2017 | Nagy |
| 2018/0064694 A1 | 3/2018 | Markowitz et al. |
| 2018/0118756 A1 | 5/2018 | Markowitz et al. |
| 2018/0125829 A1 | 5/2018 | Markowitz |
| 2019/0126044 A1 | 5/2019 | Lozano |
| 2019/0275014 A1 | 9/2019 | Markowitz et al. |
| 2019/0365769 A1 | 12/2019 | Markowitz et al. |
| 2020/0030348 A1 | 1/2020 | Markowitz et al. |
| 2020/0061073 A1 | 2/2020 | Markowitz et al. |
| 2020/0095206 A1 | 3/2020 | Markowitz et al. |
| 2020/0140453 A1 | 5/2020 | Markowitz et al. |
| 2020/0147063 A1 | 5/2020 | Markowitz et al. |
| 2020/0165249 A1* | 5/2020 | Panarese ............... C07D 471/14 |
| 2021/0032265 A1 | 2/2021 | Markowitz |
| 2021/0094968 A1 | 4/2021 | Markowitz |
| 2021/0100778 A1 | 4/2021 | Markowitz |
| 2021/0100779 A1 | 4/2021 | Markowitz |
| 2021/0106587 A1 | 4/2021 | Markowitz |
| 2021/0108177 A1 | 4/2021 | Di Santo et al. |
| 2021/0165249 A1 | 6/2021 | Wang et al. |
| 2021/0283113 A1 | 9/2021 | Markowitz et al. |
| 2021/0317132 A1 | 10/2021 | Markowitz |
| 2021/0003378 A1 | 12/2021 | Arlt et al. |
| 2021/0386070 A1 | 12/2021 | Arlt et al. |

FOREIGN PATENT DOCUMENTS

| | | |
|---|---|---|
| AU | 2016/248080 A1 | 11/2017 |
| AU | 2014/342811 B2 | 1/2019 |
| AU | 2018/200368 B2 | 7/2019 |
| AU | 2018/215678 A1 | 8/2019 |
| AU | 2018/249956 A1 | 11/2019 |
| AU | 2019/250163 A1 | 11/2019 |
| AU | 2016/229918 B2 | 10/2020 |
| AU | 2019/247838 A1 | 10/2020 |
| AU | 2019/202208 B2 | 12/2020 |
| AU | 2021/201332 A1 | 3/2021 |
| AU | 2019/384821 A1 | 6/2021 |
| AU | 2021/204985 A1 | 8/2021 |
| AU | 2017/300377 B2 | 4/2022 |
| AU | 2022/201982 A1 | 4/2022 |
| AU | 2018/272108 B2 | 9/2022 |
| AU | 2021/200610 B2 | 9/2022 |
| CA | 2007351 A1 | 7/1990 |
| CA | 2870666 A1 | 10/2013 |
| CA | 2927730 A1 | 4/2016 |
| CA | 2979203 A1 | 9/2016 |
| CA | 2974266 A1 | 7/2017 |
| CA | 2984594 A1 | 10/2017 |
| CA | 3031091 A1 | 1/2018 |
| CA | 3052466 A1 | 8/2018 |
| CA | 3059255 A1 | 10/2018 |
| CA | 3068445 A1 | 11/2018 |
| CA | 2984588 C | 10/2019 |
| CA | 3095308 A1 | 10/2019 |
| CA | 3120858 A1 | 5/2020 |
| CL | 2020002741 A1 | 1/2021 |
| CL | 2021001288 A1 | 1/2022 |

(56) References Cited

FOREIGN PATENT DOCUMENTS

| | | |
|---|---|---|
| CL | 2021003378 A1 | 8/2022 |
| CN | 1589793 A | 3/2005 |
| CN | 102888208 B | 2/2015 |
| CN | 107921025 A | 4/2018 |
| CN | 108012528 A | 5/2018 |
| CN | 110573154 A | 12/2019 |
| CN | 110582277 A | 12/2019 |
| CN | 110891568 A | 3/2020 |
| CN | 111132982 A | 5/2020 |
| CN | 11273944 A | 4/2021 |
| CN | 113507931 A | 10/2021 |
| EP | 0142811 A2 | 5/1985 |
| EP | 0271273 A2 | 6/1988 |
| EP | 0378508 A2 | 7/1990 |
| EP | 0434624 A1 | 6/1991 |
| EP | 0648488 B1 | 11/2000 |
| EP | 1080728 A1 | 3/2001 |
| EP | 1175890 A1 | 1/2002 |
| EP | 1175891 A1 | 1/2002 |
| EP | 0854700 B1 | 5/2002 |
| EP | 0680745 B1 | 11/2002 |
| EP | 2564841 B1 | 5/2015 |
| EP | 2838533 B1 | 10/2017 |
| EP | 3267995 A1 | 1/2018 |
| EP | 3280398 A1 | 2/2018 |
| EP | 3283074 A1 | 2/2018 |
| EP | 3295940 A1 | 3/2018 |
| EP | 3484473 A1 | 5/2019 |
| EP | 3057973 B1 | 9/2019 |
| EP | 3548035 A1 | 10/2019 |
| EP | 3576737 A1 | 12/2019 |
| EP | 3606520 A1 | 2/2020 |
| EP | 3630773 A1 | 4/2020 |
| EP | 3781154 A1 | 2/2021 |
| EP | 3883577 A1 | 9/2021 |
| FR | 2838641 A1 | 10/2003 |
| FR | 2860431 A1 | 4/2005 |
| JP | S60-172984 A | 9/1985 |
| JP | H02-288810 A | 11/1990 |
| JP | H04-234888 A | 8/1992 |
| JP | H09-295921 A | 11/1997 |
| JP | H10-287532 A | 10/1998 |
| JP | 2821690 B2 | 11/1998 |
| JP | 2003/286171 A | 10/2003 |
| JP | 2004/528319 A | 9/2004 |
| JP | 2005/515182 A | 5/2005 |
| JP | 2005/325099 A | 11/2005 |
| JP | 2004/528319 A5 | 1/2006 |
| JP | 2006/522750 A | 10/2006 |
| JP | 2006/522750 A5 | 5/2007 |
| JP | 2007/527850 A | 10/2007 |
| JP | 2008/507518 A | 3/2008 |
| JP | 2008/527011 A | 7/2008 |
| JP | 2008/536855 A | 9/2008 |
| JP | 2008/536855 A5 | 5/2009 |
| JP | 2009/520016 A | 5/2009 |
| JP | 2009/535335 A | 10/2009 |
| JP | 2009/535335 A5 | 1/2010 |
| JP | 2010/053332 A | 3/2010 |
| JP | 2010/520864 A | 6/2010 |
| JP | 2007/527850 A5 | 7/2010 |
| JP | 2011/500610 A | 1/2011 |
| JP | 2013/506004 A | 2/2013 |
| JP | 2013/506004 A5 | 10/2013 |
| JP | 2015514770 A | 5/2015 |
| JP | 2016/531864 A | 10/2016 |
| JP | 2016/537328 A | 12/2016 |
| JP | 2017/514809 A | 6/2017 |
| JP | 6203820 B2 | 9/2017 |
| JP | 2018/511581 A | 4/2018 |
| JP | 2018/511616 A | 4/2018 |
| JP | 2018/511616 A5 | 5/2019 |
| JP | 6517197 B2 | 5/2019 |
| JP | 2019/135253 A | 8/2019 |
| JP | 2020/502070 A | 1/2020 |
| JP | 2020/503851 A | 2/2020 |
| JP | 2020/514323 A | 5/2020 |
| JP | 2020/516617 A | 6/2020 |
| JP | 2020/516617 A5 | 7/2020 |
| JP | 6789542 B2 | 11/2020 |
| JP | 2020/502070 A5 | 1/2021 |
| JP | 2021/020942 A | 2/2021 |
| JP | 2020/514323 A5 | 3/2021 |
| JP | 2021/038247 A | 3/2021 |
| JP | 2021/519797 A | 8/2021 |
| JP | 2022/507888 A | 1/2022 |
| JP | 2021/519797 A5 | 4/2022 |
| JP | 7139308 B2 | 9/2022 |
| KR | 2008/0112764 A | 12/2008 |
| KR | 2010/0137090 A | 12/2010 |
| KR | 2013/0103945 A | 9/2013 |
| RU | 2006/127472 A | 2/2008 |
| WO | WO 1990/006100 A1 | 6/1990 |
| WO | WO 1993/013664 A2 | 7/1993 |
| WO | WO 1995/011003 A1 | 4/1995 |
| WO | 1998/0027092 A1 | 6/1998 |
| WO | WO 1998/033497 A1 | 8/1998 |
| WO | WO 2001/017480 A2 | 3/2001 |
| WO | WO 2001/072268 A1 | 10/2001 |
| WO | WO 2001/074307 A2 | 10/2001 |
| WO | WO 2001/074313 A2 | 10/2001 |
| WO | WO 2001/074314 A2 | 10/2001 |
| WO | WO 2001/074315 A2 | 10/2001 |
| WO | 2004/012671 A2 | 2/2004 |
| WO | 2004012671 A2 | 2/2004 |
| WO | WO 2004/089415 A2 | 10/2004 |
| WO | WO 2004/089416 A2 | 10/2004 |
| WO | WO 2004/089471 A2 | 10/2004 |
| WO | WO 2004/099204 A1 | 11/2004 |
| WO | 2005/0021552 A1 | 3/2005 |
| WO | WO 2005/028676 A2 | 3/2005 |
| WO | WO 2005/030773 A1 | 4/2005 |
| WO | WO 2005/046434 A2 | 5/2005 |
| WO | 2005/062735 A2 | 7/2005 |
| WO | WO 2005/090333 A1 | 9/2005 |
| WO | 2006/019832 A1 | 2/2006 |
| WO | WO 2006/048264 A2 | 5/2006 |
| WO | WO 2006/048266 A2 | 5/2006 |
| WO | WO 2006/074226 A2 | 7/2006 |
| WO | WO 2006/078676 A2 | 7/2006 |
| WO | WO 2006/096649 A2 | 9/2006 |
| WO | WO 2006/098961 A2 | 9/2006 |
| WO | WO 2006/138275 A2 | 12/2006 |
| WO | WO 2007/013665 A2 | 2/2007 |
| WO | WO 2007/019180 A2 | 2/2007 |
| WO | WO 2007/027855 A2 | 3/2007 |
| WO | WO 2007/038519 A1 | 4/2007 |
| WO | WO 2007/072095 A1 | 6/2007 |
| WO | WO 2007/100775 A2 | 9/2007 |
| WO | WO 2007/101224 A2 | 9/2007 |
| WO | WO 2007/127183 A1 | 11/2007 |
| WO | WO 2008/063671 A2 | 5/2008 |
| WO | WO 2008/156614 A2 | 12/2008 |
| WO | WO 2009/029669 A1 | 3/2009 |
| WO | WO 2009/073460 A2 | 6/2009 |
| WO | WO 2009/082691 A1 | 7/2009 |
| WO | WO 2009/111648 A1 | 9/2009 |
| WO | WO 2009/120877 A2 | 10/2009 |
| WO | WO 2010/023181 A1 | 3/2010 |
| WO | WO 2010/045017 A1 | 4/2010 |
| WO | WO 2010/052569 A2 | 5/2010 |
| WO | WO 2010/077101 A2 | 7/2010 |
| WO | WO 2010/080996 A1 | 7/2010 |
| WO | WO 2010/091808 A1 | 8/2010 |
| WO | WO 2010/111711 A2 | 9/2010 |
| WO | WO 2011/041304 A2 | 4/2011 |
| WO | WO 2011/042860 A2 | 4/2011 |
| WO | WO 2011/094847 A1 | 8/2011 |
| WO | WO 2011/147753 A1 | 12/2011 |
| WO | WO 2012/146933 A1 | 11/2012 |
| WO | WO 2013/034927 A1 | 3/2013 |
| WO | WO 2013/082243 A1 | 6/2013 |
| WO | WO 2013/083991 A1 | 6/2013 |
| WO | 2013/0112699 A2 | 8/2013 |

(56) References Cited

FOREIGN PATENT DOCUMENTS

| | | | |
|---|---|---|---|
| WO | WO 2013/158649 A1 | 10/2013 | |
| WO | WO-2013158649 A1 * | 10/2013 | .............. A61P 19/08 |
| WO | 2013/180336 A1 | 12/2013 | |
| WO | WO 2014/081617 A1 | 5/2014 | |
| WO | WO 2014/081878 A2 | 5/2014 | |
| WO | WO 2014/160183 A1 | 10/2014 | |
| WO | WO 2014/160947 A1 | 10/2014 | |
| WO | WO 2015/005239 A1 | 1/2015 | |
| WO | 2015/065716 A1 | 5/2015 | |
| WO | WO 2015/077382 A2 | 5/2015 | |
| WO | WO 2015/161142 A1 | 10/2015 | |
| WO | WO 2016/106340 A2 | 6/2016 | |
| WO | WO 2016/124939 A1 | 8/2016 | |
| WO | 2016144958 A1 | 9/2016 | |
| WO | 2016168472 A1 | 10/2016 | |
| WO | 2017/152044 A1 | 9/2017 | |
| WO | 2018017582 A1 | 1/2018 | |
| WO | WO 2018/102552 A1 | 6/2018 | |
| WO | WO 2018/145080 A1 | 8/2018 | |
| WO | WO 2018/187810 A1 | 10/2018 | |
| WO | 2018218251 A1 | 11/2018 | |
| WO | WO 2018/227134 A1 | 12/2018 | |
| WO | WO 2019/010482 A1 | 1/2019 | |
| WO | WO 2019/195565 A1 | 10/2019 | |
| WO | WO 2020/051207 A2 | 3/2020 | |
| WO | 2020/106998 A1 | 5/2020 | |
| WO | WO 2020/160151 | 8/2020 | |
| WO | WO 2020/252146 A1 | 12/2020 | |
| WO | WO 2021/151014 A1 | 7/2021 | |
| WO | WO 2021/168430 A1 | 8/2021 | |
| WO | WO 2021/236779 A1 | 11/2021 | |
| WO | WO 2021/252936 A1 | 12/2021 | |
| WO | WO 2022/032230 A1 | 2/2022 | |

OTHER PUBLICATIONS

Dai; Dig Dis Sci 2015, 60, 1236-1246. doi: 10.1007/s10620-014-3478-7 (Year: 2015).*
Hoult; Br.J.Pharmac. 1978, 64, 6-8. doi: doi.org/10.1111/j.1476-5381.1978.tb08633.x (Year: 1978).*
Katz; Practical Gastroenterology, 2005, 14-25. https://ficomputing.net/pdf/Jan05/Jan05Katz.pdf (Year: 2005).*
Niesen; PLoS ONE 2010, 5(11), e13719. doi: 10.1371/journal.pone.0013719 (Year: 2010).*
Sood; Journal of Clinical Gastroenterology 2002, 35, 328-331. doi:10.1097/01.MCG.0000028364.90843.74 (Year: 2002).*
Na; Biochemical Pharmacology 2011, 82, 1352-1360. https://doi.org/10.1016/j.bcp.2011.08.005 (Year: 2011).*
Nakanishi; Semin Immunopathol 2013, 35, 123-137. https://doi.org/10.1007/s00281-012-0342-8 (Year: 2013).*
Yan; Proc Natl Acad Sci USA 2009, 106, 9409-9413. https://doi.org/10.1073/pnas.0902367106 (Year: 2009).*
Applicant: Case Western Reserve University; Australian Patent Application No. 2018215678; Australian Office Action dated Mar. 23, 2021; 8 pgs.
Applicant: Case Western Reserve University; Australian Patent Application No. 2017300377; Australian Office Action dated Apr. 9, 2022; 7 pgs.
Cudaback E, Jorstad NL, Yang Y, Montine TJ, Keene CD. Therapeutic implications of the prostaglandin pathway in Alzheimer's disease. Biochem Pharmacol. 2014;88(4):565-572. doi:10.1016/j.bcp.2013.12.014; 9 pgs.
H. Cho, et al.; "Inhibition of NAD+-dependent 15-hydroxyprostaglandin dehydrogenase (15-PGDH) by cyclooxygenase inhibitors and chemopreventive agents"; Elsevier; vol. 67, Issue 6, Dec. 3, 2002, pp. 461-465.
Japanese Patent Application No. 2019-503202; JP OA dated Jul. 6, 2021; 12 pgs.
Japanese Patent Application No. 2019-554986; JP OA dated Jun. 22, 2021; 10 pgs.

Chinese Office Action for Application No. 201680034932.5 dated May 8, 2020.
Applicant: Case Western Reserve University; Title: Inhibitors of Short-Chain Dehydrogenase Activity for Treating Fibrosis; Australian Patent Application No. 2016229918; Examination report No. 2 for your standard patent application; Jul. 30, 2020, 8 pgs.
Sanford Markowitz, "Inhibitors of Short-Chain Dehydrogenase Activity for Modulating Hematopoietic Stem Cells and Hematopoiesis"; U.S. Appl. No. 16/581,024, filed Sep. 24, 2019; 7 pgs.
Sanford Markowitz, "Compositions and Methods of Modulating 15-PGOH Activity"; U.S. Appl. No. 16/421,867, filed May 24, 2019; Jul. 2, 2020; 65 pgs.
Cho et al: "Thiazolidinediones as a novel class of NAD+dependent 15-hydroxyprostaglandin dehydrogenase inhibitors", Archives of Biochemistry and Biophysics, Academic Press, US, vol. 405, Jan. 1, 2002 (Jan. 1, 2002), pp. 247-251, XP002292688, ISSN: 0003-9861, DOI: 10.1016/S0003-9861 (02)00352-1.
European Office Action for Application No. 17 194 305.3-1110 dated Apr. 9, 2020.
Applicant: Case Western Reserve University; "Inhibitors of Short-Chain Dehydrogenase Activity for Treating Coronary Disorders"; European Patent Application No. 18781322; Extended European Search Report dated Dec. 9, 2020; 12 pgs.
Applicant: Case Western Reserve University; "Inhibitors of Short-Chain Dehydrogenase Activity for Treating Coronary Disorders"; PCT International Application No. PCT/US2018/026739; PCT International Filing Date: Apr. 9, 2018; Date of Completion of Search: Jun. 15, 2018; 9 pgs.
Applicant: Case Western Reserve University; "Compositions and Methods of Modulating 15-PGDH Activity" Canadian Patent Application No. 2870666; Office Action dated Nov. 18, 2020; 4 pgs.
Applicant: Case Western Reserve University; "Inhibitors of Short-Chain Dehydrogenase Activity for Treating Fibrosis"; Chinese Patent Application No. 201680026631.8; Chinese Office Action dated Dec. 11, 2020; 12 pgs.
Applicant: Case Western Reserve University; Canadian Application No. 2927730 "Compositions and Methods of Modulating Short-Chain Dehydrogenase Activity"; Canadian Office Action dated Dec. 3, 2020; 5 pgs.
Applicant: Case Western Reserve University; European Office Action; dated Dec. 17, 2020; 5 pgs.
Kalugin, V.E., Shestopalov, A.M. & Litvinov, V.P. Functionalized sulfur-containing compounds. 13. Synthesis of substituted 3-amino-2-(organylsulfinyl)-and-(organylsulfonyl)thieno[2,3-b]pyridines. Russ Chem Bull 55, 529-534 (2006). https://doi.org/10.1007/s11172-006-0287-y.
Mordente et al. "Human Heart Cytosolic Reductases and Anthracycline Cardiotoxicity," IUBMB Life, Jan. 3, 2008 (Jan. 3, 2008), vol. 52, pp. 83-88.
Olson et al. "Protection from Doxorubicin-Induced Cardiac Toxicity in Mice with a Null Allele of Carbonyl Reductase 1," Cancer Research, Oct. 15, 2003 (Oct. 15, 2003), vol. 63, pp. 6602-6606.
Piska et al. "Metabolic carbonyl reduction of anthracyclines role in cardiotoxicity and cancer resistance: Reducing enzymes as putative targets for novel cardioprotective and chemosensitizing agents," Invest New Drugs, Mar. 10, 2017 (Mar. 10, 2017), vol. 35, No. 3, pp. 375-385.
International Search Report, Written Opinion, and International Preliminary Report on Patentability issued in PCT International Application No. PCT/US2013/036790, ISA/KR Korean Intellectual Property Office, Daejeon Metropolitan City, Republic of Korea. 13 pages, (2013)
International Search Report, Written Opinion, and International Preliminary Report on Patentability issued in PCT/US2014/060761, ISA/US United States Patent and Trademarl Office, Alexandria, VA. 14 pages, (2014).
International Search Report and Written Opinion and International Preliminary Report on Patentability issued in PCT International Application No. PCT/US2016/021374, ISA/US United States Patent and Trademark Office, Alexandria, VA. 15 pages, (2015)

(56) References Cited

OTHER PUBLICATIONS

International Search Report, Written Opinion, and International Preliminary Report on Patentability issued in PCT/US2016/027549, ISA/US United States Patent and Trademark Office, Alexandria, VA. 16 pages, (2016)

International Search Report, Written Opinion, and International Preliminary Report on Patentability issued in PCT/US2017/042620, ISA/US United States Patent and Trademark Office, Alexandria, VA. 24 pages, (2017)

International Search Report, Written Opinion, and International Preliminary Report on Patentability issued in PCT/US2017/063959, ISA/US United States Patent and Trademark Office, Alexandria, VA. 31 pages, (2017).

International Search Report, Written Opinion, and International Preliminary Report on Patentability issued in PCT/US2018/017044, ISA/US United States Patent and Trademark Office, Alexandria, VA. 15 pages, (2018)

International Search Report and Written Opinion and International Preliminary Report on Patentability issued in PCT International Application No. PCT/US2018/026739, ISA/US United States Patent and Trademark Office, Alexandria, VA. 17 pages, (2018)

International Search Report, Written Opinion, and International Preliminary Report on Patentability issued in PCT/US2018/034944, ISA/US United States Patent and Trademark Office, Alexandria, VA. 15 pages, (2018)

International Search Report, Written Opinion, and International Preliminary Report on Patentability issued in PCT/US2019/025812, ISA/US United States Patent and Trademark Office, Alexandria, VA. 16 pages, (2019)

International Search Report and Written Opinion and International Preliminary Report on Patentability issued in PCT/US2019/062686, ISA/RU Federal Institute of Industrial Property, Moscow, RU. 15 pages, (2019).

International Search Report, Written Opinion, and International Preliminary Report on Patentability issued in PCT/US2021/019084, ISA/US United States Patent and Trademark Office, Alexandria, VA. 13 pages, (2021).

International Search Report, Written Opinion, and International Preliminary Report on Patentability issued in PCT/US2021/033170, ISA/EP European Patent Office, NL. 28 pages, (2021)

International Search Report and Written Opinion issued in PCT/US2021/045231, ISA/US United States Patent and Trademark Office, Alexandria, VA. 9 pages, (2021)

International Search Report and Written Opinion issued in PCT/US2022/12423, ISA/US United States Patent and Trademark Office, Alexandria, VA. 12 pages, (2022).

Abulwerdi, F.A., et al., "Development of Small Molecules with a Non-Canonical Binding Mode to HIV-1 Trans Activation Response (TAR) RNA," *Journal of Medicinal Chemistry*, Dec. 22, 2016, pp. 11148-11160, 59(24), American Chemical Society, Washington, DC, US.

Ahmad, Muzamil, et al., "The $PGE_2EP2$ receptor and its selective actibvation are beneficial against ischemic stroke," *Experimental & Translational Stroke Medicine*, 2010, 8 pages, vol. 2, No. 12, BioMed Central, UK.

"AKos Screening Samples ca. 3.5 million compounds Version Dec. 2007," Web page <www.akosgmbh.de/AKosSamples/index.html>, 3 pages, Dec. 19, 2007, retrieved from the Internet Archive Wayback Machine via Page Vault <http://web.archive.org/web20071219115313/http://www.akosgmbh.de/AKosSamples/index.html> on Sep. 29, 2022.

Almeida, Camila Bononi, et al., "High Expression of the cGMP-specific Phosphodiesterase, PDE9A, in Sickle Cell Disease (SCD) and the Effects of its Inhibition in Erythroid Cells and SCD Neutrophils," *British Journal of Haematology*, Sep. 2008, pp. 836-844, 142(5), Blackwell Publishing Ltd, Oxford, UK.

Almeida, Camila Bononi, et al., "Hydroxyurea and a cGMP-amplifying Agent Have Immediate Benefits on Acute Vaso-Occlusive Events in Sickle Cell Disease Mice," *Blood*, Oct. 4, 2012, 23 pages, 120(14), American Society of Hematology, Washington, DC, US.

Al-Najjar, Belal O., et al., "Pharmacophore Modeling and 3D-QSAR Studies of 15-Hydroxyprostaglandin Dehydrogenase (15-PGDH) Inhibitors," *Indian Journal of Chemistry*, Nov. 2017, pp. 1200-1207, vol. 56B, Scientific Publishers of India, IN.

Alvarez, F.J., and Slade, R.T., "Kinetics and Mechanism of Degradation of Zileuton, a Potent 5-Lipoxygenase Inhibitor," *Pharmaceutical Research*, 1992, pp. 1465-1473, vol. 9, No. 11, Plenum Publishing Corporation-Springer Science and Business Media, DE.

Antczak, M.I., et al., "Inhibitors of 15-Prostaglandin Dehydrogenase to Potentiate Tissue Repair", *Journal of Medicinal Chemistry*, 2017, pp. 3979-4001, vol. 60, No. 9, American Chemical Society, Washington, DC, US.

Archelas, A., et al., "Absolute Configuration of α-Methylstyrene Oxide: The Correct Absolute Configuration/ Optical Rotation Correlation", *The Journal of Organic Chemistry*, Aug. 1, 1999, pp. 6112-6114, vol. 64, No. 16, American Chemical Socierty, Washington, DC, US.

Asati, V., et al., "Molecular Modeling Studies of Some Thiazolidine-2,4-Dione Derivatives as 15-PGDH Inhibitors," *Medicinal Chemistry Research*, Aug. 29, 2015, pp. 94-108, vol. 25, Springer Science +Business Media, DE.

Astatech, "AstaTech Inc. Catalog Product Search Result," Compound: 6-BROMO-3-Methylpyrimidin-4(3H)-One, 2 pages, Oct. 18, 2022, retrieved via Page Vault https://astatechnic.comr/CPSResult.php?CRNO=183100 on Oct. 18, 2022.

Bagshaw, S. M., et al., "A comparison of the RIFLE and AKIN criteria for acute kidney injury in critically ill patients," *Nephrology Dialysis Transplantation*, May 2008, pp. 1569-1574, vol. 23, Issue 5, Oxford University Press, Oxford, UK, retrieved from https://academic.oup.com/ndt/article/23/5/1569/1809429, on Oct. 18, 2022.

Baker, Michael E. "Licorice and Enzymes Other Than 11β-Hydroxysteroid Dehydrogenase: An Evolutionary Perspective," *Steroids*, Feb. 1994, pp. 136-141, vol. 59, Issue 2, Butterworth-Heinemann, Elsevier, Ltd, Oxford, UK.

Bakhle, Y.S., "Action of Prostaglandin Dehydrogenase Inhibitors on Prostaglandin Uptake in Rat Isolated Lung," *British Journal of Pharmacology*, Apr. 1979, pp. 635-639, 65(4), British Pharmacological Society, Macmillan Journals Ltd, UK.

Baliga, B.S, et al., "Combined Effects of Arginine and Hydroxyurea on BFU-E Derived Colony Growth and HbF Synthesis in Erythroid Progenitors Isolated from Sickle Cell Blood," *Cellular and Molecular Biology*, 2010, pp. OL1290-OL1298, vol. 56, No. 3, Cellular and Molecular Biology Association, Paris, FR.

Bärnthaler, Thomas, et al., "Inhibiting Eicosanoid Degradation Exerts Antifibrotic Effects in a Pulmonary Fibrosis Mouse Model and Human Tissue," *Journal of Allergy and Clinical Immunology*, Mar. 2020, pp. 818-833, vol. 145, No. 3, Elsevier Inc, Amsterdam, NL.

Battistini, Bruno, et al., "COX-1 and COX-2: Toward the Development of More Selective NSAIDS," *Advances in prostaglandin research were presented at the 9th International Conference on Prostaglandins and Related Compounds* in Florence, Italy, Jun. 6-10, 1994, and the 12th *International Congress of Pharmacology* in Montreal, Canada, Jul. 24-29, 1994, *Drug News & Perspectives Meeting Report*, Oct. 1994, pp. 501-512, 7(8).

Becker, C., et al., "In Vivo Imaging of Colitis and Colon Cancer Development in Mice Using High-Resolution Chromoendoscopy," *Gut*, 2005, pp. 950-954, vol. 54, BMJ, UK.

Berg, Daniel J., et al. "Rapid Development of Colitis in NSAID-Treated IL-10-Deficient Mice", *Gastroenterology*, 2002, pp. 1527-1542, vol. 123, No. 5, American Gastroenterological Association, W.B. Saunders, Philadelphia, PA.

Berk, L.B., et al., "16,16-Dimethyl Prostaglandin E2 and/or Syngeneic Bone Marrow Transplantation Increase Mouse Survival After Supra—Lethal Total Body Irradiation," *International Journal of Radiation Oncology Biology Physics*, Jun. 1990, pp. 1387-1392, vol. 18, No. 6, Pergamon Press plc, Oxford, UK.

Berry, C.N., et al., "Inhibition of Prostaglandin 15-Hydroxydehydrogenase by Sulphasalazine and a Novel Series of Potent Analogues," *Biochemical Pharmacology*, Oct. 1, 1983, pp. 2863-2871, vol. 32, No. 19, Pergamon Press Ltd., GB.

(56) References Cited

OTHER PUBLICATIONS

Bertram, Lars, et al., "Systematic meta-analyses of Alzheimer disease genetic association studies: the AlzGene database," *Nature Genetics*, Jan. 2007, pp. 17-23, vol. 39, No. 1, Nature Publishing Group, UK.

Bertram, Lars, et al., "Is α-T catenin (VR22) an Alzheimer's disease risk gene?", *Journal of Medical Genetics, Electronic Letters*, Jan. 2007, pp. 1-4, vol. 44, No. 1, BMJ Group, UK.

Blackwell, G.J., and Flower, R.J., "A Rapid Method for the Estimation of Prostaglandin 15-Hydroxydehydrogenase Activity and its Application to Pharmacology," *British Journal of Pharmacology*, 1976, pp. 589-597, vol. 57, Issue 4, British Pharmacological Society, UK.

Blake, Martin I., et al., "Studies with Deuterated Drugs", *Journal of Pharmaceutical Sciences*, Mar. 1975, pp. 367-391, vol. 64, No. 3, Elsevier, Amsterdam, NL.

Borm, Michelle E.A., and Bouma, Gerd, "Animal Models of Inflammatory Bowel Disease," *Drug Discovery Today: Disease Models*, Dec. 2004, pp. 437-443, vol. 1, Issue 4, Elsevier, Amsterdam, NL.

Bray, James E., et al., "The Human Short-Chain Dehydrogenase/Reductase (SPR) Superfamily: A Bioinformatics Summary," *Chemico-Biological Interactions*, Mar. 16, 2009, pp. 99-109, vol. 178, Issues 1-3, Elsevier, Amsterdam, NL.

Breyer, Richard M., et al., "Prostanoid Receptors: Subtypes and Signaling," *Annual Review of Pharmacology and Toxicology*, 2001, 32 pages including pp. 661-690, vol. 41, Annual Reviews, San Mateo, CA, US.

Brown, J.R., et al., "COX-2: A Molecular Target for Colorectal Cancer Prevention," *Journal of Clinical Oncology*, Apr. 20, 2005, pp. 2840-2855, vol. 23, No. 12, American Society of Clinical Oncology, Lippincott Williams and Wilkins, Philadelphia, PA, US.

Cahn, R.S., and Ingold, C.K., "Specification of Configuration about Quadricovalent Asymmetric Atoms," *Journal of the Chemical Society*, 1951, pp. 612-622, Chemical Society, UK.

Cahn, R.S., et al., "The Specification of Asymmetric Configuration in Organic Chemistry," *Experientia*, 1956, pp. 81-94, vol. 12, No. 3, Springer Science + Business Media, Berlin, DE.

Cahn, R.S., "An Introduction to the Sequence Rule: A System for the Specification of Absolute Configuration," *Journal of Chemical Education*, Mar. 1964, pp. 116-125, vol. 41, No. 3, American Chemical Society, Washington, DC.

Cahn, R.S., et al., "Specification of Molecular Chirality," *Angew. Chem. Inter. Edit.*, 1966, pp. 385-415, vol. 5, No. 4, Wiley-VCH, Weinheim, DE.

Cahn, R.S., et al., Errata "Specification of Molecular Chirality,", *Angew. Chem. Inter. Edit.*, 1966, p. 511, vol. 5, No. 5, Wiley-VCH, Weinheim, DE.

Cancer Genome Atlas Network, "Comprehensive molecular characterization of human colon and rectal cancer," *Nature*, Jul. 19, 2012, pp. 330-337, vol. 487, Macmillan Publishers Limited, UK.

Cancer Genome Atlas Network, "Comprehensive molecular portraits of human breast tumours," *Nature*, Oct. 4, 2012, pp. 61-70, vol. 490, Macmillan Publishers Limited, UK.

Cancer Genome Atlas Network, "Integrated genomic analyses of ovarian carcinoma," *Nature*, Jun. 30, 2011, pp. 609-615, vol. 474, and *Erratum, Nature*, Oct. 11, 2012, p. 292, vol. 490, Macmillan Publishers Limited, UK.

Castellone, M.D., et al., "Prostaglandin $E_2$ Promotes Colon Cancer Cell Growth Through a $G_s$-Axin-β Catenin Signaling Axis," *Science*, Dec. 2, 2005, pp. 1504-1510, vol. 310, Issue 5753, American Association for the Advancement of Science, Washington, DC, US.

Chang, Kyung Hee., et al., "Vasculopathy-Associated Hyperangiotensinemia Mobilizes Haematopoietic Stem Cells/Progenitors Through Endothelial $AT_2R$ and Cytoskeletal Dysregulation," *Nature Communications*, Jan. 9, 2015, 11 pages, 6, Article 5914, Macmillan Publishers Limited, Nature Research, London, UK.

"ChemBridge | Screening Libraries: Key Facts," Web page <www.chembridge.com/screening_libraries/>, 2 pages, Jan. 22, 2013, retrieved from the Internet Archive Wayback Machine via Page Vault <http://web.archive.org/web/20130122020518/https://www.chembridge.com/screening_libraries/> on Sep. 29, 2022.

Chemtob, Sylvain, et al., "Deficiency in Prostaglandin $E_2(PGE_2)$ Receptors, Mainly $EP_2$ Subtype, on Brain Synaptosomes in Early Development: Implications on Cerebral Metabolism," *Seminars in Perinatology*, Feb. 1994, pp. 23-29, vol. 18, No. 1, W.B. Saunders Company, Philadelphia, PA, US.

Chen, H., et al., "Prostaglandin E2 Mediates Sensory Nerve Regulation of Bone Homeostasis," *Nature Communications*, Jan. 14, 2019, pp. 1-13, vol. 10, Issue 1, Article No. 181, Nature Research, London, UK.

Chi, Xiuling, et al., "15-Hydroxyprostaglandin Dehydrogenase (15-PGDH) is Up-Regulated by Flurbiprofen and Other Non-Steroidal Anti-Inflammatory Drugs in Human Colon Cancer HT29 Cells," *Archives of Biochemistry and Biophysics*, Jul. 15, 2009, pp. 139-145, vol. 487, No. 2, Elsevier, Amsterdam, NL.

Childs, April C., et al., "Doxorubicin Treatment in Vivo Causes Cytochrome c Release and Cardiomyocyte Apoptosis, as Well as Increased Mitochondrial Efficiency, Superoxide Dismutase Activity, and Bcl-2:Bax Ratio," *Cancer Research*, Aug. 15, 2002, pp. 4592-4598, vol. 62, American Association for Cancer Research, Philadelphia, PA, US.

Cho, Hoon, et al., "Role of glutamine 148 of human 15-hydroxyprostaglandin dehydrogenase in catalytic oxidation of prostaglandin E2", *Bioorganic & Medicinal Chemistry*, 2006, pp. 6486-6491, vol. 14, Elsevier Ltd, Amsterdam, NL.

Choi, Dubok, et al., "Control of the Intracellular Levels of Prostaglandin $E_2$ Through Inhibition of the 15-Hydroxyprostaglandin Dehydrogenase for Wound Healing," *Bioorganic and Medicinal Chemistry*, 2013, 8 pages, Elsevier, Amsterdam, NL.

Clifford, P.C., et al., "Treatment of Vasospastic Disease with Prostaglandin $E_1$," *British Medical Journal*, Oct. 18, 1980, pp. 1031-1034, vol. 281, British Medical Association, UK.

Colombe, L., "Prostaglandin Metabolism in Human Hair Follicle," *Experimental Dermatology*, 2007, pp. 762-769, vol. 16, No. 9, Blackwell Munksgaard, Copenhagen, DK.

Combrinck, M., et al. "Levels of CSF Prostaglandin $E_2$, Cognitive Decline, and Survival in Alzheimer's disease," *Journal of Neurology, Neurosurgery, and Psychiatry*, Jun. 8, 2005, pp. 85-88, vol. 77, pp. 85-88, BMJ Group, London, UK.

Cooper, H. S. et al., "Clinicopathoiogic Study of Dextran Sulfate Sodium Experimental Murine Colitis," *Laboratory Investigation*, (1993), pp. 238-249, vol. 69, No. 2, The United States and Canadian Academy of Pathology, Inc., USA.

Coteron, J.M., et al., "Structure-Guided Lead Optimization of Triazolopyrimidine—Ring Substituents Identifies Potent *Plasmodium falciparum* Dihydroorotate Dehydrogenase Inhibitors with Clinical Candidate Potential", *Journal of Medicinal Chemistry*, Aug. 11, 2011, pp. 5540-5561, vol. 54, No. 15, American Chemical Society, Washington, DC, US.

Croft, D., et al., "The Reactome pathway knowledgebase," *Nucleic acids research*, 2014, pp. D472-477, vol. 42, Oxford University Press, UK.

Cutler, Corey, et al., "Prostaglandin-Modulated Umbilical Cord Blood Hematopoietic Stem Cell Transplantation," *Blood*, 2013, 30 pages, American Society of Hematology, Washington, DC, US.

Dai, Liying, et al., "Inverse Expression of Prostaglandin $E_2$-Related Enzymes Highlights Differences Between Diverticulitis and Inflammatory Bowel Disease," *Digestive Diseases and Sciences*, 2015, pp. 1236-1246, vol. 60, Springer Science + Business Media, Berlin, DE.

Dalvi, Siddhartha, et al., "Exogenous Arachidonic Acid Mediates Permeability of Human Brain Microvessel Endothelial Cells through Prostaglandin $E_2$ Activation of $EP_3$ and $EP_4$ Receptors," *Journal of Neurochemistry*, Apr. 27, 2015, pp. 867-879, vol. 135, International Society for Neurochemistry, Wiley-Blackwell, Hoboken, NJ, US.

Deng, Yang, et al., "Lipopolysaccharide Stimulates Bovine Endometrium Explants through Toll-Like Receptor 4 Signaling and $PGE_2$ Synthesis," *Prostaglandins, Leukotrienes, and Essential Fatty Acids*, May 2021, Abstract only—2pages, vol. 168, Elsevier Ltd., Amsterdam, NL.

Desai, A., et al., "A Second-Generation 15-PGDH Inhibitor Promotes Bone Marrow Transplant Recovery Independently of Age,

(56) References Cited

OTHER PUBLICATIONS

Transplant Dose, and Granulocyte Colony-Stimulating Factor Support," *Haematologica*, 2018, pp. 1054-1064,103(6), Ferrata Storti Foundation, IT.

Dong, Yuanqiang, et al., "Effects of SW033291 on the Myogenesis of Muscle-Derived Stem Cells and Muscle Regeneration," *Stem Cell Research and Therapy*, 2020, 17 pages, vol. 11, Issue 76, BioMedCentral, London, UK.

Douville, Christopher, et al., "Assessing Aneuploidy with Repetitive Element Sequencing," *Proceedings of the National Academy of Sciences*, Mar. 3, 2020, pp. 4858-4863, vol. 117, No. 9, United States National Academy of Sciences, Washington, DC, US.

Dowd, Noreen P., et al., "Inhibition of Cyclooxygenase-2 Aggravates Doxorubicin-Mediated Cardiac Injury in Vivo," *The Journal of Clinical Investigation*, Aug. 15, 2001, pp. 585-590, vol. 108, No. 4, American Socierty for Clinical Investigation, US.

Doxorubicin Hydrochloride Package Insert and Package Label Display Panel, Revised: Jan. 2021, 16 pages, Teva Pharmaceuticals USA, Inc., Labeler: Actavis Pharma, Inc.

Duveau, Damien Y., et al., "Discovery of two small molecule inhibitors, ML387 and ML388, of human $NAD^+$-dependent 15-hydroxyprostaglandin dehydrogenase," *Probe Reports from the NIH Molecular Libraries Program*, 2013, 26 pages, National Center for Biotechnology Information, US.

Duveau, Damien Y., et al., "Structure-activity relationship studies and biological characterization of human $NAD^+$-dependent 15 hydroxyprostaglandin dehydrogenase inhibitors", *Bioorganic and Medicinal Chemistry Letters*, Jan. 15, 2014, pp. 630-635, vol. 24, Elsevier, Amsterdam, NL.

Echeverria, Valentina, et al., "Stimulation of $PGE_2$ Receptors $EP_2$ and $EP_4$ Protects Cultured Neurons Against Oxidative Stress and Cell Death Following β-Amyloid Exposure," *European Journal of Neuroscience*, 2005, pp. 2199-2206, vol. 22, Federation of European Neuroscience Societies, Wiley-Blackwell, Hoboken, NJ.

"Enamine—Screening Compounds," Web page <http://www.enamine.net/index.php?option=com_content&task=view&id=22&menuid=51&PHPSESSID=64a4f248f69d671a413f487bb62c4d90>, 2 pages Jun. 30, 2007, retrieved from the Internet Archive Wayback Machine via Page Vault <http://web.archive.org/web/200706301718 13/https://www.enamine.net/index.php!option=com_contect&task=view&id=22&menuid=51&PHPSESSID=64a4f248f69d671a413f487bb62c4d90> on Sep. 29, 2022.

Ensor, C.M, et al., "Site-Directed Mutagenesis of the Conserved Tyrosine 151 of Human Placental $NAD^+$-dependent 15-Hydroxyprostaglandin Dehydrogenase Yields a Catalytically Inactive Enzyme", *Biochemical and Biophysical Research Communications*, Apr. 30, 1991, pp. 840-845, vol. 176, No. 2, Academic Press, Inc., Elsevier, Amsterdam, NL.

Ensor, Charles Mark, et al., "Bacterial expression and site-directed mutagenesis of two critical residues (tyrosine-151 and lysine-155) of human placental $NAD^+$-dependent 15-hydroxyprostaglandin dehydrogenase", *Biochimica et Biophysica Acta*, 1994, pp. 151-156, vol. 1208, Elsevier Science B.B., Amsterdam, NL.

Eridani, S., and Mosca, A., "Fetal hemoglobin reactivation and cell engineering in the treatment of sickle dell anemia," *Journal of Blood Medicine*, Feb. 28, 2011, pp. 23-30, vol. 2, Dove Medical Press, UK.

Esrick, Erica B., et al., "Inactivation of HDAC1 or HDAC2 induces gamma globulin expression without altering cell cycle or proliferation," *American Journal of Hematology*, Jul. 2015, pp. 624-628, vol. 90, No. 7, Wiley Pharmaceuticals, Inc., Hobokenm NJ, US.

European Directorate for the Quality of Medicines & HEALTHCARE, Structure / Nomenclature Guide, "A Guide to the Graphic Representation and Nomenclature of Chemical Formulae in the European Pharmacopoeia," *European Pharmacopoeia*, 2011, 40 pages, $2^{nd}$ Edition, Council of Europe, Strasbourg, FR.

Fauchier, L., et al., "Use of Anticoagulants and Antiplatelet Agents in Stable Outpatients with Coronary Artery Disease and Atrial Fibrillation. International CLARIFY Registry," *PLOS One*, Apr. 27, 2015, 23 pages, 10(4), Public Library of Science, San Francisco, CA, US.

Filippini, A., et al., "Covid-19 Acute Respiratory Distress Syndrome: Can Iloprost Have a Role for This Treatment?" *Respiratory Medicine Case Reports*, 2021, 101358, 4 pages, vol. 32, Elsevier, NL.

Fitzpatrick, F.A., et al., "The Stability of 13,14-Dihydro-15 Keto-$PGE_2$," *Prostaglandins*, Jun. 1980, pp. 917-931, vol. 19, No. 6., Elsevier Inc., NL.

Frias, M.A., et al., "The $PGE_2$-Stat3 Interaction in Doxorubicin-Induced Myocardial Apoptosis," *Cardiovascular Research*, 2008, pp. 69-77, vol. 80, Published on behalf of the European Society of Cardiology, Oxford University Press, Oxford, UK.

Frisch, Benjamin, et al., "In Vivo Prostaglandin $E_2$ Treatment Alters the Bone Marrow Microenvironment and Preferentially Expands Short-Term Hematopoietic Stem Cells," *Blood*, Nov. 5, 2009, 12 pages including pp. 4054-4063, vol. 114, No. 19, American Society of Hematology, Washington, DC, US.

Galiè, Nazzareno, et al., "Guidelines for the diagnosis and treatment of pulmonary hypertension," *European Heart Journal*, 2009, pp. 2493-2537, vol. 30, European Society of Cardiology, Oxford University Press, Oxford, UK.

Gentile, P., et al., "In Vivo Modulation of Murine Myelopoiesis Following Intravenous Administration of Prostaglandin E2", *Blood*, 1983, 8 pages including pp. 1100-1107, vol. 62, No. 5, American Society of Hematology, Washington, DC, US.

Ghiso, Jorge, et al., "Cerebral amyloidosis, amyloid angiopathy, and their relationship to stroke and dementia," *Journal of Alzheimer's Disease*, 2001, pp. 65-73, vol. 3, No. 1, IOS Press, Amsterdam, NL.

Girgis, Adel S., et al., "Synthesis of new 3-pyridinecarboxylates of potential vasodilation properties," *European Journal of Medicinal Chemistry*, 2008, vol. 43, pp. 1818-1827, Elsevier, NL.

Giugliano, Robert P., et al., "Edoxaban versus Warfarin in Patients with Atrial Fibrillation," *The New England Journal of Medicine*, Nov. 28, 2013, pp. 2093-2104, vol. 369, No. 22, Massachusetts Medical Society, Waltham, MA, US.

Goessling, Wolfram, et al., "Genetic Interaction of PGE2 and Wnt Signaling Regulates Developmental Specification of Stem Cells and Regeneration," *Cell*, Mar. 20, 2009, pp. 1136-1147, vol. 136, Issue 6, Cell Press, Elsevier Inc., Cambridge, MA, US.

Goessling, Wolfram, et al., "Prostaglandin E2 Enhances Human Cord Blood Stem Cell Xenotransplantsand Shows Long-Term Safety in Preclinical Nonhuman Primate Transplant Models," *Cell Stem Cell*, Apr. 8, 2011, pp. 445-458, vol. 8, Cell Press, Elsevier Inc., Cambridge, MA, US.

Gu, Xiaosong, et al., "Prostaglandin E2 Reduces Cardiac Contractility via EP3 Receptor," *Circulation: Heart Failure*, Aug. 2016, 8 pages, e003291, vol. 9, Issue 8, American Heart Association, Lippincott Williams & Wilkins, Philadelphia, PA, US.

Guo, Jian-You, et al., "Chronic unpredictable mild stress induces parallel reductions of 15-PGDH in the hypothalamus and lungs in rats," *Behavioural Brain Research*, 2015, pp. 278-284, vol. 286, Elsevier B.V., NL.

Hagedorn, E. J., et al., "Getting More for Your Marrow: Boosting Hematopoietic Stem Cell Numbers with PGE2", *Experimental Cell Research*, 2014, 7 pages, Elsevier Inc., Amsterdam, NL.

Hall, P. R et al., "Small Molecule Inhibitors of Hantavirus Infection", *Bioorganic & Medicinal Chemistry Letters*, Dec. 1, 2010, pp. 7085-7091, vol. 20, No. 23, Elsevier, Amsterdam, NL.

Hamed, S., et al., "Erythropoietin Improves Myocardial Performance in Doxorubicin-Induced Cardiomyopathy," *European Heart Journal*, 2006, pp. 1876-1883, vol. 27, Oxford University Press, Oxford, UK.

Hamid, N., et al., "A Neural System Dynamics Modeling Platform and its Applications in Randomized Controlled Trial Data Analysis," *Informatics in Medicine Unlocked*, 2021, 13 pages, 100612, vol. 24, Elsevier Ltd., Amsterdam, NL.

Hamza, Adel, et al., "Understanding human 15-hydroxyprostaglandin dehydrogenase binding with $NAO^+$and $PGE_2$ by homology modeling, docking and molecular dynamics simulation," *Bioorganic & Medicinal Chemistry*, pp. 4544-4551, vol. 13, Elsevier Ltd., Amsterdam, NL, (2003).

(56) References Cited

OTHER PUBLICATIONS

Hanai, H., et al., "Curcumin Maintenance Therapy for Ulcerative Colitis: Randomized, Multicenter, Double-Blind, Placebo-Controlled Trial," *Clinical Gastroenterology and Hepatology*, Dec. 2006, pp. 11502-1506, vol. 4, Issue 5, Elsevier, Amsterdam, NL.

Hao, C.M., "Physiological Regulation of Prostaglandins in the Kidney," *Annual Review of Physiology*, 2008, 25 pages including pp. 357-377, vol. 70, Annual Reviews, San Mateo, CA, US.

Hao, G., et al., "Protective Effects of Berberine Against Doxorubicin-Induced Cardiotoxcity in Rats by Inhibiting Metabolism of Doxorubicin," *Xenobiotica*, 2015, pp. 1024-1029, vol. 45, Issue 11, Informa, London, UK.

Harrowven, D. C. "'Cascade' Radical Reactions in Synthesis: Condensed Thiophenes from Ketenethioacetals," *Tetrahedron Letters*, 1993, pp. 5653-5656, vol. 34, No. 35, Elsevier, Amsterdam, NL.

Hassan, M., et al., "Modulatory Effects of Meloxicam on Cardiotoxicity and Antitumor Activity of Doxorubicin in Mice," *Cancer Chemotherapy and Pharmacology*, Jul. 23, 2014, pp. 559-569, vol. 74, Springer Science + Business Meda, Berlin, DE.

Heyman, Samuel N., et al., "Animal models of renal dysfunction: acute kidney injury," *Expert Opinon on Drug Discovery*, 2009, pp. 629-641, 4(6), Taylor & Francis, UK.

Heyman, Samuel N., et al., "Acute Kidney Injury: Lessons from Experimental Models," *Experimental Models for Renal Diseases: Pathogenesis and Diagnosis*, 2011, pp. 286-296, vol. 169, Karger, Basel, CH.

Hoffman, Corey M., et al., "Minireview: Complexity of Hematopoietic Stem Cell Regulation in the Bone Marrow Microenvironment", *Molecular Endocrinology*, 2014, pp. 1-11, vol. 28, The Endocrine Society, Washington, DC, US.

Hoggatt, J., et al., "Prostaglandin $E_2$ Enhances Hematopoietic Stem Cell Homing, Survival, and Proliferation," *Blood*, May 28, 2009, cover page, pp. 5444-5455, vol. 113, No. 22, American Society for Hematology, Washington, DC, US.

Hoggatt, J., et al., "Differential Stem- and Progenitor-Cell Trafficking by Prostaglandin E2", *Nature*, 00 Month 2013, 7 pages, vol. 000, Nature Portfolio, London, UK.

Hoggatt, J., et al., "Prostaglandin E2 Enhances Long-Term Repopulation but Does not Permanently Alter Inherent Stem Cell Competitiveness", *Blood*, Oct. 24, 2013, pp. 2997-3000, vol. 122, No. 17, American Society of Hematology, Washington, DC, US.

Hoggatt, Jonathan, et al., "Recovery from Hematopoietic Injury by Modulating Prostaglandin $E_2$ Signaling Post-Irradiation", *Blood Cells, Molecules and Diseases*, 2013, pp. 147-153, vol. 50, Elsevier Inc., Amsterdam, NL.

Hong, Yu Ah, et al., Paricalcitol Pretreatment Attenuates Renal Ischemia-Reperfusion Injury via Prostaglandin $E_2$ Receptor E4 Pathway, *Oxidative Medicine and Cellular Longevity*, 2017, 17 pages, vol. 2017, Hindawi Publishing Corporation, London, UK.

Hoult, J.R.S., and MOORE, p. K., "Sulphasalazine is a Potent Inhibitor of Prostaglandin 15-Hydroxydehydrogenase: Possible Basis for Therapeutic Action in Ulcerative Colitis," *British Journal of Pharmacology*, 1978, pp. 6-8, vol. 64, Macmillan Journals Ltd, UK.

Hoyt, A.L., et al., "On the nature of the chain-extending species in organolithium initiated stereospecific reagent-controlled homologation reactions using α-chloroalkyl aryl sulfoxides," *Tetrahedron Letters*, 2015, vol. I 56, pp. 2980-2982, Elsevier Ltd., NL.

Huang, X., et al., "Safety and Efficacy of Bivalirudin Monotherapy in Patients with Non-ST-Segment Elevation Acute Coronary Syndromes with Positive Biomarkers Undergoing Percutaneous Coronary Intervention: A Report From The Acute Catheterization and Urgent Intervention Triage Strategy Trial," *Coronary Artery Disease*, Jan. 1, 2020, pp. 59-65, vol. 31, Issue 1, Wolters Kluwer Health, Inc., Lippincott Williams & Wilkins, Philadelphia, PA, US.

Huang, W.J., and Tang, X.X., "Virus Infection Induced Pulmonary Fibrosis," *Journal of Translational Medicine*, 2021, 15 pages, vol. 19, Issue 496, BioMedCentral, UK.

Hughes, P.A., et al., "Experimental Colitis Models," *TRP Channels in Drug Discovery*: vol. II, Chapter 23, Jan. 1, 2012, pp. 379-390, Humana Press, Springer, Munich, DE.

Hunt, T. K., et al., "Coagulation and Macrophage Stimulation of Angiogenesis and Wound Healing," *The Surgical Wound, ed. F. Dineen & G. Hildrick-Smith*, 1981, 21 pages including pp. 1-18, Lea & Febiger, Philadelphia, PA.

"Inflammatory Bowel Disease," Web page <https://www.healthline.com/health/inflammatory-bowel-disease>, 6 pages, Jan. 7, 2015, retrieved from the Internet Archive Wayback Machine via Page Vault <http://web.archive.org/web/20070630171813/http://www.enamine.net/index.php!option=com_content&task=view&id=22&menuid=51&PHPSESSID=64a4f248f69d671a413f487bb62c4d90> on Oct. 25, 2022.

Iqubal, A., et al., "Clinical Updates on Drug-Induced Cardiotoxicity," *International Journal of Pharmaceutical Sciences and Research*, 2018, pp. 16-26, vol. 9, Issue 1, Society of Pharmaceutical Sciences and research, Panchkula, Haryana, IN.

Jadapalli, J.K., et al., "Doxorubicin Triggers Splenic Contraction and Irreversible Dysregulation of COX and LOX That Alters the Inflammation—Resolution Program in the Myocardium," *American Journal of Physiology—Heart and Circulatory Physiology*, 2018, pp. H1091-H1100, vol. 315, American Physiological Society, Rockville, MD, US.

Jadhav, A., et al., "Potent and Selective Inhibitors of $NAD^+$-Dependent 15-Hydroxyprostaglandin Dehydrogenase (HPGD)", *Molecular Libraries, Pathways to Discovery*, Jul. 8, 2011, 36 pages, NIH.

Jain, D., et al., "Cardiac Complications of Cancer Therapy: Pathophysiology, Identification, Prevention, Treatment, and Future Directions," *Current Cardiology Reports*, 2017, 12 pages, vol. 19, Issue 36, Springer Science + Business Media, Berlin, DE.

Johnston, Dudley E., "Wound Healing in Skin," *Plastic and Reconstructive Surgery, Veterinary Clinics of North American: Small Animal Practice*, Jan. 1990, pp. 1-25, vol. 20, No. 1, W.B. Saunders Ltd., US.

Jolly, L., et al. "Influenza Promotes Collagen Deposition via αvβ6 Integrin-Mediated Transforming Growth Factor β activation," *The Journal of Biological Chemistry*, Dec. 19, 2014, pp. 35246-35263, vol. 289, No. 51, pp. 35246-35263, American Society for Biochemistry and Molecular Biology, Rockville, MD, US.

Julkunen, I., et al., "Inflammatory Response to Influenza A Virus Infection," *Vaccine*, 2001, pp. S32-S37, vol. 19, Elsevier Science Ltd., Amsterdam, NL.

Jung, P., et al., "Isolation and in vitro Expansion of Human Colonic Stem Cells," *Nature Medicine*, Oct. 2011, pp. 1225-1227, vol. 17, No. 10, Nature Publishing Group, London, UK.

Kabashima, K., et al., "The Prostaglandin Receptor EP4 Suppresses Colitis, Mucosal Damage and CD4 Cell Activation in the Gut", *The Journal of Clinical Investigation*, Apr. 2002, pp. 883-893, vol. 109, No. 7, American Society for Clinical Investigation, US.

Kalugin, V.E., et al., "Utilization of Potassium Carbonate for the Synthesis of 2-(organylsulfonyl)thieno[2,3-b]pyridine Derivatives," *Russian Chemical Bulletin, International Edition*, Feb. 2019, pp. 357-364, vol. 68, No. 2, Springer Science + Business Media, Berlin, DE.

Kang, G.-J., et al., "High-Mobility Group Box 1 Suppresses Resolvin D1-Induced Phagocytosis via Induction of Resolvin D1-Inactivating Enzyme, 15-Hydroxyprostaglandin Dehydrogenase," *Biochimica et Biophysica Acta*, 2015, pp. 1981-1988, vol. 1852, No. 9, Elsevier B.V., Amsterdam, NL.

Karna, Sandeep, et al., "Novel Potent 15-Hydroxyprostaglandin Dehydrogenase Inhibitors," *Journal of Advanced Engineering and Technology*, 2010, pp. 301-304, vol. 3, No. 3.

Karna, Sandeep, "In-vitro Wound Healing Effect of 15-Hydroxyprostaglandin Dehydrogenase Inhibitor from Plant," *Pharmacognosy Magazine*, Apr. 7, 2017, pp. S122-S126, vol. 13, Issue 49, Supplement 1, Wolters Kluwer—Medkenow Publications, Mumbai, IN.

Katz, J.A., "The Practical Use of Corticosteroids in the Treatment of Inflammatory Bowel Disease," *Practical Gastroenterology*, Jan. 2005, pp. 14, 16, 18, 21, 22, 25, Shugar Publishing, Westhampton Beach, NY, US.

(56) References Cited

OTHER PUBLICATIONS

Kawaguchi, H., et al., "The Role of Prostaglandins in the Regulation of Bone Metabolism," *Clinical Orthopaedics and Related Research*, 1995, pp. 36-46, No. 313, J.B. Lippincott and Company, Philadelphia, PA.

Keller, M.D., J., et al., "Short-term Effect of Local Application of $PGE_2$ on Callus in Rabbit Osteotomy," *Eur J Exp Musculoskel Res*, 1992, vol. 1, pp. 86-92.

Kim, M. et al., "Decreased Catalytic Activity of the Insulin-degrading Enzyme in Chromosome 10-Linked Alzheimer Disease Families," *The Journal of Biological Chemistry*, Mar. 16, 2007, pp. 7825-7832, vol. 282, No. 11, The American Society for Biochemistry and Molecular Biology, Inc., USA.

Kim, H.J., et al., "Inhibition of 15-PGDH Prevents Ischemic Renal Injury by the $PGE_2/EP_4$ Signaling Pathway Mediating Vasodilation, Increased Renal Blood Flow, and Increased Adenosine/$A_{2A}$ Receptors," *American Journal of Physiology—Renal Physiology*, 2020, F1054-F1066, vol. 319, American Physiological Society, Rockville, MD.

Kimball, Frances A., et al., "Plasma Concentrations of 9-Deoxo-16,16-Dimethyl-9-methylene-$PGE_2$ in Rhesus Monkeys after Administration by Various Routes," *Prostaglandins*, Sep. 1980, pp. 559-569, vol. 20, No. 3, Elsevier, Amsterdam, NL.

Kishore, A.H., et al., "Prostaglandin Dehydrogenase is a Target for Successful Induction of Cervical Ripening," *Proceedings of the National Academy of Sciences*, Jul. 17, 2017, pp. E6427-E6436, vol. 114, No. 29, United States National Academy of Sciences, Washington, DC, US.

Kishore, B.K, et al., "Ticagrelor Reduces Urinary Concentration and Arginine Vasopressin (AVP) Levels: Potential Use in AVP Excess States," *Kidney Week*, Oct. 23, 2018, Poster SA-PO1018, San Diego, CA, in the Journal of the American Society of Nephrology, 2018, p. 1002, vol. 29, American Society of Nephrology, Washington, DC, US.

Konturek, P.C., et al., "Prostaglandins as Mediators of Cox-2 Derived Carcinogenesis in Gastrointestinal Tract," Journal of Physiology and Pharmacology, Sep. 1, 2005, 12 pages, vol. 56, Suppl. 5.

Konturek, S.J., et al., "Prostaglandins and Ulcer Healing," Journal of Physiology and Pharmacology, 2005, 22 pages, vol. 56, No. 5.

Kurland, J.I., et al., "Role for Monocyte-Macrophage-Derived Colony-Stimulating Factor and Prostaglandin E in the Positive and Negative Feedback Control of Myeloid Stem Cell Proliferation," *Blood*, 1978, 21 pages including pp. 388-407, vol. 52, American Society of Hematology, Washington, DC, US.

Lakatos et al., "The Role of PPARs in Lung Fibrosis," *PPAR Research*, Jul. 2, 2007, pp. 1-10, Hindawi Publishing Corporation, London, UK.

Lam, P.-Y., et al., "Cyp1 Inhibition Prevents Doxorubicin-Induced Cardiomyopathy in a Zebrafish Heart Failure Model," *ChemBioChem*, Jul. 1, 2020, pp. 1905-1910, vol. 21, Issue 13, Wiley-VCH, Weinheim, DE.

Lewis, J.D., et al., "An Open-Label Trial of the PPARγ Ligand Rosiglitazone for Active Ulcerative Colitis," *he American Journal of Gastroenterology*, 2001, pp. 3323-3328, vol. 96, No. 12, Elsevier Science Inc., NL.

Li, J., et al., "Neutrophil AKT2 Regulates Heterotypic Cell-Cell Interactions During Vascular Inflammation," *Journal of Clinical Investigation*, Apr. 2014, 15 pages including pp. 1483-1496, vol. 124, Issue 4, American Society for Clincal Investigation, US.

Li, T., et al., "PGE2 Increases Inflammatory Damage in *Escherichia coli*—infected Bovine Endometrial Tissue in vitro Via the EP4-PKA Signaling Pathway," *Biology of Reproduction*, 2019, pp. 175-186, vol. 100, Issue 1, Oxford University Press, Oxford, UK.

Li, T., et al., "Prostaglandin E2 Promotes Nitric Oxide Synthase 2, Platelet-Activating Factor Receptor, and Matrix Metalloproteinase-2 Expression in *Escherichia coli*—challenged ex vivo Endometrial Explants via the Prostaglandin $E_2$ Receptor 4/Protein Kinase A Signaling Pathway," *Theriogenology*, Aug. 2019, pp. 65-73, vol. 134, Elsevier, Amsterdam, NL.

Li, N., et al., "Ferritinophagy-Mediated Ferroptosis is Involved in Sepsis-Induced Cardiac Injury," *Free Radical Biology and Medicine*, 2020, pp. 303-318, vol. 160, Elsevier, Amsterdam, NL. Submitted in 2 parts.

Lian, W.-S., et al., "The Prostaglandin Agonist Beraprost Aggravates Doxorubicin—Mediated Apoptosis by Increasing iNOS Expression in Cardiomyocytes," *Current Vascular Pharmacology*, Jan. 1, 2015, pp. 54-63, vol. 13, No. 1, Bentham Science Publishers, UK.

Liu, Y.-C et al., "Triazolopyrimidines as a New Herbicidal Lead for Combating Weed Resistance Associated with Acetohydroxyacid Synthase Mutation", *Journal of Agricultural and Food Chemistry*, 2016, pp. 4845-4857, vol. 64, No. 24, American Chemical Society, Washington, DC, US.

Liu, C., et al., "Development and Stimulation of a Sensitive and Rapid UHPLC-MS/MS Method for the Simultaneous Quantification of the Common Active and Inactive Metabolites of Vicagrel and Clopidogrel in Human Plasma," *Journal of Pharmaceutical and Biomedical Analysis*, Feb. 5, 2018, pp. 394-402, vol. 149, Elsevier, Amsterdam, NL.

Liu, C., et al., "Pharmacokinetics and Pharmacokinetic/Pharmacodynamic Relationship of Vicagrel, a Novel Thineopyridine $P2Y_{12}$ Inhibitor, Compared with Clopidogrel in Healthy Chinese Subjects Following Single Oral Dosing," *European Journal of Pharmaceutical Sciences*, Jan. 15, 2019, pp. 151-160, vol. 127, Elsevier, Amsterdam, NL.

Lopes, J.A., et al., "The RIFLE and AKIN Classifications for Acute Kidney Injury: A Critical and Comprehensive Review," *Clinical Kidney Journal*, 2013, pp. 8-14, vol. 6, Oxford University Press, Oxford, UK.

Lorente, A., et al., "Synthesis of Heterocyclic Compounds. XXXIX [1]. Synthesis of 5-Cvano-2-Phenyl-4-Thioxo-3,4-Dihydropyrimidines," *Journal of Heterocyclic Chemistry*, 1985, pp. 49-51, vol. 22, Wiley-Blackwell, Hoboken, NJ, US.

Lovgren, A.K., et al., "COX-2-Derived Prostacyclin Protects Against Bleomycin-Induced Pulmonary Fibrosis," *American Journal of Physiology—Lung Cellular and Molecular Physiology*, pp. L144-L156, Feb. 10, 2006, vol. 291, The American Physiological Society, Rockville, MD, US.

Lu, L., et al., "Animal Models of Gastrointestinal Inflammation and Cancer," *Life Sciences*, 2014, pp. 1-6, vol. 108, Issue 1, Elsevier, Amsterdam, NL.

Luca, G., "The Future of Targeted Therapy: Combining Novel Agents," *Oncology*, 2002, pp. 47-56, vol. 63 (Supplement 1), Karger Publishers, Basel, CH.

Luu, A.Z., "Role of Endothelium in Doxorubicin-Induced Cardiomyopathy," *JACC: Basic to Translational Science*, Dec. 2018, pp. 861-870, vol. 3, No. 6, Elsevier on behalf of American College of Cardiology, Amsterdam, NL.

Ma, F., et al., "Discovery and Structure—Activity Relationships Study of Thieno[2,3-b]pyridine Analogues as Hepatic Gluconeogenesis Inhibitors," *European Journal of Medicinal Chemistry*, May 25, 2018, Abstract, vol. 152, Elsevier, Amsterdam, NL.

Makala, L., et al., "FK228 Analogues Induce Fetal Hemoglobin in Human Erythroid Progenitors," *Anemia*, 2012, Article ID 428137, 13 pages, vol. 2012, Hindawi Publishing Corporation, London, UK.

Mallipeddi, P.L., et al., "Structural Insights into Novel 15-Prostaglandin Dehydrogenase Inhibitors," *Molecules*, 2021, 17 pages, 5903, Multidisciplinary Digital Publishing Institute, Basel, CH.

Markowitz, S., et al., "Aspirin and Colon Cancer—Targeting Prevention", *The New England Journal of Medicine*, May 24, 2007, pp. 2195-2198, vol. 356, No. 21, Massachusetts Medical Society, MA, US.

Markowitz, S., et al., "Molecular Origins of Cancer—Molecular Basis of Colorectal Cancer," *The New England Journal of Medicine*, Dec. 17, 2009, pp. 2449-2460, vol. 361, No. 25, Massachusetts Medical Society, MA, US.

Mayo Clinic, "Diseases and Conditions—Chronic Kidney Disease," Web page <www.mayoclinic.org/diseases-conditions/kidney-disease/basic/causes/con20026778>, Jan. 7, 2015, retrieved from the Internet Archive Wayback Machine via Page Vault <http://web.archive.org/web/20150107203836/www.mayoclinic.org/diseases-conditions/kidney-disease/basics/causes/con-20026778> on Oct. 25, 2022.

(56) References Cited

OTHER PUBLICATIONS

Mayo Clinic, "Diseases and Conditions—Chronic kidney disease", Jan. 30, 2015, http://www.mayoclinic.org/diseases-conditsons/kidney-disease/basics/causes/con-20026778, accessed Dec. 11, 2015.

Mayo Clinic, "Chronic kidney disease—Care at Mayo Clinic," Oct. 25, 2022, retrieved from Page Vault https://www.mayoclinic.org/diseases-conditions/chronic-kidney-disease/care-at-mayo-clinic/mac-20354531 on Oct. 25, 2022.

Mayo Clinic, "Chronic kidney disease—Diagnosis and treatment," Oct. 25, 2022, retrieved from Page Vault https://www.mayoclinic.org/diseases-conditions/chronic-kidney-disease/diagnosis-treatment/drc-20354527 on Oct. 25, 2022.

Mayo Clinic, "Chronic kidney disease—Doctors and departments," Oct. 25, 2022, retrieved from Page Vault https://www.mayoclinic.org/diseases-conditions/chronic-kidney-disease/doctors-departments/ddc-20354530 on Oct. 25, 2022.

Mayo Clinic, "Chronic kidney disease—Symptoms and causes," Oct. 25, 2022, retrieved from Page Vault https://www.mayoclinic.org/diseases-conditions/chronic-kidney-disease/symptoms-causes/syc-20354521 on Oct. 25, 2022.

McCaffrey, T.A., et al., "Genomic Profiling Reveals the Potential Role of TCL1A and MDR1 Deficiency in Chemotherapy-Induced Cardiotoxicity," *International Journal of Biological Sciences*, 2013, pp. 350-360, vol. 9, Issue 4, Ivyspring International Publisher Pty Ltd, AU.

McCullough, Louise, et al., "Neuroprotecive Function of the $PGE_2$ EP2 Receptor in Cerebral Ischemia," *The Journal of Neuroscience*, Jan. 7, 2004, pp. 257-268, vol. 24, No. 1, Society for Neuroscience, Washington, D.C., US.

Michelet, J.F., et al., "Expression of $NAD^+$ Dependent 15-Hydroxyprostaglandin Dehydrogenase and Protection of Prostaglandins in Human Hair Follicle," *Experimental Dermatology*, 2008, pp. 821-828, vol. 17, No. 10, Wiley, Hoboken, NJ, US.

Mitchell, C., and Willenbring, H., "A Reproducible and Well-Tolerated Method for 2/3 Partial Hepatectomy in Mice," *Nature Protocols*, 2008, pp. 1167-1170, vol. 3, No. 7, Nature Publishing Group, London, UK.

Montrose, D.C., et al., "The Role of PGE2 in Intestinal Inflammation and Tumorigenesis," *Prostaglandins and Other Lipid Mediators*, 2015, 23 pages, Elsevier, Amsterdam, NL.

Morishita, Yoshiyuki, et al., "Establishment of Acute Kidney Injury Mouse Model by 0.75% Adenine Ingestion," *Renal Failure*, 2011, pp. 1013-1018, vol. 33, No. 10, Informa Healthcare USA, Inc., US.

Moustafa, Y.M., et al., "15-PGDH Inhibitors: The Antiulcer Effects of Carbenoxolone, Pioglitazone and Verapamil in Indomethacin Induced Peptic Ulcer Rats," *European Review for Medical and Pharmacological Sciences*, 2013, pp. 2000-2009, vol. 17, Verduci Editore, Rome, IT.

Myung, Seung-Jae, et al., "15-Hydroxyprostaglandin dehydrogenase is an in vivo suppressor of colon tumorigenesis," *Proceedings of the National Academy of Sciences*, Aug. 8, 2006, pp. 12098-12102, vol. 103, No. 32, United States National Academy of Sciences, Washington, DC, US.

Na, H.-K., et al., "15-Hydroxyprostaglandin Dehydrogenase as a Novel Molecular Target for Cancer Chemoprevention and Therapy," *Biochemical Pharmacology*, 2011, pp. 1352-1360, vol. 82, Elsevier, Amsterdam, NL.

Nakanishi, M., and Rosenberg, D.W., "Multifaceted Roles of $PGE_2$ in Inflammation and Cancer," *Seminars in Immunopathology*, 2013, pp. 123-137, vol. 35, Springer, Berlin, DE.

Nasrallah, Rania, et al., "$PGE_2$, Kidney Disease, and Cardiovascular Risk: Beyond Hypertension and Diabetes," *Journal of the American Society of Nephrology*, 2016, pp. 666-676, vol. 27, American Society of Nephrology, US.

Neilan, T.G., et al., "Disruption of COX-2 Modulates Gene Expression and the Cardiac Injury Response to Doxorubicin," *American Journal of Physiology—Heart and Circulatory Physiology*, Apr. 14, 2006, pp. H532-H536, vol. 291, American Physiological Society, Rockville, MD, US.

Niesen., F.H., et al., "High-Affinity Inhibitors of Human $NAD^+$-Dependent 15-Hydroxyprostaglandin Dehydrogenase: Mechanisms of Inhibition and Structure-Activity Relationships", *PLoS ONE*, Nov. 2010, e13719, 12 pages, vol. 5, issue 11, Public Library of Science, San Francisco, CA, US.

Noe, A., et al., "High Incidence of Severe Cyclosporine Neurotoxicity in Children Affected by Haemoglobinopaties Undergoing Myeloablative Haematopoietic Stem Cell Transplantation: Early Diagnosis and Prompt Intervention Ameliorates Neurological Outcome," *Italian Journal of Pediatrics*, Feb. 6, 2010, Article No. 14, pp. 1-6, vol. 36, BioMedCentral, London, UK.

Nogradi, K., et al., "Thieno[2,3-b]pyridines as Negative Allosteric Modulators of Metabotropic GluR5 Receptors: Hit-To-Lead Optimization," *Bioorganic and Medicinal Chemistry Letters*, 2014, pp. 3845-3849, vol. 24, Elsevier, Amsterdam, NL.

North, T.E., et al., "Prostaglandin E2 Regulates Vertebrate Haematopoietic Stem Cell Homeostasis," *Nature*, Jun. 21, 2007, pp. 1007-1011, vol. 447, Nature Research, London, UK.

North, Trista E., "PGE2-Regulated wnt Signaling and N-Acetylcysteine Are Synergistically Hepatoprotective in Zebrafish Acetaminophen Injury", *Proceedings of the National Academy of Sciences*, Oct. 5, 2010, pp. 17315-17320, vol. 107, No. 40, United States National Academy of Sciences, Washington, DC, US.

Obeid, J., et al., "TYR-179 and LYS-183 are Essential for Enzymatic Activity of 11 β-Hydroxysteroid Dehydroxysteroid Dehydrogenase," *Biochemical and Biophysical Research Communications*, Oct. 15, 1992, Abstract, vol. 188, Issue 1, Academic Press, Elsevier, Amsterdam, NL.

Oh, S.Y., et al., "Comparison of Experimental Mouse Models of Inflammatory Bowel Disease," *International Journal of Molecular Medicine*, 2014, pp. 333-340, vol. 33, Issue 2, Spandidos Publcations, UK.

Otani, T., et al., "Levels of $NAD^+$-dependent 15-Hydroxyprostaglandin Dehydrogenase are Reduced in Inflammatory Bowel Disease: Evidence for Involvement of TNF-α", *American Journal of Physiology—Gastrointestinal and Liver Physiology*, 2006, G361-G368, vol. 290, American Physiological Society, Rockville, MD, US.

Packer, Milton, et al., "Consensus recommendations for the management of chronic heart failure. On behalf of the membership of the advisory council to improve outcomes nationwide in heart failure," *The American Journal of Cardiology*, Jan. 21, 1999, pp. 1a-38A, vol. 83 (2a), Elsevier Inc., NL.

Park, S.H., et al., "Effect of Thiazolidinedione Phenylacetate Derivatives on Wound-Healing Activity," *Archives of Pharmacal Research*, 2019, pp. 790-814, vol. 42, Springer Science + Business Media, Berlin, DE.

Parveen, H., et al., "Synthesis and Characterization of a New Series of Hydroxy Pyrazolines," *Synthetic Communications*, 2008, pp. 3973-3983, vol. 38, Taylor and Francis, London, UK.

Patani, L., et al., "Bioisosterism: A Rational Approach in Drug Design," *Chemical Reviews*, 1996, pp. 3147-3176, vol. 96, No. 8, American Chemical Society, Washington, DC, US.

Pelus, L.M., et al., "Pleiotropic Effects of Prostaglandin $E_2$ in Hematopoiesis; Prostaglandin $E_2$ and Other Eicosanoids Regulate Hematopoietic Stem and Progenitor Cell Function," *Prostaglandins and Other Lipid Mediators*, 2011, pp. 3-9, vol. 96, Elsevier, Amsterdam, NL.

Pelus, L.M., et al., "Pulse Exposure of Haematopoietic Grafts to Prostaglandin $E_2$ in vitro Facilitates Engraftment and Recovery," *Cell Proliferation*, 2011, pp. 22-29, vol. 44, Suppl. 1, Wiley, Hoboken, NJ, US.

Perse, M., and Cerar, A., "Dextran Sodium Sulphate Colitis Mouse Model: Traps and Tricks," *Journal of Biomedicine and Biotechnology*, 2012, Article ID 718617, 13 pages, vol. 2012, Hindawi Publishing Corporation, London, UK.

Piao, Y.L., et al., "Wound Healing Effects of New 15-Hydroxyprostaglandin Dehydrogenase Inhibitors," *Prostaglandins, Leukotrienes and Essential Fatty Acids*, 2014, pp. 325-332, vol. 91, Elsevier, Amsterdam, NL.

Piao, Y.L., et al., "Cell-based Biological Evaluations of 5-(3-bromo-4-phenethoxybenzylidene)thiazolidine-2,4-dione as Promising Wound Healing Agent," *Bioorganic and Medicinal Chemistry*, May 1, 2015, pp. 2098-2103, vol. 23, Issue 9, Elsevier, Amsterdam, NL.

(56) References Cited

OTHER PUBLICATIONS

Porter, G.A., "Contrast-Associated Nephropathy," *The American Journal of Cardiology*, Sep. 5, 1989, pp. 22E-26E, vol. 64, Issue 9, Elsevier, Amsterdam, NL.

Porter, R.L., et al., "Prostaglandin E2 Increases Hematopoietic Stem Cell Survival and Accelerates Hematopoietic Recovery After Radiation Injury," *Stem Cells*, 2013, pp. 372-383, vol. 31, AlphaMed Press, Hoboken, NJ, US.

Randhawa, P.K., et al., "A Review on Chemical-Induced Inflammatory Bowel Disease Models in Rodents," *Korean Journal of Physiology and Pharmacology*, Aug. 2014, pp. 279-288, vol. 18, Issue 4, The Korean Journal of Physiology and Pharmacology, KR.

Renneville, A., et al., "EHMT1 and EHMT2 Inhibition Induces Fetal Hemoglobin Expression," *Blood*, Oct. 15, 2015, pp. 1930-1939, vol. 126, No. 16, American Society of Hematology, Washington, DC, US.

Rieder, F., et al., "Animal Models of Intestinal Fibrosis: New Tools for the Understandig of Pathogenesis and Therapy of Human Disease," *American Journal of Physiology—Gastrointestinal and Liver Physiology*, Aug. 9, 2012, G786-G801, 303(4, Pt. 1), American Physiological Society, Rockville, MD, US.

Roberts, C.R., "Is Asthma a Fibrotic Disease," *Chest*, Mar. 1995, vol. 107, pp. 111S-117S, American College of Chest Physicians, Glenview, IL, US.

Robison, T.W., and Giri, S.N., "Effects of Chronic Administration of Doxorubicin on Plasma Levels of Prostaglandins, Thromboxane $B_2$, and Fatty Acids in Rats," *Cancer Chemotherapy and Pharmacology*, May 1987, pp. 213-220, vol. 19, Springer Science +Business Media, Berlin, DE.

Rocchiccioli, F., et al., "Quantitative Gas Chromatography-Chemical Ionization Mass Spectrometry of 2-Ketoglutarate from Urine as its O-trimethylsilyl-quinoxalinol Derivative", *Journal of Chromatography*, Dec. 11, 1981, pp. 325-332, vol. 226, No. 2, Elsevier, Amsterdam, NL.

Rogaeva, Ekaterina, et al., "The neuronal sortilin-related receptor SORL1 is genetically associated with Alzheimer disease," *Nature Genetics*, Feb. 2007, pp. 168-177, vol. 39, No. 2, Nature Publishing Group, UK.

Ronzoni, L., et al., "Modulation of Gamma Globulin Genes Expression by Histone Deacetylase Inhibitors: An in vitro Study," Mar. 7, 2014, pp. 714-721, vol. 165, *British Journal of Hematology*, John Wiley & Sons, UK.

Rossi, F., et al., "Cardiotoxicity of Doxorubicin: Effects of Drugs Inhibiting the Release of Vasoactive Substances," *Pharmacology & Toxicology*, Aug. 1994, Abstract, vol. 75, Issue 2, Pharmacology & Toxicology, DK.

Sasaki, S., et al., "Prostaglandin $E_2$ Inhibits Lesion Formation in Dextran Sodium Sulphate-Induced Colitis in Rats and Reduces the Levels of Mucosal Inflammatory Cytokines", *Scandinavian Journal of Immunology*, 2000, pp. 23-28, vol. 51, Wiley, UK.

Schaefer, C.F., et al., "PID: The Pathway Interaction Database," *Nucleic Acids Research*, 2009, pp. D674-D679, vol. 37, Oxford University Press, Oxford, UK.

Seo, S.Y., et al., "Effect of 15-Hydroxyprostaglandin Dehydrogenase Inhibitor on Wound Healing," *Prostaglandins, Leukotrienes, and Essential Fatty Acids*, 2015, pp. 35-41, vol. 97, Elsevier, Amsterdam, NL.

Seto, M., et al., "Orally Active CCR5 Antagonists as Anti-HIV-1 Agents. Part 3: Synthesis and Biological Activities of 1-Benzazepine Derivatives Containing a Sulfoxide Moiety," *Bioorganic and Medicinal Chemistry*, 2005, pp. 363-386, vol. 13, Elsevier, Amsterdam, NL.

Shannon, P., et al., "Cytoscape: A Software Environment for Integrated Models of Biomolecular Interaction Networks," *Genome Research*, 2003, 8 pages including pp. 2498-2504, vol. 13, Cold Spring Harbor Laboratory Press, Cold Spring Harbor, NY, US.

Sharkey, L.C., et al., "Differential Cardiotoxicity in Response to Chronic Doxorubicin Treatment in Male Spontaneous Hypertension-Heart Failure (SHHF), Spontaneously Hypertensive (SHR), and Wistar Kyoto (WKY) Rats," *Toxicology and Applied Pharmacology*, 2013, pp. 47-57, vol. 273, Issue 1, Elsevier, Amsterdam, NL.

Smith, J.N.P., et al., "Inhibition of 15-PGDH Protects Mice from Immune-Mediated Bone Marrow Failure," *Biology of Blood and Marrow Transplantation*, 2020, pp. 1552-1556, vol. 26, Elsevier, Amsterdam, NL.

Smith, J.N.P., "Therapeutic Targeting of 15-PGDH in Murine Pulmonary Fibrosis," *Scientific Reports*, 2020, 11657, 10 pages, vol. 10, Nature Research, London, UK.

Smusz, S., et al., "Fingerprint-based Consensus Virtual Screening Towards Structurally New 5-$HT_6$R Ligands," *Bioorganic and Medicinal Chemistry Letters*, 2015, pp. 1827-1830, vol. 25, Issue 9, Elsevier, Amsterdam, NL.

Solomon, L., et al., "The Dextran Sulphate Sodium (DSS) Model of Colitis: An Overview," *Comparative Clinical Pathology*, Mar. 4, 2010, pp. 235-239, vol. 19, Springer, Munich, DE.

Somasundaram, S., et al., "The DNMT1-Associated lincRNA DACOR1 Reprograms Genome-Wide DNA Methylation in Colon Cancer," *Clinical Epigenetics*, 2018, 15 pages, 10:127, BioMedCentral, London, UK.

Sood, A., et al., "A Prospective, Open-Label Trial Assessing Dexamethasone Pulse Therapy in Moderate to Sever Ulcerative Colitis," *Journal of Clinical Gastroenterology*, Oct. 2002, pp. 328-331, vol. 35, Issue 4, Lippincott Williams & Wilkins, Philadelphia, PA, US.

"Specs," Web page <www.specs.net/>, 2 pages, Dec. 25, 2003, retrieved from the Internet Archive Wayback Machine without Page Vault <http://web.archive.org/web/20031225052253/http://www.specs.net/> on Oct. 26, 2022.

"Specs," Web page <www.specs.net/>, 2 pages, Dec. 25, 2003, retrieved from the Internet Archive Wayback Machine via Page Vault <http://web.archive.org/web/20031225052253/http://www.specs.net/> on Sep. 29, 2022.

Speth, J. M., et al., "Pharmacologic Increase in HIF1α Enhances Hematopoietic Stem and Progenitor Homing and Engraftment," *Blood*, Jan. 9, 2014, six pages including pp. 203-207, vol. 123, No. 2, American Society of Hematology, Washington, DC, US.

St George-Hyslop, P.H., et al., "The Genetic Defect Causing Familial Alzheimer's Disease Maps on Chromosome 21," *Science*, Feb. 20, 1987, pp. 885-890, vol. 235, Issue 4791, American Association for the Advancement of Science, Washington, DC, US.

Tai, H.-H., et al., "Prostaglandin Catabolizing Enzymes", *Prostaglandins and Other Lipid Mediators*, 2002, pp. 483-493, Elsevier Science Inc., Amsterdam, NL.

Tanaka, N., et al., "Crystal Structures of the Binary and Ternary Complexes of 7α-Hydroxysteroid Dehydrogenase from *Escherichia coli,*" *Biochemistry*, Jun. 18, 1996, pp. 7715-7730, vol. 35, Issue 24, American Chemical Society, Washington, DC, US.

Tanaka, Y., et al., "Systems Analysis of ATF3 in Stress Response and Cancer Reveals Opposing Effects on Pro-Apoptotic Genes in p53 Pathway," *PLoS One*, Oct. 2011, e26848, 12 pages, vol. 6, Issue 10, Public Library of Science, San Francisco, CA, US.

Tatsuwaki, H., et al., "Reduction of 15-Hydroxyprostaglandin Dehydrogenase Expression is an Independent Predictor of Poor Survival Associated with Enhanced Cell Proliferation in Gastric Adenocarcinoma," *Cancer Science*, Feb. 2010, pp. 550-558, vol. 101, No. 2, Wiley-Blackwell, Hoboken, NJ, US.

Tessner, T.G., et al., "Prostaglandins Prevent Decreased Epithelial Cell Proliferation Associated With Dextran Sodium Sulfate Injury in Mice", *Gastroenterology*, Oct. 1998, pp. 874-882, vol. 115, No. 4, Elsevier, Amsterdam, NL.

Tong, M., et al., "15-Hydroxyprostaglandin Dehydrogenase Can Be Induced by Dexamethasone and Other Glucocorticoids at the Therapeutic Level in A549 Human Lung Adenocarcinoma Cells," *Archives of Biochemistry and Biophysics*, Mar. 1, 2005, pp. 50-55, vol. 435, issue 1, Elsevier, Amsterdam, NL.

Valatas, V., et al., "Experimental Colitis Models: Insights into the Pathogenesis of Inflammatory Bowel Disease and Translational Issues," *European Journal of Pharmacology*, 2015, pp. 253-264, vol. 759, Elsevier, Amsterdam, NL.

(56) References Cited

OTHER PUBLICATIONS

Varadan, V., et al., "The Integration of Biological Pathway Knowledge in Cancer Genomics," *IEEE Signal Processing Magazine*, Jan. 2012, 20 pages, vol. 29, Issue 1, IEEE Signal Processing Society, Piscataway, NJ, US.

Vaske, C.J., et al., "Inference of patient-specific pathway activities from multi-dimensional cancer genomics data using PARADIGM," *Bioinformatics*, 2010, pp. i237-i245, vol. 26, Oxford University Press, Oxford, UK.

Vukicevic, S., et al., "Role of EP2 and EP4 Receptor—Selective Agonists of Prostaglandin $E_2$ in Acute and Chronic Kidney Failure," *Kidney International*, 2006, pp. 1099-1106, vol. 70, Elsevier on behalf of the International Society of Nephrology, Amsterdam, NL.

Wallace, J.L., "Prostaglandins, NSAIDs, and Gastric Mucosal Protection: Why Doesn't the Stomach Digest Itself?" *Physiol Reviews*, 2008, pp. 1547-1565, vol. 88, No. 4, The American Physiological Society, Rockville, MD, US.

Wang, Y.F., et al., "Meta-Analysis of Drug-Eluting Versus Bare Mtal Stents in Patients with Indications for Oral Anticoagulation Undergoing Coronary Stenting," *Acta Cardiologica*, 2014, pp. 237-244, vol. 69, Issue 3, Belgian Society of Cardiology, BE, Springer.

Wang, Q., et al., "Discovery of Novel Allosteric Effectors Based on the Predicted Allosteric Sites for *Escherichia coli* D-3-Phosphoglycerate Dehydrogenase", *PLOS ONE*, Apr. 14, 2014, p. e94829, vol. 9, issue 4, Public Library of Science, San Francisco, CA, US.

Wang, J., et al., "Design, Synthesis, and Pharmacological Evaluation of Novel Piperlongumine Derivatives as Potential Antiplatelet Aggregation Candidate," *Chemical Biology and Drug Design*, 2016, pp. 883-840, vol. 87, Issue 6, John Wiley & Sonse A/S, Hoboken, NJ.

Wang, J., et al., "Chemopreventive Efficacy of the Cyclooxygenase-2 (Cox-2) Inhibitor, Celecoxib, is Predicted By Adenoma Expression of Cox-2 and 15-PGDH," *Cancer Epidemiology, Biomarkers, and Prevention*, Jul. 2018, 20 pages, vol. 27, Issue 7, American Association for Cancer Research, Philadelphia, PA, US.

Wei, Q., and Dong, Z., "Mouse Model of Ischemic Acute Kidney Injury: Technical Notes and Tricks," *American Journal of Physiology—Renal Physiology*, Sep. 19, 2012, F1487-F1494, vol. 303, American Physiological Society, Rockville, MD, US.

Westbrook, A.M., et al., "Mouse Models of Intestinal Inflammation and Cancer," *Archives of Toxicology*, 2016, 22 pages, vol. 90, Issue 9, Springer-Verlag, DE.

Wirtz, S., and Neurath, M.F., "Mouse Models of Inflammatory Bowel Disease," *Advanced Drug Delivery Reviews*, 2007, pp. 1073-1083, vol. 59, Issue 11, Elsevier B.V., Amsterdam, NL.

Wu, Y., et al., "Synthesis and SAR of Thiazolidinedione Derivatives as 15-PGDH Inhibitors," *Bioorganic and Medicinal Chemistry*, Feb. 15, 2010, Abstract, vol. 18, Issue 4, Elsevier Ltd., Amsterdam, NL.

Wu, Y., et al. "Synthesis and Biological Evaluation of Novel Thiazolidinedione Analogues as 15-Hydroxyprostaglandin Dehydrogenase Inhibitors," *Journal of Medicinal Chemistry*, 2011, pp. 5260-5264, vol. 54, American Chemical Society, Washington, DC, US.

Yan, M., et al., "15-Hydroxyprostaglandin dehydrogenase, a COX-2 oncogene antagonist, is a TGF-β-induced suppressor of human gastrointestinal cancers", *Proceedings of the National Academy of Sciences*, Dec. 14, 2004, pp. 17468-17473, vol. 101, No. 50, United States National Academy of Sciences, Washington, DC, US.

Yan, C., et al., "Cyclooxygenases, Microsomal Prostaglandin E Synthase-1, and Cardiovascular Function," *The Journal of Clinical Investigation*, 2006, pp. 1391-1399, vol. 116, Issue 5, American Society for Clinical Investigation, US.

Yan, Min, et al., "15-Hydroxyprostaglandin dehydrogenase inactivation as a mechanism of resistance to celecoxib chemoprevention of colon tumors", *Proceedings of the National Academy of Sciences*, Jun. 9, 2009, pp. 9409-9413, vol. 106, No. 23, United States National Academy of Sciences, Washington, DC, US.

Yang, H., et al., "Altered Hippocampal Long-Term Synaptic Plasticity in Mice Deficient in the PGE2 EP2 Receptor," *Journal of Neurochemistry*, 2009, pp. 295-304, vol. 108, Wiley-Blackwell, Hoboken, NJ, US.

Yao, R., et al., "Comparison of Clinical Efficacy of Different Statins on Cardiovascular Events Following Percutaneous Coronary Intervention," *International Journal of Clinical and Experimental Medicine*, 2017, 11286, vol. 10, Issue 7, e-Century Publishing Corporation, Madison, WI, US, Article Retracted.

Yeh, F.-L., et al., "Keloid-Derived Fibroblasts Have a Diminished Capacity to Produce Prostaglandin $E_2$," *Burns*, 2006, pp. 299-304, vol. 32, Elsevier Ltd., Amsterdam, NL.

Zhang, Y., "Inhibition of the Prostaglandin Degrading Enzyme 15-PGDH Potentiates Tissue Regeneration," *Science*, Jun. 12, 2015, p. 1223, pp. aaa2340-1 to aaa2340-8, vol. 348, Issue 6240, American Association for the Advancement of Science, Washington, DC, US.

Zhang, Y., et al., "Prasugrel Suppresses Development of Lithium-Induced Nephrogenic Diabetes Insipidus in Mice," *Purinergic Signalling*, 2017, pp. 239-248, vol. 13, Springer Science + Business Media, Berlin, DE.

Zhang, Y., et al., "Impacts of CYP2C19 Genetic Polymorphisms on Bioavailability and Effect on Platelet Adhesion of Vicagrel, a Novel Thienopyridine $P2Y_{12}$ Inhibitor," *British Journal of Clinical Pharmacology*, 2020, pp. 1860-1874, vol. 86, The British Pharmacological Society, Wiley-Blackwell, Hoboken, NJ, US.

Zhao, L., et al., "Design, Synthesis and SAR of Thienopyridines as Potent CHK1 Inhibitors," *Bioorganic and Medicinal Chemistry Letters*, Dec. 15, 2010, pp. 7216-7221, vol. 20, Issue 24, Elsevier Ltd., Amsterdam, NL.

Zhou, Y., and Gong, Y., "Asymmetric Copper(II)-Catalysed Nitroaldol (Henry) Reactions Utilizing a Chiral $C_1$-Symmetric Dinitrogen Ligand," *European Journal of Organic Chemistry*, 2011, pp. 6092-6099, vol. 2011, Issue 30, Wiley-VCH Verlag GmbH & Co. KGaA, Weinheim, DE.

CAS Registry No. 296798-64-6 [online database], STN Entry Date Oct. 18, 2000 [retrieved on Oct. 21, 2022], Retrieved from SciFinder <https://scifinder-n.cas.org/>, substance detail downloaded to PDF.

CAS Registry No. 299406-22-7 [online database], STN Entry Date Oct. 26, 2000 [retrieved on Oct. 24, 2022], Retrieved from SciFinder <https://scifinder-n.cas.org/>, substance detail downloaded to pdf.

CAS Registry No. 299920-58-4 [online database], STN Entry Date Oct. 27, 2000 [retrieved on Sep. 21, 2022], Retrieved from SciFinder <https://scifinder-n.cas.org/>, substance detail downloaded to PDF.

CAS Registry No. 299920-59-5 [online database], STN Entry Date Oct. 27, 2000 [retrieved on Sep. 21, 2022], Retrieved from SciFinder <https://scifinder-n.cas.org/>, substance detail downloaded to PDF.

CAS Registry No. 299920-61-9 [online database], STN Entry Date Oct. 27, 2000 [retrieved on Sep. 16, 2022], Retrieved from SciFinder <https://scifinder-n.cas.org/>, substance detail downloaded to PDF.

CAS Registry No. 299920-78-8 [online database], STN Entry Date Oct. 27, 2000 [retrieved on Sep. 21, 2022], Retrieved from SciFinder <https://scifinder-n.cas.org/>, substance detail downloaded to PDF.

CAS Registry No. 306766-39-2 [online database], STN Entry Date Dec. 5, 2000 [retrieved on Oct. 24, 2022], Retrieved from SciFinder <https://scifinder-n.cas.org/>, substance detail downloaded to pdf.

CAS Registry No. 313245-69-1 [online database], STN Entry Date Jan. 9, 2001 [retrieved on Oct. 24, 2022], Retrieved from SciFinder <https://scifinder-n.cas.org/>, substance detail downloaded to pdf.

CAS Registry No. 313245-70-4 [online database], STN Entry Date Jan. 9, 2001 [retrieved on Sep. 16, 2022], Retrieved from SciFinder <https://scifinder-n.cas.org/>, substance detail downloaded to PDF.

CAS Registry No. 331447-76-8 [online database], STN Entry Date Apr. 16, 2001 [retrieved on Sep. 16, 2022], Retrieved from SciFinder <https://scifinder-n.cas.org/>, substance detail downloaded to PDF.

CAS Registry No. 331655-85-7 [online database], STN Entry Date Apr. 17, 2001 [retrieved on Sep. 16, 2022], Retrieved from SciFinder <https://scifinder-n.cas.org/>, substance detail downloaded to PDF.

CAS Registry No. 331655-86-8 [online database], STN Entry Date Apr. 17, 2001 [retrieved on Apr. 16, 2022], Retrieved from SciFinder <https://scifinder-n.cas.org/>, substance detail downloaded to PDF.

(56) References Cited

OTHER PUBLICATIONS

CAS Registry No. 332945-05-8 [online database], STN Entry Date Apr. 26, 2001 [retrieved on Oct. 24, 2022], Retrieved from SciFinder <https://scifinder-n.cas.org/>, substance detail downloaded to pdf.
CAS Registry No. 348151-19-9 [online database], STN Entry Date Jul. 25, 2001 [retrieved on Sep. 21, 2022], Retrieved from SciFinder <https://scifinder-n.cas.org/>, substance detail downloaded to PDF.
CAS Registry No. 350511-89-6 [online database], STN Entry Date Aug. 6, 2001 [retrieved on Sep. 16, 2022], Retrieved from SciFinder <https://scifinder-n.cas.org/>, substance detail downloaded to PDF.
CAS Registry No. 369400-43-1 [online database], STN Entry Date Nov. 13, 2001 [retrieved on Sep. 16, 2022], Retrieved from SciFinder <https://scifinder-n.cas.org/>, substance detail downloaded to PDF.
CAS Registry No. 369402-41-5 [online database], STN Entry Date NNov. 13, 2001 [retrieved on Sep. 16, 2022], Retrieved from SciFinder <https://scifinder-n.cas.org/>, substance detail downloaded to PDF.
CAS Registry No. 370572-70-6 [online database], STN Entry Date Nov. 16, 2001 [retrieved on Sep. 21, 2022], Retrieved from SciFinder <https://scifinder-n.cas.org/>, substance detail downloaded to PDF.
CAS Registry No. 370870-44-3 [online database], STN Entry Date Nov. 19, 2001 [retrieved on Sep. 21, 2022], Retrieved from SciFinder <https://scifinder-n.cas.org/>, substance detail downloaded to PDF.
CAS Registry No. 371116-23-3 [online database], STN Entry Date Nov. 20, 2001 [retrieved on Sep. 16, 2022], Retrieved from SciFinder <https://scifinder-n.cas.org/>, substance detail downloaded to PDF.
CAS Registry No. 371117-75-8 [online database], STN Entry Date Nov. 20, 2001 [retrieved on Sep. 21, 2022], Retrieved from SciFinder <https://scifinder-n.cas.org/>, substance detail downloaded to PDF.
CAS Registry No. 371118-22-8 [online database], STN Entry Date Nov. 20, 2001 [retrieved on Sep. 21, 2022], Retrieved from SciFinder <https://scifinder-n.cas.org/>, substance detail downloaded to PDF.
CAS Registry No. 371144-00-2 [online database], STN Entry Date Nov. 20, 2001 [retrieved on Sep. 16, 2022], Retrieved from SciFinder <https://scifinder-n.cas.org/>, substance detail downloaded to PDF.
CAS Registry No. 371208-33-2 [online database], STN Entry Date Nov. 21, 2001 [retrieved on Sep. 16, 2022], Retrieved from SciFinder <https://scifinder-n.cas.org/>, substance detail downloaded to PDF.
CAS Registry No. 371213-13-7 [online database], STN Entry Date Nov. 21, 2001 [retrieved on Sep. 21, 2022], Retrieved from SciFinder <https://scifinder-n.cas.org/>, substance detail downloaded to PDF.
CAS Registry No. 371222-38-7 [online database], STN Entry Date Nov. 21, 2001 [retrieved on Sep. 21, 2022], Retrieved from SciFinder <https://scifinder-n.cas.org/>, substance detail downloaded to PDF.
CAS Registry No. 371232-15-4 [online database], STN Entry Date Nov. 21, 2001 [retrieved on Sep. 21, 2022], Retrieved from SciFinder <https://scifinder-n.cas.org/>, substance detail downloaded to PDF.
CAS Registry No. 371926-65-7 [online database], STN Entry Date Nov. 27, 2001 [retrieved on Sep. 16, 2022], Retrieved from SciFinder <https://scifinder-n.cas.org/>, substance detail downloaded to PDF.
CAS Registry No. 384861-16-9 [online database], STN Entry Date Jan. 20, 2002 [retrieved on Sep. 21, 2022], Retrieved from SciFinder <https://scifinder-n.cas.org/>, substance detail downloaded to PDF.
CAS Registry No. 420824-06-2 [online database], STN Entry Date May 23, 2002 [retrieved on Sep. 16, 2022], Retrieved from SciFinder <https://scifinder-n.cas.org/>, substance detail downloaded to PDF.
CAS Registry No. 420825-11-2 [online database], STN Entry Date May 23, 2002 [retrieved on Sep. 21, 2022], Retrieved from SciFinder <https://scifinder-n.cas.org/>, substance detail downloaded to PDF.
CAS Registry No. 420825-38-3 [online database], STN Entry Date May 23, 2002 [retrieved on Sep. 21, 2022], Retrieved from SciFinder <https://scifinder-n.cas.org/>, substance detail downloaded to PDF.
CAS Registry No. 442152-75-2 [online database], STN Entry Date Aug. 2, 2002 [retrieved on Sep. 21, 2022], Retrieved from SciFinder <https://scifinder-n.cas.org/>, substance detail downloaded to PDF.
CAS Registry No. 442152-82-1 [online database], STN Entry Date Aug. 2, 2002 [retrieved on Sep. 16, 2022], Retrieved from SciFinder <https://scifinder-n.cas.org/>, substance detail downloaded to PDF.
CAS Registry No. 442152-88-7 [online database], STN Entry Date Aug. 2, 2002 [retrieved on Sep. 16, 2022], Retrieved from SciFinder <ttps://scifinder-n.cas.org/>, substance detail downloaded to PDF.
CAS Registry No. 442152-94-5 [online database], STN Entry Date Aug. 2, 2002 [retrieved on Sep. 16, 2022], Retrieved from SciFinder <https://scifinder-n.cas.org/>, substance detail downloaded to PDF.
CAS Registry No. 442153-01-7 [online database], STN Entry Date Aug. 2, 2002 [retrieved on Sep. 16, 2022], Retrieved from SciFinder <https://scifinder-n.cas.org/>, substance detail downloaded to PDF.
CAS Registry No. 442153-03-9 [online database], STN Entry Date Aug. 2, 2002 [retrieved on Sep. 21, 2022], Retrieved from SciFinder <https://scifinder-n.cas.org/>, substance detail downloaded to PDF.
CAS Registry No. 448191-85-3 [online database], STN Entry Date Sep. 9, 2002 [retrieved on Sep. 21, 2022], Retrieved from SciFinder <https://scifinder-n.cas.org/>, substance detail downloaded to PDF.
CAS Registry No. 448191-89-7 [online database], STN Entry Date Sep. 9, 2002 [retrieved on Sep. 21, 2022], Retrieved from SciFinder <https://scifinder-n.cas.org/>, substance detail downloaded to PDF.
CAS Registry No. 452922-28-0 [online database], STN Entry Date Sep. 19, 2002 [retrieved on Sep. 16, 2022], Retrieved from SciFinder <https://scifinder-n.cas.org/>, substance detail downloaded to PDF.
CAS Registry No. 457958-02-0 [online database], STN Entry Date Oct. 2, 2002 [retrieved on Sep. 16, 2022], Retrieved from SciFinder <https://scifinder-n.cas.org/>, substance detail downloaded to PDF.
CAS Registry No. 457958-03-1 [online database], STN Entry Date Oct. 2, 2002 [retrieved on Sep. 16, 2022], Retrieved from SciFinder <https://scifinder-n.cas.org/>, substance detail downloaded to PDF.
CAS Registry No. 457958-04-2 [online database], STN Entry Date Oct. 2, 2002 [retrieved on Sep. 16, 2022], Retrieved from SciFinder <https://scifinder-n.cas.org/>, substance detail downloaded to PDF.
CAS Registry No. 457958-05-3 [online database], STN Entry Date Oct. 2, 2002 [retrieved on Sep. 16, 2022], Retrieved from SciFinder <https://scifinder-n.cas.org/>, substance detail downloaded to PDF.
CAS Registry No. 457958-06-4 [online database], STN Entry Date Oct. 2, 2002 [retrieved on Sep. 21, 2022], Retrieved from SciFinder <https://scifinder-n.cas.org/>, substance detail downloaded to PDF.
CAS Registry No. 457958-16-6 [online database], STN Entry Date Oct. 2, 2002 [retrieved on Sep. 16, 2022], Retrieved from SciFinder <https://scifinder-n.cas.org/>, substance detail downloaded to PDF.
CAS Registry No. 457958-17-7 [online database], STN Entry Date Oct. 2, 2002 [retrieved on Sep. 19, 2022], Retrieved from SciFinder <https://scifinder-n.cas.org/>, substance detail downloaded to PDF.
CAS Registry No. 457958-18-8 [online database], STN Entry Date Oct. 2, 2002 [retrieved on Sep. 21, 2022], Retrieved from SciFinder <https://scifinder-n.cas.org/>, substance detail downloaded to PDF.
CAS Registry No. 457958-30-4 [online database], STN Entry Date Oct. 2, 2002 [retrieved on Sep. 16, 2022], Retrieved from SciFinder <https://scifinder-n.cas.org/>, substance detail downloaded to PDF.
CAS Registry No. 457958-31-5 [online database], STN Entry Date Oct. 2, 2002 [retrieved on Sep. 21, 2022], Retrieved from SciFinder <https://scifinder-n.cas.org/>, substance detail downloaded to PDF.
CAS Registry No. 457958-32-6 [online database], STN Entry Date Oct. 2, 2002 [retrieved on Sep. 16, 2022], Retrieved from SciFinder <https://scifinder-n.cas.org/>, substance detail downloaded to PDF.
CAS Registry No. 457958-38-2 [online database], STN Entry Date Oct. 2, 2002 [retrieved on Sep. 16, 2022], Retrieved from SciFinder <https://scifinder-n.cas.org/>, substance detail downloaded to PDF.
CAS Registry No. 457958-39-3 [online database], STN Entry Date Oct. 2, 2002 [retrieved on Sep. 16, 2022], Retrieved from SciFinder <https://scifinder-n.cas.org/>, substance detail downloaded to PDF.
CAS Registry No. 457958-40-6 [online database], STN Entry Date Oct. 2, 2002 [retrieved on Sep. 21, 2022], Retrieved from SciFinder <https://scifinder-n.cas.org/>, substance detail downloaded to PDF.
CAS Registry No. 457958-41-7 [online database], STN Entry Date Oct. 2, 2002 [retrieved on Sep. 16, 2022], Retrieved from SciFinder <https://scifinder-n.cas.org/>, substance detail downloaded to PDF.
CAS Registry No. 457958-49-5 [online database], STN Entry Date Oct. 2, 2002 [retrieved on Sep. 16, 2022], Retrieved from SciFinder <https://scifinder-n.cas.org/>, substance detail downloaded to PDF.
CAS Registry No. 457958-50-8 [online database], STN Entry Date Oct. 2, 2002 [retrieved on Sep. 21, 2022], Retrieved from SciFinder <https://scifinder-n.cas.org/>, substance detail downloaded to PDF.

(56) References Cited

OTHER PUBLICATIONS

CAS Registry No. 459147-27-4 [online database], STN Entry Date Oct. 4, 2002 [retrieved on Sep. 16, 2022], Retrieved from SciFinder <https://scifinder-n.cas.org/>, substance detail downloaded to PDF.
CAS Registry No. 459147-39-8 [online database], STN Entry Date Oct. 4, 2002 [retrieved on Sep. 16, 2022], Retrieved from SciFinder <https://scifinder-n.cas.org/>, substance detail downloaded to PDF.
CAS Registry No. 459147-74-1 [online database], STN Entry Date Oct. 4, 2002 [retrieved on Sep. 21, 2022], Retrieved from SciFinder <https://scifinder-n.cas.org/>, substance detail downloaded to PDF.
CAS Registry No. 459150-70-0 [online database], STN Entry Date Oct. 4, 2002 [retrieved on Sep. 21, 2022], Retrieved from SciFinder <https://scifinder-n.cas.org/>, substance detail downloaded to PDF.
CAS Registry No. 459150-74-4 [online database], STN Entry Date Oct. 4, 2002 [retrieved on Sep. 16, 2022], Retrieved from SciFinder <https://scifinder-n.cas.org/>, substance detail downloaded to PDF.
CAS Registry No. 459150-94-8 [online database], STN Entry Date Oct. 4, 2002 [retrieved on Sep. 16, 2022], Retrieved from SciFinder <https://scifinder-n.cas.org/>, substance detail downloaded to PDF.
CAS Registry No. 459151-05-4 [online database], STN Entry Date Oct. 4, 2002 [retrieved on Sep. 21, 2022], Retrieved from SciFinder <https://scifinder-n.cas.org/>, substance detail downloaded to PDF.
CAS Registry No. 459152-84-2 [online database], STN Entry Date Oct. 4, 2002 [retrieved on Sep. 16, 2022], Retrieved from SciFinder <https://scifinder-n.cas.org/>, substance detail downloaded to PDF.
CAS Registry No. 459153-20-9 [online database], STN Entry Date Oct. 4, 2002 [retrieved on Sep. 16, 2022], Retrieved from SciFinder <https://scifinder-n.cas.org/>, substance detail downloaded to PDF.
CAS Registry No. 459153-24-3 [online database], STN Entry Date Oct. 4, 2002 [retrieved on Sep. 21, 2022], Retrieved from SciFinder <https://scifinder-n.cas.org/>, substance detail downloaded to PDF.
CAS Registry No. 459153-30-1 [online database], STN Entry Date Oct. 4, 2002 [retrieved on Sep. 16, 2022], Retrieved from SciFinder <https://scifinder-n.cas.org/>, substance detail downloaded to PDF.
CAS Registry No. 459153-75-4 [online database], STN Entry Date Oct. 4, 2002 [retrieved on Sep. 21, 2022], Retrieved from SciFinder <https://scifinder-n.cas.org/>, substance detail downloaded to PDF.
CAS Registry No. 459154-25-7 [online database], STN Entry Date Oct. 4, 2002 [retrieved on Sep. 16, 2022], Retrieved from SciFinder <https://scifinder-n.cas.org/>, substance detail downloaded to PDF.
CAS Registry No. 459154-76-8 [online database], STN Entry Date Oct. 4, 2002 [retrieved on Sep. 16, 2022], Retrieved from SciFinder <https://scifinder-n.cas.org/>, substance detail downloaded to PDF.
CAS Registry No. 459154-80-4 [online database], STN Entry Date Oct. 4, 2002 [retrieved on Sep. 16, 2022], Retrieved from SciFinder <https://scifinder-n.cas.org/>, substance detail downloaded to PDF.
CAS Registry No. 459155-72-7 [online database], STN Entry Date Oct. 10, 2002 [retrieved on Sep. 16, 2022], Retrieved from SciFinder <https://scifinder-n.cas.org/>, substance detail downloaded to PDF.
CAS Registry No. 459155-77-2 [online database], STN Entry Date Oct. 4, 2002 [retrieved on Sep. 16, 2022], Retrieved from SciFinder <https://scifinder-n.cas.org/>, substance detail downloaded to PDF.
CAS Registry No. 459155-84-1 [online database], STN Entry Date Oct. 4, 2002 [retrieved on Sep. 21, 2022], Retrieved from SciFinder <https://scifinder-n.cas.org/>, substance detail downloaded to PDF.
CAS Registry No. 693820-48-3 [online database], STN Entry Date Jun. 16, 2004 [retrieved on Sep. 16, 2022], Retrieved from SciFinder <https://scifinder-n.cas.org/>, substance detail downloaded to PDF.
CAS Registry No. 924846-44-6 [online database], STN Entry Date Mar. 5, 2007 [retrieved on Sep. 16, 2022], Retrieved from SciFinder <https://scifinder-n.cas.org/>, substance detail downloaded to PDF.
CAS Registry No. 957625-42-2 [online database], STN Entry Date Dec. 11, 2007 [retrieved on Sep. 21, 2022], Retrieved from SciFinder <https://scifinder-n.cas.org/>, substance detail downloaded to PDF.
CAS Registry No. 957939-31-0 [online database], STN Entry Date Dec. 13, 2007 [retrieved on Sep. 16, 2022], Retrieved from SciFinder <https://scifinder-n.cas.org/>, substance detail downloaded to PDF.
CAS Registry No. 957948-58-2 [online database], STN Entry Date Dec. 13, 2007 [retrieved on Sep. 16, 2022], Retrieved from SciFinder <https://scifinder-n.cas.org/>, substance detail downloaded to PDF.
CAS Registry No. 957957-90-3 [online database], STN Entry Date Dec. 13, 2007 [retrieved on Sep. 21, 2022], Retrieved from SciFinder <https://scifinder-n.cas.org/>, substance detail downloaded to PDF.
CAS Registry No. 1015864-36-4 [online database], STN Entry Date Apr. 20, 2008 [retrieved on Sep. 16, 2022], Retrieved from SciFinder <https://scifinder-n.cas.org/>, substance detail downloaded to PDF.
CAS Registry No. 1015864-38-6 [online database], STN Entry Date Apr. 20, 2008 [retrieved on Sep. 21, 2022], Retrieved from SciFinder <https://scifinder-n.cas.org/>, substance detail downloaded to PDF.
CAS Registry No. 1020685-61-3 [online database], STN Entry Date May 14, 2008 [retrieved on Sep. 16, 2022], Retrieved from SciFinder <https://scifinder-n.cas.org/>, substance detail downloaded to PDF.
CAS Registry No. 1020685-65-7 [online database], STN Entry Date May 14, 2008 [retrieved on Sep. 16, 2022], Retrieved from SciFinder <https://scifinder-n.cas.org/>, substance detail downloaded to PDF.
CAS Registry No. 1020686-01-4 [online database], STN Entry Date May 14, 2008 [retrieved on Sep. 16, 2022], Retrieved from SciFinder <https://scifinder-n.cas.org/>, substance detail downloaded to PDF.
CAS Registry No. 1020686-06-9 [online database], STN Entry Date May 14, 2008 [retrieved on Sep. 21, 2022], Retrieved from SciFinder <https://scifinder-n.cas.org/>, substance detail downloaded to PDF.
CAS Registry No. 1020686-10-5 [online database], STN Entry Date May 15, 2008 [retrieved on Sep. 21, 2022], Retrieved from SciFinder <https://scifinder-n.cas.org/>, substance detail downloaded to PDF.
CAS Registry No. 1020686-49-0 [online database], STN Entry Date May 14, 2008 [retrieved on Sep. 16, 2022], Retrieved from SciFinder <https://scifinder-n.cas.org/>, substance detail downloaded to PDF.
CAS Registry No. 1020686-53-6 [online database], STN Entry Date May 14, 2008 [retrieved on Sep. 21, 2022], Retrieved from SciFinder <https://scifinder-n.cas.org/>, substance detail downloaded to PDF.
CAS Registry No. 1020686-57-0 [online database], STN Entry Date May 14, 2008 [retrieved on Sep. 16, 2022], Retrieved from SciFinder <https://scifinder-n.cas.org/>, substance detail downloaded to PDF.
CAS Registry No. 1020686-77-4 [online database], STN Entry Date May 14, 2008 [retrieved on Sep. 16, 2022], Retrieved from SciFinder <https://scifinder-n.cas.org/>, substance detail downloaded to PDF.
CAS Registry No. 1020686-81-0 [online database], STN Entry Date May 14, 2008 [retrieved on Sep. 21, 2022], Retrieved from SciFinder <https://scifinder-n.cas.org/>, substance detail downloaded to PDF.
CAS Registry No. 1020687-17-5 [online database], STN Entry Date May 14, 2008 [retrieved on Sep. 16, 2022], Retrieved from SciFinder <https://scifinder-n.cas.org/>, substance detail downloaded to PDF.
CAS Registry No. 1112019-47-2 [online database], STN Entry Date Feb. 26, 2009 [retrieved on Sep. 16, 2022], Retrieved from SciFinder <https://scifinder-n.cas.org/>, substance detail downloaded to PDF.
CAS Registry No. 1115479-64-5 [online database], STN Entry Date Mar. 4, 2009 [retrieved on Sep. 16, 2022], Retrieved from SciFinder <https://scifinder-n.cas.org/>, substance detail downloaded to PDF.
CAS Registry No. 1221411-67-1 [online database], STN Entry Date May 5, 2010 [retrieved on Sep. 16, 2022], Retrieved from SciFinder <https://scifinder-n.cas.org/>, substance detail downloaded to PDF.
CAS Registry No. 1221411-70-6 [online database], STN Entry Date May 5, 2010 [retrieved on Sep. 16, 2022], Retrieved from SciFinder <https://scifinder-n.cas.org/>, substance detail downloaded to PDF.
CAS Registry No. 1347499-81-3 [online database], STN Entry Date Dec. 2, 2011 [retrieved on Sep. 21, 2022], Retrieved from SciFinder <https://scifinder-n.cas.org/>, substance detail downloaded to PDF.
CAS Registry No. 1348234-90-1 [online database], STN Entry Date Dec. 4, 2011 [retrieved on Sep. 21, 2022], Retrieved from SciFinder <https://scifinder-n.cas.org/>, substance detail downloaded to PDF.
CAS Registry No. 1348857-03-3 [online database], STN Entry Date Dec. 5, 2011 [retrieved on Sep. 21, 2022], Retrieved from SciFinder <https://scifinder-n.cas.org/>, substance detail downloaded to PDF.
CAS Registry No. 1349215-63-9 [online database], STN Entry Date Dec. 5, 2011 [retrieved on Sep. 21, 2022], Retrieved from SciFinder <https://scifinder-n.cas.org/>, substance detail downloaded to PDF.
CAS Registry No. 1421694-45-2 [online database], STN Entry Date Feb. 22, 2013 [retrieved on Sep. 16, 2022], Retrieved from SciFinder <https://scifinder-n.cas.org/>, substance detail downloaded to PDF.
CAS Registry No. 1471306-25-8 [online database], STN Entry Date Nov. 11, 2013 [retrieved on Sep. 16, 2022], Retrieved from SciFinder <https://scifinder-n.cas.org/>, substance detail downloaded to PDF.

(56) References Cited

OTHER PUBLICATIONS

CAS Registry No. 1471306-27-0 [online database], STN Entry Date Nov. 11, 2013 [retrieved on Sep. 16, 2022], Retrieved from SciFinder <https://scifinder-n.cas.org/>, substance detail downloaded to PDF.
CAS Registry No. 1471306-29-2 [online database], STN Entry Date Nov. 11, 2013 [retrieved on Sep. 16, 2022], Retrieved from SciFinder <https://scifinder-n.cas.org/>, substance detail downloaded to PDF.
CAS Registry No. 1471306-31-6 [online database], STN Entry Date Nov. 11, 2013 [retrieved on Sep. 16, 2022], Retrieved from SciFinder <https://scifinder-n.cas.org/>, substance detail downloaded to PDF.
CAS Registry No. 1471306-33-8 [online database], STN Entry Date Nov. 11, 2013 [retrieved on Sep. 16, 2022], Retrieved from SciFinder <https://scifinder-n.cas.org/>, substance detail downloaded to PDF.
CAS Registry No. 1471306-35-0 [online database], STN Entry Date Nov. 11, 2013 [retrieved on Sep. 16, 2022], Retrieved from SciFinder <https://scifinder-n.cas.org/>, substance detail downloaded to PDF.
CAS Registry No. 1471306-37-2 [online database], STN Entry Date Nov. 11, 2013 [retrieved on Sep. 16, 2022], Retrieved from SciFinder <https://scifinder-n.cas.org/>, substance detail downloaded to PDF.
CAS Registry No. 1471306-39-4 [online database], STN Entry Date Nov. 11, 2013 [retrieved on Sep. 16, 2022], Retrieved from SciFinder <https://scifinder-n.cas.org/>, substance detail downloaded to PDF.
CAS Registry No. 1611464-74-4 [online database], STN Entry Date Jun. 20, 2014 [retrieved on Oct. 25, 2022], Retrieved from SciFinder <https://scifinder-n.cas.org/>, substance detail downloaded to PDF.
CAS Registry No. 1714959-81-5 [online database], STN Entry Date May 28, 2015 [retrieved on Sep. 16, 2022], Retrieved from SciFinder <https://scifinder-n.cas.org/>, substance detail downloaded to PDF.
CAS Registry No. 1714959-82-6 [online database], STN Entry Date May 28, 2015 [retrieved on Sep. 16, 2022], Retrieved from SciFinder <https://scifinder-n.cas.org/>, substance detail downloaded to PDF.
CAS Registry No. 1714959-83-7 [online database], STN Entry Date May 28, 2015 [retrieved on Sep. 16, 2022], Retrieved from SciFinder <https://scifinder-n.cas.org/>, substance detail downloaded to PDF.
CAS Registry No. 1714959-86-0 [online database], STN Entry Date May 28, 2015 [retrieved on Sep. 16, 2022], Retrieved from SciFinder <https://scifinder-n.cas.org/>, substance detail downloaded to PDF.
CAS Registry No. 1714959-92-8 [online database], STN Entry Date May 28, 2015 [retrieved on Sep. 16, 2022], Retrieved from SciFinder <https://scifinder-n.cas.org/>, substance detail downloaded to PDF.
CAS Registry No. 1714959-93-9 [online database], STN Entry Date May 28, 2015 [retrieved on Sep. 16, 2022], Retrieved from SciFinder <https://scifinder-n.cas.org/>, substance detail downloaded to PDF.
CAS Registry No. 1714959-95-1 [online database], STN Entry Date May 28, 2015 [retrieved on Sep. 16, 2022], Retrieved from SciFinder <https://scifinder-n.cas.org/>, substance detail downloaded to PDF.
CAS Registry No. 1714959-96-2 [online database], STN Entry Date May 28, 2015 [retrieved on Sep. 16, 2022], Retrieved from SciFinder <https://scifinder-n.cas.org/>, substance detail downloaded to PDF.
CAS Registry No. 1714961-85-9 [online database], STN Entry Date May 28, 2015 [retrieved on Sep. 16, 2022], Retrieved from SciFinder <https://scifinder-n.cas.org/>, substance detail downloaded to PDF.
CAS SciFinder Search Result on Jan. 27, 2022, at 5:14 pm (2 results)-1-Preparation of thienopyridines and related compounds, their commpositions and methods of modulating short-chain dehydrogenase activity (WO 2018/218251);-2-Compositions and methods of adulating short-chain dehydrogenase activity (WO 2016/168472).
CAS SciFinder Search Result on Jan. 27, 2022, at 11:52 am (1 result)-1-Preparation of thienopyridines and similar bicyclic heterocyclic compounds as modulators of 15-hydroxyprostaglandin dehydrogenase type I for therapy (WO 2015/065716).
CAS SciFinder Search Result on Jan. 27, 2022, at 3:02 pm (2 results)-1-Preparation of thienopyridines and similar bicyclic heterocyclic compounds as modulators of 15-hydroxyprostaglandin dehydrogenase type I for therapy (WO 2015/065716);-2-Preparation of enopyridines and related compounds, their compositions and methods of modulating short-chain dehydrogenase activity (WO 2018/218251).
CAS SciFinder Search Result on Jan. 27, 2022, at 3:25 pm (1 result)-1-Preparation of thienopyridines and similar bicyclic heterocyclic mpounds as modulators of 15-hydroxyprostaglandin dehydrogenase type I for therapy (WO 2015/065716).
CAS SciFinder Search Result on Jan. 27, 2022, at 3:30 pm (2 results)-1-Preparation of thienopyridines and similar bicyclic heterocyclic compounds as modulators of 15-hydroxyprostaglandin dehydrogenase type I for therapy (WO 2015/065716);-2-Preparation of enopyridines and related compounds, their compositions and methods of modulating short-chain dehydrogenase activity (WO 2018/218251).
CAS SciFinder Search Result on Jan. 27, 2022, at 4:08 pm (2 results)-1-Preparation of thienopyridines and similar bicyclic heterocyclic mpounds as modulators of 15-hydroxyprostaglandin dehydrogenase type I for therapy (WO 2015/065716);-2-Preparation of thienopridines and related compounds, their compositions and ethods of modulating short-chain dehydrogenase activity (WO 2018/218251).
CAS SciFinder Search Result on Jan. 27, 2022, at 4:11 pm (2 results)-1-Preparation of thienopyridines and similar bicyclic heterocyclic compounds as modulators of 15-hydroxyprostaglandin dehydrogenase type I for therapy (WO 2015/065716);-2-Preparation of thienopyridines and related compounds, their compositions and methods of modulating short-chain dehydrogenase activity (WO 2018/218251).
CAS SciFinder Search Result on Jan. 27, 2022, at 4:14 pm (2 results)-1-Preparation of thienopyridines and similar bicyclic heterocyclic compounds as modulators of 15-hydroxyprostaglandin dehydrogenase type I for therapy (WO 2015/065716);-2-Preparation of thienopyridines and related compounds, their compositions and methods of modulating short-chain dehydrogenase activity (WO 2018/218251).
CAS SciFinder Search Result on Jan. 27, 2022, at 4:16 pm (2 results)-1-Preparation of thienopyridines and similar bicyclic heterocyclic compounds as modulators of 15-hydroxyprostaglandin dehydrogenase type I for therapy (2015/065716);-2-Preparation of thienopyridines and related compounds, their compositions and methods of modulating short-chain dehydrogenase activity (WO 2018/218251).
CAS SciFinder Search Result on Jan. 27, 2022, at 4:50 pm (2 results)-1-Preparation of thienopyridines and similar bicyclic heterocyclic compounds as modulators of 15-hydroxyprostaglandin dehydrogenase type I for therapy (WO 2015/065716);-2-Preparation of thienopyridines and related compounds, their compositions and methods of modulating short-chain dehydrogenase activity (WO 2018/218251).
CAS SciFinder Search Result on Jan. 27, 2022, at 5:09 pm (2 results)-1-Preparation of thienopyridines and similar bicyclic heterocyclic compounds as modulators of 15-hydroxyprostaglandin dehydrogenase type I for therapy (WO 2015/065716);-2-Preparation of thienopyridines and related compounds, their compositions and methods of modulating short-chain dehydrogenase activity (WO 2018/218251).
CAS SciFinder Search Result on Jan. 27, 2022, at 5:52 pm (2 results)-1-Preparation of thienopyridines and related compounds, their compositions and methods of modulating short-chain dehydrogenase activity (WO 2018/218251);- 2-Compositions and methods of modulating short-chain dehydrogenase activity (WO 2016/168472).
CAS SciFinder Search Result on Jan. 27, 2022, at 5:58 pm (2 results)-1-Preparation of thienopyridines and related compounds, their compositions and methods of modulating short-chain dehydrogenase activity (WO 2018/218251);- 2-Compositions and methods of modulating short-chain dehydrogenase activity (WO 2016/168472).
CAS SciFinder Search Result on Jan. 27, 2022, at 6:03 pm (6 results)-1-Preparation of thienopyridines and similar bicyclic heterocyclic compounds as modulators of 15-hydroxyprostaglandin dehydrogenase type I for therapy (WO 2015/065716);-2-Inhibitors of 15-Prostaglandin Dehydrogenase to Potentiate Tissue Repair (Antczak et al.);-3-Compositions and methods of modulating short-chain dehydrogenase activity (WO 2016/168472);-4-Preparation of thienopyridines and related compounds, their compositions and

(56) References Cited

OTHER PUBLICATIONS methods of modulating short-chain dehydrogenase activity (WO 2018/218251);-5-Preparation of alkylsulfinyl-, alkylsulfonyl- and alkylthio-thieno[2,3-b]pyridinamines inhibitors of short-chain dehydrogenase activity for promoting neurogenesis and inhibiting nerve cell death (WO 2018/017582);-6-Preparation of thienopyridine compounds having sulfur-containing Substituent as inhibitors of short-chain dehydrogenase activity for treating fibrosis (WO 2016/144958).
CAS SciFinder Search Result on Jan. 27, 2022, at 7:17 pm (6 results)-1-Compositions and methods of modulating short-chain dehydrogenase activity (WO 2016/168472);-2-Preparation of thienopyridines and similar bicyclic heterocyclic compounds as modulators of 15-hydroxyprostaglandin dehydrogenase type I for therapy (WO 2015/065716);-3-Inhibitors of 15-Prostaglandin Dehydrogenase to Potentiate Tissue Repair (Antczak et al.);-4-Preparation of thienopyridines and related compounds, their compositions and methods of modulating short-chain dehydrogenase activity (WO 2018/218251);-5-Preparation of alkylsulfinyl-, alkylsulfonyl- and alkylthio- thieno[2,3-b]pyridinamines as inhibitors of short-chain dehydrogenase activity for promoting neurogenesis and inhibiting nerve cell death (WO 2018/017582);-6-Preparation of thienopyridine compounds having sulfur-containing substituent as inhibitors of short-chain dehydrogenase activity for treating fibrosis (WO 2016/144958).
CAS SciFinder Search Result on Jan. 27, 2022, at 7:21 pm (2 results)-1-Preparation of thienopyridines and similar bicyclic heterocyclic compounds as modulators of 15-hydroxyprostaglandin dehydrogenase type I for therapy (WO 2015/065716);-2-Preparation of thienopyridines and related compounds, their compositions and methods of modulating short-chain dehydrogenase activity (WO 2018/218251).
CAS SciFinder Search Result on Jan. 27, 2022, at 7:30 pm (1 result)-1-Preparation of thienopyridines and similar bicyclic heterocyclic compounds as modulators of 15-hydroxyprostaglandin dehydrogenase type I for therapy (WO 2015/065716).
CAS SciFinder Search Result on Jan. 27, 2022, at 7:31 pm (1 result)-1-Preparation of thienopyridines and similar bicyclic heterocyclic compounds as modulators of 15-hydroxyprostaglandin dehydrogenase type I for therapy (WO 2015/065716).
CAS SciFinder Search Result on Jan. 27, 2022, at 7:32 pm (1 result)-1-Preparation of thienopyridines and similar bicyclic heterocyclic compounds as modulators of 15-hydroxyprostaglandin dehydrogenase type I for therapy (WO 2015/065716).
CAS SciFinder Search Result on Jan. 27, 2022, at 7:39 pm (6 results)-1-Preparation of thienopyridines and similar bicyclic heterocyclic compounds as modulators of 15-hydroxyprostaglandin dehydrogenase type I for therapy (WO 2015/065716);-2-Inhibitors of 15-Prostaglandin Dehydrogenase to Potentiate Tissue Repair (Antczak et al.);-3-Compositions and methods of modulating short-chain dehydrogenase activity (WO 2016/168472);-4-Preparation of thienopyridines and related compounds, their compositions and methods of modulating short-chain dehydrogenase activity (WO 2018/218251);-5-Preparation alkylsulfinyl-, alkylsulfonyl- and alkylthio-thieno[2,3-b]pyridinamines as inhibitors of short-chain dehydrogenase activity for promoting neurogenesis and inhibiting nerve cell death (WO 2018/017582);-6-Preparation of thienopyridine compounds having sulfur-containing substituent as inhibitors of short-chain dehydrogenase activity for treating fibrosis (WO 2016/144958).
CAS SciFinder Search Result on Jan. 27, 2022, at 7:47 pm (2 results)-1-Preparation of thienopyridines and similar bicyclic heterocyclic compounds as modulators of 15-hydroxyprostaglandin dehydrogenase type I for therapy (WO 2015/065716);-2-Preparation of thienopyridines and related compounds, their compositions and methods of modulating short-chain dehydrogenase activity (WO 2018/218251).
CAS SciFinder Search Result on Jan. 27, 2022, at 7:50 pm (2 results)-1-Preparation of thienopyridines and similar bicyclic heterocyclic compounds as modulators of 15-hydroxyprostaglandin dehydrogenase type I for therapy;-2-Preparation of thienopyridines and related compounds, their compositions and methods of modulating short-chain dehydrogenase activity.
CAS SciFinder Search Result on Jan. 27, 2022, at 7:52 pm (2 results)-1-Preparation of thienopyridines and related compounds, their commpositions and methods of modulating short-chain dehydrogenase activity (WO 2015/065716);-2-Preparation of thienopyridines and similar bicyclic heterocyclic compounds as modulators of 15-hydroxyprostaglandin dehydrogenase type I for therapy (WO 2018/218251).
CAS SciFinder Search Result on Jan. 27, 2022, at 7:55 pm (2 results)-1-Preparation of thienopyridines and related compounds, their compositions and methods of modulating short-chain dehydrogenase activity (WO 2018/218251);- 2-Preparation of thienopyridines and similar bicyclic heterocyclic compounds as modulators of 15-hydroxyprostaglandin dehydrogenase type 1 for therapy (WO 2015/065716).
CAS SciFinder Search Result on Jan. 27, 2022, at 3:28 pm (0 results).
NCBI Database Accession No. CID 654955 [online database], create date Jun. 4, 2005, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 1826991 [online database], create date Jul. 12, 2005, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 3337838 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 3337839 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 3337991 [online database], create date Sep. 7, 2005, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 3337992 [online database], create date Sep. 7, 2005, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 3337993 [online database], create date Sep. 7, 2005, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 3337994 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 3337995 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 3337996 [online database], create date Sep. 7, 2005, modify date Sep. 10, 2022, [retrieved on Sep. 16, 2022], Retrieved from PubChem <https://pubchem.ncbi.nlm.nih.gov>, compound summary printed to pdf.
NCBI Database Accession No. CID 3337997 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 3337998 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 46864148 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 52943190 [online database], create date Jun. 16, 2011, modify date Sep. 10, 2022, [retrieved on

(56) References Cited

OTHER PUBLICATIONS

Sep. 15, 2022], Retrieved from PubChem <https://pubchem.ncbi.nlm.nih.gov>, compound summary printed to pdf.
NCBI Database Accession No. CID 72188203 [online database], create date Dec. 9, 2013, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 72188204 [online database], create date Dec. 9, 2013, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 92272562 [online database], create date Dec. 10, 2015, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 92272564 [online database], create date Dec. 10, 2015, modify date Sep. 10, 2022, [retrieved on Sep. 16, 2022], Retrieved from PubChem <https://pubchem.ncbi.nlm.nih.gov>, compound summary printed to pdf.
NCBI Database Accession No. CID 118050369 [online database], create date Feb. 23, 2016, modify date Sep. 10, 2022, [retrieved Sep. 15, 2022], Retrieved from PubChem <https://pubchem.ncbi.nlm.nih.go>, compound summary printed to pdf.
NCBI Database Accession No. CID 118050655 [online database], create date Feb. 23, 2016, modify date Sep. 10, 2022, [retrieved Sep. 15, 2022], Retrieved from PubChem <https://pubchem.ncbi.nlm.nih.go>, compound summary printed to pdf.
NCBI Database Accession No. CID 118050656 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 118050707 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 118050770 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 118050833 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 118050838 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 118050952 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 118051074 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 118051078 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 118059027 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 118059055 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 118059089 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 118059090 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 118059098 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 122624302 [online database], create date Dec. 8, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 123677271 [online database], create date Jan. 25, 2017, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 129266585 [online database], create date Aug. 4, 2017, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 129266602 [online database], create date Aug. 4, 2017, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 130296193 [online database], create date Oct. 7, 2017, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 130296194 [online database], create date Oct. 7, 2017, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 132012504 [online database], create date Jan. 29, 2018, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 134314069 [online database], create date Jun. 23, 2018, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 134474501 [online database], create date Jun. 23, 2018, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 134576829 [online database], create date Jun. 23, 2018, modify date Sep. 10, 2022, [retrieved Sep. 16, 2022], Retrieved from PubChem <https://pubchem.ncbi.nlm.nih.gov>, compound summary printed to pdf.
NCBI Database Accession No. CID 135387726 [online database], create date Dec. 15, 2018, modify date Sep. 10, 2022, [retrieved Sep. 16, 2022], Retrieved from PubChem <https://pubchem.ncbi.nlm.nih.gov>, compound summary printed to pdf.
NCBI Database Accession No. CID 135387830 [online database], create date Dec. 15, 2018, modify date Sep. 10, 2022, [retrieved Sep. 16, 2022], Retrieved from PubChem <https://pubchem.ncbi.nlm.nih.gov>, compound summary printed to pdf.
NCBI Database Accession No. CID 139476465 [online database], create date Nov. 2, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142484843 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142485754 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142485836 [online database], create date Dec. 6, 2019, modify date Sep. 17, 2022, [retrieved Sep.

(56) References Cited

OTHER PUBLICATIONS 19, 2022], Retrieved from PubChem <https://pubchem.ncbi.nlm.nih.gov>, compound summary printed to pdf.
NCBI Database Accession No. CID 142485845 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142485847 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142485863 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142485864 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142485868 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142485879 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142485896 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142485929 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142485938 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142485953 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142485954 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 144839639 [online database], create date Dec. 7, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 145656773 [online database], create date Dec. 12, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 145656809 [online database], create date Dec. 12, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 146410683 [online database], create date Jun. 27, 2020, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 146580152 [online database], create date Jun. 27, 2020, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 146580711 [online database], create date Jun. 27, 2020, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 146602898 [online database], create date Jun. 27, 2020, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 146602900 [online database], create date Jun. 27, 2020, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 146731064 [online database], create date Aug. 12, 2020, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 146835156 [online database], create date Aug. 12, 2020, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 147432252 [online database], create date Aug. 12, 2020, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 147594754 [online database], create date Aug. 12, 2020, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 148490795 [online database], create date Aug. 12, 2020, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 149178699 [online database], create date Aug. 12, 2020, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 152798992 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153596863 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153596870 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153596898 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153596904 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153596919 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153596924 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153596928 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153596948 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153596953 [online database], create date Aug. 13, 2020, modify date Sep. 17, 2022, [retrieved

(56) References Cited

OTHER PUBLICATIONS

Sep. 22, 2022], Retrieved from PubChem <https://pubchem.ncbi.nlm.nih.gov>, compound summary printed to pdf.
NCBI Database Accession No. CID 153596968 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153596975 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597016 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597047 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597069 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597090 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597104 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597123 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597128 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597141 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597150 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597177 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597180 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597205 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597208 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597214 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597233 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 155786794 [online database], create date Feb. 22, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 156156400 [online database], create date Aug. 21, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 156837702 [online database], create date Nov. 10, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 156837721 [online database], create date Nov. 10, 20210, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 156837722 [online database], create date Nov. 10, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 156837731 [online database], create date Nov. 10, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 156837741 [online database], create date Nov. 10, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 156837742 [online database], create date Nov. 10, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157158417 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157167058 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157167059 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157167060 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157213480 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157216800 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157257517 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157294602 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157302941 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157386272 [online database], create date Dec. 3, 2021, modify date Sep. 17, 2022, [retrieved Sep.

(56) References Cited

OTHER PUBLICATIONS 22, 2022], Retrieved from PubChem <https://pubchem.ncbi.nlm.nih.gov>, compound summary printed to pdf.
NCBI Database Accession No. CID 157400808 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157440570 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157440572 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157456496 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157498212 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157526683 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157600443 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157604959 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157688874 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157717185 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157767490 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157848053 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157864542 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157864543 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157872044 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157901254 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157944805 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157949758 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157955983 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158049978 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158088730 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158134580 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158145130 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158221946 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158221947 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158258231 [online database], create date Dec. 3, 2021, modify dated Sep. 17, 2022, [retrieved Sep. 22, 2022], Retrieved from PubChem <https://pubchem.ncbi.nlm.nih.gov>, compound summary printed to pdf.
NCBI Database Accession No. CID 158329834 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158370045 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158404656 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158415066 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158432471 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158531185 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158540614 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158568511 [online database], create date Dec. 3, 2021, modify dated Sep. 17, 2022, [retrieved Sep. 22, 2022], Retrieved from PubChem <https://pubchem.ncbi.nlm.nih.gov>, compound summary printed to pdf.
NCBI Database Accession No. CID 158628602 [online database], create date Dec. 3, 2021, modify date Sep. 17, 2022, [retrieved Sep.

(56) References Cited

OTHER PUBLICATIONS 22, 2022], Retrieved from PubChem <https://pubchem.ncbi.nlm.nih.gov>, compound summary printed to pdf.
NCBI Database Accession No. CID 158653266 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158660366 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158784514 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158829687 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158910891 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 159056851 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 159130668 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 159144809 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 159154352 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 159191585 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 159215478 [online database], create date Dec. 3, 2021, modify Sep. 17, 2022, [retrieved Sep. 22, 2022], Retrieved from PubChem <https://pubchem.ncbi.nlm.nih.gov>, compound summary printed to pdf.
NCBI Database Accession No. CID 159233281 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 159233282 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 159474011 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 159590113 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 159820000 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 159891397 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 160071422 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 160071423 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 160155004 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 160156242 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 161100344 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 162062070 [online database], create date Dec. 3, 2021, modify Sep. 17, 2022, [retrieved Sep. 22, 2022], Retrieved from PubChem <https://pubchem.ncbi.nlm.nih.gov>, compound summary printed to pdf.
NCBI Database Accession No. CID 162728470 [online database], create date Apr. 5, 2022, modify date Sep. 17, 2022, [retrieved Sep. 22, 2022], Retrieved from PubChem <https://pubchem.ncbi.nlm.nih.gov>, compound summary printed to pdf.

* cited by examiner

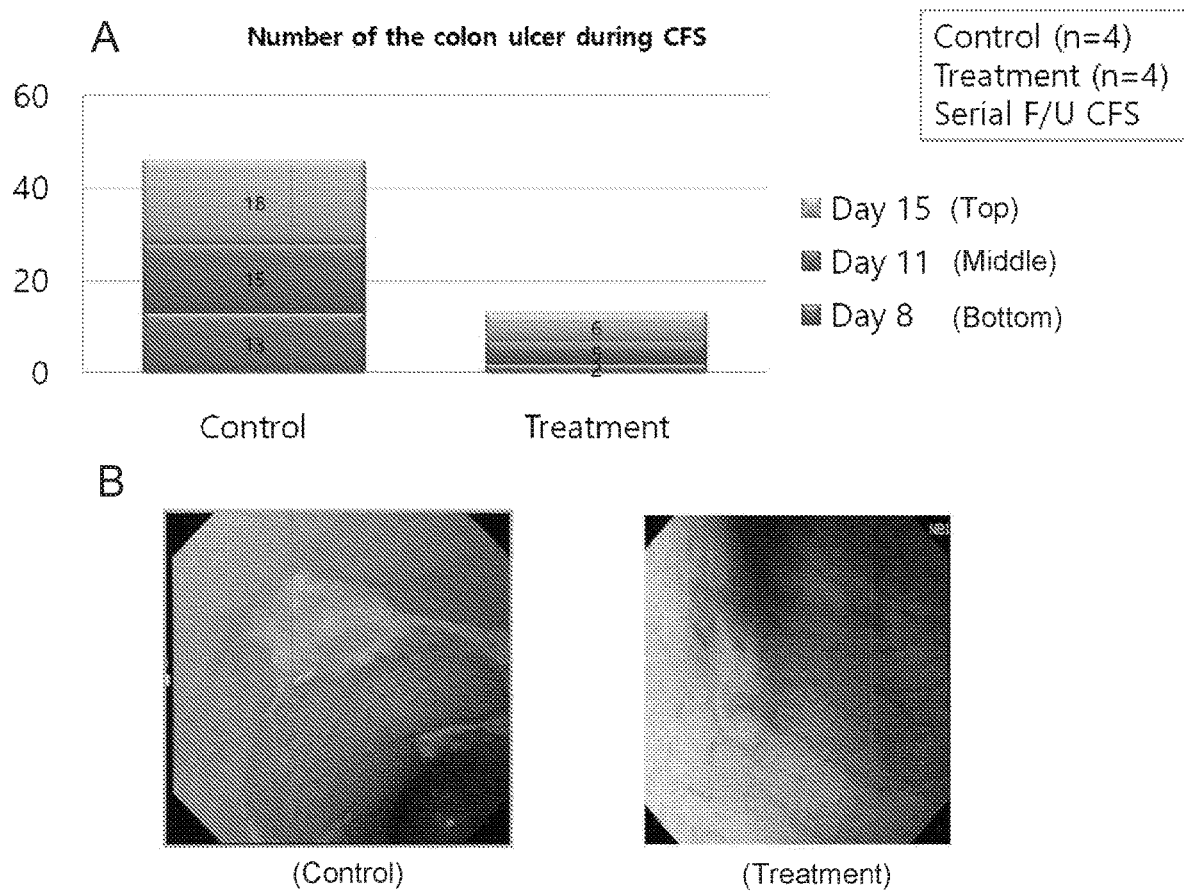
Figs. 4A-B

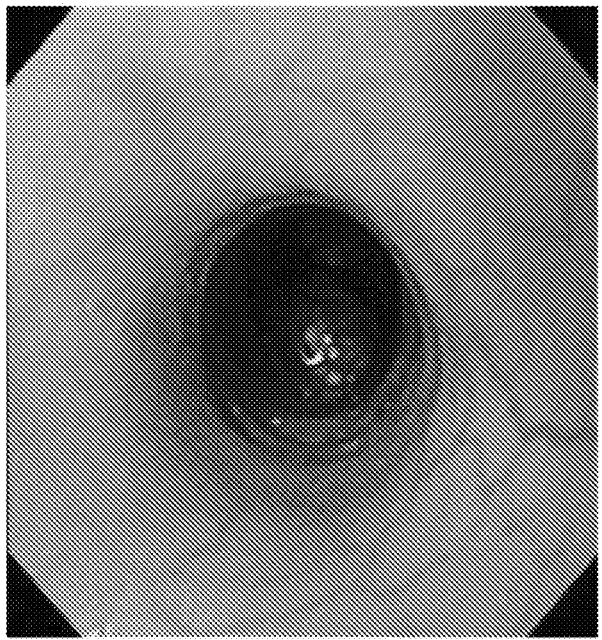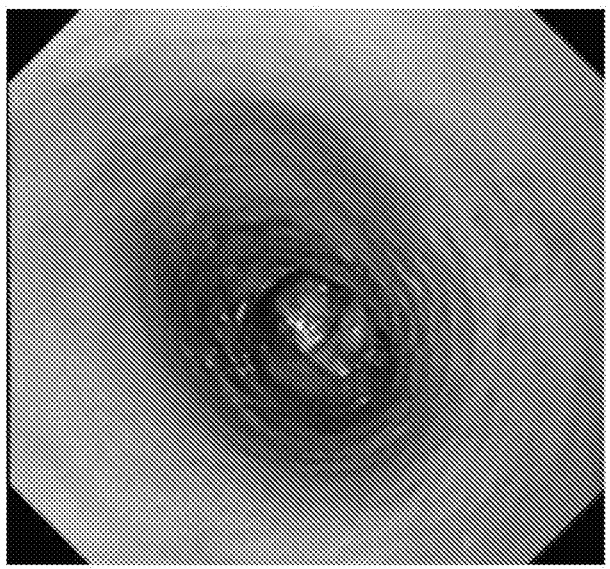
Figs. 6A-B

COMBINATIONS OF 15-PGDH INHIBITORS WITH CORTICOSTEROIDS AND/OR TNF INHIBITORS AND USES THEREOF

CROSS-REFERENCE TO RELATED APPLICATIONS

This application is a U.S. national stage application under 35 U.S.C. § 371 of International Application No. PCT/US2017/063959, filed Nov. 30, 2017, which in turn claims priority to U.S. Provisional Application No. 62/428,259, filed on Nov. 30, 2016, and U.S. Provisional Application No. 62/510,166, filed on May 23, 2017. All three of these documents are incorporated by reference herein in their entireties.

GOVERNMENT FUNDING

This invention was made with government support under Grant No. DK150964 AND CA150964, awarded by The National Institutes of Health. The United States government has certain rights in the invention.

BACKGROUND

Short-chain dehydrogenases (SCDs) are a family of dehydrogenases that share only 15% to 30% sequence identity, with similarity predominantly in the coenzyme binding domain and the substrate binding domain. In addition to their role in detoxification of ethanol, SCDs are involved in synthesis and degradation of fatty acids, steroids, and some prostaglandins, and are therefore implicated in a variety of disorders, such as lipid storage disease, myopathy, SCD deficiency, and certain genetic disorders.

The SCD, 15-hydroxy-prostaglandin dehydrogenase (15-PGDH), (hydroxyprostaglandin dehydrogenase 15-(nicotinamide adeninedinucleotide); 15-PGDH; Enzyme Commission number 1.1.1.141; encoded by the HPGD gene), represents the key enzyme in the inactivation of a number of active prostaglandins, leukotrienes and hydroxyeicosatetraenoic acids (HETEs) (e.g., by catalyzing oxidation of $PGE_2$ to 15-keto-prostaglandin E2, 15k-PGE). The human enzyme is encoded by the HPGD gene and consists of a homodimer with subunits of a size of 29 kDa. The enzyme belongs to the evolutionarily conserved superfamily of short-chain dehydrogenase/reductase enzymes (SDRs), and according to the recently approved nomenclature for human enzymes, it is named SDR36C1. Thus far, two forms of 15-PGDH enzyme activity have been identified, NAD+-dependent type I 15-PGDH, which is encoded by the HPGD gene, and the type II NADP-dependent 15-PGDH, also known as carbonyl reductase 1 (CBR1, SDR21C1). However, the preference of CBR1 for NADP and the high Km values of CBR1 for most prostaglandin suggest that the majority of the in vivo activity can be attributed to type I 15-PGDH encoded by the HPGD gene, that hereafter, and throughout all following text, simply denoted as 15-PGDH.

SUMMARY

Embodiments described herein relate to the use of 15-PGDH inhibitors in combination with corticosteroids and TNF inhibitors to treat inflammation, reduce aberrant activity of the immune system, and/or promote wound healing in a subject in need thereof. It was found that corticosteroids administered to a subject can induce 15-PGDH expression in tissue of the subject. Administration of a 15-PGDH inhibitor in combination with a corticosteroid was found to enhance anti-inflammatory and/or immunosuppressive effects of the corticosteroid while attenuating corticosteroid induced adverse and/or cytotoxic effects. Treatment of inflammatory disorders, immune disorders, and/or wounds by administration of 15-PGDH inhibitors in combination with corticosteroids can increase therapeutic efficacy of the corticosteroids and can allow the corticosteroids to be administered, in some instances, at lower dosages to achieve similar effects, and, in other instances, at higher dosages and for prolonged periods of times with attenuated and/or reduced adverse or cytotoxic effects.

In some embodiments, an inflammatory and/or immune disease or disorder treated with the combination of 15-PGDH inhibitor and a corticosteroid and TNF inhibitor can include intestinal, gastrointestinal, or bowel disorders. As described below, it was found that inhibitors of short-chain dehydrogenase activity, such as 15-PGDH inhibitors, can be administered to a subject in need thereof alone or in combination with corticosteroids and/or tumor necrosis factor (TNF)-alpha antagonists to treat intestinal, gastrointestinal, or bowel disorders, such as oral ulcers, gum disease, gastritis, colitis, ulcerative colitis, gastric ulcers, inflammatory bowel disease, and Crohn's disease.

In other embodiments, the 15-PGDH inhibitor can be used as a glucocorticoid sensitizer to treat glucocorticoid insensitivity, restore corticosteroid sensitivity, enhance glucocorticoid sensitivity, and/or reverse glucocorticoid insensitivity in a subject experiencing corticosteroid dependence or corticoid resistance or unresponsiveness or intolerance to corticosteroids. For example, a 15-PGDH inhibitor can be administered to a subject in combination with a corticosteroid to treat glucocorticoid insensitivity, restore corticosteroid sensitivity, enhance glucocorticoid sensitivity, and/or reverse glucocorticoid insensitivity in a subject experiencing corticosteroid dependence or corticoid resistance or unresponsiveness or intolerance to corticosteroids.

The 15-PGDH inhibitor can also be administered in combination with a corticosteroid and/or TNF inhibitor to a subject to promote wound healing, tissue repair, and/or tissue regeneration and/or engraftment or regeneration of a tissue graft.

In some embodiments, the 15-PGDH inhibitor can be administered to a subject at an amount effective to increase prostaglandin levels in the subject and attenuate corticosteroid induced adverse and/or cytotoxic effects. The 15-PGDH inhibitor can include a compound having formula (I):

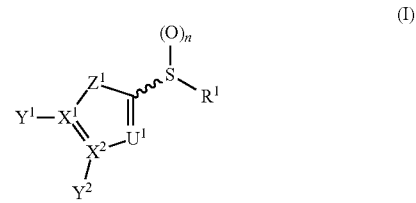

wherein n is 0-2;
$Y^1$, $Y^2$, and $R^1$ are the same or different and are each selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O) ($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), combinations thereof, and wherein $Y^1$ and $Y^2$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl;

$U^1$ is N, C—R$^2$, or C—NR$^3$R$^4$, wherein R$^2$ is selected from the group consisting of a H, a lower alkyl group, O, (CH$_2$)$_{n1}$OR' (wherein n1=1, 2, or 3), CF$_3$, CH$_2$—CH$_2$X, O—CH$_2$—CH$_2$X, CH$_2$—CH$_2$—CH$_2$X, O—CH$_2$—CH$_2$X, X, (wherein X=H, F, Cl, Br, or I), CN, (C=O)—R', (C=O)N(R')$_2$, O(CO)R', COOR' (wherein R' is H or a lower alkyl group), and wherein R$^1$ and R$^2$ may be linked to form a cyclic or polycyclic ring, wherein R$^3$ and R$^4$ are same or different and are each selected from the group consisting of H, a lower alkyl group, O, (CH$_2$)$_{n1}$OR' (wherein n1=1, 2, or 3), CF$_3$, CH$_2$—CH$_2$X, CH$_2$—CH$_2$—CH$_2$X, (wherein X=H, F, Cl, Br, or I), CN, (C=O)—R', (C=O)N(R')$_2$, COOR' (wherein R' is H or a lower alkyl group), and R$^3$ or R$^4$ may be absent;

$X^1$ and $X^2$ are independently N or C, and wherein when $X^1$ and/or $X^2$ are N, $Y^1$ and/or $Y^2$, respectively, are absent;

$Z^1$ is O, S, CR$^a$R$^b$ or NR$^a$, wherein R$^a$ and R$^b$ are independently H or a $C_{1-8}$ alkyl, which is linear, branched, or cyclic, and which is unsubstituted or substituted; and pharmaceutically acceptable salts thereof.

In other embodiments, the 15-PGDH inhibitor can include a compound having the following formula (V):

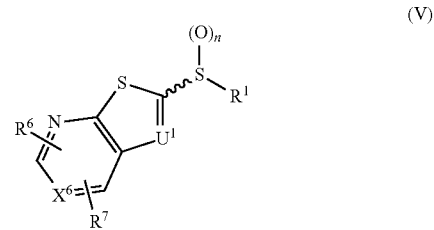

(V)

wherein n is 0-2

$X^6$ is independently is N or CR$^c$ $R^1$, $R^6$, $R^7$, and $R^c$ are each independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C—), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkylethers, phosphates, phosphate esters, groups incorporating amino acids or other moieties expected to bear positive or negative charge at physiological pH, combinations thereof, and wherein $R^6$ and $R^7$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl;

$U^1$ is N, C—R$^2$, or C—NR$^3$R$^4$, wherein R$^2$ is selected from the group consisting of a H, a lower alkyl group, O, (CH$_2$)$_{n1}$OR' (wherein n1=1, 2, or 3), CF$_3$, CH$_2$—

CH$_2$X, O—CH$_2$—CH$_2$X, CH$_2$—CH$_2$—CH$_2$X, O—CH$_2$—CH$_2$X, X, (wherein X=H, F, Cl, Br, or I), CN, (C=O)—R', (C=O)N(R')$_2$, O(CO)R', COOR' (wherein R' is H or a lower alkyl group), and wherein R$^1$ and R$^2$ may be linked to form a cyclic or polycyclic ring, wherein R$^3$ and R$^4$ are the same or different and are each selected from the group consisting of H, a lower alkyl group, O, (CH$_2$)$_{n1}$OR' (wherein n1=1, 2, or 3), CF$_3$, CH$_2$—CH$_2$X, CH$_2$—CH$_2$—CH$_2$X, (wherein X=H, F, Cl, Br, or I), CN, (C=O)—R', (C=O)N(R')$_2$, COOR' (wherein R' is H or a lower alkyl group), and R$^3$ or R$^4$ may be absent;

and pharmaceutically acceptable salts thereof.

In some embodiments, R$^1$ is selected from the group consisting of branched or linear alkyl including —(CH$_2$)$_{n1}$CH$_3$ (n$_1$=0-7),

wherein n$_2$=0-6 and X is any of the following: CF$_y$H$_z$ (y+z=3), CCl$_y$H$_z$ (y+z=3), OH, OAc, OMe, R$^{71}$, OR$^{72}$, CN, N(R$^{73}$)$_2$,

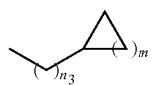

(n$_3$=0-5, m=1-5), and

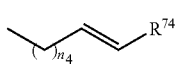

(n$_4$=0-5).

In other embodiments, R$^6$ and R$^7$ can each independently be one of the following:

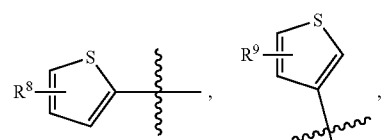

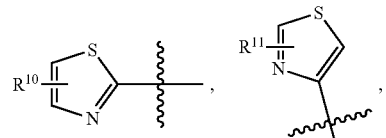

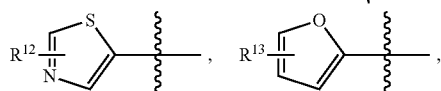

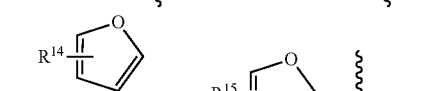

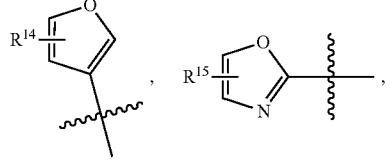

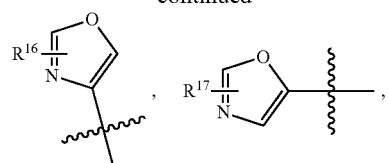

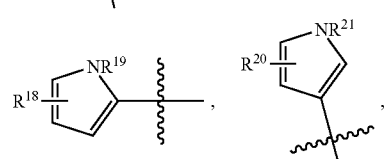

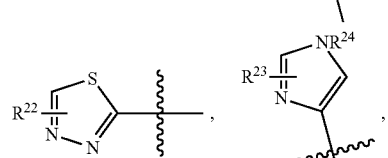

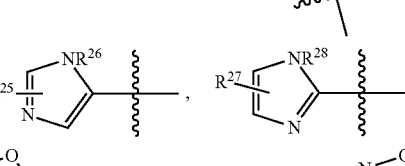

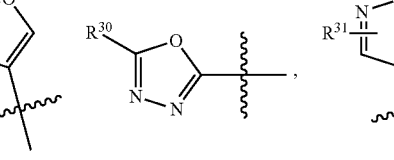

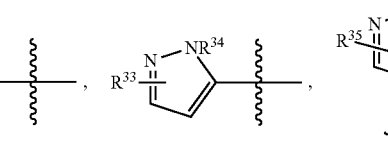

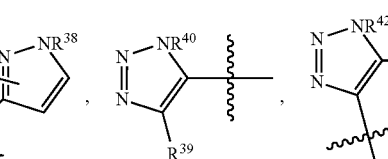

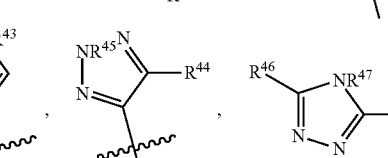

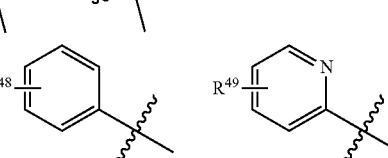

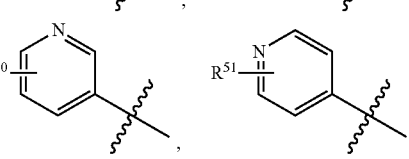

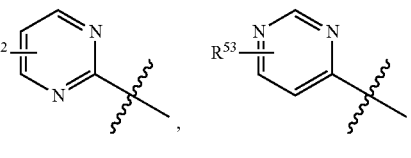

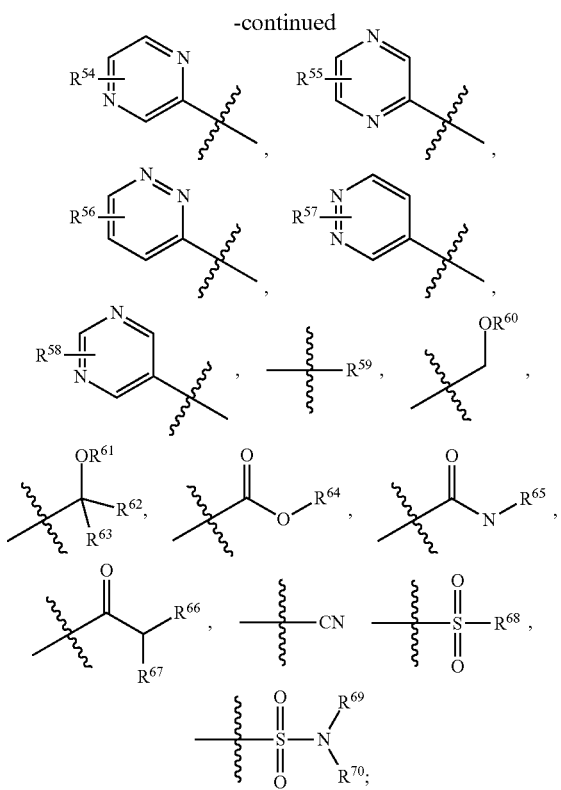

each $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, and $R^{74}$, are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O)($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfonamido (—SO$_2$N(R)$_2$ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkyl ethers (—[(CH$_2$)O]$_m$), phosphates, phosphate esters [—OP(O)(OR)$_2$ where R=H, methyl or other alkyl], groups incorporating amino acids or other moieties expected to bear positive or negative charge at physiological pH, and combinations thereof, and pharmaceutically acceptable salts thereof.

In some embodiments, the 15-PGDH inhibitor can inhibit the enzymatic activity of recombinant 15-PGDH at an $IC_{50}$ of less than 1 μM, or preferably at an $IC_{50}$ of less than 250 nM, or more preferably at an $IC_{50}$ of less than 50 nM, or more preferably at an $IC_{50}$ of less than 10 nM, or more preferably at an $IC_{50}$ of less than 5 nM at a recombinant 15-PGDH concentration of about 5 nM to about 10 nM.

In other embodiments, the corticosteroid can be selected from the group consisting of aclovate, alclometasone dipropionate, amcinafel, amcinafide, amcinonide, aristocort A, augmented betamethasone dipropionate, beclamethasone, beclopmethasone dipropionate, betamethasone, betamethasone benzoate, betamethasone-17-benzoate, betamethasone dipropionate, betamethasone sodium phosphate and acetate, betamethasone valerate, betamethasone-17-valerate, chloroprednisone, clobetasol propionate, clobetasone propionate, clocortelone, cordran, corticosterone, cortisol, cortisol acetate, cortisol cypionate, cortisol sodium phosphate, cortisol sodium succinate, cortisone, cortisone acetate, cortodoxone, cyclocort, deflazacort, difluprednate, descinolone, desonide, desowen, desoximetasone, desoxycorticosterone acetate, desoxycorticosterone pivalate, 11-desoxycortisol, dexamethasone, dexamethasone acetate, dexamethasone sodium phosphate, dichlorisone, diflorasone diacetate, dihydroxycortisone, diprolen, diprolene, diprosone, esters of betamethasone, florone, flucetonide, flucloronide, flucortolone, fludrocortisone, fludrocortisone acetate, flumethalone, flumethasone, flumethasone pivalate, flunisolide, fluocinolone acetonide, fluocinolone acetonide acetate, fluocinonide, fluorametholone, fluorocortisone, fluperolone, fluprednisolone, flurandrenolide, fluroandrenolone acetonide, fluticasone propionate, fuprednisolone, halcinonide, halobetasol propionate, halog, hydrocortamate, hydrocortisone, hydrocortisone acetate, hydrocortisone butyrate, hydrocortisone valerate, hydrocortisone-17-valerate, kenalog, lidex, locold, locorten, maxiflor, medrysone, meprednisone, methylprednisolone, 6α-methylprednisolone, methylprednisolone acetate, methylprednisolone sodium succinate, methylprednisone, mometasone furoate, paramethasone, paramethasone acetate, prednidone, prednisone, prednisolone, prednisolone acetate, prednisolone sodium phosphate, prednisolone sodium succinate, prednisolone tebutate, prednisone, psorcon, synalar, temovate, tetrahydrocortisol, topicort, topicort LP, triamcinolone, triamcinolone acetonide, triamcinolone diacetate, triamcinolone hexacotonide, tridesilone, valisone, and westcort.

versus SW033291 (squares) treated mice all treated with 2% dextran sulfate sodium (DSS) in the drinking water.

Figure 2:
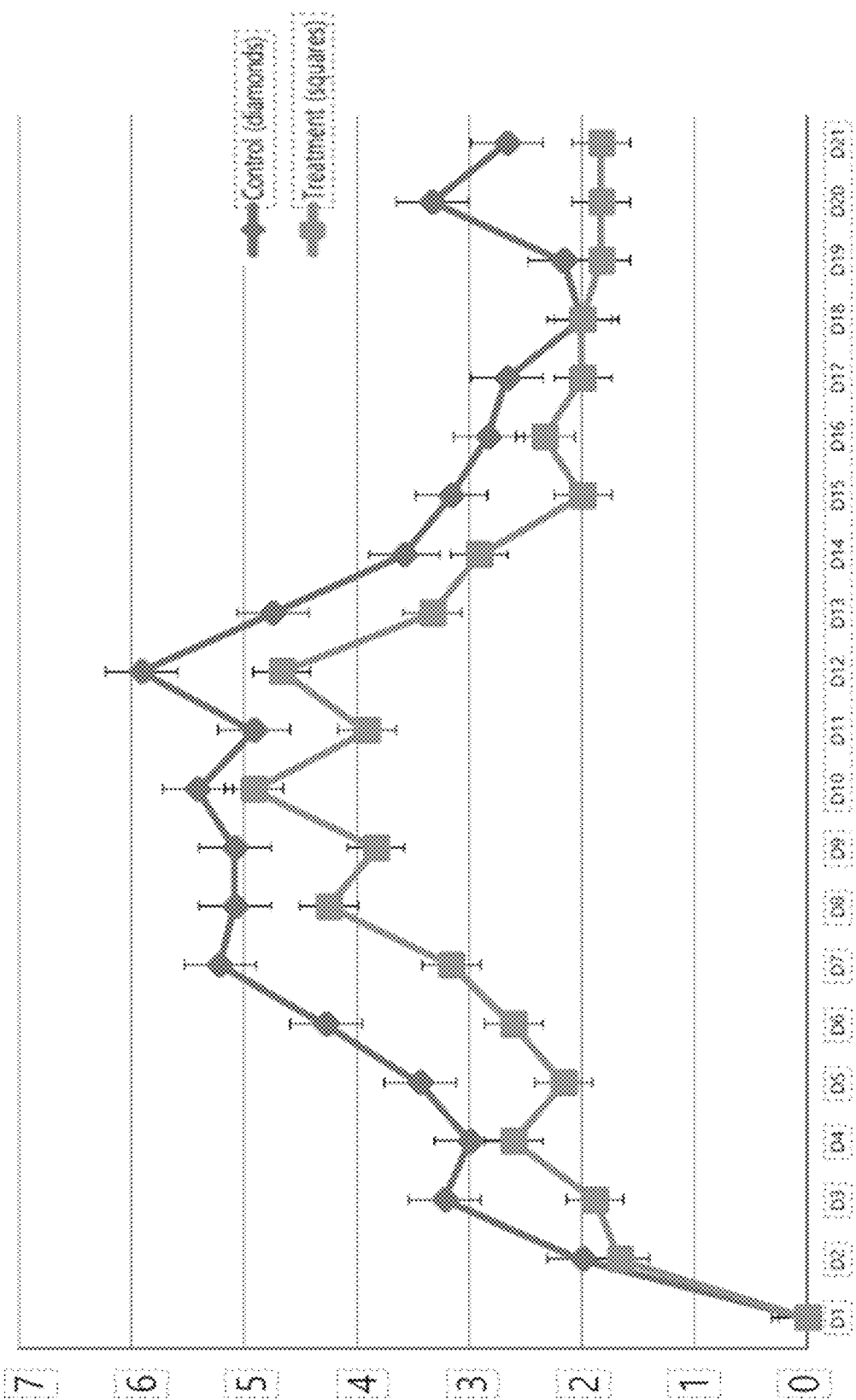

FIG. 2 illustrates a graph of the daily disease activity index of the cohort of control (diamonds) versus SW033291 (squares) treated mice all treated with 2% DSS in the drinking water.

FIG. 3 illustrates a graph showing the average changes from baseline weight of the cohort of DSS treated mice receiving a control vehicle (diamonds) versus SW033291 (squares).

FIGS. 4(A-B) illustrate: (A) a graph showing the number of ulcers in a colon of DSS treated mice receiving a control vehicle versus SW033291; and (B) photographs showing ulcers of DSS treated mice receiving control (left) or SW033291 (right).

Figure 5:
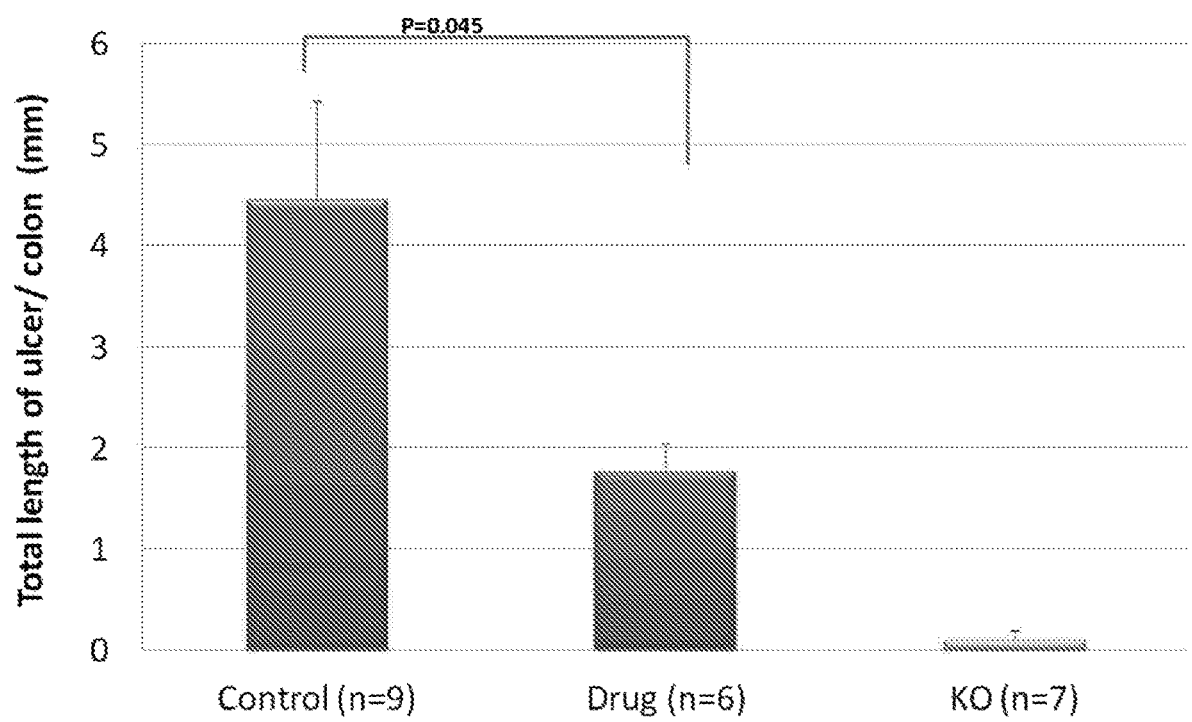

FIG. 5 illustrates a graph showing quantitation of ulcer burden on day 15 of DSS treated mice receiving a control vehicle or SW033291.

FIGS. 6(A-B) illustrate photographs showing colonoscopic findings and mouse endoscopic index of colitis severity (MEICs) for a DSS treated mouse receiving a control vehicle or SW033291.

Figure 7:
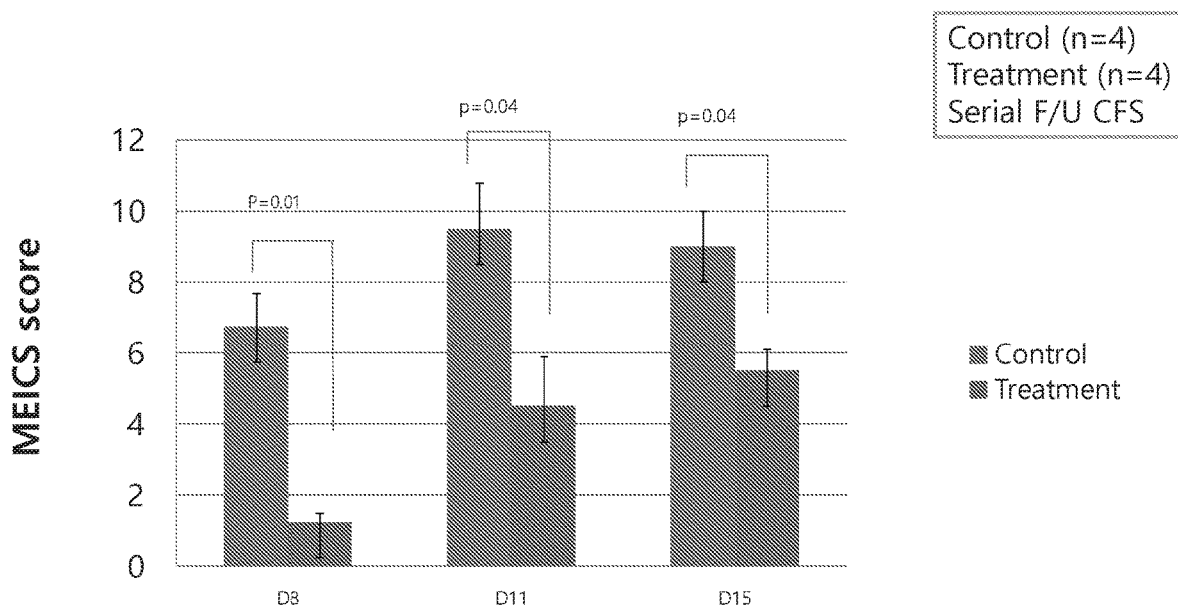

FIG. 7 illustrates a graph showing MEICS score of DSS treated mice receiving a control vehicle or SW033291.

Figure 8:
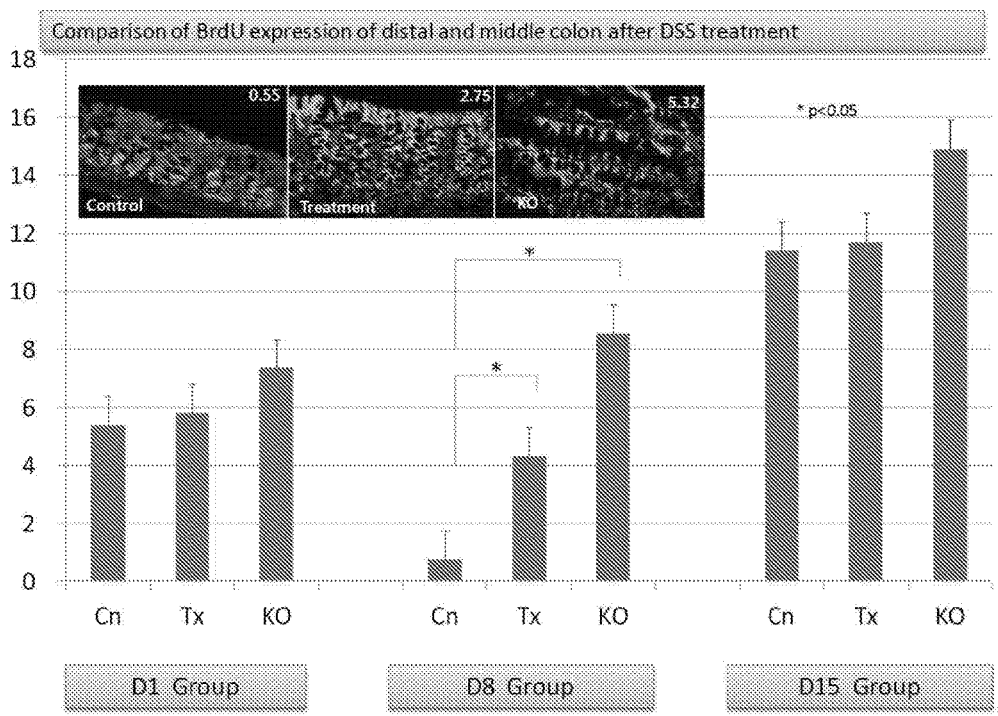

FIG. 8 illustrates photomicrographs of high powered fields from the mid-colon on day 8 of the DSS protocol from control mice, SW033291 treated mice (treatment) and 15-PGDHknockout mice (KO) and a graph depicting sum of the average number of BrdU positive cells per crypt in the distal plus middle colons of control (Cn), SW033219 treated mice (Tx), and 15-PGDH knockout mice (KO) on day 1, day 8, and day 15 of the DSS treatment protocol.

Figure 9:
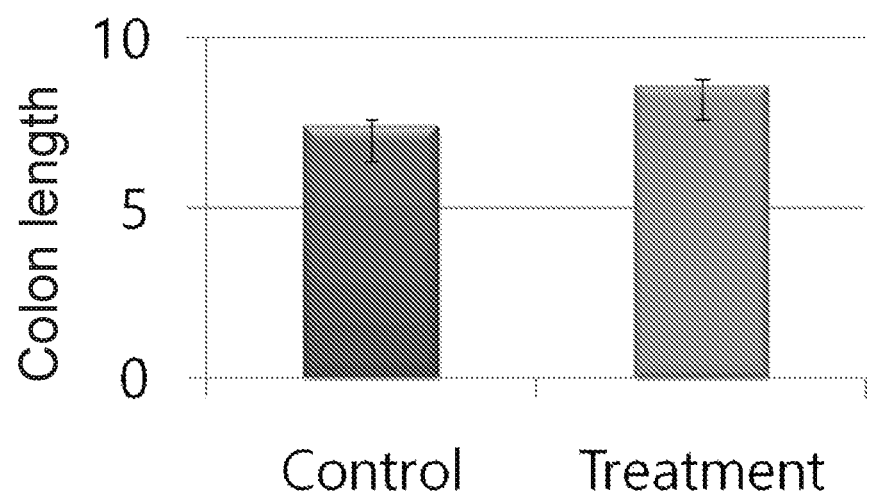

FIG. 9 illustrates a graph showing colon length at day 22 of DSS treated mice receiving a control vehicle or SW033291.

Figure 10:
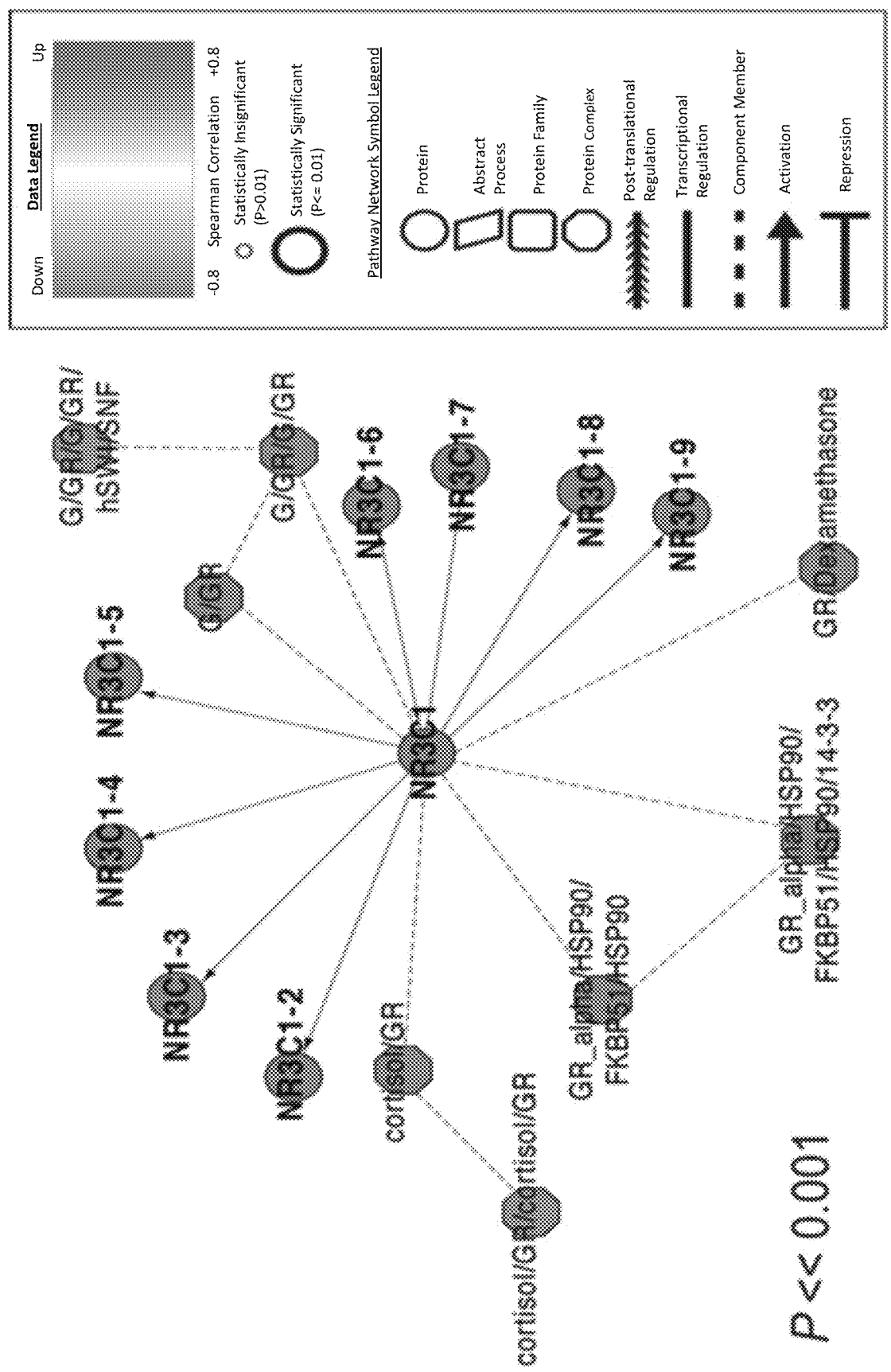

FIG. 10 is a schematic illustration showing PARADIGM SuperPathway sub-networks whose activities are significantly correlated with 15-PGDH gene expression in normal colon tissues.

Figure 11:
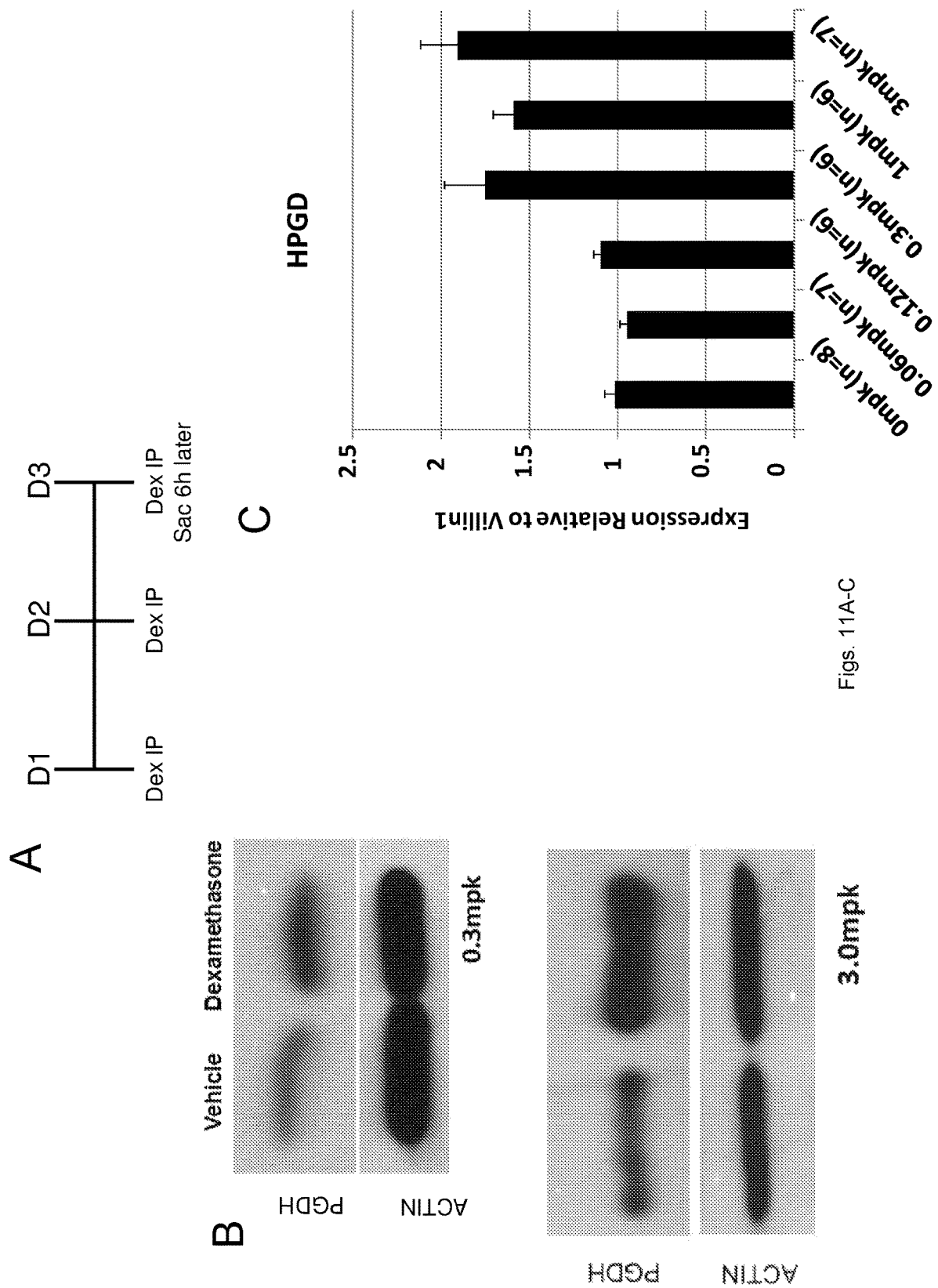

FIGS. 11(A-C) illustrate: (A) a schema of a study in which mice received three daily doses of dexamethasone and were sacrificed 6 hours after the third dose for analysis; (B) representative western blot analysis showing dexamethasone induction of 15-PGDH protein in mouse colon, at two different doses of dexamethasone; and (C) graphical summary of real time RT-PCR from all mice in the study showing an approximate doubling of colon 15-PGDH expression level by dexamethasone treatment.

Figure 12:
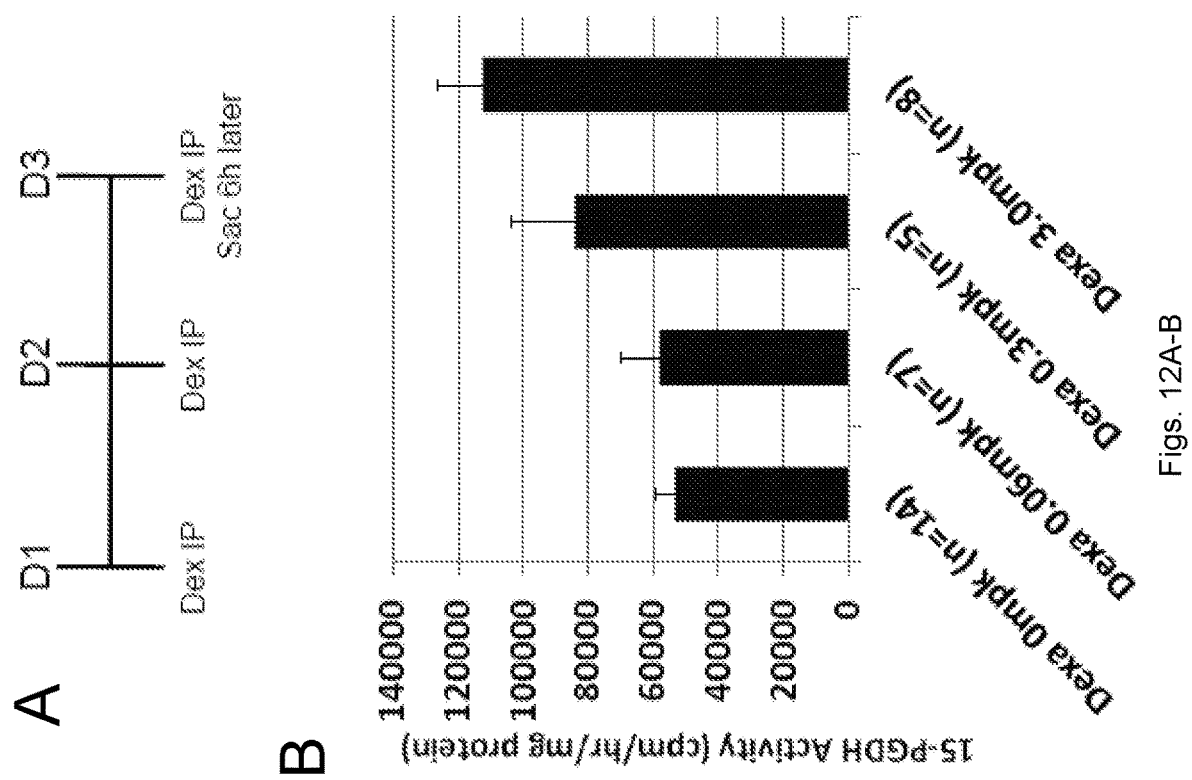

FIGS. 12(A-B) illustrate: (A) a schema of a study in which mice received three daily doses of dexamethasone and were sacrificed 6 hours after the third dose for analysis; and (B) a graph showing near doubling of 15-PGDH enzyme activity in colons of dexamethasone treated mice.

Figure 13:
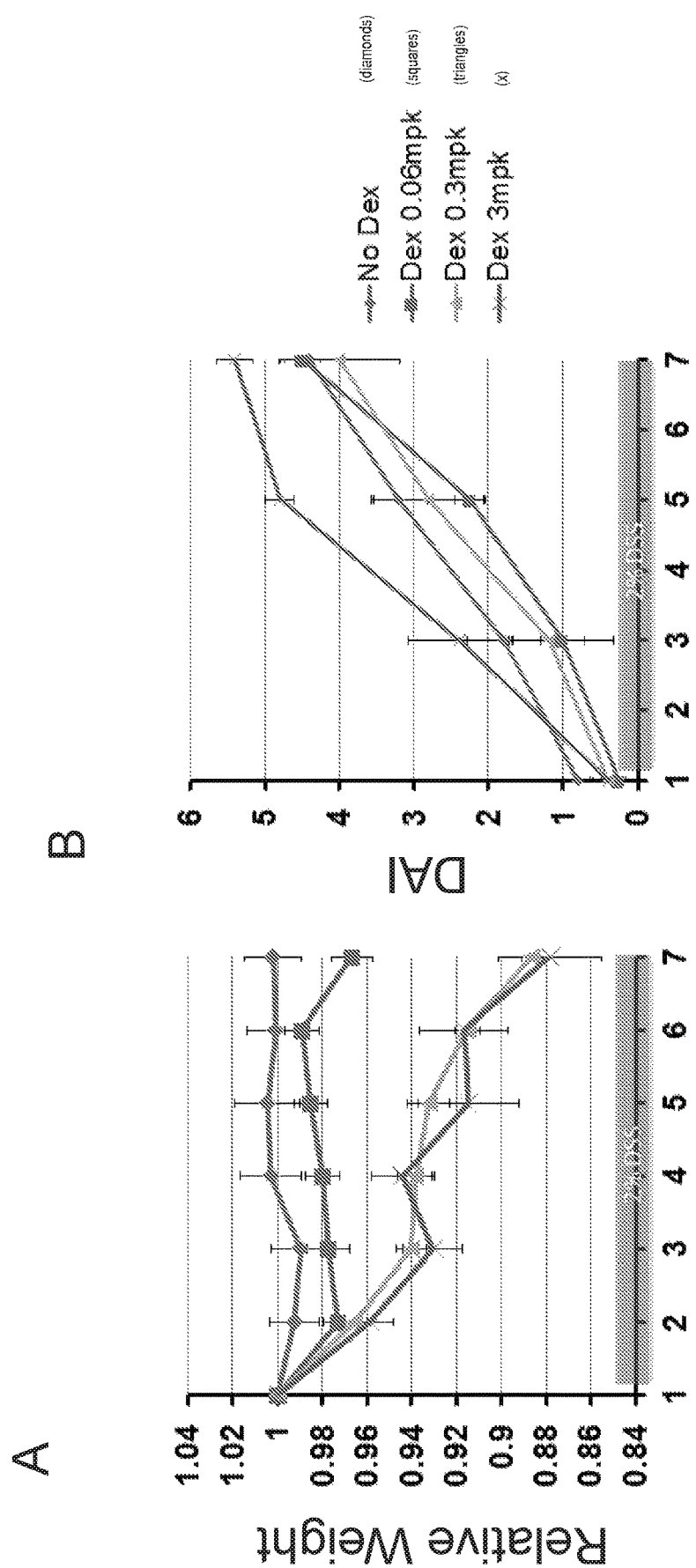

FIGS. 13(A-B) illustrate graphs showing higher dexamethasone doses exacerbate colitis induction by DSS.

Figure 14:
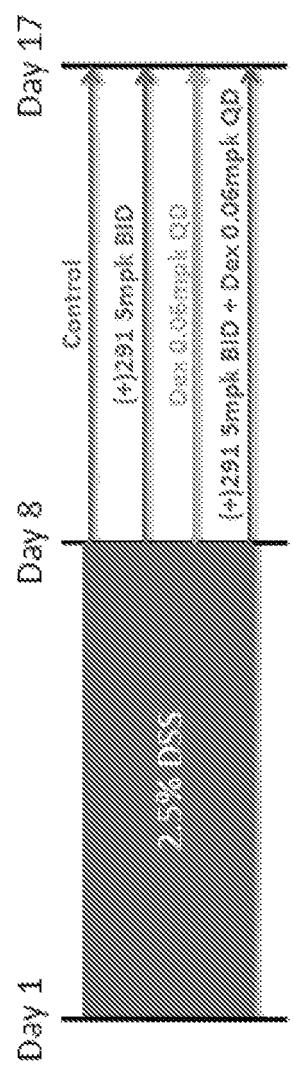

FIG. 14 illustrate a schema of a study in which mice receive 7 days of 2.5% DSS in drinking water (from day 1 to day 8), a regime that induces murine colitis, and followed by treatment with vehicle, (+) SW033291, dexamethasone, or both (+) SW033291 and dexamethasone.

Figure 15:
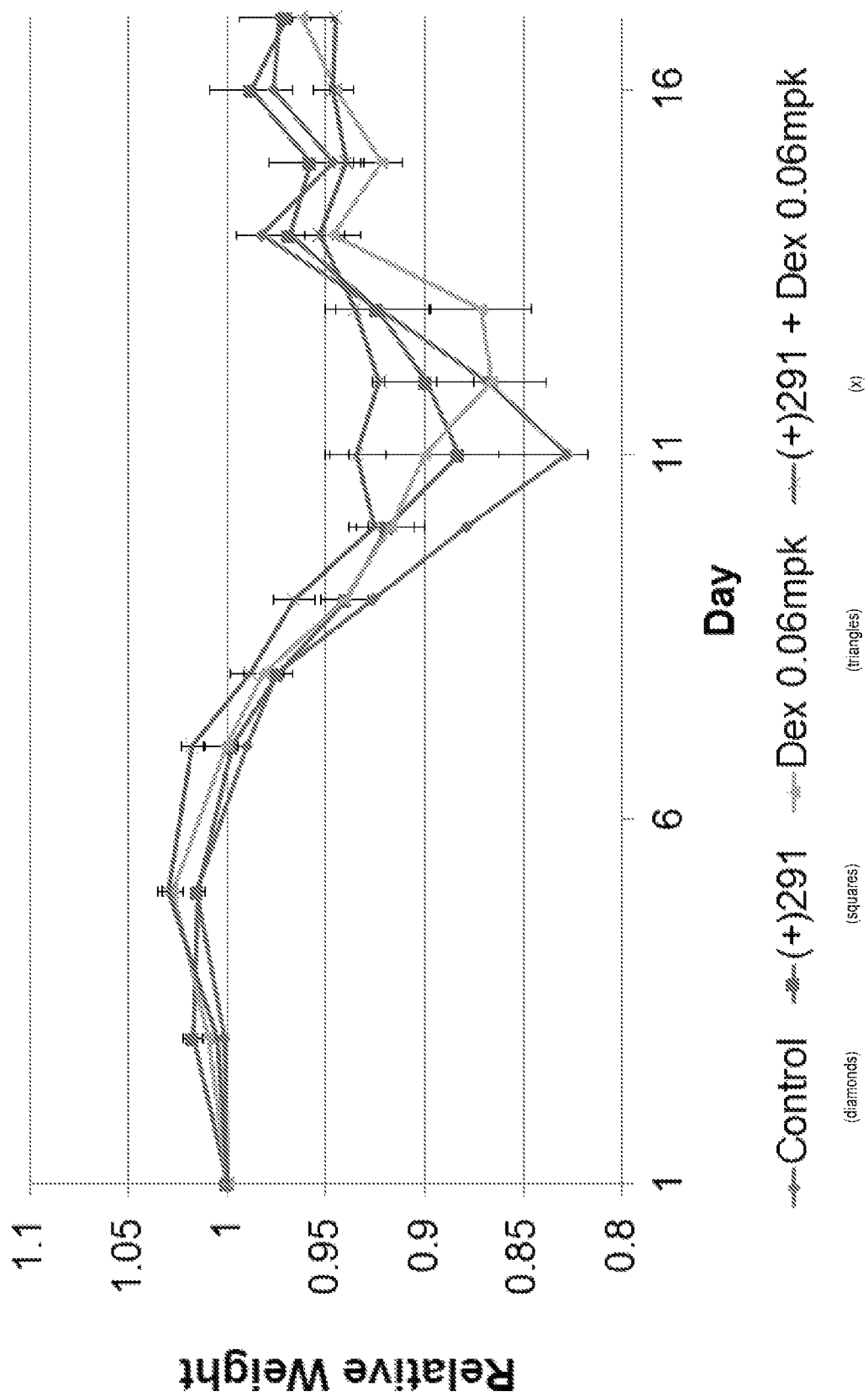

FIG. 15 illustrates plots showing daily weights of mice on the study from days 1-17 in mice administered (+) SW033291 and dexamethasone treatment individually or in combination.

Figure 16:
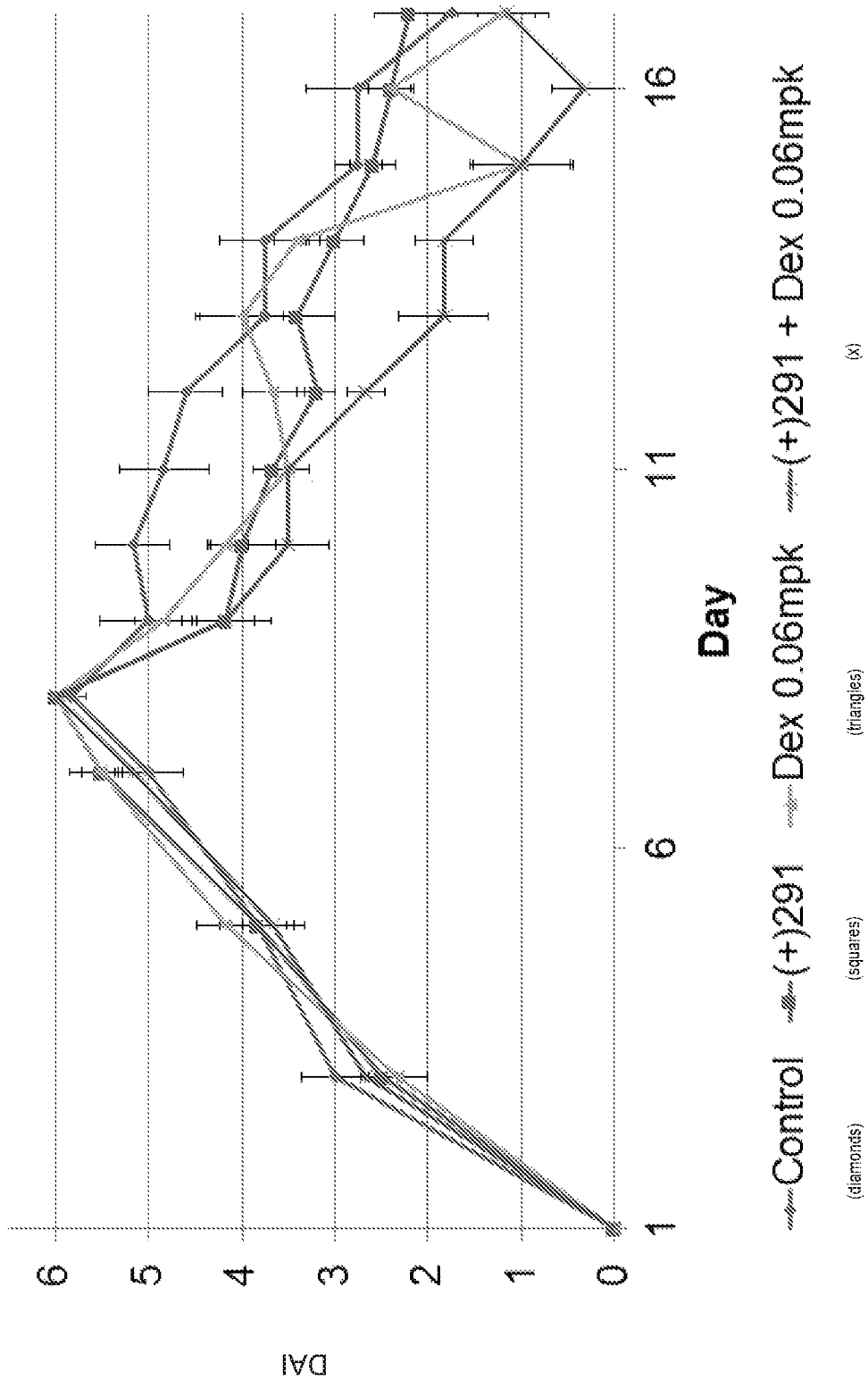

FIG. 16 illustrates plots of disease activity (DAI) as measured by the disease activity index in which diarrhea (on a 0-3 scale) and fecal blood (on a 0-3 scale) are combined (on a 0-6 scale) in mice administered (+) SW033291 and dexamethasone treatment individually or in combination.

Figure 17:
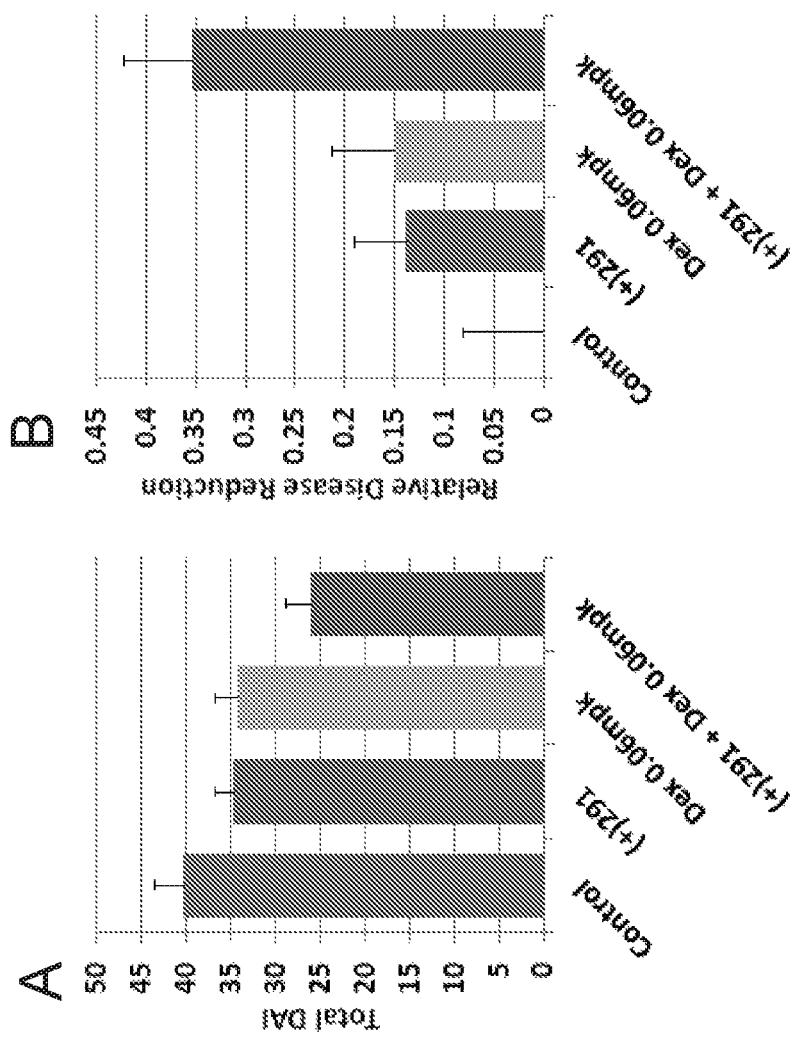

FIGS. 17(A-B) illustrate graphs showing area under the DAI curve (total DAI) at left, and showing the percent decrease in total DAI (relative disease reduction) graph at right of the results of FIG. 16.

Figure 18:
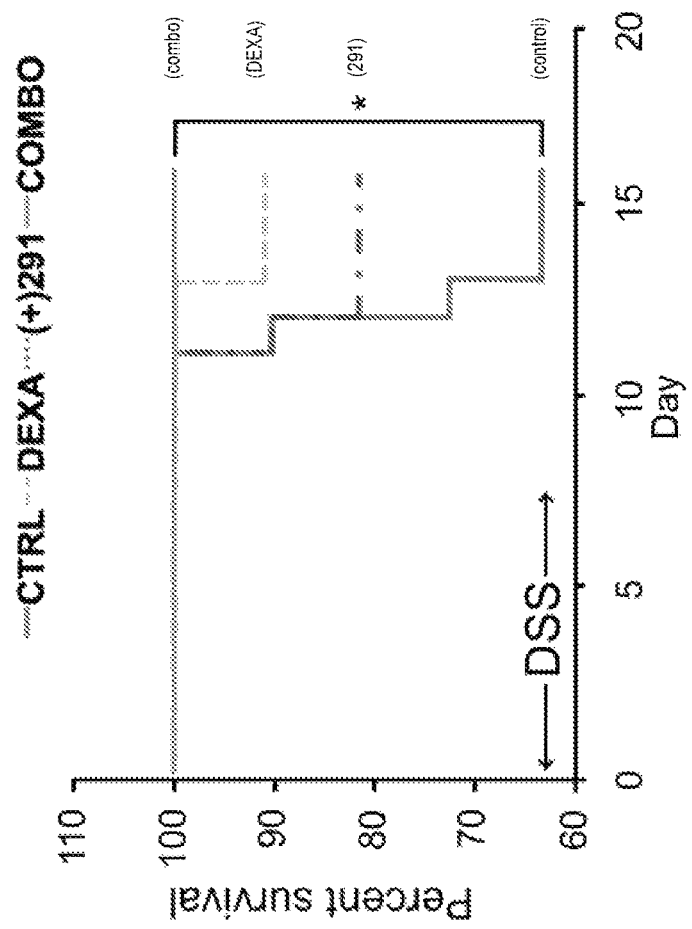

FIG. 18 illustrates a graph showing the survival of mice on a daily basis for each treatment arm through day 16 of the disease model.

Figure 19:
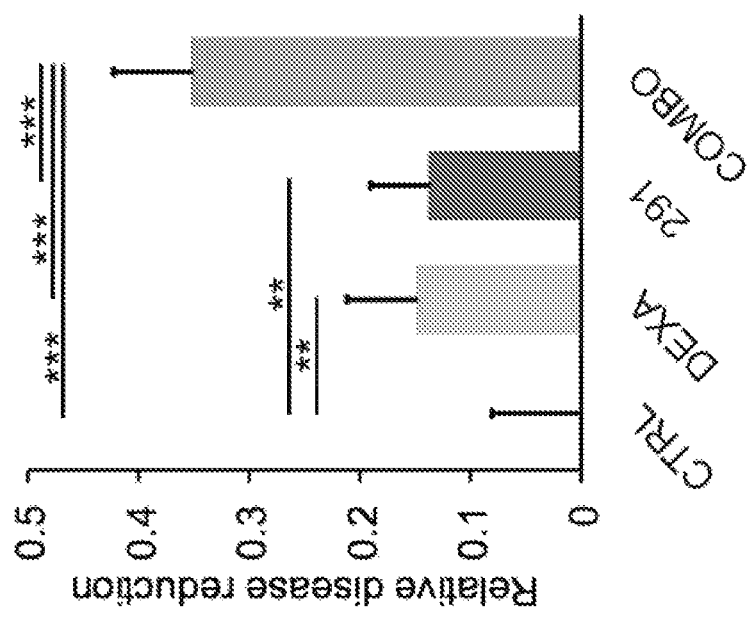

FIG. 19 illustrates a graph of data shown in FIG. 17B with the addition of p values and reordering of arms.

Figure 20:
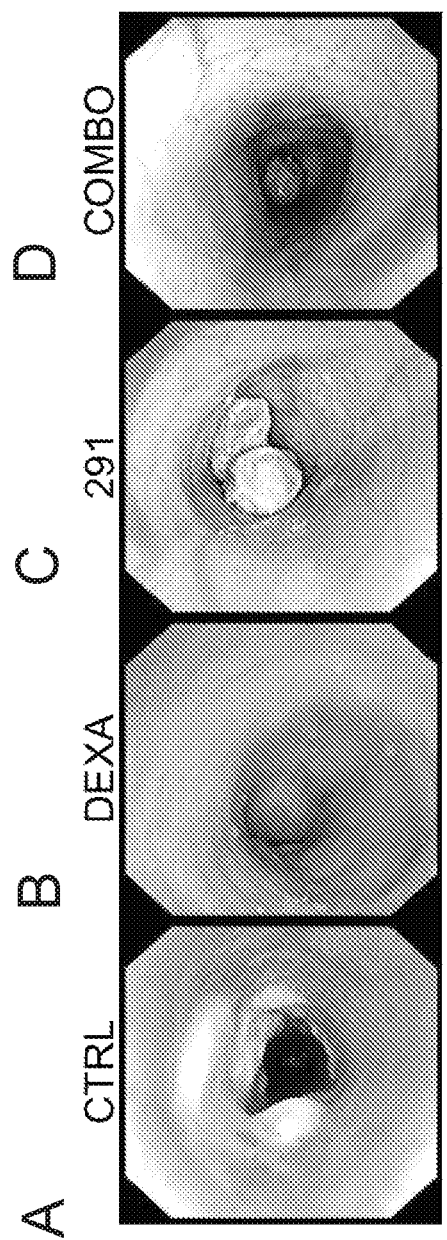

FIGS. 20(A-D) show representative endoscopic image for each treatment group on day 13 of treatment.

Figure 21:
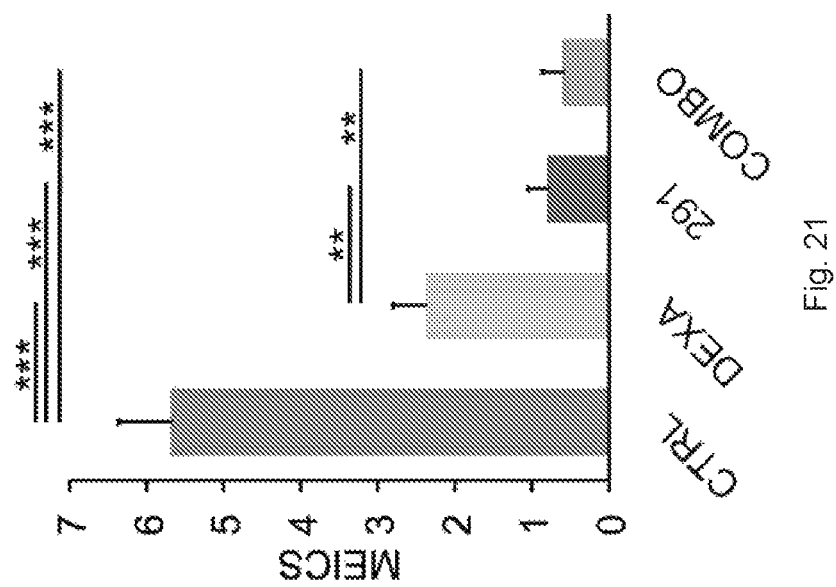

FIG. 21 illustrates a graph showing murine endoscopic index of colitis severity (MEICS) scores on day 13 for each treatment group. p<0.01, *p<0.005 by ANOVA and Student's t-test.

FIGS. 22A-D show representative histological pictures of distal colons on day 13 of each treatment group (A) control, (B) dexamethasone, (C) SW033291, and (D) combination.

Figure 23:
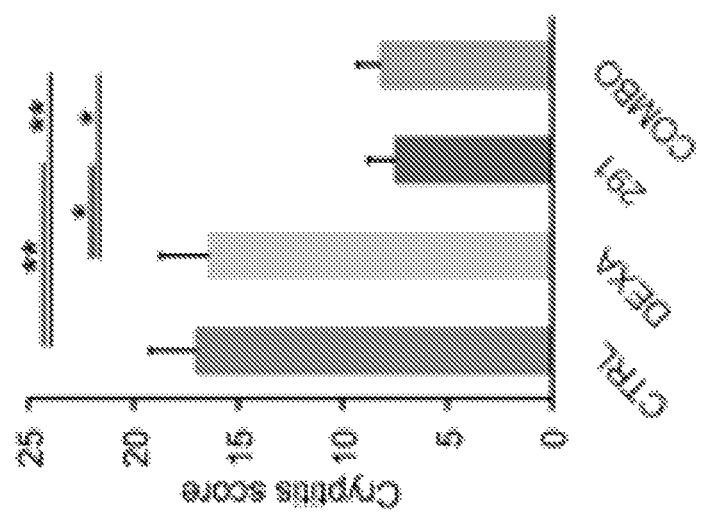

FIG. 23 graphs semi-quantitatively scored histological extent of inflammatory damage to the crypts.

Figure 24:
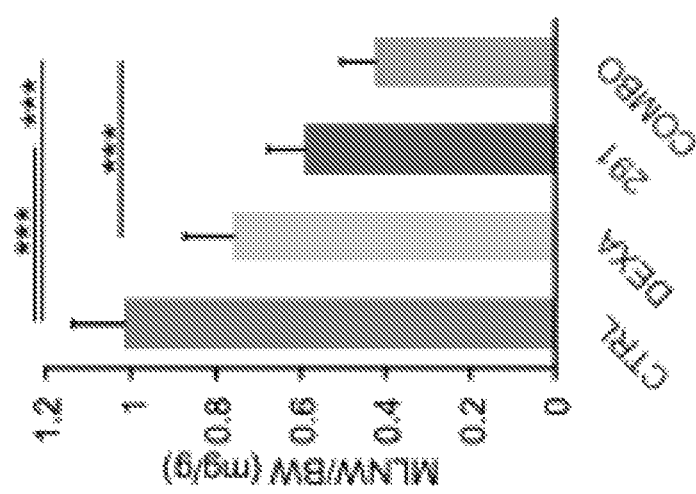

FIG. 24 graphs the severity of mesenteric lymphadenopathy assessed by collective mesenteric lymph node weight normalized by body weight on day 13 of each treatment group.

DETAILED DESCRIPTION

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center" whereas a sulfur bound to three or four different substitutents, e.g., sulfoxides or sulfinimides, is likewise termed a "chiral center".

The term "chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2n-1$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative" refers to compounds that have a common core structure, and are substituted with various groups as described herein.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively. Prodrugs can also include a precursor (forerunner) of a compound described herein that undergoes chemical conversion by metabolic processes before becoming an active or more active pharmacological agent or active compound described herein.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl)N-Mannich bases, Schiff bases and enaminones of amino functional groups, oximes, acetals, ketals and enol esters of ketone and aldehyde functional groups in compounds, and the like, as well as sulfides that are oxidized to form sulfoxides or sulfones.

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarhonyl (FMOC), nitro-veratryloxycarbonyl (NVOC), and the like. Those of skill in the art can identify other suitable amine protecting groups.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The term "analogue" refers to a chemical compound that is structurally similar to another but differs slightly in composition (as in the replacement of one atom by an atom of a different element or in the presence of a particular functional group, or the replacement of one functional group by another functional group). Thus, an analogue is a compound that is similar or comparable in function and appearance, but not in structure or origin to the reference compound.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The terms "$IC_{50}$," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The teem "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and alkylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl). If not otherwise indicated, the term "aryl" includes unsubstituted, substituted, and/or heteroatom-containing aromatic substituents.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

The term "halo" or "halogen" refers to fluoro, chloro, bromo, and iodo. "Counterion" is used to represent a small, negatively charged species such as fluoride, chloride, bromide, iodide, hydroxide, acetate, and sulfate. The term sulfoxide refers to a sulfur attached to 2 different carbon atoms and one oxygen and the S—O bond can be graphically represented with a double bond (S=O), a single bond without charges (S—O) or a single bond with charges [S(+)—O(−)].

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO−), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—CN), isocyano (—$N^+C^-$), cyanato (—O—CN), isocyanato (—$ON^+C^-$), isothiocyanato (—S—CN), azido (—N=$N^+$=$N^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—$NO_2$), nitroso (—NO), sulfo (—$SO_2$—OH), sulfonato (—$SO_2$—$O^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)($O^-$)$_2$), phosphinato (—P(O)($O^-$)), phospho (—$PO_2$), and phosphino (—$PH_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "stable compound" and "stable structure" are meant to indicate a compound that is sufficiently robust to survive isolation, and as appropriate, purification from a reaction mixture, and formulation into an efficacious therapeutic agent.

The terms "free compound" is used herein to describe a compound in the unbound state.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

All percentages and ratios used herein, unless otherwise indicated, are by weight.

The terms "gene expression" or "protein expression" includes any information pertaining to the amount of gene transcript or protein present in a sample, as well as information about the rate at which genes or proteins are produced or are accumulating or being degraded (e.g., reporter gene data, data from nuclear runoff experiments, pulse-chase data etc.). Certain kinds of data might be viewed as relating to both gene and protein expression. For example, protein levels in a cell are reflective of the level of protein as well as the level of transcription, and such data is intended to be included by the phrase "gene or protein expression information". Such information may be given in the form of amounts per cell, amounts relative to a control gene or protein, in unitless measures, etc.; the term "information" is not to be limited to any particular means of representation and is intended to mean any representation that provides relevant information. The term "expression levels" refers to a quantity reflected in or derivable from the gene or protein expression data, whether the data is directed to gene transcript accumulation or protein accumulation or protein synthesis rates, etc.

The terms "healthy" and "normal" are used interchangeably herein to refer to a subject or particular cell or tissue that is devoid (at least to the limit of detection) of a disease condition.

The term "nucleic acid" refers to polynucleotides such as deoxyribonucleic acid (DNA), and, where appropriate, ribonucleic acid (RNA). The term should also be understood to include analogues of either RNA or DNA made from nucleotide analogues, and, as applicable to the embodiment being described, single-stranded (such as sense or antisense) and double-stranded polynucleotides. In some embodiments, "nucleic acid" refers to inhibitory nucleic acids. Some categories of inhibitory nucleic acid compounds include antisense nucleic acids, RNAi constructs, and catalytic nucleic acid constructs. Such categories of nucleic acids are well-known in the art.

The term "corticosteroid resistance to the anti-inflammatory effects of corticosteroids" refers to no clinical improvement after treatment with high-dose glucocorticoid.

The term "corticosteroid dependence" refers to a condition that initially responds to corticosteroids but relapses quickly upon drug withdrawal or dose tapering.

The term "corticosteroid refractory response" refers to a condition that does not respond to an adequate induction dose of corticosteroids. It includes relatively or totally refractory responses to glucocorticoid therapy, and often needs to be controlled by add-on treatment.

Other types of corticosteroid ineffectiveness include the need for a very high dose treatment, "difficult to treat" and "do not respond well" or severe cases, and impaired in vitro and in vivo responsiveness.

The term "corticosteroid intolerance" refers to toxicity of the therapy and/or risks for developing corticosteroid-related adverse events such as opportunistic infections and bone loss.

Embodiments described herein relate to the use of 15-PGDH inhibitors in combination with corticosteroids to treat inflammation and/or reduce aberrant activity of the immune system in a subject in need thereof. It was found that corticosteroids administered to a subject can induce 15-PGDH expression in tissue of the subject. Administration of a 15-PGDH inhibitor in combination with a corticosteroid was found to enhance anti-inflammatory and/or immunosuppressive effects of the corticosteroid while attenuating corticosteroid induced adverse and/or cytotoxic effects. Treatment of inflammatory and/or immune disorders by administration of 15-PGDH inhibitors in combination with corticosteroids can increase therapeutic efficacy and can allow the corticosteroids to be administered, in some instances, at lower dosages to achieve similar effects, and, in other instances, at higher dosages and for prolonged periods of times with attenuated and/or reduced adverse or cytotoxic effects. Additional embodiments herein relate to the use of 15-PGDH inhibitors in combination with TNF alpha inhibitors to treat inflammation and/or reduce aberrant activity of the immune system in a subject in need thereof.

In some embodiments, the 15-PGDH inhibitors can be administered in combination with corticosteroids and/or TNF inhibitors to treat intestinal, gastrointestinal, or bowel disorders. The intestinal, gastrointestinal, or bowel disorders treated can include oral ulcers, gum disease, gastritis, colitis, ulcerative colitis, gastric ulcers, inflammatory bowel disease, and Crohn's disease. As described below, it was found that that inhibitors of short-chain dehydrogenase activity, such as 15-PGDH inhibitors, can be administered to a subject in need thereof alone or in combination with corticosteroids to treat intestinal, gastrointestinal, or bowel disorders, such as oral ulcers, gum disease, gastritis, colitis, ulcerative colitis, gastric ulcers, inflammatory bowel disease, and Crohn's disease.

The 15-PGDH inhibitors described herein can be used in a pharmaceutical composition for the prevention or the treatment of oral, intestinal, and/or gastrointestinal injury or diseases, or inflammatory bowel disease (IBD), such as Crohn's disease, oral ulcers, gum disease, gastritis, colitis, ulcerative colitis, and gastric ulcers. Gastritis and gastric ulcer, representatives of the gastrointestinal diseases, are defined as the conditions where gastrointestinal mucus membrane is digested by gastric acid to form ulcer. In the stomach walls generally consisting of mucosa, submucosa, muscle layer and serosa, gastric ulcer even damages submucosa and muscle layer, while gastritis damages mucosa only. Although the morbidity rates of gastritis and gastric ulcer are relatively high, the causes thereof have not been clarified yet. Until now, they are known to be caused by an imbalance between aggressive factors and defensive factors, that is, the increase in aggressive factors such as the increase in gastric acid or pepsin secretion, or the decrease in defensive factors such as structural or morphological deficit of the gastric mucus membrane, the decrease in mucus and bicarbonate ion secretion, the decrease in prostaglandin production, or the like.

Currently available therapeutic agents for gastritis and gastric ulcer comprise various drugs for strengthening the defensive factors such as an antacid, which does not affect, gastric acid secretion but neutralizes gastric acid that has been already produced, an inhibitor of gastric acid secretion, a promoter of prostaglandin secretion, and a coating agent for stomach walls. Especially, prostaglandins are known to be essential in maintaining the mechanism for protecting and defending gastric mucus membrane (Wallace J L., 2008, Physiol Rev., 88(4), 1547-65, S. J. Konturek et al., 2005, Journal of Physiology and Pharmacology, 56(5)). In view of the above, since the 15-PGDH inhibitors described herein show a suppressive or inhibitory activity against 15-PGDH, which degrades prostaglandins that protect gastric mucus membrane, they can be effective for the prevention or the treatment of gastrointestinal diseases, inter alia, gastritis and gastric ulcer.

Additionally, corticosteroids and TNF alpha antagonists are both used in the treatment of ulcerative colitis and IBD patients. In mouse models, 15-PGDH inhibitors speed healing of ulcerative colitis. We have found that administering corticosteroids to mice elevates levels of colon 15-PGDH, an effect that should reduce the therapeutic effectiveness of corticosteroids in colitis treatment. This suggests that combining a corticosteroid with a 15-PGDH inhibitor should be more effective in colitis (and IBD) treatment than using either agent alone.

Similarly, we have shown that TNF-alpha suppresses colon 15-PGDH expression. This suggests that TNF-alpha antagonists will increase colon 15-PGDH expression, an effect that should reduce the therapeutic effectiveness of corticosteroids in colitis treatment. This suggests that combining a TNF-alpha antagonist, e.g., the chimeric antibody REMICADE (infliximab), with a 15-PGDH inhibitor should be more effective in colitis (and IBD) treatment than using either agent alone.

In other embodiments, the 15-PGDH inhibitors and corticosteroids or 15-PGDH inhibitors and TNF inhibitors can be provided in a topical composition or formulation that is used to treat inflammation and/or aberrant immune system activity associated with medical conditions, such as atopic dermatitis, psoriasis, eczematous dermatitis, nummular dermatitis, irritant contact dermatitis, allergic contact dermatitis (such as poison ivy exposure, poison oak exposure, and poison sumac exposure), seborrheic dermatitis, stasis dermatitis, and other steroid responsive dermatoses.

In other embodiments, the 15-PGDH inhibitors and corticosteroids or 15-PGDH inhibitors and TNF inhibitors provided in a topical composition can be used to treat, for example, acne vulgaris, alopecia, alopecia greata, vitiligo, eczema, xerotic eczema, keratosis pilaris, lichen planus, lichen sclerosus, lichen *striatus*, lichen simplex chronicus, prurigo nodularis, discoid lupus erythematosus, lymphocytic infiltrate of Jessner/Kanof, lymphacytoma cutis, pyoderma gangrenosum, pruritis ani, sarcoidosis, chondrodermatitis nodularis helices, and other inflammatory dermatological disorders.

Medical conditions treated by the 15-PGDH inhibitors and corticosteroids or 15-PGDH inhibitors and TNF inhibitors can also include, for example, keloids, hypertrophic scars, pretibial myxedema and other infiltrative dermatological disorders. Additional medical conditions include, for example, granuloma annulare, necrobiosis lipoidica diabeticorum, sarcoidosis, and other noninfectious granulomas.

In still other embodiments, the 15-PGDH inhibitors described herein can be administered in combination with corticosteroids or TNF inhibitors for wound healing, tissue regeneration, and/or tissue repair. Among various prostaglandins, $PGE_2$ is known to serve as a mediator for wound healing. Therefore, subjects who are receiving steroids, including those healing of wounds from undergoing surgery, can be administered a 15-PGDH inhibitor to enhance $PGE_2$ and promote would healing.

Additionally, increased prostaglandin levels have been shown to stimulate signaling through the Wnt signaling pathway via increased beta-catenin mediated transcriptional activity. Wnt signaling is known to be a key pathway employed by tissue stem cells. Hence, 15-PGDH inhibitors described herein may be utilized to increase tissue stem cell numbers for purposes that would include promoting tissue regeneration or repair in subjects receiving corticosteroid treatment. In addition, 15-PGDH inhibitors described herein may be utilized to promote tissue regeneration or repair in additional organs that would include but are not limited to brain, eye, cornea, retina, lung, heart, stomach, small intestine, pancreas, beta-cells of the pancreas, kidney, bone, cartilage, and peripheral nerve.

In other embodiments, the 15-PGDH inhibitor can be used as a glucocorticoid sensitizer to treat glucocorticoid insensitivity, restore corticosteroid sensitivity, enhance glucocorticoid sensitivity, and/or reverse the glucocorticoid insensitivity in a subject experiencing corticosteroid dependence or corticoid resistance or unresponsiveness or intolerance to corticosteroids. Therapeutic effects of the 15-PGDH inhibitors when used as a glucocorticoid sensitizer include any, but are not limited to, steroid-sparing in corticosteroid-dependent patients, better responsiveness or tolerance to corticosteroids, achieving efficacy by using a lower dose of corticosteroid, preventing individuals at risk for developing refractory responses or resistance or exacerbations in response to antigen exposures, infections, exercise, or irritants, achieving optimal immune functions, easier responses for the subject or patient when steroid administration is tapered or withdrawn, or after prolonged administration of corticosteroids, decreased risks for developing corticosteroid-related adverse events such as opportunistic infections, bone loss, pathologic fracture, diabetes, cataract, and combinations thereof.

In some embodiments, the 15-PGDH inhibitor can be administered to a subject in combination with the corticosteroid to treat glucocorticoid insensitivity, restore corticosteroid sensitivity, enhance glucocorticoid sensitivity, and/or reverse the glucocorticoid insensitivity in a subject experiencing corticosteroid dependence or corticoid resistance or unresponsiveness or intolerance to corticosteroids. The glucocorticoid insensitivity related conditions can include a range of immune-inflammatory disorders/diseases treated with steroids when the therapy fails to achieve disease control or is not effective or intolerant or dependent to corticosteroids, and combinations thereof.

In other embodiments, the 15-PGDH inhibitor and corticosteroid or the 15-PGDH inhibitor and TNF inhibitor can be administered to a subject that exhibits one or more glucocorticoid insensitivity related diseases, disorders, or conditions selected from the group consisting of glucocorticoid resistant asthma, refractory rheumatoid arthritis, refractory inflammatory bowel disease, chronic obstructive pulmonary disease, acute respiratory distress syndrome, interstitial pulmonary fibrosis, cystic fibrosis, refractory ulcerative colitis, children with severe Crohn's disease, corticosteroid refractory asthma, desquamative interstitial pneumonia refractory to corticosteroid, refractory inflammatory myopathies, refractory myasthenia gravis, refractory pemphigus vulgaris, methotrexate-refractory RA patients, refractory nephrotic syndrome, refractory multiple sclerosis, refractory sprue-like disease, steroid-resistant sarcoidosis, refractory mucosal lesions of pemphigus vulgaris, refractory Schnitzler syndrome, resistant dermatitis of the head and neck, severe refractory atopic dermatitis, refractory Idiopathic thrombocytopenia purpura, refractory orbital myositis, refractory or recurrent lymphomas, critically ill patients with sepsis or acute respiratory distress syndrome (ARDS) and relative adrenal insufficiency, rosacea, polymyalgia rheumatic, giant cell arteritis, polymyositis, dermatomyositis, Kawasaki syndrome, Guillain-Barre syndrome, chronic inflammatory demyelinating polyneuropathy, multifocal motor neuropathy, Stiff man syndrome, corticosteroid dependent systemic lupus erythematosus, corticosteroid dependent multiple sclerosis, symptomatic corticosteroid dependent asthma, primary Sjogren's syndrome, systemic vasculitis, polymyositis, organ transplants, graft-versus-host disease, inflammatory diseases, autoimmune diseases, hyperproliferative diseases, lupus, osteoarthritis, rhinosinusitis, polyarteritis nodosa, Wegener's granulomatosis, giant cell arteritis, allergic rhinitis, urticaria, hereditary angioedema, tendonitis, bursitis, autoimmune chronic active hepatitis, cirrhosis, transplant rejection, psoriasis, dermatitus, malignancies, leukemia, myelomas, lymphomas, acute adrenal insufficiency, rheumatic fever, granulomatous disease, immune proliferation/apotosis, hypothalamic-pituitary-adrenal (HPA) axis suppression and regulation, hypercortisolemia, modulation of the Th1/Th2 cytokine balance, chronic kidney disease, spinal cord injury, cerebral edema, thrombocytopenia, Little's syndrome, Addison's disease, autoimmune hemolytic anemia, uveitis, pemphigus vulgaris, nasal polyps, sepsis, bacterial infections, viral infections, rickettsial infections, parasitic infections, type II diabetes, obesity, metabolic syndrome, depression, schizophrenia, mood disorders, Cushing's syndrome, anxiety, sleep disorders, memory and learning enhancement, glucocorticoid-induced glaucoma, atopic dermatitis, drug hypersensitivity reactions, serum sickness, bullous dermatitis herpetiformis, contact dermatitis, exfoliative erythroderma, mycosis fungoides, pemphigus, nonsuppurative thyroiditis, sympathetic ophthalmia, uveitis, ocular inflammatory conditions unresponsive to topical steroids, allergic bronchopulmonary aspergillosis, fulminating or disseminated pulmonary tuberculosis when used concurrently with appropriate chemotherapy, hypersensitivity pneumonitis, idiopathic bronchiolitis obliterans with organizing pneumonia, idiopathic eosinophilic pneumonias, idiopathic pulmonary fibrosis, *Pneumocystis carinii* pneumonia (PCP) associated with hypoxemia occurring in an HIV(+) individual who is also under treatment with appropriate anti-PCP antibiotics, a diuresis or remission of proteinuria in nephrotic syndrome, without uremia, of the idiopathic type or that due to lupus erythematosus, ankylosing spondylitis, polymyalgia rheumatic, psoriatic arthritis, relapsing polychondritis, trichinosis with neurologic or myocardial involvement, and tuberculous meningitis.

The 15-PGDH inhibitors used in the methods described herein can be identified using assays in which putative inhibitor compounds are applied to cells expressing 15-PGDH and then the functional effects on 15-PGDH activity are determined. Samples or assays comprising 15-PGDH that are treated with a potential inhibitor are compared to control samples without the inhibitor to examine the extent of effect. Control samples (untreated with modulators) are assigned a relative 15-PGDH activity value of 100%. Inhibition of 15-PGDH is achieved when the 15-PGDH activity value relative to the control is about 80%, optionally 50% or 25%, 10%, 5% or 1%.

Agents tested as inhibitors of 15-PGDH can be any small chemical molecule or compound. Typically, test compounds will be small chemical molecules, natural products, or peptides. The assays are designed to screen large chemical libraries by automating the assay steps and providing compounds from any convenient source to assays, which are typically run in parallel (e.g., in microtiter formats on microtiter plates in robotic assays).

In some embodiments, the 15-PGDH inhibitor can include a compound having the following formula (I):

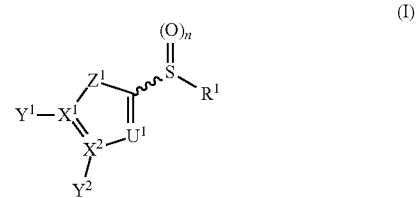

wherein n is 0-2;

Y$^1$, Y$^2$, and R$^1$ are the same or different and are each selected from the group consisting of hydrogen, substituted or unsubstituted C$_1$-C$_{24}$ alkyl, C$_2$-C$_{24}$ alkenyl, C$_2$-C$_{24}$ alkynyl, C$_3$-C$_{20}$ aryl, heteroaryl, heterocycloalkenyl containing from 5-6 ring atoms (wherein from 1-3 of the ring atoms is independently selected from N, NH, N(C$_1$-C$_6$ alkyl), NC(O) (C$_1$-C$_6$ alkyl), O, and S), C$_6$-C$_{24}$ alkaryl, C$_6$-C$_{24}$ aralkyl, halo, —Si(C$_1$-C$_3$ alkyl)$_3$, hydroxyl, sulfhydryl, C$_1$-C$_{24}$ alkoxy, C$_2$-C$_{24}$ alkenyloxy, C$_2$-C$_{24}$ alkynyloxy, C$_5$-C$_{20}$ aryloxy, acyl (including C$_2$-C$_{24}$ alkylcarbonyl (—CO-alkyl) and C$_6$-C$_{20}$ arylcarbonyl (—CO-aryl)), acyloxy (—O-acyl), C$_2$-C$_{24}$ alkoxycarbonyl (—(CO)—O-alkyl), C$_6$-C$_{20}$ aryloxycarbonyl (—(CO)—O-aryl), C$_2$-C$_{24}$ alkylcarbonato (—O—(CO)—O-alkyl), C$_6$-C$_{20}$ arylcarbonato (—O—(CO)—O-aryl), carboxy (—COOH), carboxylato (—COO$^−$), carbamoyl (—(CO)—NH$_2$), C$_1$-C$_{24}$ alkyl-carbamoyl (—(CO)—NH(C$_1$-C$_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^−$), cyanato (—O—CN), isocyanato (—O—N$^+$=C—), isothiocyanato (—S—CN), azido (—N=N$^+$=N$^−$), formyl (—(CO)—H), thioformyl (—(CS)—H), amino (—NH$_2$), C$_1$-C$_{24}$ alkyl amino, C$_5$-C$_{20}$ aryl amino, C$_2$-C$_{24}$ alkylamido (—NH—(CO)-alkyl), C$_6$-C$_{20}$ arylamido (—NH—(CO)-aryl), imino (—CR=NH where R is hydrogen, C$_1$-C$_{24}$ alkyl, C$_5$-C$_{20}$ aryl, C$_6$-C$_{24}$ alkaryl, C$_6$-C$_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, arlyl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkylethers, phosphates, phosphate esters, groups incorporating amino acids or other moieties expected to bear positive or negative charge at physiological pH, combinations thereof, and wherein $Y^1$ and $Y^2$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl;

$U^1$ is N, C—R$^2$, or C—NR$^3$R$^4$, wherein R is selected from the group consisting of a H, a lower alkyl group, O, (CH$_2$)$_{n1}$OR' (wherein n1=1, 2, or 3), CF$_3$, CH$_2$—CH$_2$X, O—CH$_2$—CH$_2$X, CH$_2$—CH$_2$—CH$_2$X, O—CH$_2$—CH$_2$X, X, (wherein X=H, F, Cl, Br, or I), CN, (C=O)—R', (C=O)N(R')$_2$, O(CO)R', COOR' (wherein R' is H or a lower alkyl group), and wherein $R^1$ and $R^2$ may be linked to form a cyclic or polycyclic ring, wherein $R^3$ and $R^4$ are the same or different and are each selected from the group consisting of H, a lower alkyl group, O, (CH$_2$)$_{n1}$OR' (wherein n1=1, 2, or 3), CF$_3$, CH$_2$—CH$_2$X, CH$_2$—CH$_2$—CH$_2$X, (wherein X=H, F, Cl, Br, or I), CN, (C=O)—R', (C=O)N(R')$_2$, COOR' (wherein R' is H or a lower alkyl group), and $R^3$ or $R^4$ may be absent;

$X^1$ and $X^2$ are independently N or C, and wherein when $X^1$ and/or $X^2$ are N, $Y^1$ and/or $Y^2$, respectively, are absent;

$Z^1$ is O, S, CR$^a$R$^b$ or NR$^a$, wherein R$^a$ and R$^b$ are independently H or a $C_{1-8}$ alkyl, which is linear, branched, or cyclic, and which is unsubstituted or substituted; and pharmaceutically acceptable salts thereof.

Examples of 15-PGDH inhibitors having formula (I) include the following compounds:

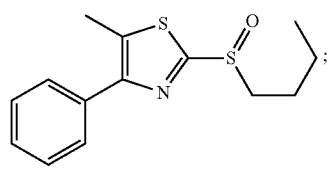

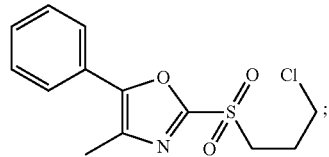

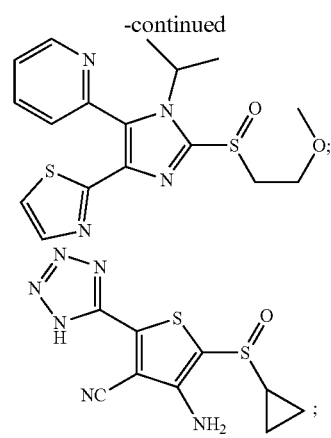

and pharmaceutically acceptable salts thereof.

In other embodiments, the 15-PGDH inhibitor can include a compound having the following formula (II):

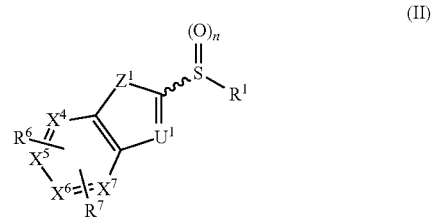

wherein n is 0-2

$X^4$, $X^5$, $X^6$, and $X^7$ are independently N or CR$^c$;

$R^1$, $R^6$, $R^7$, and R' are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N(C$_1$-C$_6$ alkyl), NC(O)(C$_1$-C$_6$ alkyl), O, and S), $C_6$-$C_{24}$ alkaryl, $C_6$-$C_{24}$ aralkyl, halo, —Si(C$_1$-C$_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_2$ alkyl-carbamoyl (—(CO)—NH(C$_1$-C$_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C—), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N (aryl), where R=hydrogen, alkyl, aryl, alkaryl, etc.), nitro (—NO$_2$), nitroso (—NO), sulfo (—SO$_2$—OH), sulfonato (—SO$_2$—O$^-$), C$_1$-C$_{24}$ alkylsulfanyl (—S-alkyl; also termed "alkylthio"), arylsulfanyl (—S-aryl; also termed "arylthio"), C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$-aryl), sulfonamide (—SO$_2$—NH$_2$, —SO$_2$NY$_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkylethers, phosphates, phosphate esters, groups incorporating amino acids or other moieties expected to bear positive or negative charge at physiological pH, combinations thereof, and wherein R$^6$ and R$^7$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl;

U$^1$ is N, C—R$^2$, or C—NR$^3$R$^4$, wherein R$^2$ is selected from the group consisting of a H, a lower alkyl group, O, (CH$_2$)$_{n1}$OR' (wherein n1=1, 2, or 3), CF$_3$, CH$_2$—CH$_2$X, O—CH$_2$—CH$_2$X, CH$_2$—CH$_2$—CH$_2$X, O—CH$_2$—CH$_2$X, X, (wherein X=H, F, Cl, Br, or I), CN, (C=O)—R', (C=O)N(R')$_2$, O(CO)R', COOR' (wherein R' is H or a lower alkyl group), and wherein R$^1$ and R$^2$ may be linked to form a cyclic or polycyclic ring, wherein R$^3$ and R$^4$ are the same or different and are each selected from the group consisting of H, a lower alkyl group, O, (CH$_2$)$_{n1}$OR' (wherein n1=1, 2, or 3), CF$_3$, CH$_2$—CH$_2$X, CH$_2$—CH$_2$—CH$_2$X, (wherein X=H, F, Cl, Br, or I), CN, (C=O)—R', (C=O)N(R')$_2$, COOR' (wherein R' is H or a lower alkyl group), and R$^3$ or R$^4$ may be absent;

Z$^1$ is O, S, CR$^a$R$^b$ or NR$^a$, wherein R$^a$ and R$^b$ are independently H or a C$_{1-8}$ alkyl, which is linear, branched, or cyclic, and which is unsubstituted or substituted;

and pharmaceutically acceptable salts thereof.

Examples of 15-PGDH inhibitors having formulas (II) include the following compounds:

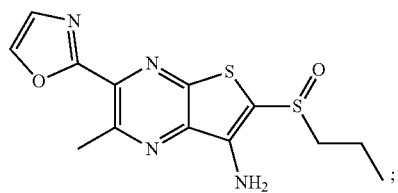

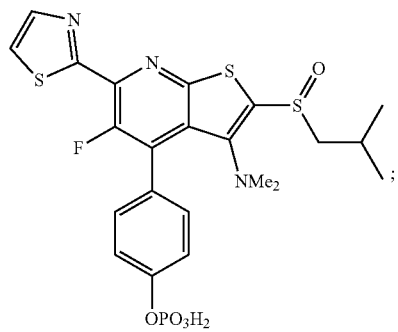

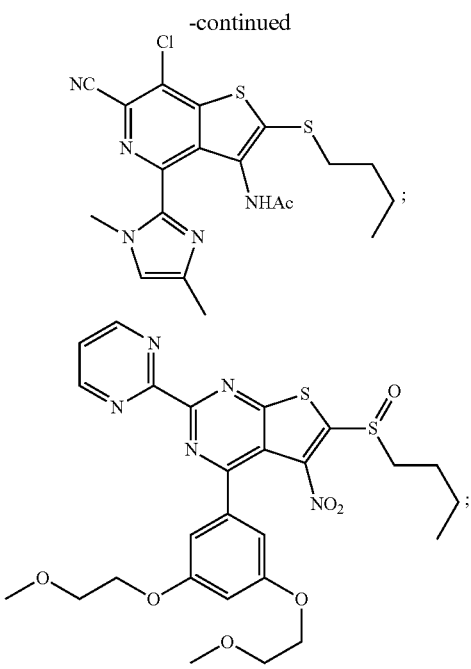

and pharmaceutically acceptable salts thereof.

In yet other embodiments, the 15-PGDH inhibitor can include a compound having the following formulas (III) or (IV):

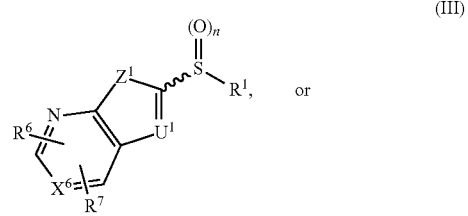

(III)

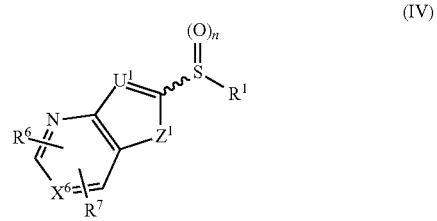

(IV)

wherein n is 0-2

X$^6$ is independently is N or CR$^c$;

R$^1$, R$^6$, R$^7$, and R$^c$ are independently selected from the group consisting of hydrogen, substituted or unsubstituted C$_1$-C$_{24}$ alkyl, C$_2$-C$_{24}$ alkenyl, C$_2$-C$_{24}$ alkynyl, C$_3$-C$_{20}$ aryl, heteroaryl, heterocycloalkenyl containing from 5-6 ring atoms (wherein from 1-3 of the ring atoms is independently selected from N, NH, N(C$_1$-C$_6$ alkyl), NC(O)(C$_1$-C$_6$ alkyl), O, and S), C$_6$-C$_{24}$ alkaryl, C$_6$-C$_{24}$ aralkyl, halo, —Si(C$_1$-C$_3$ alkyl)$_3$, hydroxyl, sulfhydryl, C$_1$-C$_{24}$ alkoxy, C$_2$-C$_{24}$ alkenyloxy, C$_2$-C$_{24}$ alkynyloxy, C$_5$-C$_{20}$ aryloxy, acyl (including C$_2$-C$_{24}$ alkylcarbonyl (—CO-alkyl) and C$_6$-C$_{20}$ arylcarbonyl (—CO-aryl)), acyloxy (—O-acyl), C$_2$-C$_{24}$ alkoxycarbonyl (—(CO)—O-alkyl), C$_6$-C$_{20}$ aryloxycarbonyl (—(CO)—O-aryl), C$_2$-C$_{24}$ alkylcarbonato (—O—

(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C—), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, aryl (or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkylethers, phosphates, phosphate esters, groups incorporating amino acids or other moieties expected to bear positive or negative charge at physiological pH, combinations thereof, and wherein $R^6$ and $R^7$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl;

$U^1$ is N, C—$R^2$, or C—NR$^3$R$^4$, wherein $R^2$ is selected from the group consisting of a H, a lower alkyl group, O, (CH$_2$)$_{n1}$OR' (wherein n1=1, 2, or 3), CF$_3$, CH$_2$—CH$_2$X, O—CH$_2$—CH$_2$X, CH$_2$—CH$_2$—CH$_2$X, O—CH$_2$—CH$_2$X, X, (wherein X=H, F, Cl, Br, or I), CN, (C=O)—R', (C=O)N(R')$_2$, O(CO)R', COOR' (wherein R' is H or a lower alkyl group), and wherein $R^1$ and $R^2$ may be linked to form a cyclic or polycyclic ring, wherein $R^3$ and $R^4$ are the same or different and are each selected from the group consisting of H, a lower alkyl group, O, (CH$_2$)$_{n1}$OR' (wherein n1=1, 2, or 3), CF$_3$, CH$_2$—CH$_2$X, CH$_2$—CH$_2$—CH$_2$X, (wherein X=H, F, Cl, Br, or I), CN, (C=O)—R', (C=O)N(R')$_2$, COOR' (wherein R' is H or a lower alkyl group), and $R^3$ or $R^4$ may be absent;

$Z^1$ is O, S, CR$^a$R$^b$ or NR$^a$, wherein R$^a$ and R$^b$ are independently H or a $C_{1-8}$ alkyl, which is linear, branched, or cyclic, and which is unsubstituted or substituted;

and pharmaceutically acceptable salts thereof.

In some embodiments, $R^1$ is selected from the group consisting of branched or linear alkyl including —(CH$_2$)$n_1$CH$_3$ ($n_1$=0-7),

wherein $n_2$=0-6 and X is any of the following: CF$_y$H$_z$ (y+z=3), CCl$_y$H$_z$ (y+z=3), OH, OAc, OMe, $R^{71}$, $OR^{72}$, CN, N(R$^{73}$)$_2$,

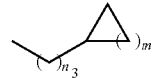

($n_3$=0-5, m=1-5), and

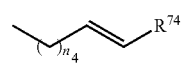

($n_4$=0-5).

In other embodiments, $R^6$ and $R^7$ can each independently be one of the following:

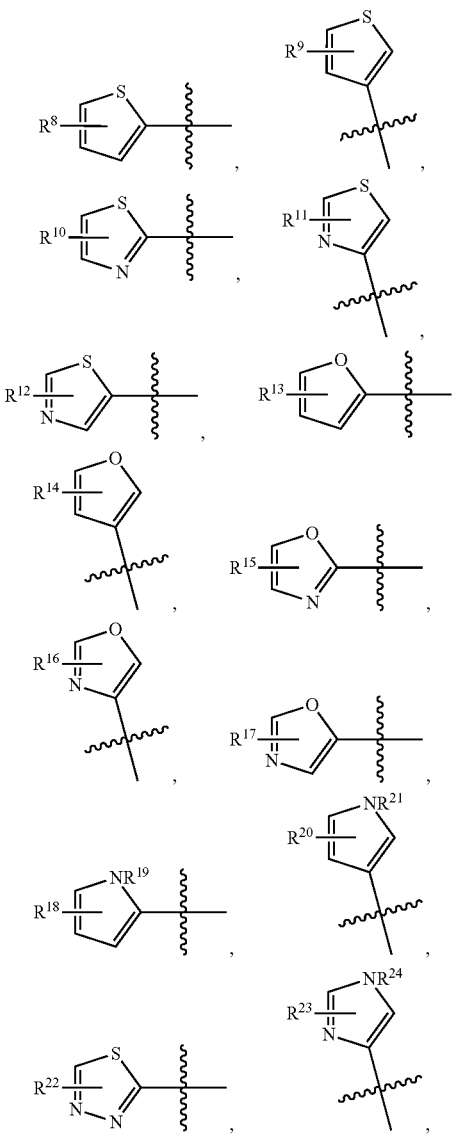

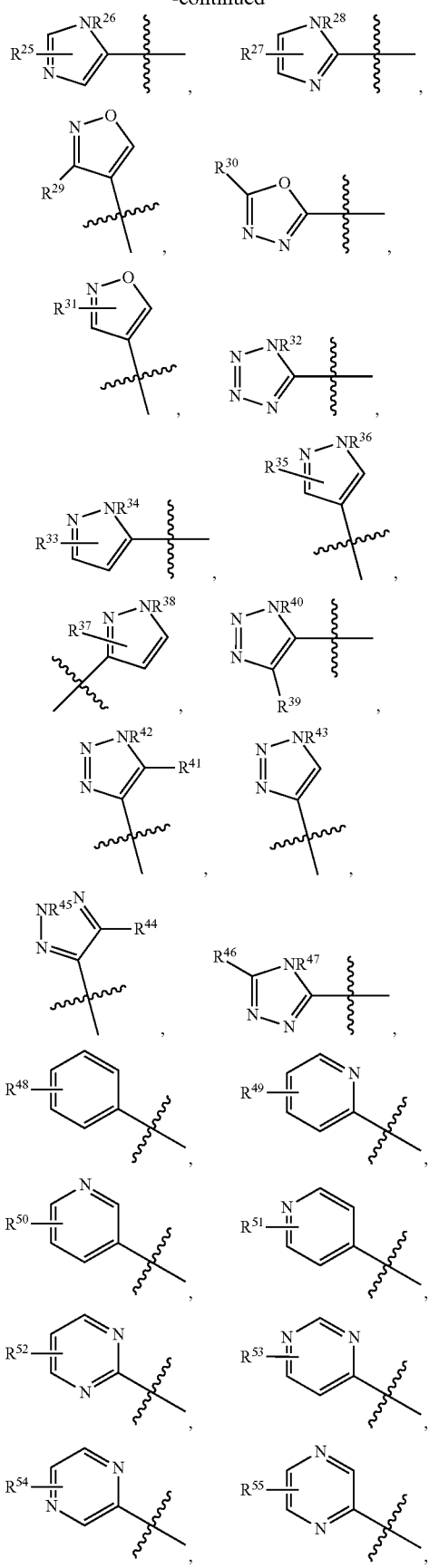

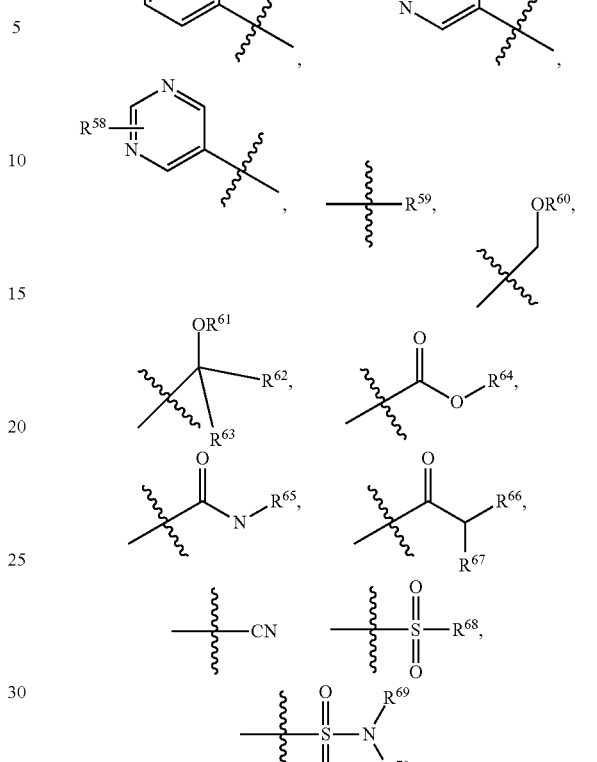

each $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, and $R^{74}$, are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O) ($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH₂), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH₂), carbamido (—NH—(CO)—NH₂), cyano(—CN), isocyano (—N⁺C⁻), cyanato (—O—CN), isocyanato (—O—N⁺=C⁻), isothiocyanato (—S—CN), azido (—N=N⁺=N⁻), formyl (—(CO)—H), thioformyl (—(CS)—H), amino (—NH₂), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)- aryl), sulfanamido (—SO$_2$N(R)$_2$ where R is independently H, alkyl, aryl or heteroaryl), imino (—CR═NH where R is hydrogen, C$_1$-C$_{24}$ alkyl, C$_5$-C$_{20}$ aryl, C$_6$-C$_{24}$ alkaryl, C$_6$-C$_{24}$ aralkyl, etc.), alkylimino (—CR═N(alkyl), where R═hydrogen, alkyl, aryl, alkaryl, aralkyl, etc.), arylimino (—CR═N(aryl), where R═hydrogen, alkyl, aryl, alkaryl, etc.), nitro (—NO$_2$), nitroso (—NO), sulfo (—SO$_2$—OH), sulfonato (—SO$_2$—O$^-$), C$_1$-C$_{24}$ alkylsulfanyl (—S-alkyl; also termed "alkylthio"), arylsulfanyl (—S-aryl; also termed "arylthio"), C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_2$O arylsulfonyl (—SO$_2$-aryl), sulfonamide (—SO$_2$—NH$_2$, —SO$_2$NY$_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkyl ethers (—[(CH$_2$)$_n$O]$_m$), phosphates, phosphate esters [—OP(O)(OR)$_2$ where R═H, methyl or other alkyl], groups incorporating amino acids or other moieties expected to bear positive or negative charge at physiological pH, and combinations thereof, and pharmaceutically acceptable salts thereof.

In still other embodiments, R$^6$ and R$^7$ can independently be a group that improves aqueous solubility, for example, a phosphate ester (—OPO$_3$H$_2$), a phenyl ring linked to a phosphate ester (—OPO$_3$H$_2$), a phenyl ring substituted with one or more methoxyethoxy groups, or a morpholine, or an aryl or heteroaryl ring substituted with such a group.

Examples of 15-PGDH inhibitors having formulas (III) or (IV) include the following compounds:

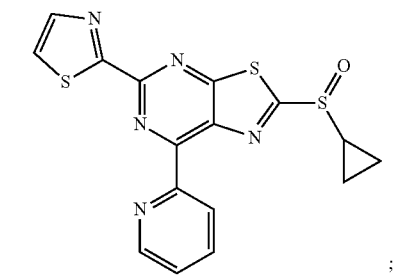

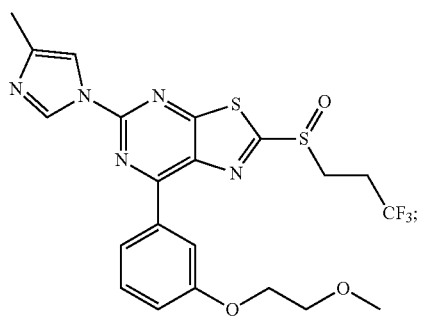

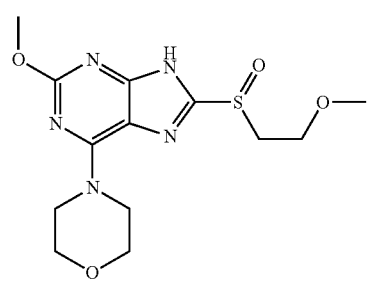

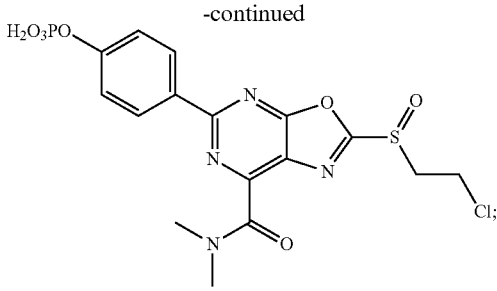

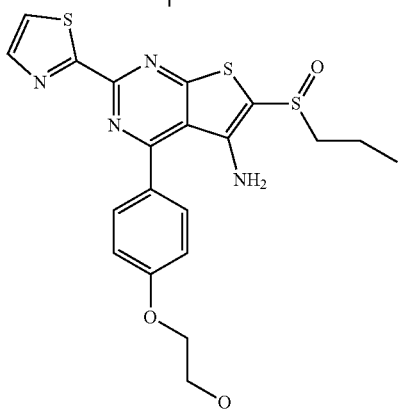

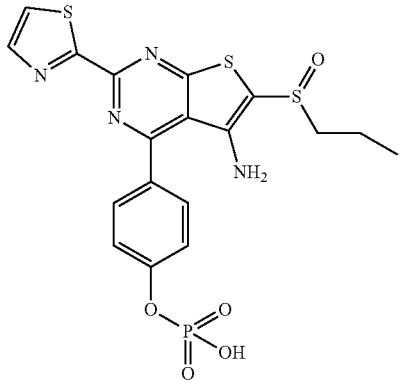

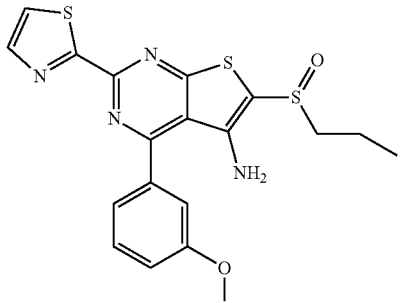

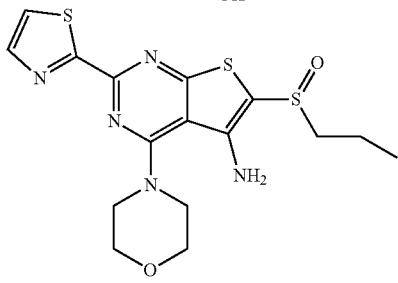

-continued

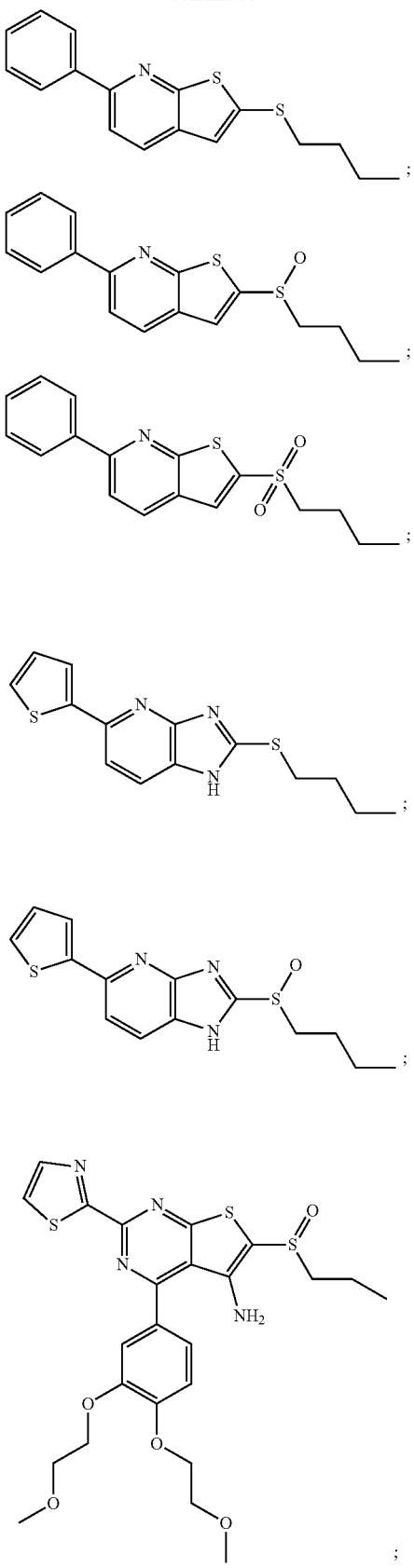

and pharmaceutically acceptable salts thereof.

In other embodiments, the 15-PGDH inhibitor can include a compound having the following formula (V):

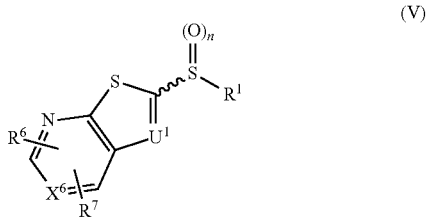

(V)

wherein n is 0-2
$X^6$ is independently is N or $CR^c$
$R^1$, $R^6$, $R^7$, and $R^c$ are each independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N⁺C⁻), cyanato (—O—CN), isocyanato (—O—N⁺=C—), isothiocyanato (—S—CN), azido (—N=N⁺=N⁻), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N (aryl), where R=hydrogen, alkyl, aryl, alkaryl, etc.), nitro (—NO$_2$), nitroso (—NO), sulfo (—SO$_2$—OH), sulfonato (—SO$_2$—O⁻), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, aryl or alkyl), phosphono (—P(O)(OH)$_2$), phosphonato (—P(O)(O⁻)$_2$), phosphinato (—P(O)(O⁻)), phospho (—PO$_2$), phosphino (—PH$_2$), polyalkylethers, phosphates, phosphate esters, groups incorporating amino acids or other moieties expected to bear positive or negative charge at physiological pH, combinations thereof, and wherein $R^6$ and $R^7$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl;

$U^1$ is N, C—$R^2$, or C—$NR^3R^4$, wherein $R^2$ is selected from the group consisting of a H, a lower alkyl group, O, $(CH_2)_{n1}OR'$ (wherein n1=1, 2, or 3), $CF_3$, $CH_2$—$CH_2X$, O—$CH_2$—$CH_2X$, $CH_2$—$CH_2$—$CH_2X$, O—$CH_2$—$CH_2X$, X, (wherein X=H, F, Cl, Br, or I), CN, (C=O)—R', (C=O)N(R')$_2$, O(CO)R', COOR' (wherein R' is H or a lower alkyl group), and wherein $R^1$ and $R^2$ may be linked to form a cyclic or polycyclic ring, wherein $R^3$ and $R^4$ are the same or different and are each selected from the group consisting of H, a lower alkyl group, O, $(CH_2)_{n1}OR'$ (wherein n1=1, 2, or 3), $CF_3$, $CH_2$—$CH_2X$, $CH_2$—$CH_2$—$CH_2X$, (wherein X=H, F, Cl, Br, or I), CN, (C=O)—R', (C=O)N(R')$_2$, COOR' (wherein R' is H or a lower alkyl group), and $R^3$ or $R^4$ may be absent;

and pharmaceutically acceptable salts thereof.

In some embodiments, $R^1$ is selected from the group consisting of branched or linear alkyl including —$(CH_2)_{n1}CH_3$ ($n_1$=0-7),

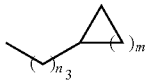

wherein $n_2$=0-6 and X is any of the following: $CF_yH_z$ (y+z=3), $CCl_yH_z$ (y+z=3), OH, OAc, OMe, $R^{71}$, $OR^{72}$, CN, $N(R^{73})_2$,

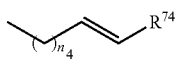

($n_3$=0-5, m=1-5), and

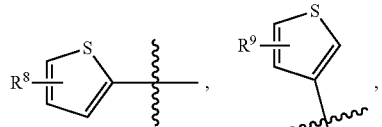

($n_4$=0-5).

In other embodiments, $R^6$ and $R^7$ can each independently be one of the following:

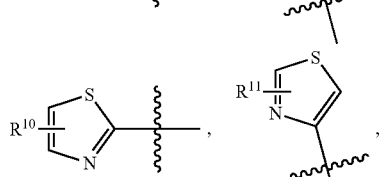

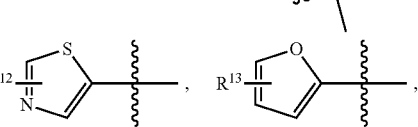

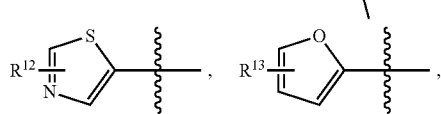

-continued

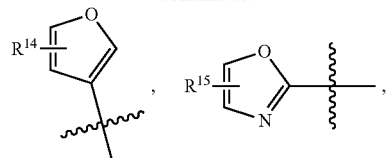

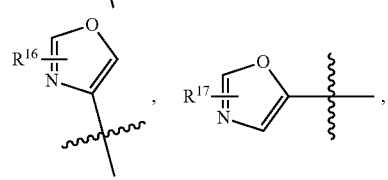

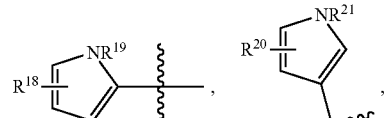

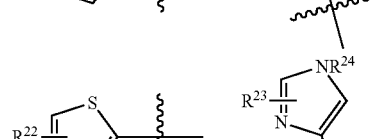

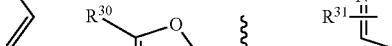

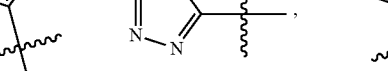

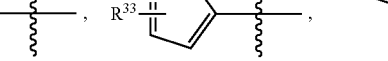

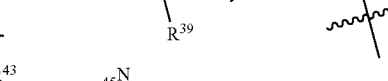

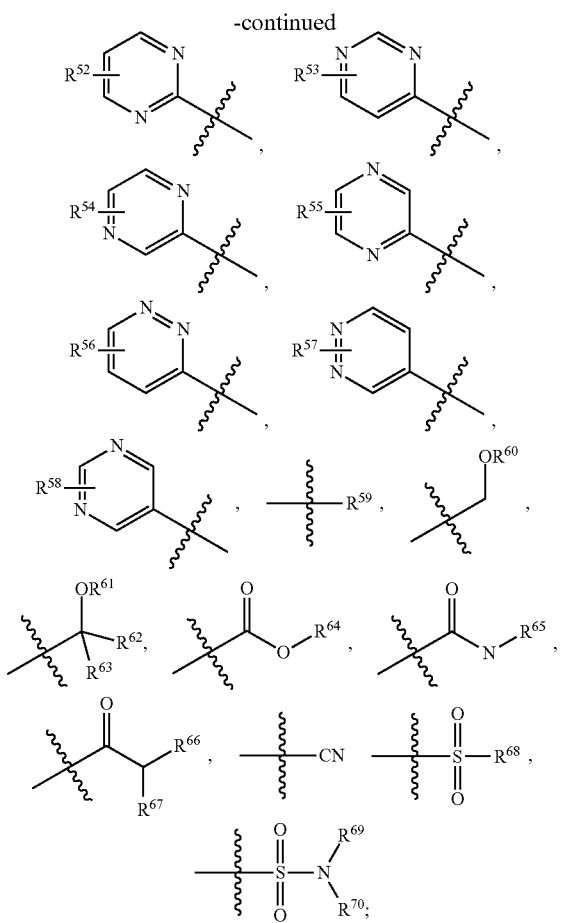

each $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, and $R^{74}$, are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O) ($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—SO$_2$N(R)$_2$ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkyl ethers (—[(CH$_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, and combinations thereof, and pharmaceutically acceptable salts thereof.

In still other embodiments, $R^6$ and $R^7$ can independently be a group that improves aqueous solubility, for example, a phosphate ester (—OPO$_3$H$_2$), a phenyl ring linked to a phosphate ester (—OPO$_3$H$_2$), a phenyl ring substituted with one or more methoxyethoxy groups, or a morpholine, or an aryl or heteroaryl ring substituted with such a group.

In other embodiments, the 15-PGDH inhibitor can include a compound having the following formula (VI):

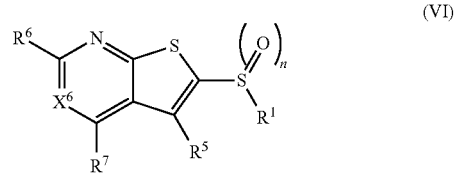

(VI)

wherein n=0-2;
$X^6$ is N or CR';
$R^1$ is selected from the group consisting of branched or linear alkyl including —(CH$_2$)$_{n1}$CH$_3$ (n$_1$=0-7),

wherein n$_2$=0-6 and X is any of the following: CF$_y$H$_z$ (y+z=3), CCl$_y$H$_z$ (y+z=3), OH, OAc, OMe, $R^{71}$, OR$^{72}$, CN, N(R$^{73}$)$_2$,

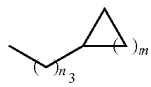

(n$_3$=0-5, m=1-5), and

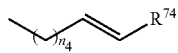

(n$_4$=0-5).

$R^5$ is selected from the group consisting of H, Cl, F, $NH_2$, and $N(R^{76})_2$;
$R^6$ and $R^7$ can each independently be one of the following:
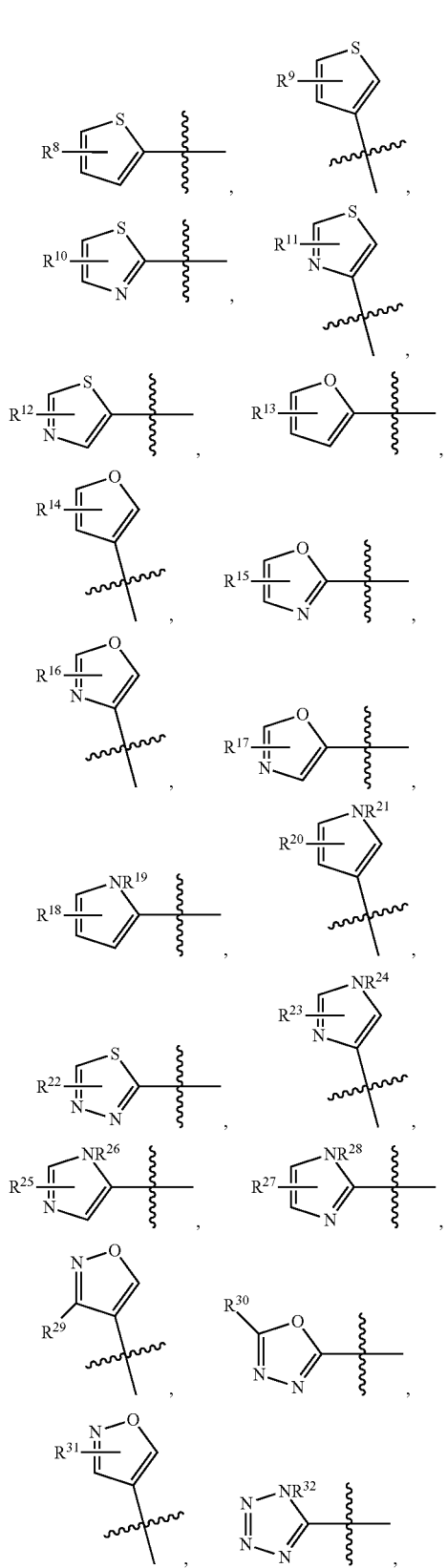
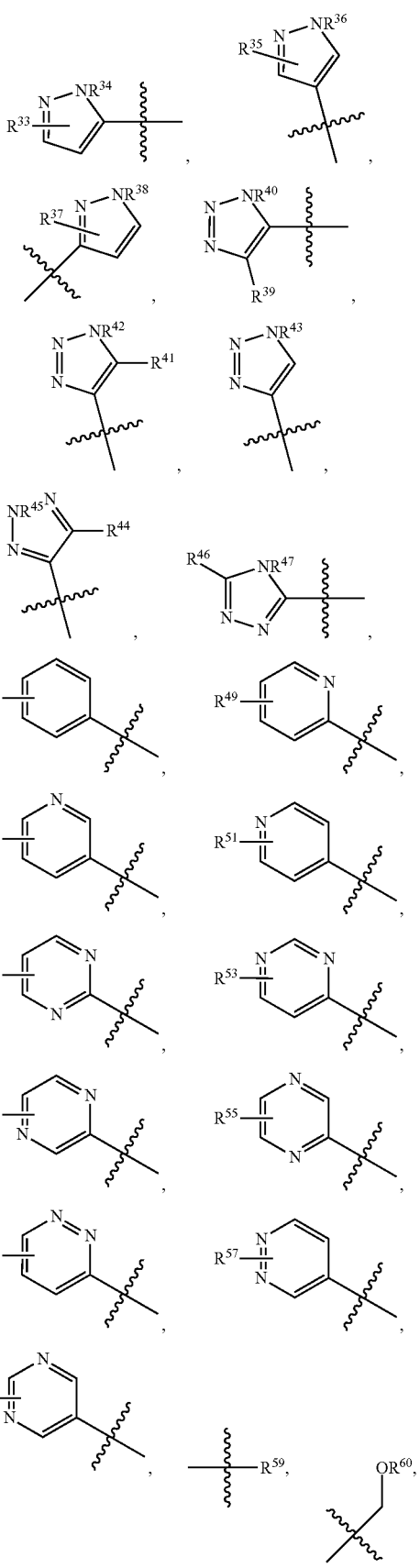

-continued

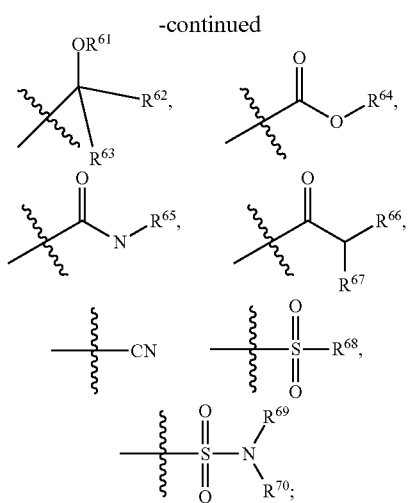

each $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, and $R^{74}$, are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O) ($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulthydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH₂), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH₂), carbamido (—NH—(CO)—NH₂), cyano(—CN), isocyano (—N⁺C⁻), cyanato (—O—CN), isocyanato (—O—N⁺=C—), isothiocyanato (—S—CN), azido (—N=N⁺=N⁻), formyl (—(CO)—H), thioformyl (—(CS)—H), amino (—NH₂), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—SO₂N(R)₂ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO₂), nitroso (—NO), sulfo (—SO₂—OH), sulfonato (—SO₂—O⁻), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO₂-alkyl), $C_5$-$C_{20}$ arylsulfonyl (—SO₂-aryl), sulfonamide (—SO₂—NH₂, —SO₂NY₂ (wherein Y is independently H, aryl or alkyl), phosphono (—P(O)(OH)₂), phosphonato (—P(O)(O⁻)₂), phosphinato (—P(O)(O⁻)), phospho (—PO₂), phosphino (—PH₂), polyalkyl ethers (—[(CH₂)ₙO]ₘ), phosphates, phosphate esters [—OP(O)(OR)₂ where R=H, methyl or other alkyl], groups incorporating amino acids or other moieties expected to bear positive or negative charge at physiological pH, and combinations thereof, and pharmaceutically acceptable salts thereof.

In other embodiments, the 15-PGDH inhibitor can include a compound having the following formula (VII):

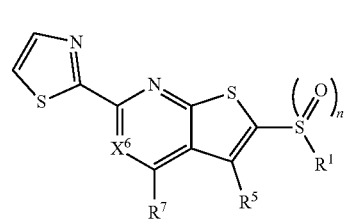

(VII)

wherein n=0-2;

$X^6$ is N or $CR^c$;

$R^1$ is selected from the group consisting of branched or linear alkyl including —(CH₂)n₁CH₃ (n₁=0-7),

wherein n₂=0-6 and X is any of the following: $CF_yH_z$ (y+z=3), $CCl_yH_z$ (y+z=3), OH, OAc, OMe, $R^{71}$, $OR^{72}$, CN, $N(R^{73})_2$,

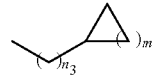

(n₃=0-5, m=1-5), and

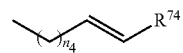

(n₄=0-5).

$R^5$ is selected from the group consisting of H, Cl, F, NH₂, and $N(R^{76})_2$;

$R^7$ can each independently be one of the following:

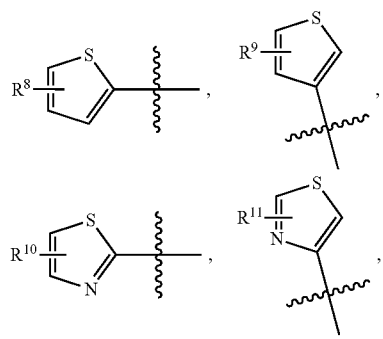

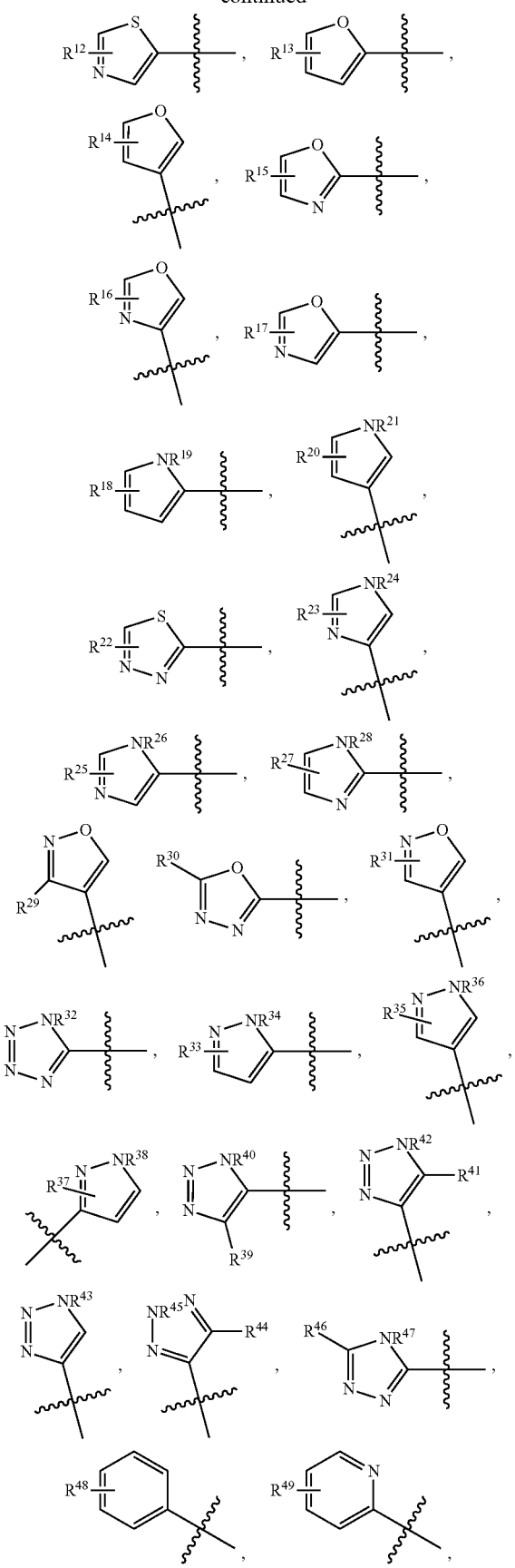
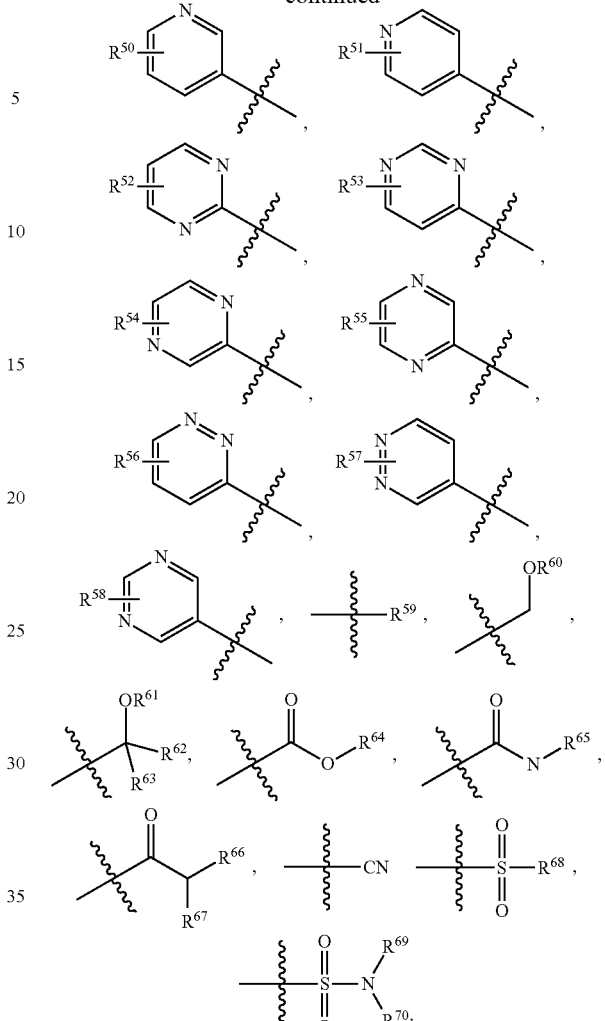

each $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, and $R^{74}$, are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O)($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—

NH-aryl), thiocarbamoyl (—(CS)—NH₂), carbamido (—NH—(CO)—NH₂), cyano(—CN), isocyano (—N⁺C⁻), cyanato (—O—CN), isocyanato (—O—N⁺=C—), isothiocyanato (—S—CN), azido (—N=N⁺=N⁻), formyl (—(CO)—H), thioformyl (—(CS)—H), amino (—NH₂), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—SO₂N(R)₂ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO₂), nitroso (—NO), sulfo (—SO₂—OH), sulfonato (—SO₂—O⁻), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO₂-alkyl), $C_5$-$C_{20}$ arylsulfonyl (—SO₂-aryl), sulfonamide (—SO₂—NH₂, —SO₂NY₂ (wherein Y is independently H, aryl or alkyl), phosphono (—P(O)(OH)₂), phosphonato (—P(O)(O⁻)₂), phosphinato (—P(O)(O⁻)), phospho (—PO₂), phosphino (—PH₂), polyalkyl ethers (—[(CH₂)ₙO]ₘ), phosphates, phosphate esters [—OP(O)(OR)₂ where R=H, methyl or other alkyl], groups incorporating amino acids or other moieties expected to bear positive or negative charge at physiological pH, and combinations thereof, and pharmaceutically acceptable salts thereof.

Examples of compounds having formulas (V), (VI), or (VII) are selected from the group consisting of:

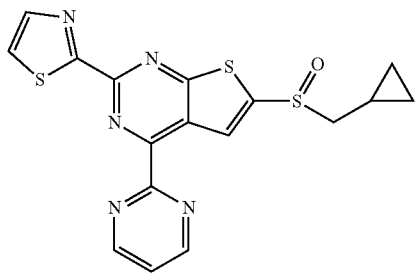

;

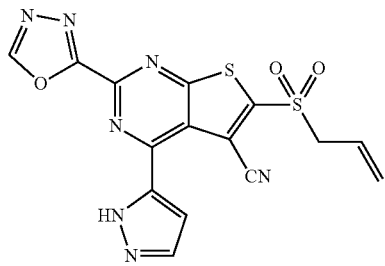

;

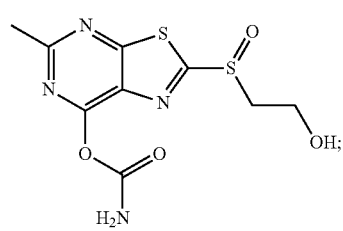

-continued

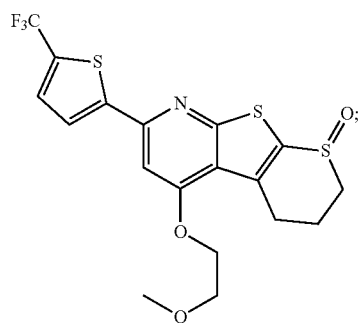

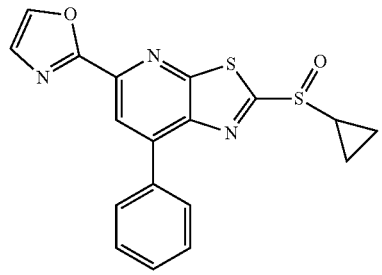

;

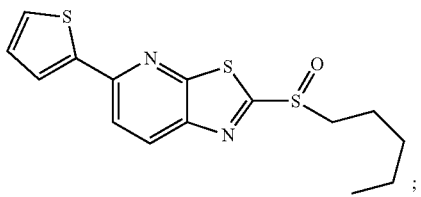

;

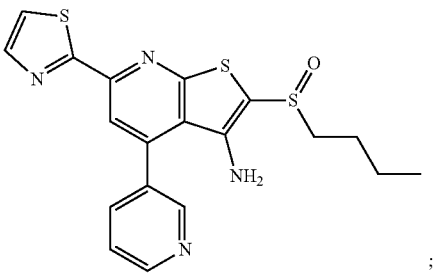

;

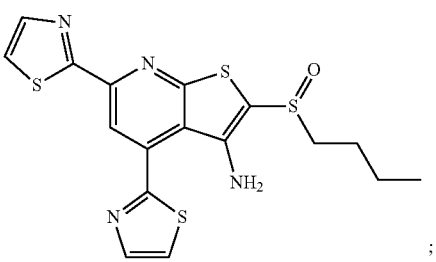

;

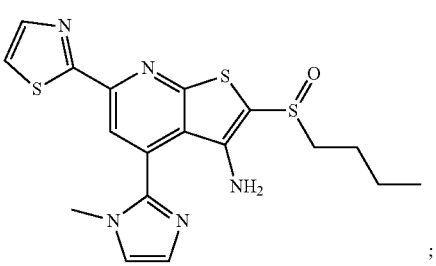

;

51
-continued
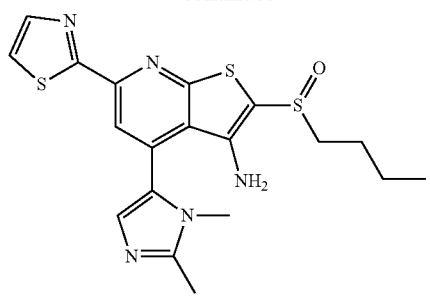
;
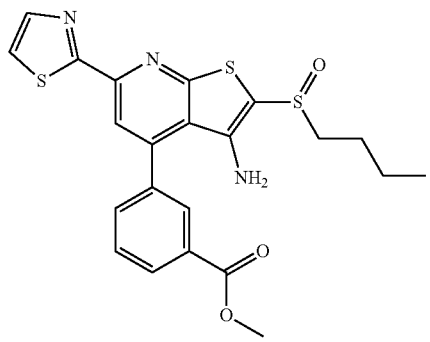
;
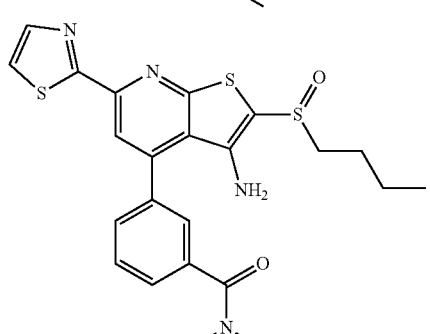
;
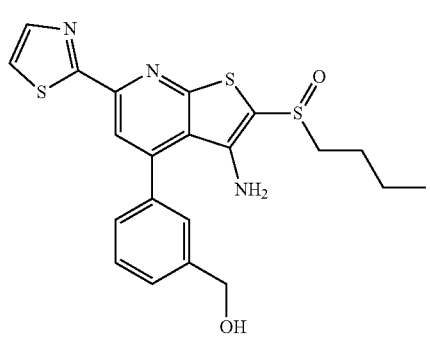
;
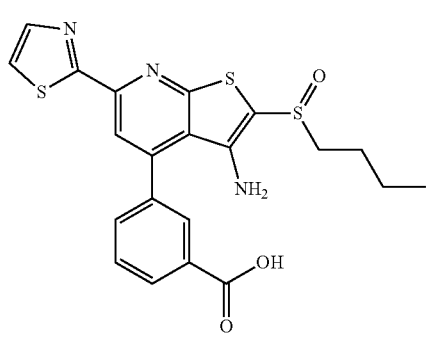
;
52
-continued
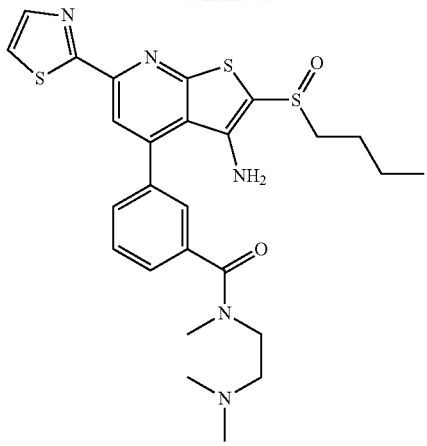
;
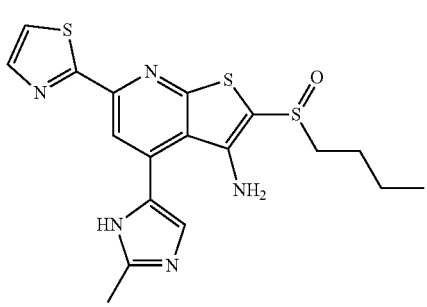
;
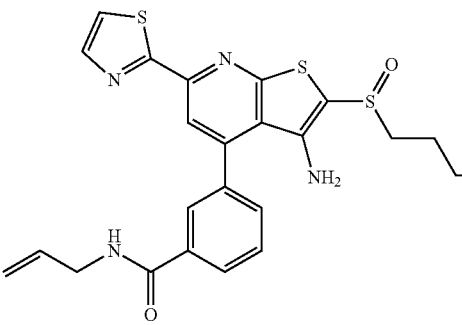
;
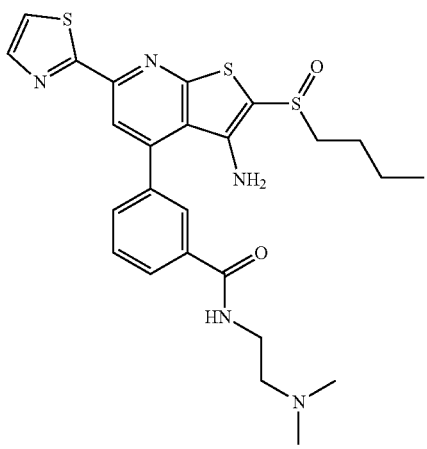
;

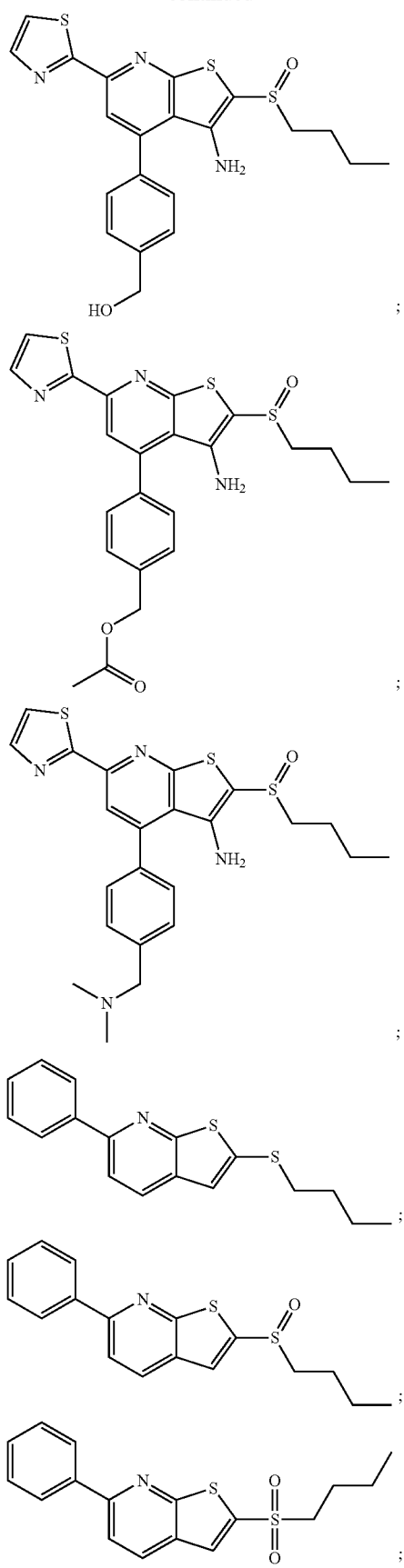
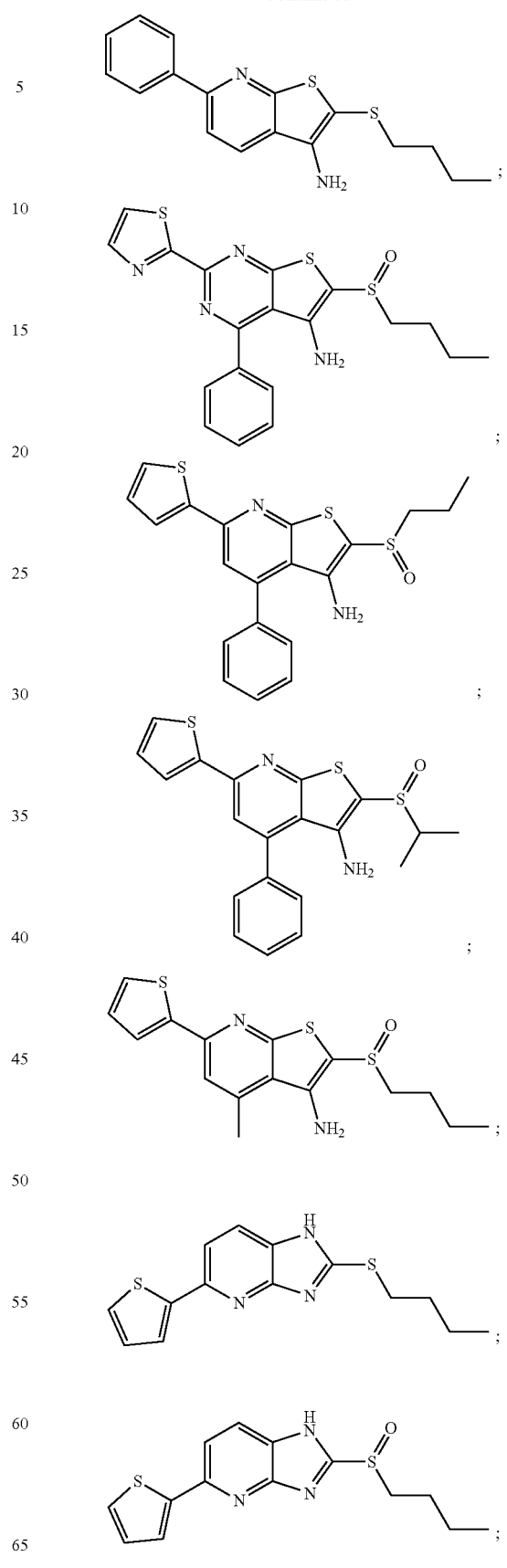

55
-continued
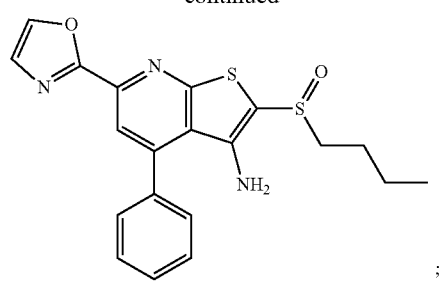
;
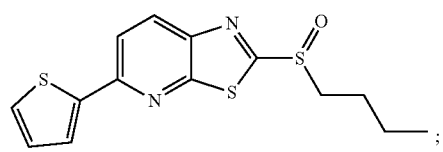
;
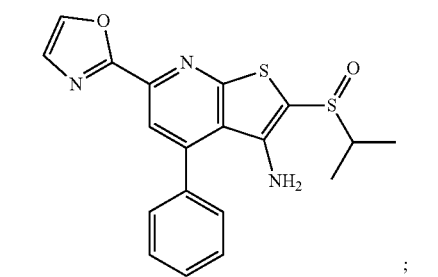
;
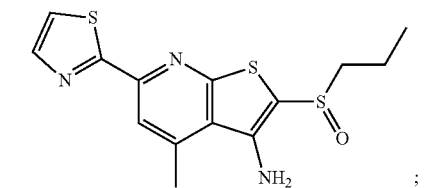
;
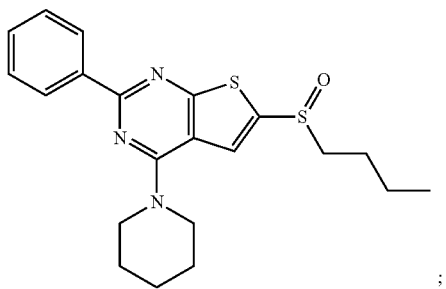
;
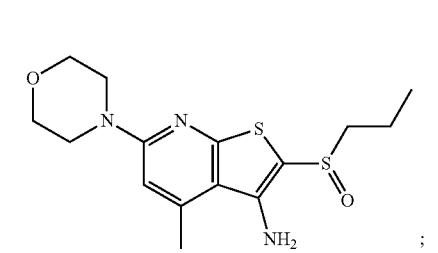
;
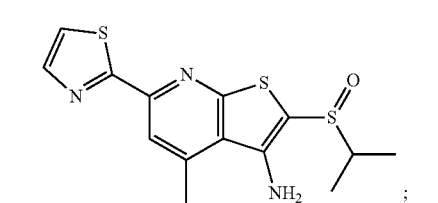
;
56
-continued
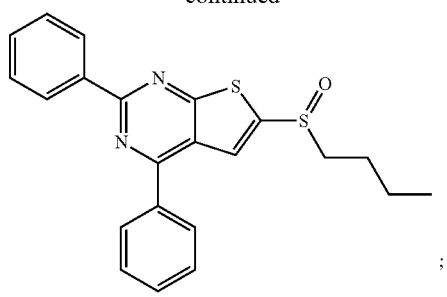
;
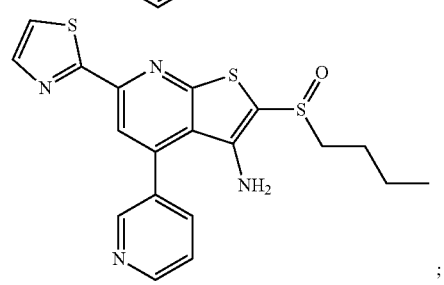
;
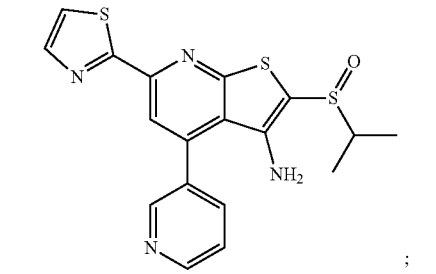
;
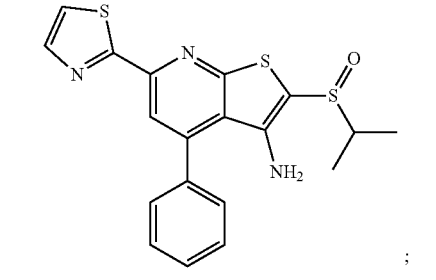
;
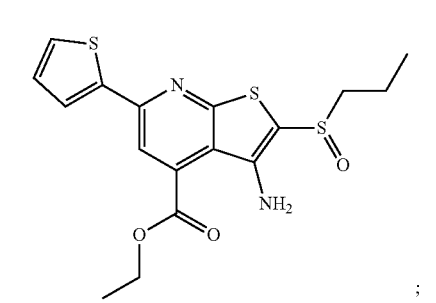
;
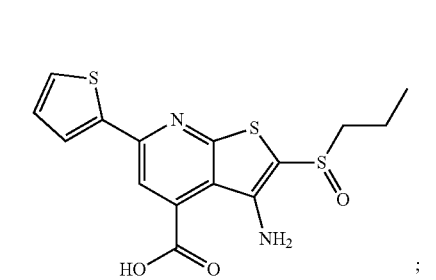
;

57
-continued
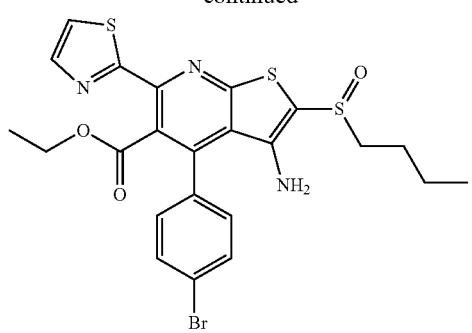
;
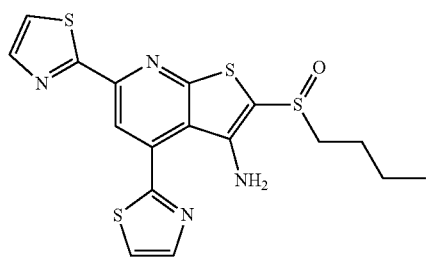
;
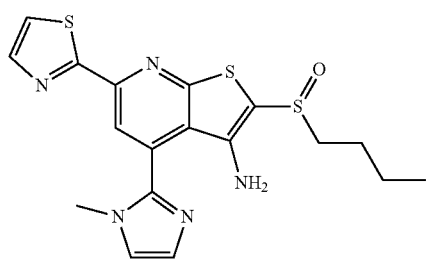
;
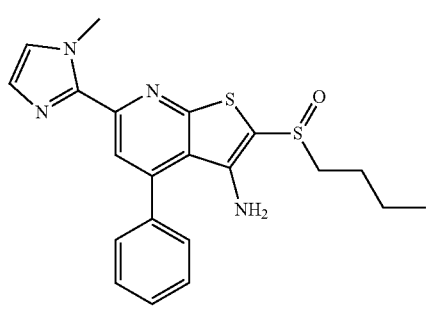
;
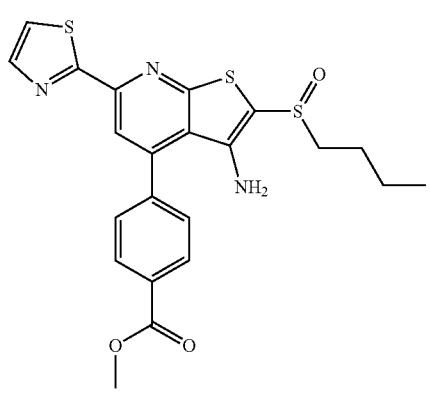
;
58
-continued
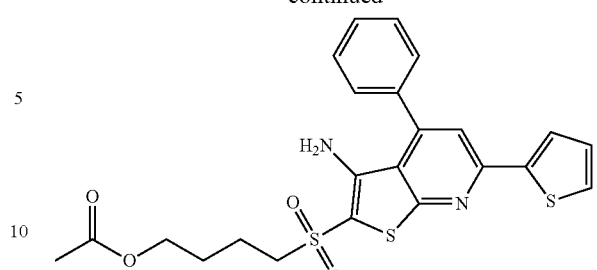
;
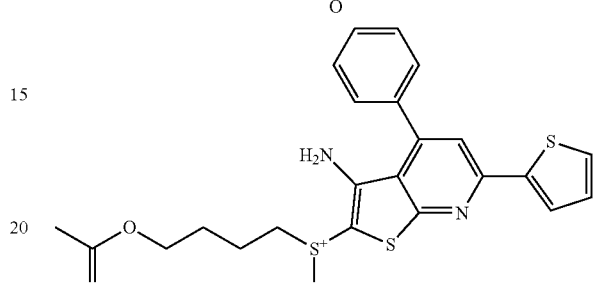
;
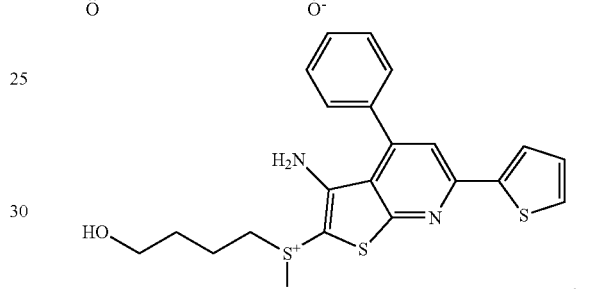
;
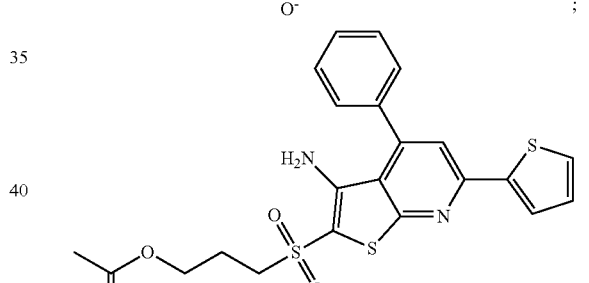
;
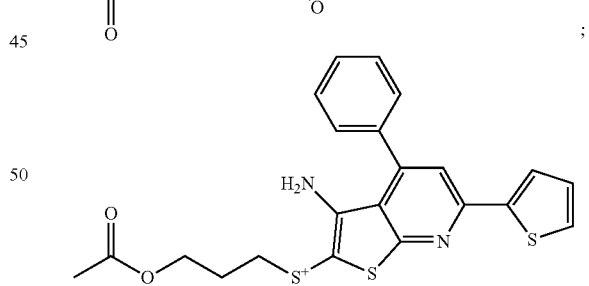
;
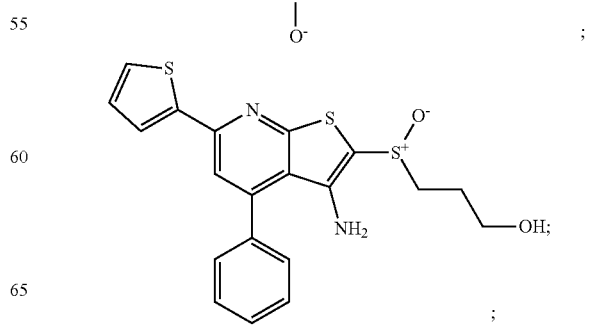
;

59
-continued
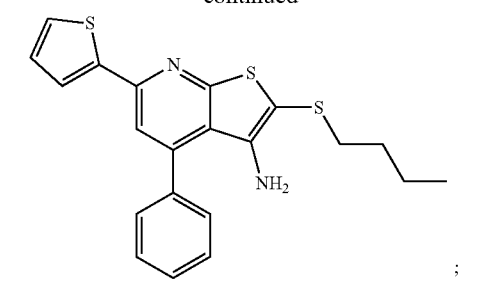
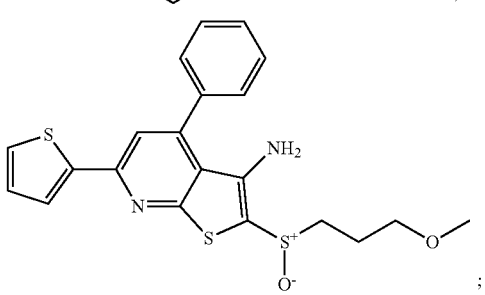
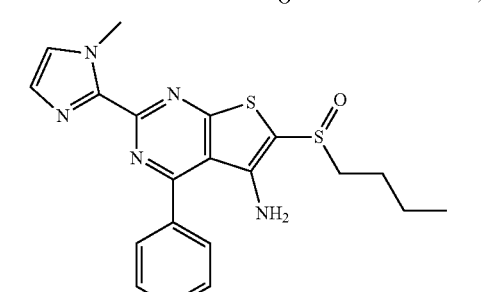
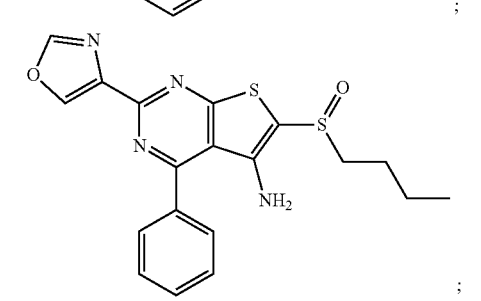
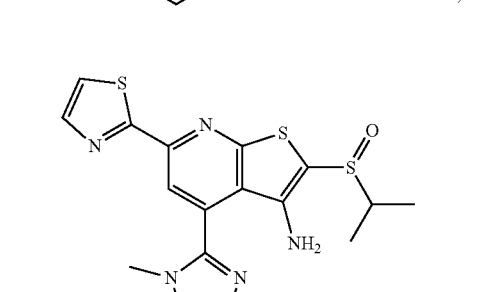
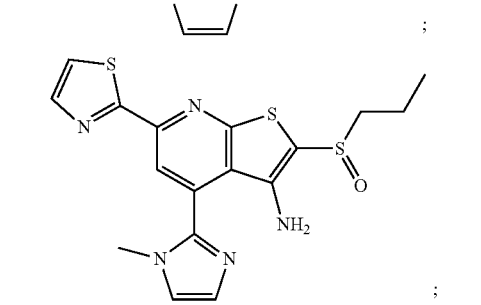
60
-continued
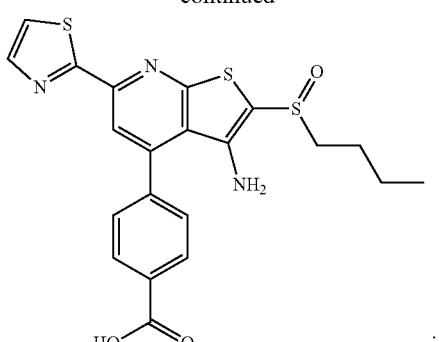
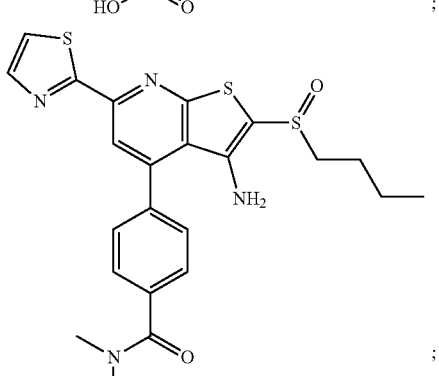
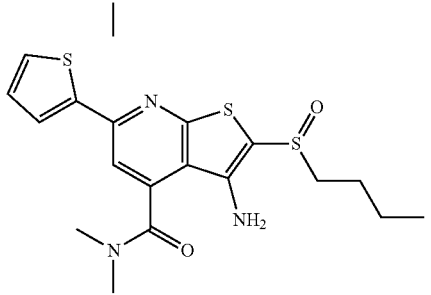
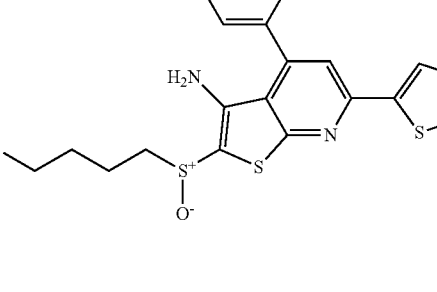
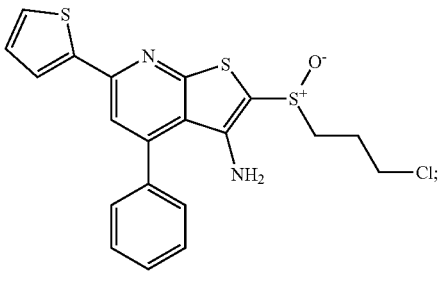

61
-continued
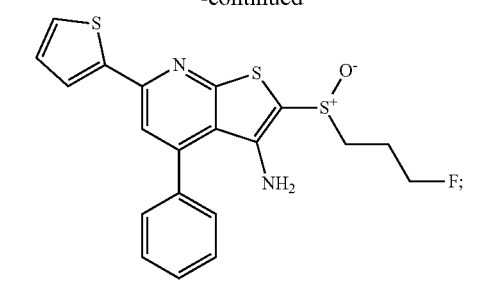
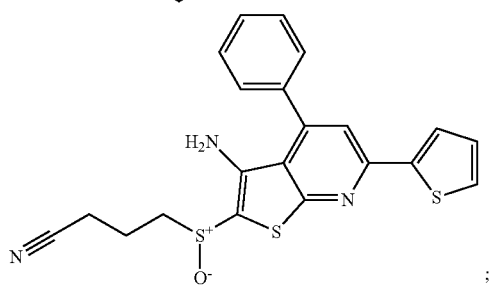
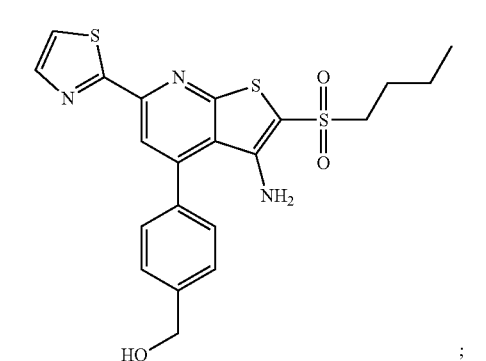
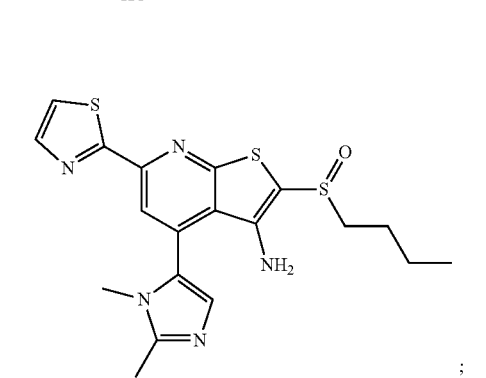
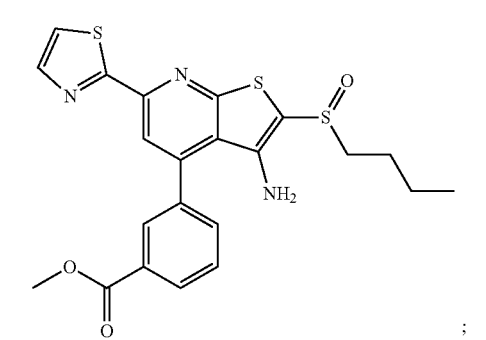
62
-continued
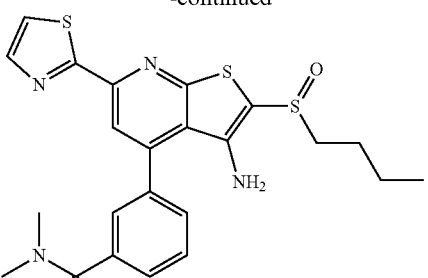
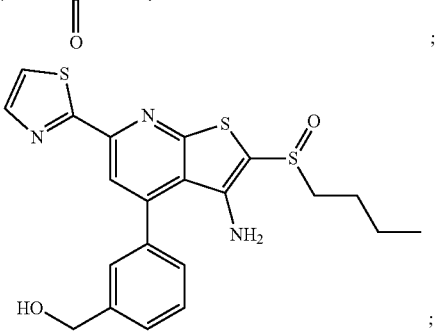
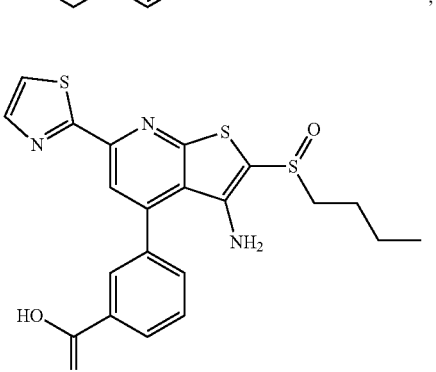
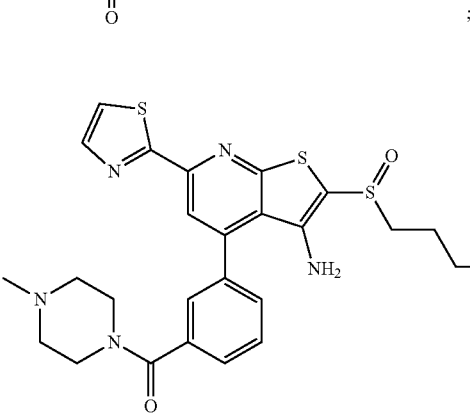
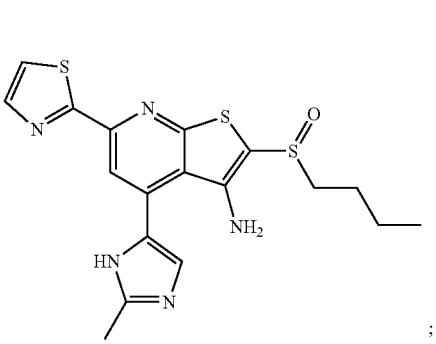

63
-continued
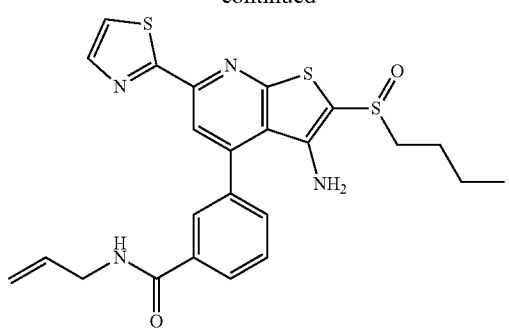
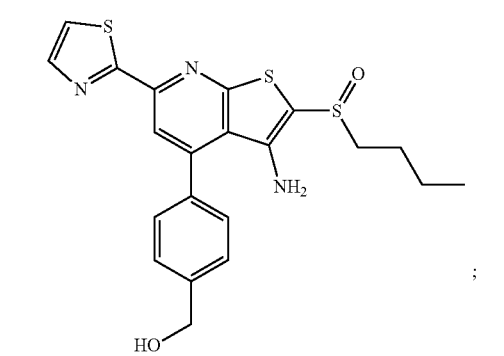
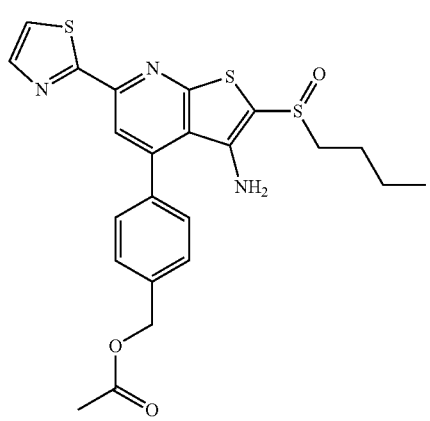
64
-continued
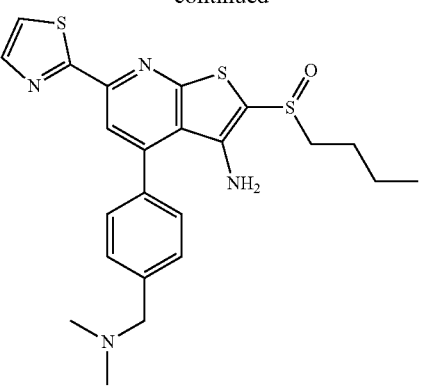
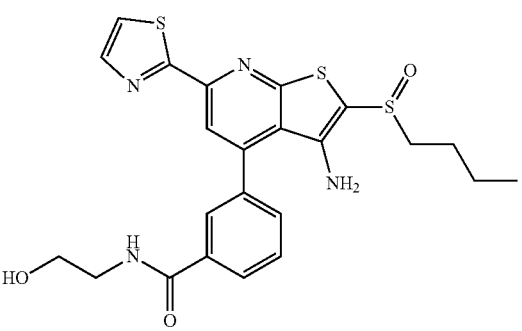
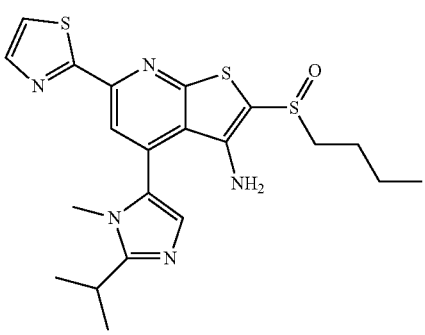
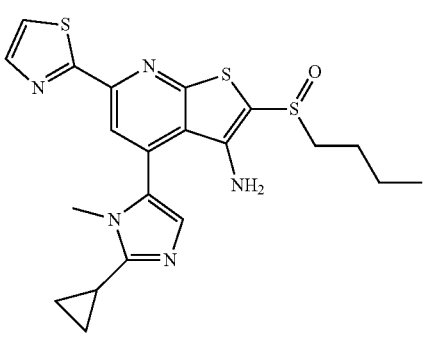

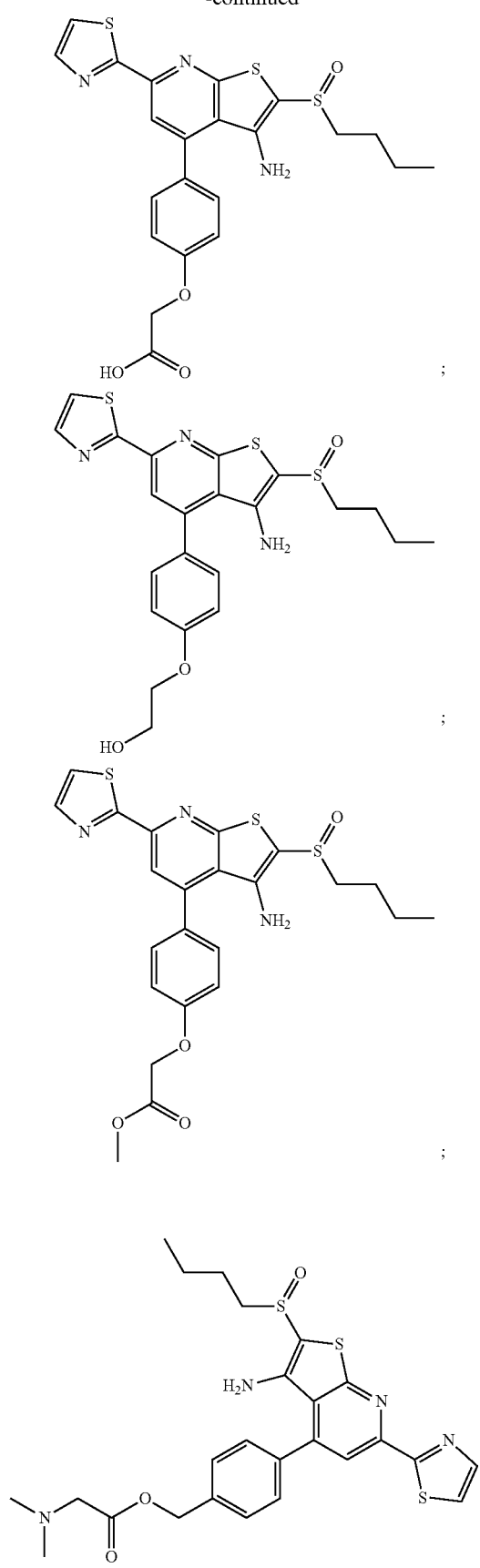
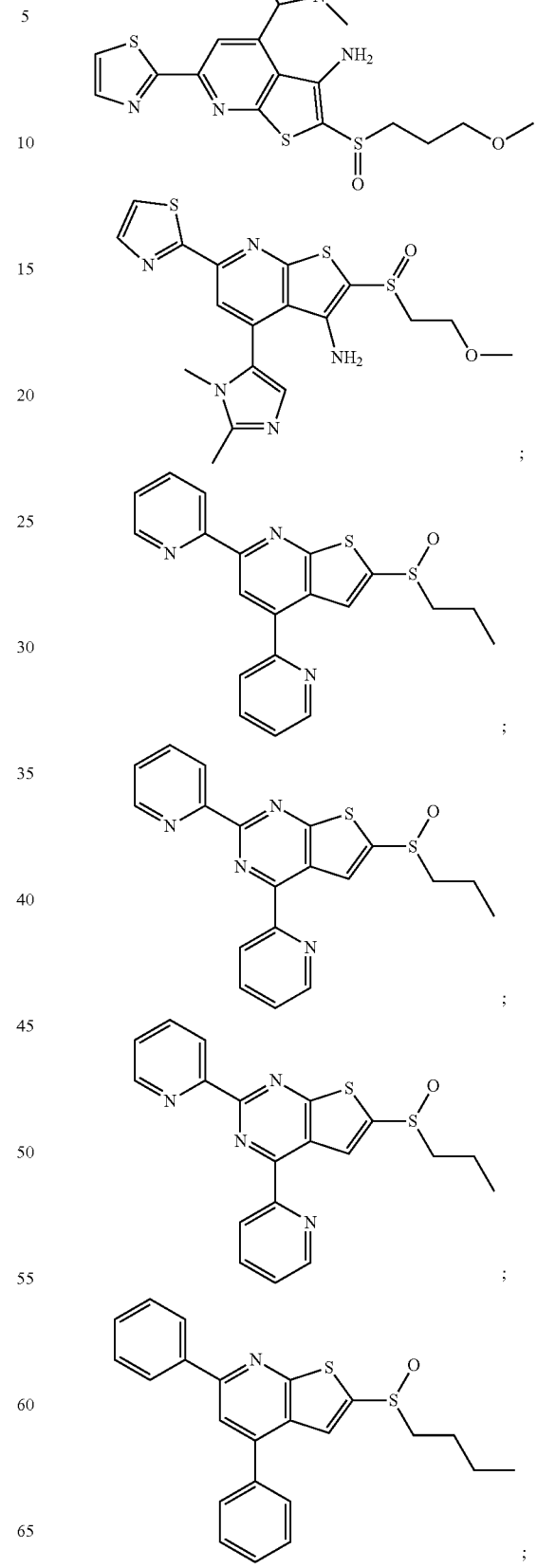

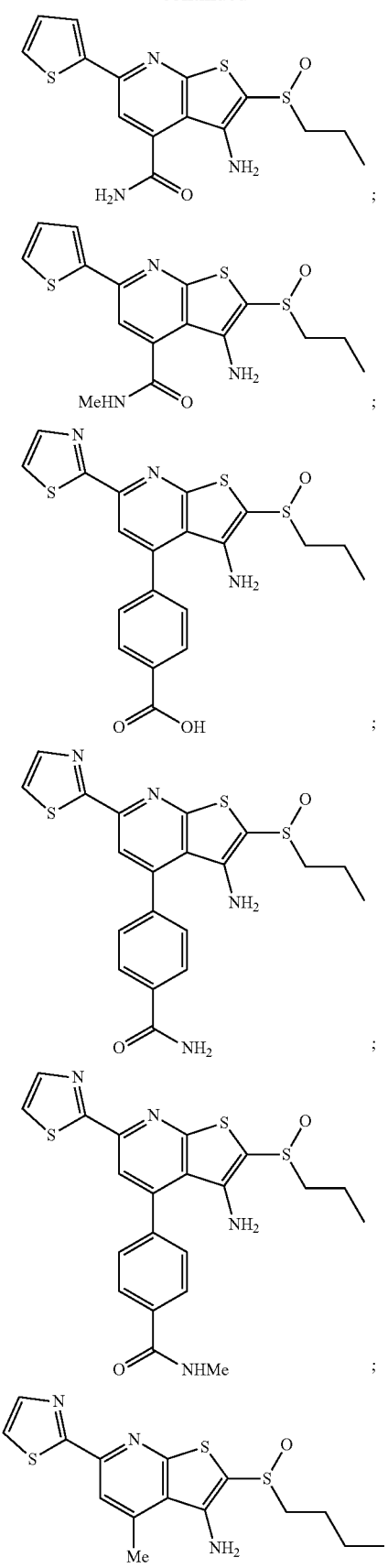
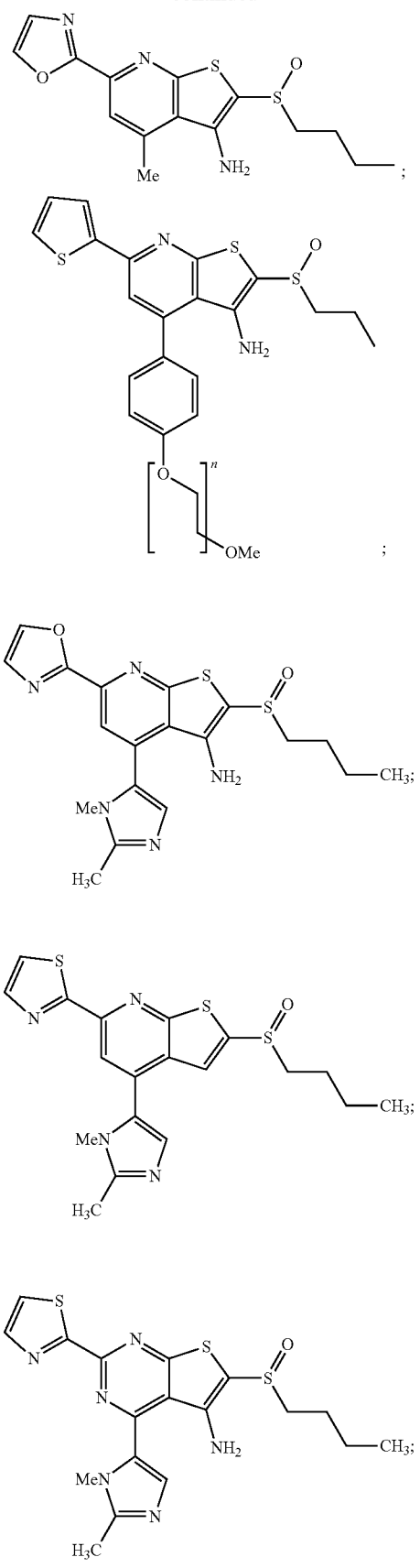

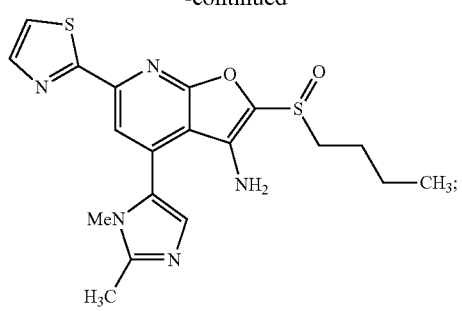
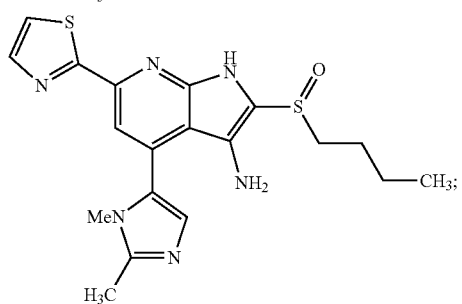
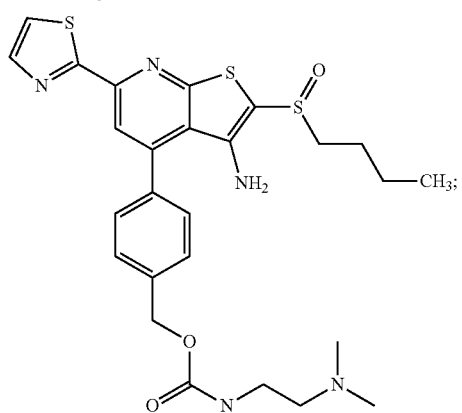
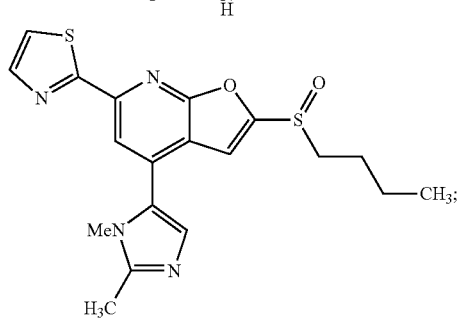
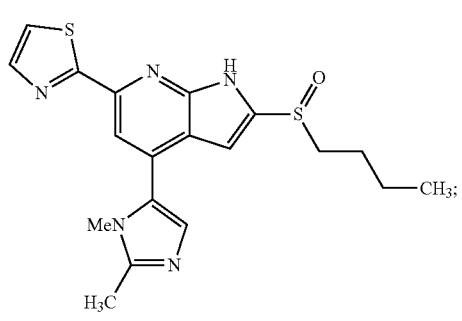
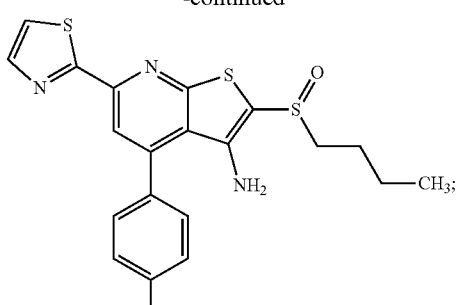
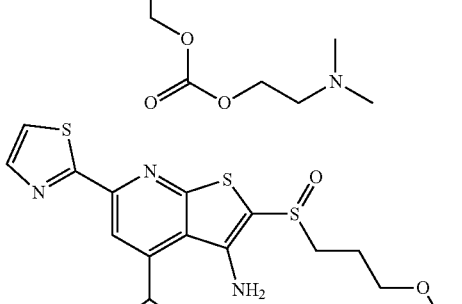
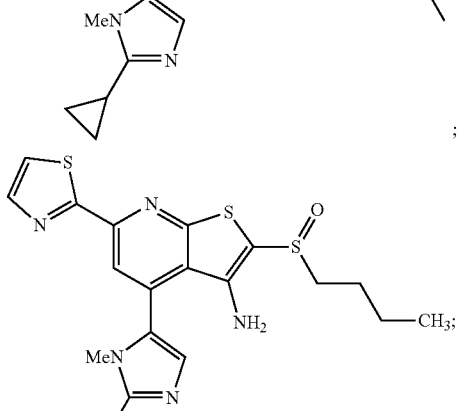
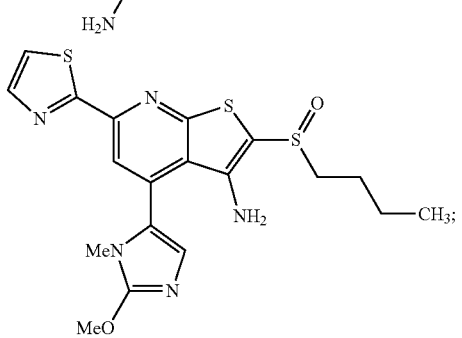
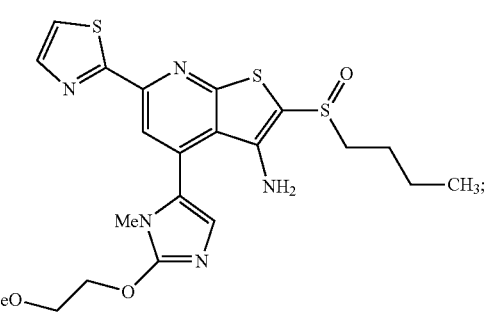

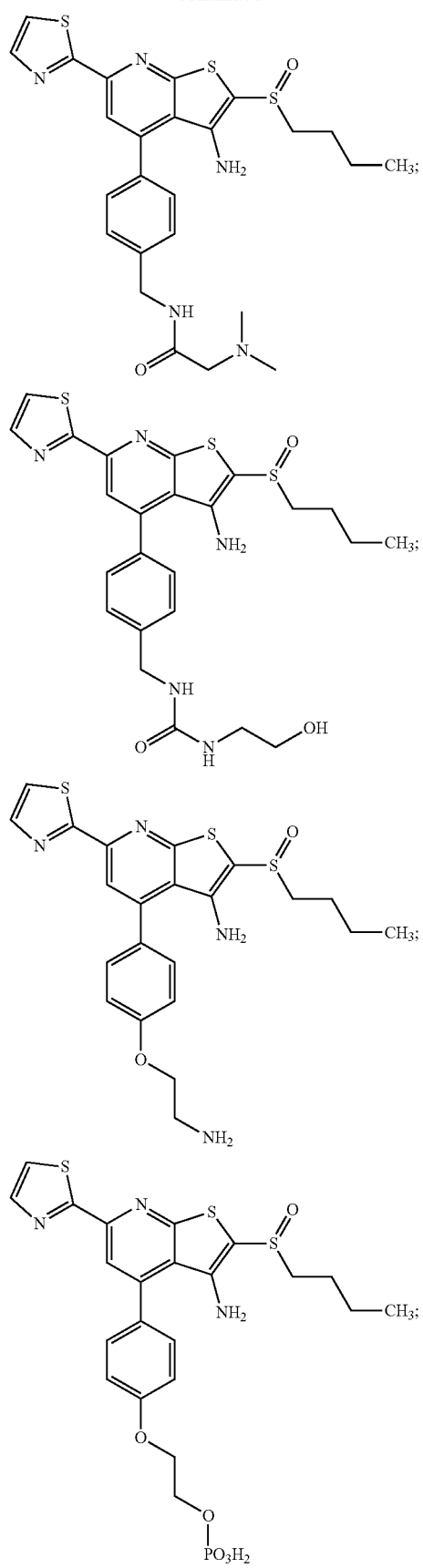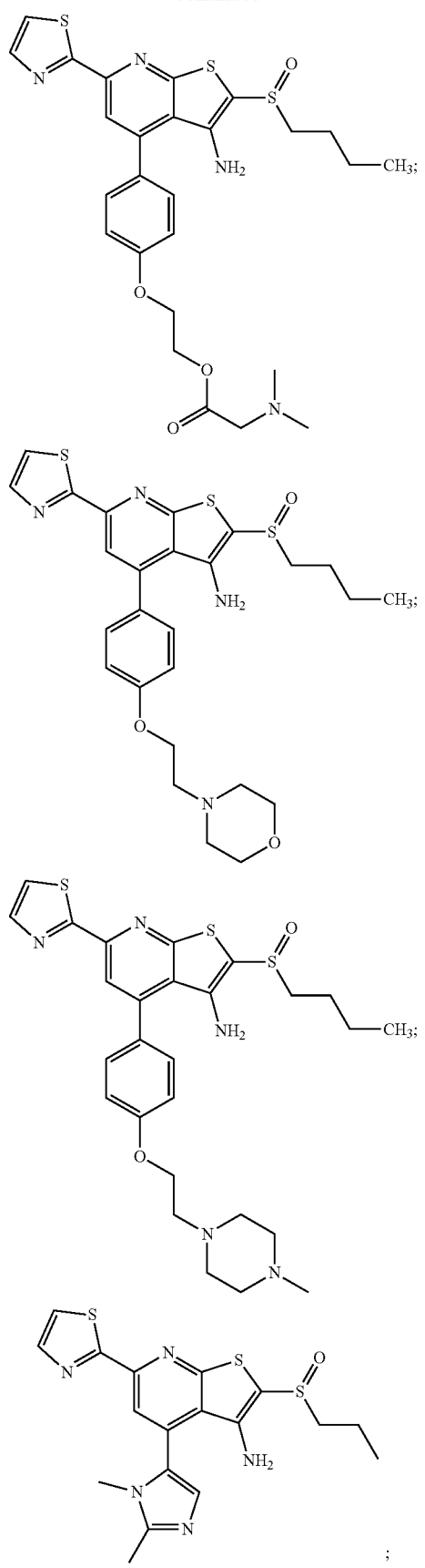 [SMILES: CCCCS(=O)c1sc2nc(-c3nccs3)cc(-c3ccc(OCCOC(=O)CN(C)C)cc3)c2c1N ; CCCCS(=O)c1sc2nc(-c3nccs3)cc(-c3ccc(OCCN4CCOCC4)cc3)c2c1N ; CCCCS(=O)c1sc2nc(-c3nccs3)cc(-c3ccc(OCCN4CCN(C)CC4)cc3)c2c1N ; CCCS(=O)c1sc2nc(-c3nccs3)cc(-c3cnc(C)n3C)c2c1N]

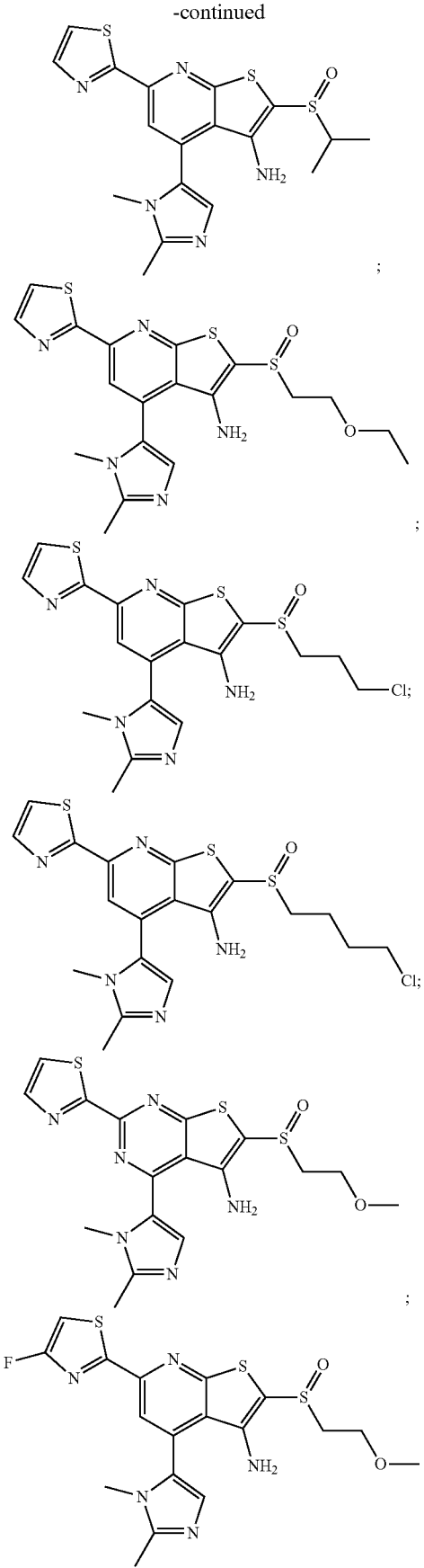
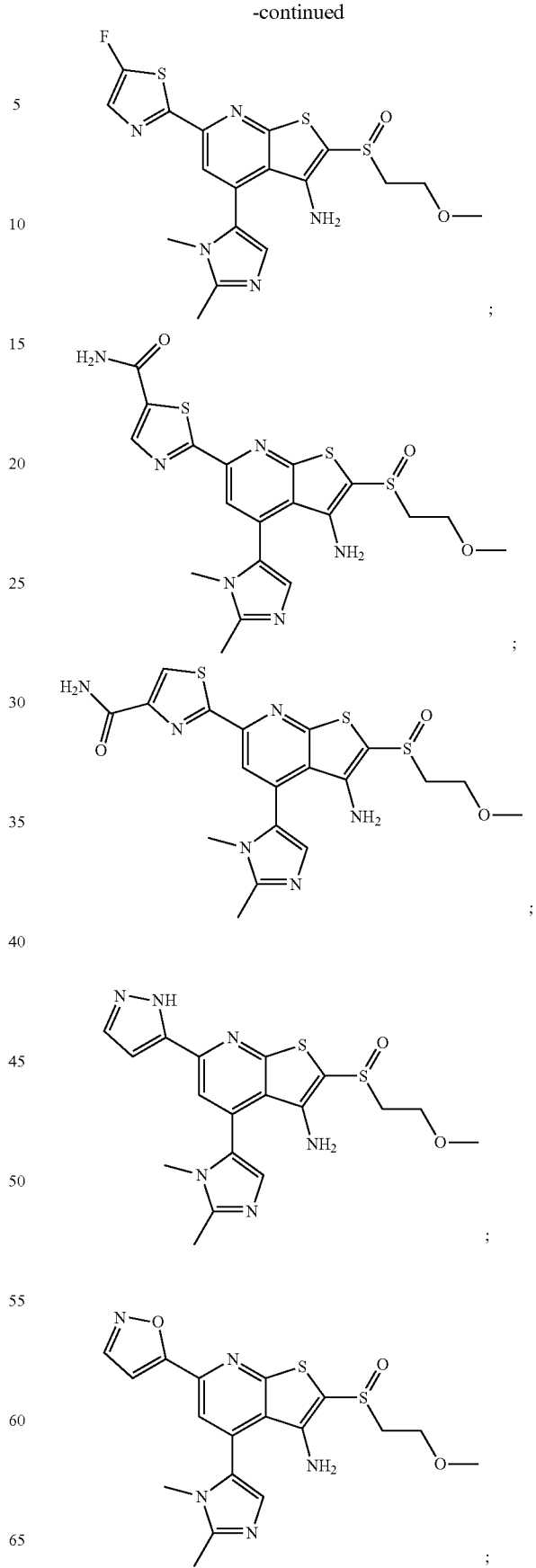

75
-continued
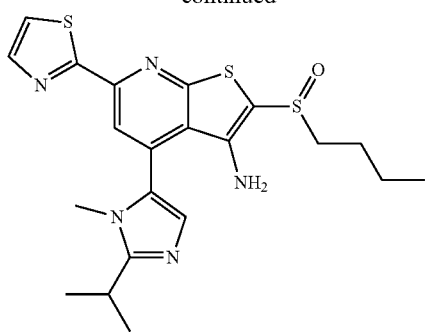
;
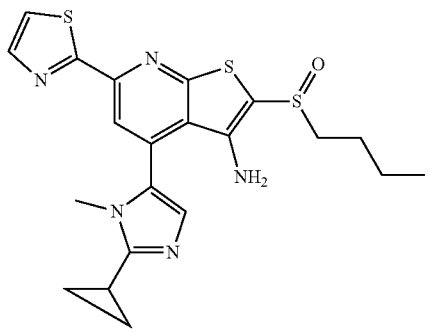
;
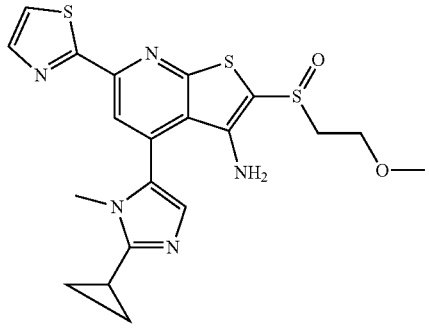
;
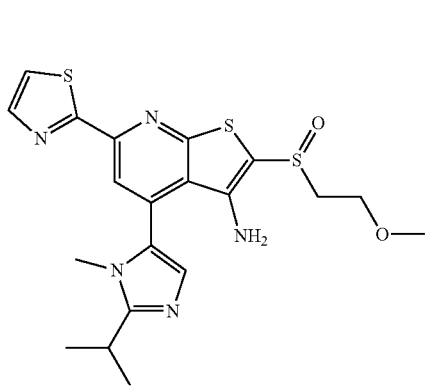
;
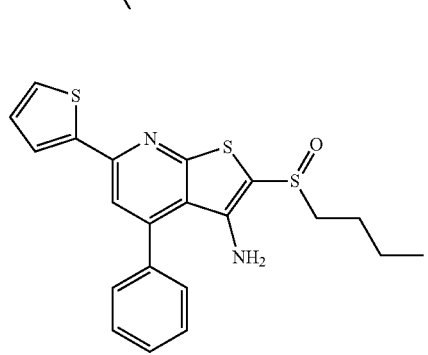
;
76
-continued
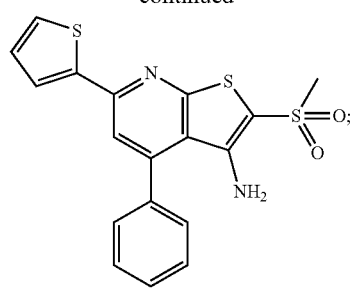
;
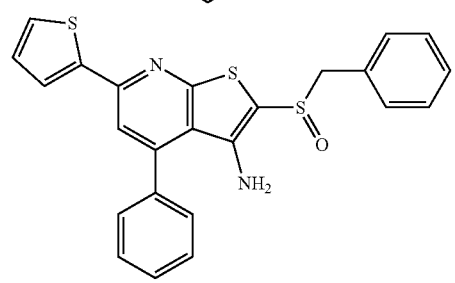
;
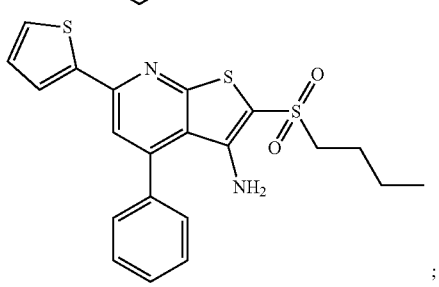
;
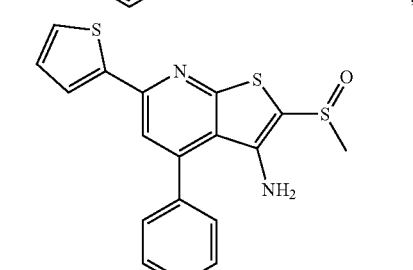
;
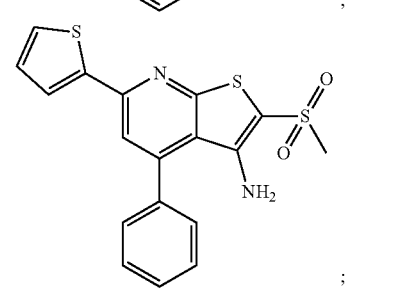
;
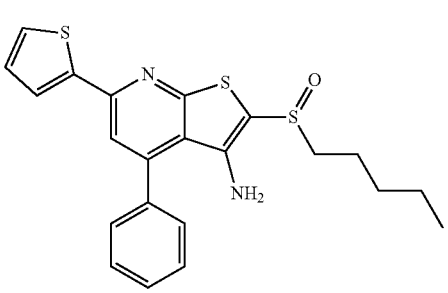
;

-continued

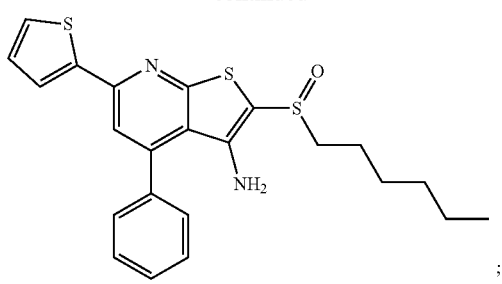

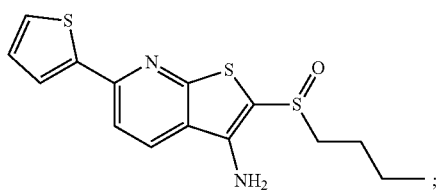

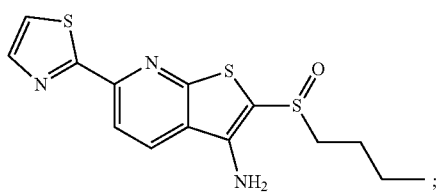

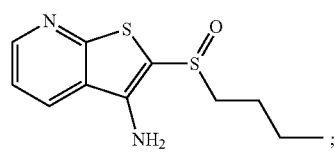

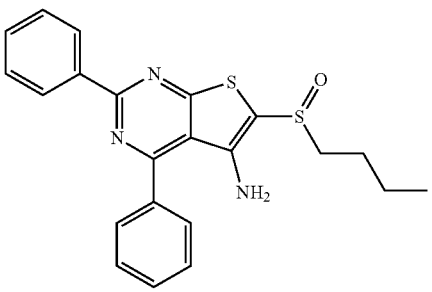

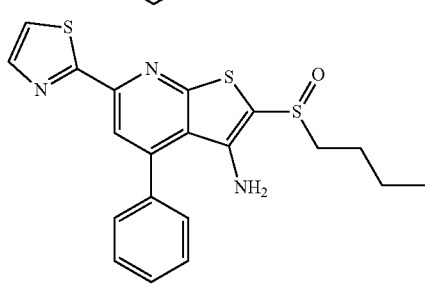

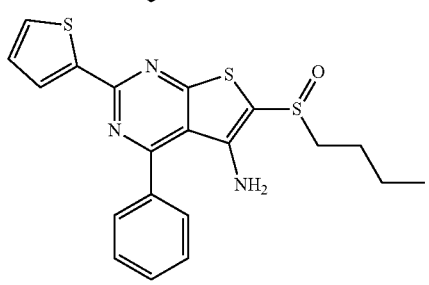

-continued

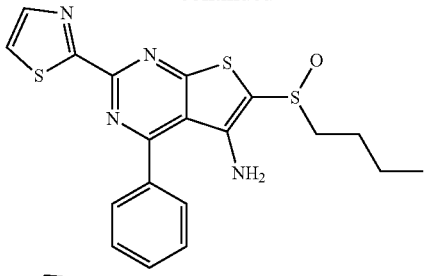

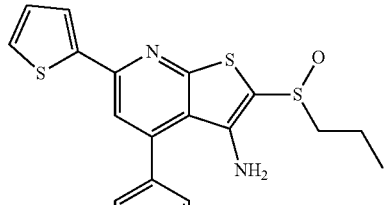

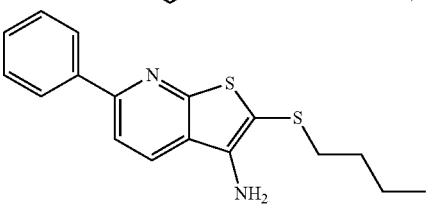

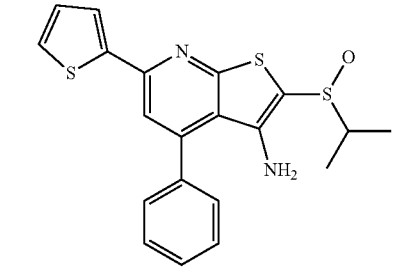

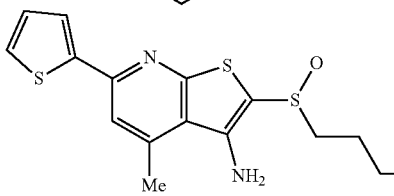

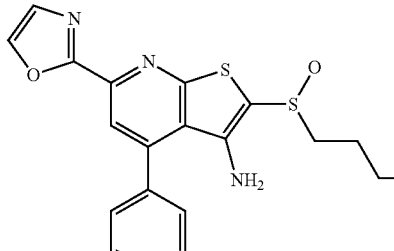

and pharmaceutically acceptable salts thereof.

In certain embodiments, the 15-PGDH inhibitor having formula (I), (11), (111), (IV), (V), (VI), and (VII) can be selected that can ia) at 2.5 µM concentration, stimulate a Vaco503 reporter cell line expressing a 15-PGDH luciferase fusion construct to a luciferase output level of greater than 70 (using a scale on which a value of 100 indicates a doubling of reporter output over baseline); iia) at 2.5 µM concentration stimulate a V9m reporter cell line expressing a 15-PGDH luciferase fusion construct to a luciferase output level of greater than 75; iiia) at 7.5 μM concentration stimulate a LS174T reporter cell line expressing a 15-PGDH luciferase fusion construct to a luciferase output level of greater than 70; and iva) at 7.5 μM concentration, does not activate a negative control V9m cell line expressing TK-renilla luciferase reporter to a level greater than 20; and va) inhibits the enzymatic activity of recombinant 15-PGDH protein at an $IC_{50}$ of less than 1 μM.

In other embodiments, the 15-PGDH inhibitor can ib) at 2.5 μM concentration, stimulate a Vaco503 reporter cell line expressing a 15-PGDH luciferase fusion construct to increase luciferase output; iib) at 2.5 μM concentration stimulate a V9m reporter cell line expressing a 15-PGDH luciferase fusion construct to increase luciferase output; iiib) at 7.5 μM concentration stimulate a LS174T reporter cell line expressing a 15-PGDH luciferase fusion construct to increase luciferase output; ivb) at 7.5 μM concentration, does not activate a negative control V9m cell line expressing TK-renilla luciferase reporter to a luciferase level greater than 20% above background; and vb) inhibits the enzymatic activity of recombinant 15-PGDH protein at an $IC_{50}$ of less than 1 μM.

In other embodiments, the 15-PGDH inhibitor can inhibit the enzymatic activity of recombinant 15-PGDH at an $IC_{50}$ of less than 1 μM, or preferably at an $IC_{50}$ of less than 250 nM, or more preferably at an $IC_{50}$ of less than 50 nM, or more preferably at an $IC_{50}$ of less than 10 nM, or more preferably at an $IC_{50}$ of less than 5 nM at a recombinant 15-PGDH concentration of about 5 nM to about 10 nM.

In other embodiments, the 15-PGDH inhibitor can increase the cellular levels of PGE-2 following stimulation of an A459 cell with an appropriate agent, for example IL1-beta.

In some embodiments, a15-PGDH inhibitor can include a compound having the following formula (VIII):

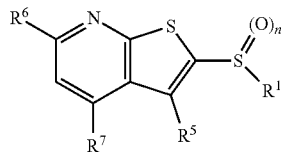

(VIII)

wherein n is 0-2;
$R^1$, $R^6$, and $R^7$ are the same or different and are each selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O) ($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkylethers, phosphates, phosphate esters, groups incorporating amino acids or other moieties expected to bear positive or negative charge at physiological pH, combinations thereof, and wherein $R^6$ and $R^7$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl; and pharmaceutically acceptable salts thereof.

15-PGDH inhibitors having formula (VIII) can be synthesized as shown:

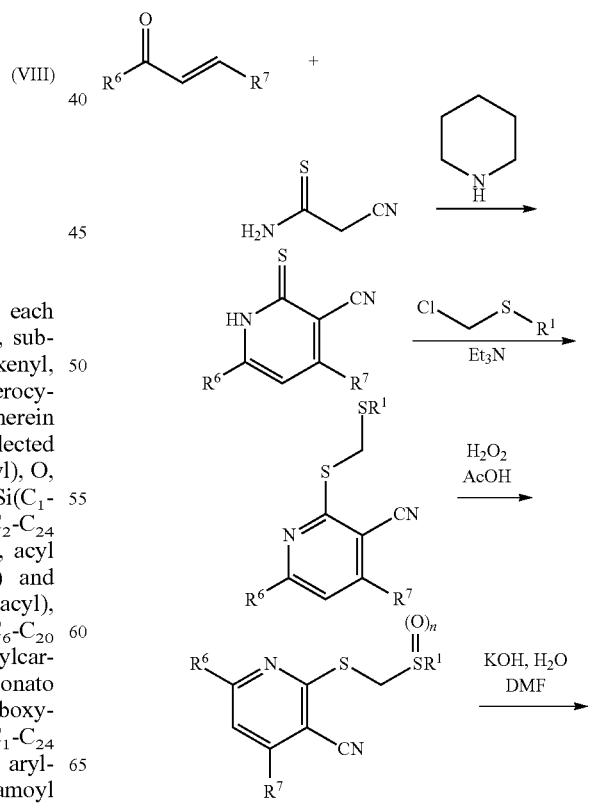

-continued

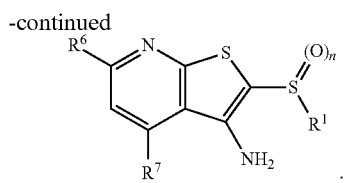

Any reaction solvent can be used in the above preparation process as long as it is not involved in the reaction. For example, the reaction solvent includes ethers such as diethyl ether, tetrahydrofuran and dioxane; halogenized hydrocarbons, such as dichloromethane and chloroform; amines such as pyridine, piperidine and triethylamine; alkylketones, such as acetone, methylethylketone and methylisobutyl; alcohols, such as methanol, ethanol and propanol; non-protonic polar solvent, such as N,N-dimethylformamide, N,N-dimethylacetamide, acetonitrile, dimethylsulfoxide and hexamethyl phosphoric acid triamide. Among non-reactive organic solvents that are ordinarily used in the organic synthesis, preferable solvents are those from which water generated in the reaction can be removed by a Dean-Stark trap. The examples of such solvents include, but are not limited to benzene, toluene, xylene and the like. The reaction product thus obtained may be isolated and purified by condensation, extraction and the like, which is ordinarily conducted in the field of the organic synthesis, if desired, by silica gel column chromatography. The individual enantiomers of PGDH inhibitors having the formula III can be separated by a preparative HPLC using chromatography columns containing chiral stationary phases.

Further, embodiments of this application include any modifications for the preparation method of the 15-PGDH inhibitors described above. In this connection, any intermediate product obtainable from any step of the preparation method can be used as a starting material in the other steps. Such starting material can be formed in situ under certain reaction conditions. Reaction reagents can also be used in the form of their salts or optical isomers.

Depending on the kinds of the substituents to be used in the preparation of the 15-PGDH inhibitors, and the intermediate product and the preparation method selected, novel 15-PGDH inhibitors can be in the form of any possible isomers such as substantially pure geometrical (cis or trans) isomers, optical isomers (enantiomers) and racemates.

In some embodiments, a 15-PGDH inhibitor having formula (VIII) can include a compound with the following formula (IX):

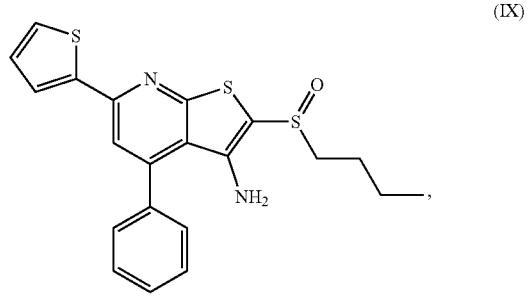 [SMILES: CCCCS(=O)c1sc2nc(-c3cccs3)cc(-c3ccccc3)c2c1N]

(IX)

and pharmaceutically acceptable salts thereof.

Advantageously, the 15-PDGH inhibitor having formula (IX) was found to: i) inhibit recombinant 15-PGDH at 1 nM concentration; ii) inhibit 15-PGDH in cell lines at 100 nM concentration, iii) increase $PGE_2$ production by cell lines; iv) is chemically stable in aqueous solutions over broad pH range; v) is chemically stable when incubated with hepatocyte extracts, vi) is chemically stable when incubated with hepatocyte cell lines; vii) shows 253 minutes plasma half-life when injected IP into mice; and viii) shows no immediate toxicity over 24 hours when injected IP into mice at 0.6 µmole/per mouse and at 1.2 µmole/per mouse and also no toxicity when injected IP into mice at 0.3 µmole/per mouse twice daily for 21 days.

In other embodiments, a 15-PGDH inhibitor having formula (IX) can include a compound with the following formula (IXa):

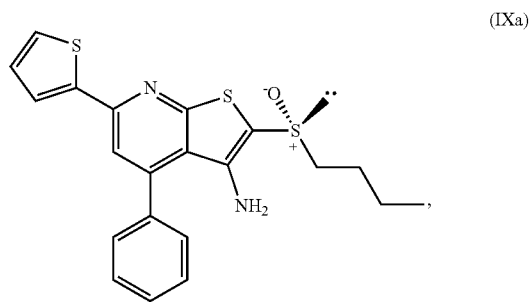

(IXa)

and pharmaceutically acceptable salts thereof.

In still other embodiments, a 15-PGDH inhibitor having formula (IX) can include a compound with the following formula (IXb):

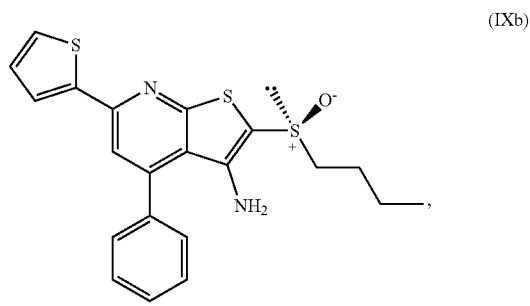

(IXb)

and pharmaceutically acceptable salts thereof.

In other embodiments, the 15-PDHG inhibitor can comprise a (+) or (−) optical isomer of a 15-PGDH inhibitor having formula (IX). In still other embodiments, the 15-PDHG inhibitor can comprise a mixture at least one of a (+) or (−) optical isomer of a 15-PGDH inhibitor having formula (IX). For example, the 15-PGDH inhibitor can comprise a mixture of: less than about 50% by weight of the (−) optical isomer of a 15-PGDH inhibitor having formula (IX) and greater than about 50% by weight of the (+) optical isomer of a 15-PGDH inhibitor having formula (IX), less than about 25% by weight of the (−) optical isomer of a 15-PGDH inhibitor having formula (IX) and greater than about 75% by weight of the (+) optical isomer of a 15-PGDH inhibitor having formula (IX), less than about 10% by weight of the (−) optical isomer of a 15-PGDH inhibitor having formula (IX) and greater than about 90% by weight of the (+) optical isomer of a 15-PGDH inhibitor having formula (IX), less than about 1% by weight of the (−) optical isomer of a 15-PGDH inhibitor having formula (IX) and greater than about 99% by weight of the (+) optical isomer of a 15-PGDH inhibitor having formula (IX), greater than about 50% by weight of the (−) optical isomer of a 15-PGDH inhibitor having formula (IX) and less than about 50% by weight of the (+) optical isomer of a 15-PGDH inhibitor having formula (IX), greater than about 75% by weight of the (−) optical isomer of a 15-PGDH inhibitor having formula (IX) and less than about 25% by weight of the (+) optical isomer of a 15-PGDH inhibitor having formula (IX), greater than about 90% by weight of the (−) optical isomer of a 15-PGDH inhibitor having formula (IX) and less than about 10% by weight of the (+) optical isomer of a 15-PGDH inhibitor having formula (IX), or greater than about 99% by weight of the (−) optical isomer of a 15-PGDH inhibitor having formula (IX) and less than about 1% by weight of the (+) optical isomer of a 15-PGDH inhibitor having formula (IX).

In a still further embodiment, the 15-PDGH inhibitor can consist essentially of or consist of the (+) optical isomer of a 15-PGDH inhibitor having formula (IX). In yet another embodiment, the PDGH inhibitor can consist essentially of or consist of the (−) optical isomer of a 15-PGDH inhibitor having formula (IX).

In other embodiments, a 15-PGDH inhibitor having formula (VIII) can include a compound with the following formula (X):

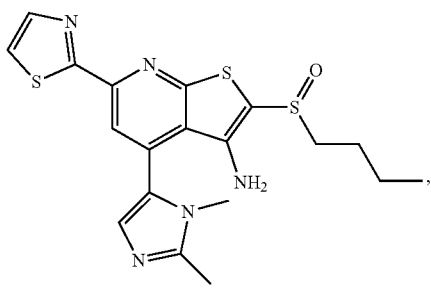

(X)

and pharmaceutically acceptable salts thereof.

Advantageously, the 15-PDGH inhibitor having formula (X) was found to: i) inhibit recombinant 15-PGDH at 3 nM concentration; ii) increase $PGE_2$ production by cell lines at 20 nM; iii) is chemically stable in aqueous solutions over broad pH range; iv) is chemically stable when incubated with mouse, rat and human liver extracts, v) shows 33 minutes plasma half-life when injected IP into mice; viii) shows no immediate toxicity over 24 hours when injected IP into mice at 50 mg/kg body weight, and ix) is soluble in water (pH=3) at 1 mg/mL.

In other embodiments, a 15-PGDH inhibitor having formula (X) can include a compound with the following formula (Xa):

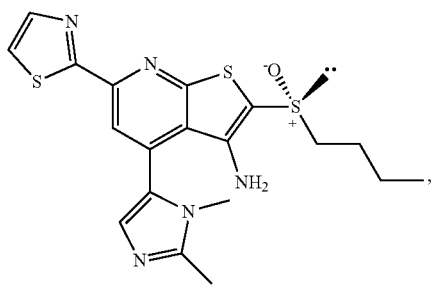

(Xa)

and pharmaceutically acceptable salts thereof.

In still other embodiments, a 15-PGDH inhibitor having formula (X) can include a compound with the following formula (Xb):

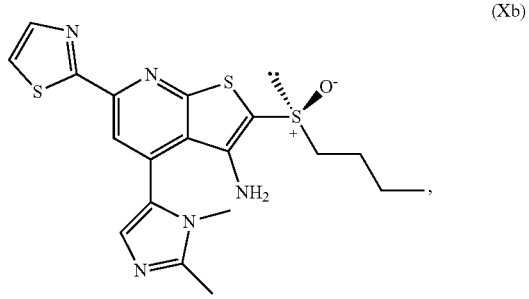

(Xb)

and pharmaceutically acceptable salts thereof.

In other embodiments, the 15-PDHG inhibitor can comprise a (+) or (−) optical isomer of a 15-PGDH inhibitor having formula (X). In still other embodiments, the 15-PDHG inhibitor can comprise a mixture at least one of a (+) or (−) optical isomer of a 15-PGDH inhibitor having formula (X). For example, the 15-PGDH inhibitor can comprise a mixture of: less than about 50% by weight of the (−) optical isomer of a 15-PGDH inhibitor having formula (X) and greater than about 50% by weight of the (+) optical isomer of a 15-PGDH inhibitor having formula (X), less than about 25% by weight of the (−) optical isomer of a 15-PGDH inhibitor having formula (X) and greater than about 75% by weight of the (+) optical isomer of a 15-PGDH inhibitor having formula (X), less than about 10% by weight of the (−) optical isomer of a 15-PGDH inhibitor having formula (X) and greater than about 90% by weight of the (+) optical isomer of a 15-PGDH inhibitor having formula (X), less than about 1% by weight of the (−) optical isomer of a 15-PGDH inhibitor having formula (X) and greater than about 99% by weight of the (+) optical isomer of a 15-PGDH inhibitor having formula (X), greater than about 50% by weight of the (−) optical isomer of a 15-PGDH inhibitor having formula (X) and less than about 50% by weight of the (+) optical isomer of a 15-PGDH inhibitor having formula (X), greater than about 75% by weight of the (−) optical isomer of a 15-PGDH inhibitor having formula (X) and less than about 25% by weight of the (+) optical isomer of a 15-PGDH inhibitor having formula (X), greater than about 90% by weight of the (−) optical isomer of a 15-PGDH inhibitor having formula (X) and less than about 10% by weight of the (+) optical isomer of a 15-PGDH inhibitor having formula (X), or greater than about 99% by weight of the (−) optical isomer of a 15-PGDH inhibitor having formula (X) and less than about 1% by weight of the (+) optical isomer of a 15-PGDH inhibitor having formula (X).

In a still further embodiment, the 15-PDGH inhibitor can consist essentially of or consist of the (+) optical isomer of a 15-PGDH inhibitor having formula (X). In yet another embodiment, the PDGH inhibitor can consist essentially of or consist of the (−) optical isomer of a 15-PGDH inhibitor having formula (X).

It will be appreciated that the other 15-PGDH inhibitors can be used in the methods described herein. These other 15-PGDH inhibitors can include known 15-PGDH inhibitors including, for example, tetrazole compounds of formulas (I) and (II), 2-alkylideneaminooxyacetamide compounds of formula (I), heterocyclic compounds of formulas (VI) and (VII), and pyrazole compounds of formula (III) described in U.S. Patent Application Publication No. 2006/0034786 and U.S. Pat. No. 7,705,041; benzylidene-1,3-thiazolidine compounds of formula (I) described in U.S. Patent Application Publication No. 2007/0071699; phenylfurylnethylthiazolidine-2,4-dione and phenylthienylmethylthiazolidine-2,4-dione compounds described in U.S. Patent Application Publication No. 2007/0078175; thiazolidenedione derivatives described in U.S. Patent Application Publication No. 2011/0269954; phenylfuran, phenylthiophene, or phenylpyrrazole compounds described in U.S. Pat. No. 7,294,641, 5-(3,5-disubstituted phenylazo)-2-hydroxybenzene-acetic acids and salts and lactones described in U.S. Pat. No. 4,725,676, and azo compounds described in U.S. Pat. No. 4,889,846.

In certain embodiments, the corticosteroid is selected from the group consisting of aclovate, alclometasone dipropionate, amcinafel, amcinafide, amcinonide, aristocort A, augmented betamethasone dipropionate, beclamethasone, beclopmethasone dipropionate, betamethasone, betamethasone benzoate, betamethasone-17-benzoate, betamethasone dipropionate, betamethasone sodium phosphate and acetate, betamethasone valerate, betamethasone-17-valerate, chloroprednisone, clobetasol propionate, clobetasone propionate, clocortelone, cordran, corticosterone, cortisol, cortisol acetate, cortisol cypionate, cortisol sodium phosphate, cortisol sodium succinate, cortisone, cortisone acetate, cortodoxone, cyclocort, deflazacort, defluprednate, descinolone, desonide, desowen, desoximetasone, desoxycorticosterone acetate, desoxycorticosterone pivalate, 11-desoxycortisol, dexamethasone, dexamethasone acetate, dexamethasone sodium phosphate, dichlorisone, diflorasone diacetate, dihydroxycortisone, diprolen, diprolene, diprosone, esters of betamethasone, florone, flucetonide, flucloronide, flucortolone, fludrocortisone, fludrocortisone acetate, flumethalone, flumethasone, flumethasone pivalate, flunisolide, fluocinolone acetonide, fluocinolone acetonide acetate, fluocinonide, fluorametholone, fluorocortisone, fluperolone, fluprednisolone, flurandrenolide, fluroandrenolone acetonide, fluticasone propionate, fuprednisolone, halcinonide, halobetasol propionate, halog, hydrocortamate, hydrocortisone, hydrocortisone acetate, hydrocortisone butyrate, hydrocortisone valerate, hydrocortisone-17-valerate, kenalog, lidex, locold, locorten, maxiflor, medrysone, meprednisone, methylprednisolone, 6 α-methylprednisolone, methylprednisolone acetate, methylprednisolone sodium succinate, methylprednisone, mometasone furoate, paramethasone, paramethasone acetate, prednidone, prednisone, prednisolone, prednisolone acetate, prednisolone sodium phosphate, prednisolone sodium succinate, prednisolone tebutate, prednisone, psorcon, synalar, temovate, tetrahydrocortisol, topicort, topicort LP, triamcinolone, triamcinolone acetonide, triamcinolone diacetate, triamcinolone hexacotonide, tridesilone, valisone, and westcort.

In other embodiments, the corticosteroids to be used in combination with the 15-PGDH inhibitors described herein are prednisolone, methylprednisolone, dexamethasone, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone furoate, rimexolone, prednisolone famesylate, ciclesonide, deprodone propionate, fluticasone, fluticasone propionate, fluticasone furoate, halobetasol propionate, loteprednol etabonate, betamethasone butyrate propionate, flunisolide, prednisone, dexamethasone sodium phosphate, triamcinolone, betamethasone 17-valerate, betamethasone, hydrocortisone acetate, hydrocortisone sodium succinate, prednisolone sodium phosphate and hydrocortisone probutate.

In certain embodiments, TNF inhibitors described herein can include, but are not limited to, anti-TNF alpha antibodies (such as infliximab, adalimumab certolizumab pegol, and/or golimumab), receptor-construct fusion proteins (such as etanercept), or small molecules, such as, but not limited to, pomalidomide, thalidomide, lenalidomide and bupropion.

The 15-PGDH inhibitors and corticosteroids and TNF inhibitors described herein can be provided in a pharmaceutical composition. A pharmaceutical composition containing the 15-PGDH inhibitors and corticosteroids described herein as an active ingredient may be manufactured by mixing the derivative with a pharmaceutically acceptable carrier(s) or an excipient(s) or diluting the 15-PGDH inhibitors and corticosteroids and TNF inhibitors described herein with a diluent in accordance with conventional methods. The pharmaceutical composition may further contain fillers, anticohesives, lubricants, wetting agents, flavoring agents, emulsifying agents, preservatives and the like. The pharmaceutical composition may be formulated into a suitable formulation in accordance with the methods known to those skilled in the art so that it can provide an immediate, controlled or sustained release of the 15-PGDH inhibitors and/or corticosteroids described herein after being administered into a mammal.

In some embodiments, the pharmaceutical composition may be formulated into a parenteral or oral dosage form. The solid dosage form for oral administration may be manufactured by adding excipient, if necessary, together with binder, disintegrants, lubricants, coloring agents, and/or flavoring agents, to the 15-PGDH inhibitors and corticosteroids described herein and shaping the resulting mixture into the form of tablets, sugar-coated pills, granules, powder or capsules. The additives that can be added in the composition may be ordinary ones in the art. For example, examples of the excipient include lactose, sucrose, sodium chloride, glucose, starch, calcium carbonate, kaolin, microcrystalline cellulose, silicate and the like. Exemplary binders include water, ethanol, propanol, sweet syrup, sucrose solution, starch solution, gelatin solution, carboxymethylcellulose, hydroxypropyl cellulose, hydroxypropyl starch, methylcellulose, ethylcellulose, shellac, calcium phosphonate and polypyrrolidone. Examples of the disintegrant include dry starch, sodium arginate, agar powder, sodium bicarbonate, calcium carbonate, sodium lauryl sulfate, stearic monoglyceride and lactose. Further, purified talc, stearates, sodium borate, and polyethylene glycol may be used as a lubricant; and sucrose, bitter orange peel, citric acid, tartaric acid, may be used as a flavoring agent. In some embodiments, the pharmaceutical composition can be made into aerosol formulations (e.g., they can be nebulized) to be administered via inhalation.

The 15-PGDH inhibitors and corticosteroids described herein described herein may be combined with flavoring agents, buffers, stabilizing agents, and the like and incorporated into oral liquid dosage forms such as solutions, syrups or elixirs in accordance with conventional methods. One example of the buffers may be sodium citrate. Examples of the stabilizing agents include tragacanth, acacia and gelatin.

In some embodiments, the 15-PGDH inhibitors and corticosteroids described herein described herein may be incorporated into an injection dosage form, for example, for a subcutaneous, intramuscular or intravenous route by adding thereto pH adjusters, buffers, stabilizing agents, relaxants, topical anesthetics. Examples of the pH adjusters and the buffers include sodium citrate, sodium acetate and sodium phosphate. Examples of the stabilizing agents include sodium pyrosulfite, EDTA, thioglycolic acid and thiolactic acid. The topical anesthetics may be procaine HCl, lidocaine HCl and the like. The relaxants may be sodium chloride, glucose and the like.

In other embodiments, the 15-PGDH inhibitors and corticosteroids described herein described herein may be incorporated into suppositories in accordance with conventional methods by adding thereto pharmaceutically acceptable carriers that are known in the art, for example, polyethylene glycol, lanolin, cacao butter or fatty acid triglycerides, if necessary, together with surfactants such as Tween.

The pharmaceutical composition may be formulated into various dosage forms as discussed above and then administered through various routes including an oral, inhalational, transdermal, subcutaneous, intravenous or intramuscular route. The dosage can be a pharmaceutically or therapeutically effective amount.

Therapeutically effective dosage amounts of the 15-PGDH inhibitor and corticosteroids described herein may be present in varying amounts in various embodiments. For example, in some embodiments, a therapeutically effective amount of the 15-PGDH inhibitor may be an amount ranging from about 10-1000 mg (e.g., about 20 mg-1,000 mg, 30 mg-1,000 mg, 40 mg-1,000 mg, 50 mg-1,000 mg, 60 mg-1,000 mg, 70 mg-1,000 mg, 80 mg-1,000 mg, 90 mg-1,000 mg, about 10-900 mg, 10-800 mg, 10-700 mg, 10-600 mg, 10-500 mg, 100-1000 mg, 100-900 mg, 100-800 mg, 100-700 mg, 100-600 mg, 100-500 mg, 100-400 mg, 100-300 mg, 200-1000 mg, 200-900 mg, 200-800 mg, 200-700 mg, 200-600 mg, 200-500 mg, 200-400 mg, 300-1000 mg, 300-900 mg, 300-800 mg, 300-700 mg, 300-600 mg, 300-500 mg, 400 mg-1,000 mg, 500 mg-1,000 mg, 100 mg-900 mg, 200 mg-800 mg, 300 mg-700 mg, 400 mg-700 mg, and 500 mg-600 mg). In some embodiments, the 15-PGDH inhibitor is present in an amount of or greater than about 10 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg. In some embodiments, the 15-PGDH inhibitor is present in an amount of or less than about 1000 mg, 950 mg, 900 mg, 850 mg, 800 mg, 750 mg, 700 mg, 650 mg, 600 mg, 550 mg, 500 mg, 450 mg, 400 mg, 350 mg, 300 mg, 250 mg, 200 mg, 150 mg, or 100 mg.

In other embodiments, a therapeutically effective amount of the corticosteroid may be an amount ranging from about 10-1000 mg (e.g., about 20 mg-1,000 mg, 30 mg-1,000 mg, 40 mg-1,000 mg, 50 mg-1,000 mg, 60 mg-1,000 mg, 70 mg-1,000 mg, 80 mg-1,000 mg, 90 mg-1,000 mg, about 10-900 mg, 10-800 mg, 10-700 mg, 10-600 mg, 10-500 mg, 100-1000 mg, 100-900 mg, 100-800 mg, 100-700 mg, 100-600 mg, 100-500 mg, 100-400 mg, 100-300 mg, 200-1000 mg, 200-900 mg, 200-800 mg, 200-700 mg, 200-600 mg, 200-500 mg, 200-400 mg, 300-1000 mg, 300-900 mg, 300-800 mg, 300-700 mg, 300-600 mg, 300-500 mg, 400 mg-1,000 mg, 500 mg-1,000 mg, 100 mg-900 mg, 200 mg-800 mg, 300 mg-700 mg, 400 mg-700 mg, and 500 mg-600 mg). In some embodiments, the corticosteroid is present in an amount of or greater than about 10 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg. In some embodiments, the corticosteroid is present in an amount of or less than about 1000 mg, 950 mg, 900 mg, 850 mg, 800 mg, 750 mg, 700 mg, 650 mg, 600 mg, 550 mg, 500 mg, 450 mg, 400 mg, 350 mg, 300 mg, 250 mg, 200 mg, 150 mg, or 100 mg.

In other embodiments, a therapeutically effective dosage amount of the 15-PGHD inhibitor and/or the corticosteroid may be, for example, about 0.001 mg/kg weight to 500 mg/kg weight, e.g., from about 0.001 mg/kg weight to 400 mg/kg weight, from about 0.001 mg/kg weight to 300 mg/kg weight, from about 0.001 mg/kg weight to 200 mg/kg weight, from about 0.001 mg/kg weight to 100 mg/kg weight, from about 0.001 mg/kg weight to 90 mg/kg weight, from about 0.001 mg/kg weight to 80 mg/kg weight, from about 0.001 mg/kg weight to 70 mg/kg weight, from about 0.001 mg/kg weight to 60 mg/kg weight, from about 0.001 mg/kg weight to 50 mg/kg weight, from about 0.001 mg/kg weight to 40 mg/kg weight, from about 0.001 mg/kg weight to 30 mg/kg weight, from about 0.001 mg/kg weight to 25 mg/kg weight, from about 0.001 mg/kg weight to 20 mg/kg weight, from about 0.001 mg/kg weight to 15 mg/kg weight, from about 0.001 mg/kg weight to 10 mg/kg weight.

In still other embodiments, a therapeutically effective dosage amount of the 15-PGHD inhibitor and/or the corticosteroid may be, for example, about 0.0001 mg/kg weight to 0.1 mg/kg weight, e.g. from about 0.0001 mg/kg weight to 0.09 mg/kg weight, from about 0.0001 mg/kg weight to 0.08 mg/kg weight, from about 0.0001 mg/kg weight to 0.07 mg/kg weight, from about 0.0001 mg/kg weight to 0.06 mg/kg weight, from about 0.0001 mg/kg weight to 0.05 mg/kg weight, from about 0.0001 mg/kg weight to about 0.04 mg/kg weight, from about 0.0001 mg/kg weight to 0.03 mg/kg weight, from about 0.0001 mg/kg weight to 0.02 mg/kg weight, from about 0.0001 mg/kg weight to 0.019 mg/kg weight, from about 0.0001 mg/kg weight to 0.018 mg/kg weight, from about 0.0001 mg/kg weight to 0.017 mg/kg weight, from about 0.0001 mg/kg weight to 0.016 mg/kg weight, from about 0.0001 mg/kg weight to 0.015 mg/kg weight, from about 0.0001 mg/kg weight to 0.014 mg/kg weight, from about 0.0001 mg/kg weight to 0.013 mg/kg weight, from about 0.0001 mg/kg weight to 0.012 mg/kg weight, from about 0.0001 mg/kg weight to 0.011 mg/kg weight, from about 0.0001 mg/kg weight to 0.01 mg/kg weight, from about 0.0001 mg/kg weight to 0.009 mg/kg weight, from about 0.0001 mg/kg weight to 0.008 mg/kg weight, from about 0.0001 mg/kg weight to 0.007 mg/kg weight, from about 0.0001 mg/kg weight to 0.006 mg/kg weight, from about 0.0001 mg/kg weight to 0.005 mg/kg weight, from about 0.0001 mg/kg weight to 0.004 mg/kg weight, from about 0.0001 mg/kg weight to 0.003 mg/kg weight, from about 0.0001 mg/kg weight to 0.002 mg/kg weight. In some embodiments, the therapeutically effective dose may be 0.0001 mg/kg weight, 0.0002 mg/kg weight, 0.0003 mg/kg weight, 0.0004 mg/kg weight, 0.0005 mg/kg weight, 0.0006 mg/kg weight, 0.0007 mg/kg weight, 0.0008 mg/kg weight, 0.0009 mg/kg weight, 0.001 mg/kg weight, 0.002 mg/kg weight, 0.003 mg/kg weight, 0.004 mg/kg weight, 0.005 mg/kg weight, 0.006 mg/kg weight, 0.007 mg/kg weight, 0.008 mg/kg weight, 0.009 mg/kg weight, 0.01 mg/kg weight, 0.02 mg/kg weight, 0.03 mg/kg weight, 0.04 mg/kg weight, 0.05 mg/kg weight, 0.06 mg/kg weight, 0.07 mg/kg weight, 0.08 mg/kg weight, 0.09 mg/kg weight, or 0.1 mg/kg weight. The effective dose for a particular individual can be varied (e.g., increased or decreased) over time, depending on the needs of the individual.

In some embodiments, a therapeutically effective dosage of the 15-PGHD inhibitor and/or the corticosteroid may be a dosage of 10 µg/kg/day, 50 µg/kg/day, 100 µg/kg/day, 250

µg/kg/day, 500 µg/kg/day, 1000 µg/kg/day or more. In various embodiments, the amount of the 15-PGDH inhibitor and/or corticosteroid is sufficient to provide a dosage to a patient of between 0.01 µg/kg and 10 µg/kg; 0.1 µg/kg and 5 µg/kg; 0.1 µg/kg and 1000 µg/kg; 0.1 µg/kg and 900 µg/kg; 0.1 µg/kg and 900 µg/kg; 0.1 µg/kg and 800 µg/kg; 0.1 µg/kg and 700 µg/kg; 0.1 µg/kg and 600 µg/kg; 0.1 µg/kg and 500 µg/kg; or 0.1 µg/kg and 400 µg/kg.

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, severity of cardiac defect and/or level of risk of cardiac defect, etc., or combinations thereof). Such doses or amounts can be determined by those of ordinary skill. In some embodiments, an appropriate dose or amount is determined in accordance with standard clinical techniques. For example, in some embodiments, an appropriate dose or amount is a dose or amount sufficient to reduce a disease severity index score by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100% or more. For example, in some embodiments, an appropriate dose or amount is a dose or amount sufficient to reduce a disease severity index score by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100%. Alternatively or additionally, in some embodiments, an appropriate dose or amount is determined through use of one or more in vitro or in vivo assays to help identify desirable or optimal dosage ranges or amounts to be administered.

Various embodiments may include differing dosing regimen. In some embodiments, the 15-PGDH inhibitor and corticosteroids described herein can be administered via continuous infusion. In some embodiments, the continuous infusion is intravenous. In other embodiments, the continuous infusion is subcutaneous. Alternatively or additionally, in some embodiments, the 15-PGDH inhibitor can be administered bimonthly, monthly, twice monthly, triweekly, biweekly, weekly, twice weekly, thrice weekly, daily, twice daily, or on another clinically desirable dosing schedule. The dosing regimen for a single subject need not be at a fixed interval, but can be varied over time, depending on the needs of the subject.

For topical application, the composition can be administered in the form of aqueous, alcoholic, aqueous-alcoholic or oily solutions or suspensions, or of a dispersion of the lotion or serum type, of emulsions that have a liquid or semi-liquid consistency or are pasty, obtained by dispersion of a fatty phase in an aqueous phase (O/W) or vice versa (W/O) or multiple emulsions, of a free or compacted powder to be used as it is or to be incorporated into a physiologically acceptable medium, or else of microcapsules or microparticles, or of vesicular dispersions of ionic and/or nonionic type. It may thus be in the form of a salve, a tincture, milks, a cream, an ointment, a powder, a patch, an impregnated pad, a solution, an emulsion or a vesicular dispersion, a lotion, aqueous or anhydrous gels, a spray, a suspension, a shampoo, an aerosol or a foam. It may be anhydrous or aqueous. It may also comprise solid preparations constituting soaps or cleansing cakes.

Pharmaceutical compositions including the 15-PGDH inhibitor and corticosteroids described herein can additionally contain, for example, at least one compound chosen from prostaglandins, in particular prostaglandin $PGE_1$, $PGE_2$, their salts, their esters, their analogues and their derivatives, in particular those described in WO 98/33497, WO 95/11003, JP 97-100091, JP 96-134242, in particular agonists of the prostaglandin receptors. It may in particular contain at least one compound such as the agonists (in acid form or in the form of a precursor, in particular in ester form) of the prostaglandin $F_2\alpha$ receptor, such as for example latanoprost, fluprostenol, cloprostenol, bimatoprost, unoprostone, the agonists (and their precursors, in particular the esters such as travoprost) of the prostaglandin $E_2$ receptors such as 17-phenyl $PGE_2$, viprostol, butaprost, misoprostol, sulprostone, 16,16-dimethyl $PGE_2$, 11-deoxy $PGE_1$, 1-deoxy $PGE_1$, the agonists and their precursors, in particular esters, of the prostacycline (IP) receptor such as cicaprost, iloprost, isocarbacycline, beraprost, eprostenol, treprostinil, the agonists and their precursors, in particular the esters, of the prostaglandin $D_2$ receptor such as BW245C ((4S)-(3-[(3R,S)-3-cyclohexyl-3-isopropyl]-2,5-dioxo)-4-imidazolidinchept-anoic acid), BW246C ((4R)-(3-[(3R,S)-3-cyclohexyl-3-isopropyl]-2,5-dioxo)-4-imidazolidinehept-anoic acid), the agonists and their precursors, in particular the esters, of the receptor for the thromboxanes A2 (TP) such as I-BOP ([1S-[1a,2a(Z), 3b(1E,3S),4a]]-7-[3-[3-hydroxy-4-[4-(iodophenoxy)-1-butenyl]-7-oxabicyclo-[2.2.1]hept-2-yl]-5-heptenoic acid).

Advantageously, the composition can include at least one 15-PGDH inhibitor and corticosteroid as defined above and at least one prostaglandin or one prostaglandin derivative such as for example the prostaglandins of series 2 including in particular $PGF_{2\alpha}$ and $PGE_2$ in saline form or in the form of precursors, in particular of the esters (example isopropyl esters), their derivatives such as 16,16-dimethyl $PGE_2$, 17-phenyl $PGE_2$ and 16,16-dimethyl $PGF_2$a 17-phenyl $PGF_2$a, prostaglandins of series 1 such as 11-deoxyprostaglandin E1, 1-deoxyprostaglandin E1 in saline or ester form, is their analogues, in particular latanoprost, travoprost, fluprostenol, unoprostone, bimatoprost, cloprostenol, viprostol, butaprost, misoprostol, their salts or their esters.

The invention is further illustrated by the following examples, which is not intended to limit the scope of the claims.

Example 1

Analysis of Effect of SW033291 on Dextan Sodium Sulfate (DSS) Induced Colitis

This Example provides data from studies of the effect of SW033291 on prevention of induction of colitis in the dextran sodium sulfate (DSS) treated mouse. In the study, 8-12 week old FVB male mice were fed with 2% DSS in drinking water for days 1-7, and then switched to normal drinking water beginning on day 8, and continued through day 22. Mice were treated with twice daily SW033291 5 mg/kg IP in a vehicle of 10% Ethanol, 5% Cremophor EL, 85% D5W, at 125 µg/200 ul, versus with vehicle alone. Clinical scoring (body weight, rectal bleeding, stool consistency) was recorded daily, endoscopic scoring (ulcer number, mucosal thickening, and vascular pattern) was assessed on days 8, 11, 15. Mice were sacrificed on days 1, 8, 15 and 22 for assessment of colon length, colon weight, ulcer number, ulcer area, and crypt damage.

Table 1 shows a summary of the baseline properties of age and weight of the 24 SW033291 treated mice and the 24 control group mice used in the study. Also provided are baseline characteristics of 4 FVB male 15-PGDH knockout (KO) mice that are used as a comparator group.

TABLE 1

FVB PGDH WT/KO male mice
8-12 weeks old

| DSS Study | WT-Control | WT-Treatment | KO | p-value |
|---|---|---|---|---|
| Number | 24 | 24 | 4 | |
| Sex | M | M | M | |
| Age (Days) | 74.1 ± 3.7 | 74.2 ± 4.0 | 73.9 ± 3.4 | 0.655 |
| Weight (gm) | 26.3 ± 1.19 | 26.8 ± 1.78 | 27.4 ± 1.4 | 0.391 |

Figure 1:
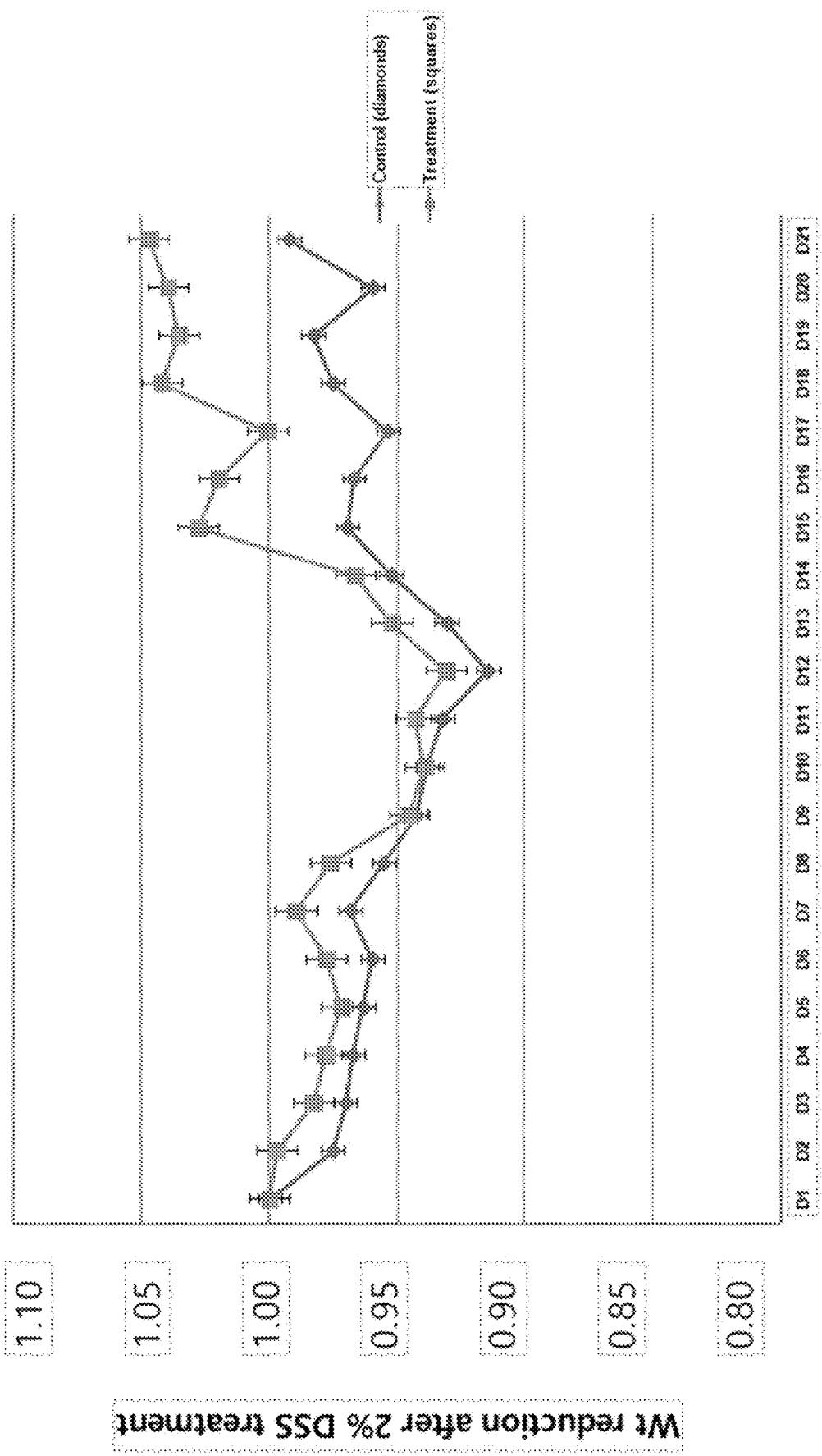
FIG. 1 illustrates a graph showing the average changes from baseline weight of the cohort of control (diamonds)

FIG. 1 shows a graph of the average changes from baseline weight of the cohort of control versus SW033291 treated mice across the 22 days of the study. SW033291 treated mice (squares) show greater weight at all time points, and in particular, show faster weight gain after washout of DSS then do the control mice (diamonds), P=0.001.

FIG. 2 shows a graph of the daily Disease Activity Index (DAI) of the cohort of control (diamonds) versus SW033291 treated mice across (squares) the 22 days of the study. The Disease Activity Index is calculated as an equally weighted average of the change from baseline weight, the consistency of stool, and the presence of rectal bleeding, with each component normalized to span an identical numerical range. SW033291 treated mice (squares) show a lower Disease Activity Index than do control (diamonds) on each day of the study, P<0.001.

FIG. 3 shows the design of the study in which colonoscopic examination of the left colon, up to the splenic flexure, was performed on live mice on days 8, 11 and 15, under isoflurane anesthesia. Daily weights of these SW033291 treated (squares) and untreated mice (diamonds) were also recorded and are shown. In addition, post-mortem colonoscopy of the full colon was performed on two SW033291 treated (squares) and two control treated mice (diamonds) on day 15, with findings confirming that DSS induced ulcerations are largely confined to the descending colon distal to the splenic flexure.

FIGS. 4(A-B) show at bottom left the colon as visualized during colonoscopy of a DSS treated control mouse that shows loss of the mucosal vascular pattern and a gross ulceration (FIG. 4B). At bottom right is shown the colonoscopic findings of a DSS treated mouse receiving SW033291, with only a small ulcer and with maintenance of the normal mucosal vascular pattern otherwise (FIG. 4B). FIG. 4A is a graph showing numbers of ulcers present on days 8 (bottom), 11 (middle), and 15 (top) in the control versus SW033291 treated mice. SW033291 treatment prevents two-thirds of ulcer formation. Additional studies of 15-PGDH knockout mice show that 15-PGDH gene knockout prevents 95% of colon ulcer formation. These findings support that the colitis prevention activity of SW033291 is mediated through its activity as a 15-PGDH inhibitor, and suggest further modifications of drug dosing and delivery may provide added colitis prevention and would also be expected to protect from other forms of intestinal injury that would include toxicity from radiation, toxicity from chemotherapy, and chemotherapy induced mucositis.

FIG. 5 shows quantitation of ulcer burden on day 15 of DSS treated mice as determined by embedding the full length of the formalin fixed colons of mice in paraffin blocks, and then microscopic inspection of a random 5 µm section along the full colon length for visualization and measurement of ulcerated mucosa. The graph shows that the average length of ulcerated mucosa is 4.48 mm per colon section in control mice (N=9 mice) and is reduced by 61% to a length of 1.74 mm per colon section in SW033291 (drug) treated mice (N=6 mice), P=0.045. Again, 15-PGDH gene knockout (KO) is highly effective in preventing colon ulceration, supporting that the therapeutic effect of SW033291 is mediated through inhibition of 15-PGDH.

FIGS. 6(A-B) show examples of scoring murine colonic mucosa according to the Murine Endoscopic Index of Colitis Severity (MEICS) (Becker C. et al. Gut 2005; 54: 950-954). FIG. 6A shows the colonoscopic findings and MEICS scoring for a DSS treated mouse receiving SW033291. FIG. 6B the colonoscopic findings and MEICS scoring of a DSS treated mouse receiving vehicle only.

FIG. 7 shows graphs of the MEICS scores for DSS treated mice receiving SW033291 (treatment, right) versus vehicle (control, left). MEICS scores show significantly less colitis activity in SW033291 treated mice on days 8, 11 and 15 of the study.

In addition to the gross visual inspection and scoring of colitis activity by the MEICS index, full length colons of mice were formalin fixed and paraffin embedded, and microscopic scoring of crypt damage was performed using the 0-4 severity scale of Cooper H S. Et al., Lab Invest. 1993; 69:238-249. For this analysis, the colons were divided into 3 segments of proximal, middle, and distal colon, each approximately 1.6 cm in length, with each segment was further subdivided into 4 sections each approximately 4 mm in length. For each section the crypt damage severity score was multiplied by the length in mm of the damaged area, creating a 0-16 cryptitis severity index. An average cryptitis severity index was calculated for each segment (proximal, middle, and distal colon), and the summed whole colon cryptitis severity index was determined on a scale of 0-48 for each mouse colon. In parallel with the visual MEICS score, the microscopic cryptitis severity index on day 8 of the DSS protocol was significantly greater in control mice (value of 9.49) than in the SW033291 treated mice (value of 3.16), P<0.05 (data described but not shown in the figure).

FIG. 8 shows assessment of the effect of SW033291 on maintaining DNA synthesis in the colonic mucosa of DSS treated mice. Mice were injected with BrdU at 100 mg/kg IP 3 hours before sacrifice and then full length colons were formalin fixed and embedded in paraffin. S-phase cells, that have incorporated BrdU into DNA, were visualized by immuno-fluorescent staining of 5 µm thick sections with an antibody that detects the BrdU. Colonic crypts were visualized by immuno-fluorescent staining with an antibody to the epithelial marker E-Cadherin. Photographic insets show photomicrographs of high powered fields taken from the mid-colon on day 8 of the DSS protocol from control mice, SW033291 treated mice (treatment) and 15-PGDH knockout mice (KO). Red immune-fluorescence identifies BrdU positive nuclei, and green immune-fluorescence identifies E-Cadherin positive colonocytes. The number of BrdU positive cell per crypt is determined by counting the number of dual labeled red and green cells per average crypt. Green only cells that are not in S-phase are not counted, and red only cells, that are likely stromal cells outside of crypts, are also not counted. On the photomicrograph shown crypts are displayed as vertically oriented in control and SW033291 treated mice, and crypts are displayed as horizontally oriented in the 15-PGDH knockout mice. In the photographs the numbers of S-phase cells are fewest in the control mice and are increased in the SW033291 treated mice, and increased further in the knockout mice. In the particular photographs shown, the crypts from control mice both lack S-phase cells and are also visually decreased in height; whereas, crypt height is increased in the crypts shown from SW033291 treated mice, and crypt heights is increased further in the crypts shown from 15-PGDH knockout mice. The graph depicts the sum of the average number of BrdU positive cells per crypt in the distal colon plus the average number of BrdU positive cells per crypt middle colons of control (Cn), SW033219 treated (Tx), and 15-PGDH knockout mice (KO) on day 1, day 8, and day 15 of the DSS treatment protocol. On day 8, SW033291 treated mice demonstrate 5.7-fold greater numbers of BrdU positive cells than do control mice, which have lost 85% of the day 1 value of BrdU positive cells per crypt. 15-PGDH knockout mice show no loss of BrdU positive cells in the crypt on day 8, consistent with the protective effect of SW033291 being mediated by inhibition of 15-PGDH.

Table 2 shows a summary of colon length (in cm) in DSS treated mice sacrificed on days 8, 15 and 22, in SW033291 treated mice, versus vehicle treated control mice, versus 15-PGDH knockout (KO) mice, where shortening of the colon is a measure of disease activity.

TABLE 2

Colon length shortening may be correlated to severity of the colon ulceration

| Time Point | Control | SW033291 | KO | P-value |
|---|---|---|---|---|
| Baseline | 8.3 + 0.2 | 8.4 + 0.2 | | 0.71 |
| Day 8 | 6.6 + 0.4 | 6.6 + 0.1 | | 1.0 |
| Day 15 | 7.1 + 0.1 | 7.5 + 0.1 | 8.5 + 0.1 | 0.001 |
| Day 22 | 7.4 + 0.2 | 8.6 + 0.3 | | 0.012 |

Vehicle treated control mice show significantly greater colon shortening at day 22 versus SW033291 treated mice, P=0.012. This comparison is also shown graphically in FIG. 9.

Table 3 shows a summary on day of sacrifice of mouse weights (gms) and colon lengths (cm) for DSS treated mice receiving SW033291 or vehicle control.

TABLE 3

| Wt @sacrifice-gm Time Point | Vehicle | SW033291 | KO |
|---|---|---|---|
| Baseline | 26.3 + 0.7 | 25.9 + 0.7 | |
| Day 8 | 25.4 + 0.7 | 26.4 + 0.5 | |
| Day 15 | 24.4 + 0.5 | 25.2 + 0.9 | |
| Day 22 * | 26.3 + 0.7 | 28.2 + 0.5 | 29.2 + 1.3 |
| Colon length-cm Time Point | | | |
| Baseline | 8.3 + 0.2 | | |
| Day 8 | 6.6 + 0.4 | 8.4 + 0.2 | |
| Day 15 | 7.1 + 0.1 | 6.6 + 0.1 | |
| Day 22 * | 7.4 + 0.2 | 7.5 + 0.1 | 8.5 + 0.1 |
| | | 8.6 + 0.3 | |

On day 22 SW033291 treated mice show greater body weight and greater colon lengths, indicative of therapeutic effect of SW033291 in protecting against DSS induced colitis.

Example 2

Identifying Signaling Networks Associated with 15-PGDH Expression

In order to identify signaling networks that are significantly correlated with 15-PGDH gene expression in colon tissues, we first to comprehensively characterized global pathway network activities across 16 normal colon tissue samples using an integrative pathway network modeling framework, PARADIGM. (Vaske, C. J., et al. Inference of patient-specific pathway activities from multi-dimensional cancer genomics data using PARADIGM. *Bioinformatics* 26, i237-245 (2010).) The PARADIGM analytics framework leverages gene expression measurements for a given sample in order to explicitly model regulatory relationships detailed in a given signaling network and estimate the biological activity state of each of the signaling network components in the tissue sample. (Varadan, V., Mittal, P., Vaske, C. J. & Benz, S. C. The integration of biological pathway knowledge in cancer genomics: A review of existing computational approaches. *IEEE Signal Processing Magazine* 29, 35-50 (2012); Cancer Genome Atlas, N. Comprehensive molecular characterization of human colon and rectal cancer. *Nature* 487, 330-337 (2012); Cancer Genome Atlas, N. Comprehensive molecular portraits of human breast tumours. *Nature* 490, 61-70 (2012); tlas, T.C.G. Integrated genomic analyses of ovarian carcinoma. *Nature* 474, 609-615 (2011)). PARADIGM incorporates known signaling network information curated within public databases such as the National Cancer Institute's Pathway Interaction Database (NCI-PID), Reactome and BioCarta pathway databases, resulting in a merged signaling network structure (SuperPathway) containing over 17000 concepts representing 7324 proteins, 1574 protein families, 7813 complexes, and 586 processes. (Schaefer, C. F., et al. PID: the Pathway Interaction Database. Nucleic acids research 37, D674-679 (2009); Croft, D., et al. The Reactome pathway knowledgebase. Nucleic acids research 42, D472-477 (2014)). Thus, PARADIGM leverages gene expression data obtained for genes within the SuperPathway network to infer sample-specific activity levels, called Integrated Pathway Levels (IPLs) for each network component in the SuperPathway network. The IPLs are typically distributed between −1 and +1, with negative IPLs corresponding to lower activity and positive IPLs corresponding to higher pathway-specific activity.

Accordingly, we used PARADIGM to analyze normalized, log 2-transformed gene expression values across normal colon tissue samples (N=16) resulting in the estimation of Integrated Pathway Levels (IPL) for each component of the SuperPathway network, and then evaluated the correlation of the IPLs across all components in the SuperPathway with the normalized 15-PGDH gene expression. The extent and statistical significance of the correlation was determined using the Spearman's rho statistic. Pathway network components with a Spearman correlation p-value≤0.01 were considered significant and the resulting sub-networks along with their regulatory relationships were plotted using Cytoscape. (Shannon, P., et al. Cytoscape: a software environment for integrated models of biomolecular interaction networks. *Genome research* 13, 2498-2504 (2003)). The resulting interconnected component sub-networks provide insights into transcription factor activities associated with 15-PGDH gene expression across normal colon tissues.

In order to further evaluate the likelihood of identifying a sub-network of a given size purely by chance, we performed 10,000 randomization experiments. In each iteration, we randomly selected the same number of network components from the SuperPathway as originally identified to be significantly associated with 15-PGDH expression. Subsequently, for each iteration, we determined the sizes and numbers of connected sub-networks derived from these random component selections. The resulting distribution of sub-network sizes obtained from the 10,000 random iterations were modeled as a Poisson distribution, thus allowing us to estimate the probability of obtaining a sub-network of a given size purely by chance.

FIG. 10 illustrates identifying that Glucocorticoid receptor NR3C1-centered sub-network activities are significantly correlated with 15-PGDH gene expression in normal human colons via examining PARADIGM SuperPathway sub-networks whose activities are significantly correlated with 15-PGDH gene expression in normal colon tissues. Pathway components showing significant activity correlation with 15-PGDH gene expression across 16 normal colon cancer tissues (Spearman Correlation P-Value≤0.01) are plotted along with their regulatory relationships in shades of red (positively correlated) and green (negatively correlated), with darker colors corresponding to higher absolute correlation. The size of the node corresponds to the statistical significance of the correlation. The p-value assigned to each sub-network is the probability of obtaining a sub-network of this size purely by chance.

Example 3

Combination of a Corticosteroid and an Inhibitor of 15-PGDH

We have previously demonstrated that SW033291, an inhibitor of 15-PGDH, has activity in treatment of DSS induced colitis, a murine model of ulcerative colitis. This example provides new findings showing inhibitors of 15-PGDH synergistically enhance corticosteroid treatment of DSS induced colitis, a murine model of ulcerative colitis.

FIG. 11A shows a schema of the study in which mice received three daily doses of dexamethasone and were sacrificed 6 hours after the third dose for analysis. FIG. 11B shows representative western blot analysis showing dexamethasone induction of 15-PGDH protein in mouse colon, at two different doses of dexamethasone. FIG. 11C is a graphical summary of real time RT-PCR from all mice in the study, showing an approximate doubling of colon 15-PGDH expression level by dexamethasone treatment.

FIG. 12A shows a schema of near doubling of 15-PGDH enzyme activity in colons of dexamethasone treated mice. FIG. 12B shows findings that corticosteroids increase colon 15-PGDH activity suggesting that these agents paradoxically induce a negative feedback loop that would act to retard healing of colon mucosa in ulcerative colitis and intestinal mucosa in Crohn's disease. These findings predict that combining corticosteroid therapy with a 15-PGDH inhibitor would be predicted to improve the efficacy of corticosteroid therapy of ulcerative colitis and Crohn's disease.

FIGS. 13(A-B) show higher dexamethasone doses exacerbate colitis induction by DSS. 8-week old FVB/NJ male mice were exposed to 2% DSS in drinking water concurrent with daily dexamethasone intraperitoneal injections at specified dose, 0 mpk (diamonds), 0.06 mpk (squares), 0.3 mpk (triangles), 3.0 mpk(x). To compare the effects of increasing dexamethasone doses on the induction of colitis, daily weights and disease activity indices (severity of diarrhea and hematochezia) were compared and are graphed as shown (mean±SEM, N=5-8), with relative daily weights shown in FIG. 13A and daily disease activity shown in FIG. 13B. Higher doses of dexamethasone significantly exacerbated the induction of colitis; mice with 0.3 or 3 mpk of dexamethasone displayed significantly worse weight loss and mice with 3 mpk developed significantly worse disease activity compared to the lower dose.

FIG. 14 shows the schematic of a study in which mice receive 7 days of 2.5% DSS in drinking water (from day 1 to day 8), a regime that induces murine colitis. Starting on day 8 mice are then treated with either: vehicle control; with a 15-PGDH inhibitor—(+) SW033291 at 5 mpk IP twice daily (abbreviated (+) 291); with dexamethasone 0.06 mpk IP daily (abbreviated dex); or with the combination of (+) SW033291 at 5 mpk IP twice daily plus dexamethasone 0.06 mpk IP daily. (mpk=mg/kg).

FIG. 15 shows daily weights of mice on the study from days 1-17, mice were treated with control (diamonds), SW033291 (squares), dexamethasone 0.06 mpk (triangles), and combination of both SW033291 and dexamethasone (x). While both (+) SW033291 (squares) and dexamethasone (triangles) treatment as single agents provide some amelioration of weight loss, the combination of (+) SW033291 plus dexamethasone (x) was significantly more effective.

FIG. 16 shows disease activity as measured by the disease activity index (DAI) in which diarrhea (on a 0-3 scale) and fecal blood (on a 0-3 scale) are combined (on a 0-6 scale). Mice were treated with control (diamonds), SW033291 (squares), dexamethasone 0.06 mpk (triangles), and combination of both SW033291 and dexamethasone (x). While both (+) SW033291 (squares) and dexamethasone (triangles) treatment as single agents provide some amelioration of DAL, the combination of (+) SW033291 plus dexamethasone (x) was significantly more effective.

FIG. 17A graphs these results showing area under the DAI curve (total DAI) and FIG. 17B the percent decrease in total DAI (relative disease reduction) graphed. Single agent (+) SW033291 reduced total DAI by 14%. Single agent dexamethasone reduced total DAT by 15%. However the combination of (+) SW033291 plus dexamethasone reduced total DAL by 35%.

FIG. 18 graphs the survival of mice with control, dexamethasone, SW033291, and combination treatment on a daily basis through day 16 of the disease model (N=12 per group). *p<0.05 by Mantel-Cox test.

FIG. 19 is a regraphing of the data of FIG. 17B, with P-values, and a reordering of the sequence of presenting the groups. Combination group (green bar) is significantly improved compared to control (blue bar) or dexamethasone (yellow bar) or (+)-SW033291 (red bar) and is superior to either of the monotherapy regimens. Means+SEM (N=6 per arm). p<0.01, *p<0.005 by ANOVA and Student's t-test.

FIGS. 20(A-D) show representative endoscopic images for each group (A) control, (B) dexamethasone, (C) SW033291, and (D) combination) on day 13 of treatment. Signs of mucosal bleeding and reduced wall transparency were evident in the control group whereas reduced wall transparency is more prominent in the dexamethasone group when compared to (+)-SW033291 or combination.

FIG. 21 shows graphs of murine endoscopic index of colitis severity (MEICS) scores as means+SEM (N=8-10 per arm) on day 13 for each treatment group (control, dexamethasone, SW033291, and combination). p<0.01, *p<0.005 by ANOVA and Student's t-test.

Figure 22:
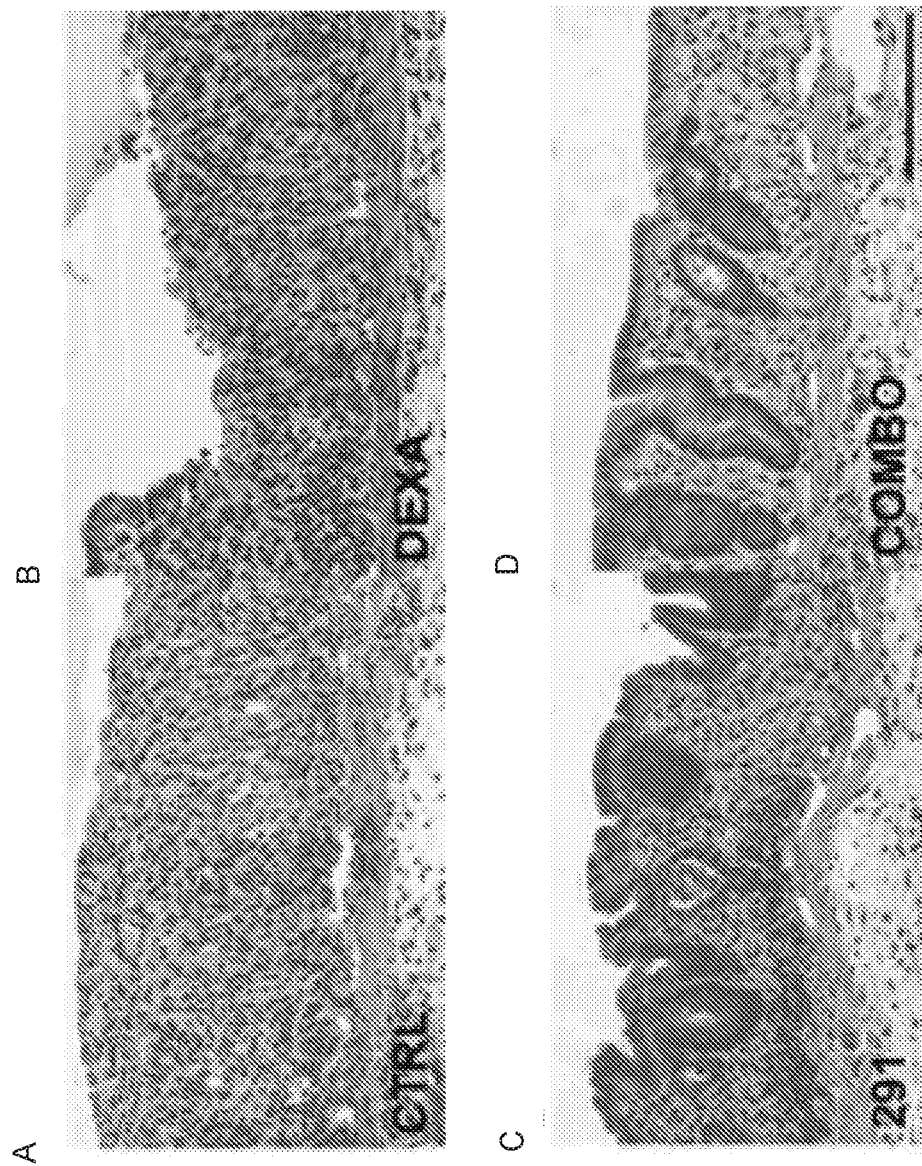

FIGS. 22(A-D) show representative histological pictures of distal colons on day 13 of each treatment group (A) control, (B) dexamethasone, (C) SW033291, and (D) combination. Destruction of epithelial crypt structures were more severely manifested in both control and dexamethasone-treated mice compared to (+)-SW033291- or combination-treated mice. Scale bar: 200 µm.

FIG. 23 shows graphs of semi-quantitatively scored histological extent of inflammatory damage to the crypts ("cryptits"). p<0.01, *p<0.005 by ANOVA and Student's t-test.

FIG. 24 shows graphs of the severity of mesenteric lymphadenopathy assessed by collective mesenteric lymph node weight normalized by body weight on day 13 of each treatment group (control, dexamethasone, SW033291, and combination). Means+SEM (N=11-16). ***p<0.005 by ANOVA and Student's t-test.

The invention claimed is:

1. A method of treating intestinal, gastrointestinal, or bowel disorders in a subject in need thereof, the method comprising administering to the subject therapeutically effective amounts of a 15-PGDH inhibitor of formula:

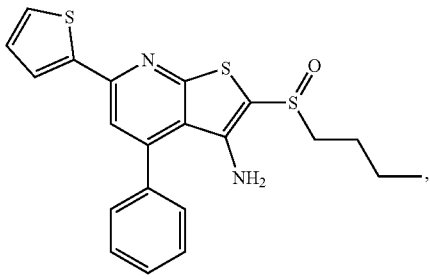 [SMILES: CCCCS(=O)c1sc2nc(-c3cccs3)cc(-c3ccccc3)c2c1N]

or a pharmaceutically acceptable salt thereof, and a corticosteroid, dexamethasone.

2. The method of claim 1, wherein the disorder comprises oral ulcers, gum disease, gastritis, colitis, ulcerative colitis, gastric ulcers, inflammatory bowel disease, Crohn's disease, or combinations thereof.

3. The method of claim 1, wherein the bowel disorder is inflammatory bowel disease.

4. The method of claim 1, wherein the corticosteroid induces 15-PGDH expression.

5. The method of claim 1, wherein the 15-PGDH inhibitor is effective to attenuate corticosteroid induced adverse and/or cytotoxic effects in a subject, or to increase therapeutic efficacy.

6. The method of claim 1, wherein the intestinal, gastrointestinal, or bowel disorder comprises inflammation of the esophagus, inflammation of the glottis, inflammation of the epiglottis, inflammation of the tonsils, inflammation of the oropharynx, eosinophilic esophagitis, gastroesophageal reflux disease (GERD), non-erosive reflux disease (NERD), erosive esophagitis, Barrett's esophagus, eosinophilic gastroenteritis, hypereosinophilic syndrome, corrosive (caustic) chemical esophagitis, radiation-induced esophagitis, chemotherapy-induced esophagitis, transient drug-induced esophagitis, persistent drug-induced esophagitis, Crohn's disease of the esophagus, pseudomembranous esophagitis, or combinations thereof.

* * * * *

UNITED STATES PATENT AND TRADEMARK OFFICE
CERTIFICATE OF CORRECTION

| | |
|---|---|
| PATENT NO. | : 11,690,847 B2 |
| APPLICATION NO. | : 16/465500 |
| DATED | : July 4, 2023 |
| INVENTOR(S) | : Markowitz et al. |

It is certified that error appears in the above-identified patent and that said Letters Patent is hereby corrected as shown below:

In the Specification

Column 1, Lines 19-22, should read as follows:
--This invention was made with government support under Grant No. DK107156 and CA150964, awarded by The National Institutes of Health. The United States government has certain rights in the invention.--

Signed and Sealed this
Twenty-second Day of August, 2023

Katherine Kelly Vidal
*Director of the United States Patent and Trademark Office*